US009873880B2

(12) United States Patent
Scaife et al.

(10) Patent No.: US 9,873,880 B2
(45) Date of Patent: Jan. 23, 2018

(54) ENGINEERING MICROORGANISMS

(71) Applicant: DSM NUTRITIONAL PRODUCTS AG, Kaiseraugst (CH)

(72) Inventors: Mark A. Scaife, Ely (GB); Roberto E. Armenta, Dartmouth (CA)

(73) Assignee: DSM Nutritional Products AG, Kaiseraugst (CH)

( * ) Notice: Subject to any disclaimer, the term of this patent is extended or adjusted under 35 U.S.C. 154(b) by 199 days.

(21) Appl. No.: 14/776,245

(22) PCT Filed: Mar. 12, 2014

(86) PCT No.: PCT/IB2014/059687
§ 371 (c)(1),
(2) Date: Sep. 14, 2015

(87) PCT Pub. No.: WO2014/141098
PCT Pub. Date: Sep. 18, 2014

(65) Prior Publication Data
US 2016/0040175 A1    Feb. 11, 2016

Related U.S. Application Data

(60) Provisional application No. 61/779,257, filed on Mar. 13, 2013.

(51) Int. Cl.
*C12P 7/64* (2006.01)
*C12N 15/79* (2006.01)
*C12N 9/02* (2006.01)

(52) U.S. Cl.
CPC .......... *C12N 15/79* (2013.01); *C12N 9/0071* (2013.01); *C12P 7/6427* (2013.01); *C12Y 114/19006* (2013.01)

(58) Field of Classification Search
CPC combination set(s) only.
See application file for complete search history.

(56) References Cited

U.S. PATENT DOCUMENTS

| | | | |
|---|---|---|---|
| 2,076,018 A | 4/1937 | Ferguson |
| 4,295,383 A | 10/1981 | Frost |
| 4,341,038 A | 7/1982 | Bloch et al. |
| 4,445,495 A | 5/1984 | Frost |
| 4,680,314 A | 7/1987 | Nonomura |
| 4,952,511 A | 8/1990 | Radmer |
| 5,070,018 A | 12/1991 | Peters et al. |
| 5,104,803 A | 4/1992 | Delente et al. |
| 5,130,242 A | 7/1992 | Barclay et al. |
| 5,151,347 A | 9/1992 | Delente et al. |
| 5,162,051 A | 11/1992 | Hoeksema |
| 5,164,308 A | 11/1992 | Kyle et al. |
| 5,168,056 A | 12/1992 | Frost et al. |
| 5,171,680 A | 12/1992 | Mullenbach et al. |
| 5,211,181 A | 5/1993 | Delente |
| 5,232,565 A | 8/1993 | Zare et al. |
| 5,244,921 A | 9/1993 | Kyle et al. |
| 5,272,073 A | 12/1993 | Frost et al. |
| 5,324,658 A | 6/1994 | Cox et al. |
| 5,327,901 A | 7/1994 | Delente |
| 5,340,594 A | 8/1994 | Barclay et al. |
| 5,340,742 A | 8/1994 | Barclay et al. |
| 5,374,657 A | 12/1994 | Kyle |
| 5,376,540 A | 12/1994 | Kyle |
| 5,393,669 A | 2/1995 | Brown |
| 5,397,591 A | 3/1995 | Kyle et al. |
| 5,407,957 A | 4/1995 | Kyle et al. |
| 5,432,094 A | 7/1995 | Delente |
| 5,466,434 A | 11/1995 | Kyle et al. |
| 5,487,987 A | 1/1996 | Frost et al. |
| 5,492,938 A | 2/1996 | Kyle et al. |
| 5,518,918 A | 5/1996 | Barclay et al. |
| 5,547,699 A | 8/1996 | Iizuka et al. |
| 5,550,156 A | 8/1996 | Kyle |
| 5,567,732 A | 10/1996 | Kyle et al. |
| 5,583,019 A | 12/1996 | Barclay et al. |
| 5,593,853 A | 1/1997 | Chen et al. |
| 5,616,496 A | 4/1997 | Frost et al. |
| 5,627,044 A | 5/1997 | Brown |
| 5,629,181 A | 5/1997 | Frost et al. |
| 5,656,319 A | 8/1997 | Barclay et al. |
| 5,658,767 A | 8/1997 | Kyle |
| 5,688,500 A | 11/1997 | Barclay et al. |
| 5,698,244 A | 12/1997 | Barclay et al. |

(Continued)

FOREIGN PATENT DOCUMENTS

| CA | 2072978 | 10/2006 |
|---|---|---|
| CN | 101400798 A | 4/2009 |

(Continued)

OTHER PUBLICATIONS

PCT/IB2014/059687, International Search Report and Written Opinion, dated Jun. 11, 2014, 13 pages.
PCT/IB2014/059687, International Preliminary Report on Patentability, dated Sep. 15, 2015, 10 pages.
Omega-3 News, Ocean Nutrition Canada Ltd., 2011.
Thraustochytriaceae Family Data Sheet, 2007, 2 pages.
Breakthrough Process to Extract Oil from Algae, http://www.miningtopnews.com/originoil-announces-breakthrough-process-to-extract-oil-from-.htm., Apr. 20, 2009.
Oilgae Glossary, Available at http://www.oilgae.com/algae/oil/extract/extract.html, Jun. 4, 2009, 8 pages.
Marine Biopharmacy, Marine Biopharmacy fermentation engineering, Beijing Chemical Industry Press, 2002, 1: 96-101, with translation (12 pages).

(Continued)

*Primary Examiner* — Kagnew H Gebreyesus
(74) *Attorney, Agent, or Firm* — Kilpatrick Townsend & Stockton, LLP

(57) ABSTRACT

Provided are Thraustochytrid and *Thraustochytrium* and relevant methods and reagents, including engineered regulatory sequences and genes from and/or operative in Thraustochytrid or *Thraustochytrium*, selectable markers useful for engineering microorganisms such as Thraustochytrids, means for mutagenizing microorganisms, strains produced by mutagenesis, and methods and compositions related to production of particular compounds in microorganisms.

37 Claims, 18 Drawing Sheets

(56) References Cited

U.S. PATENT DOCUMENTS

| | | |
|---|---|---|
| 5,711,983 A | 1/1998 | Kyle et al. |
| 5,741,713 A | 4/1998 | Brown et al. |
| 5,770,598 A | 6/1998 | Miller et al. |
| 5,776,736 A | 7/1998 | Frost et al. |
| 5,798,236 A | 8/1998 | Frost et al. |
| 5,817,474 A | 10/1998 | Brown |
| 5,821,266 A | 10/1998 | Frost |
| 5,882,703 A | 3/1999 | Barclay et al. |
| 5,908,622 A | 6/1999 | Barclay et al. |
| 5,985,348 A | 11/1999 | Barclay |
| 6,027,900 A | 2/2000 | Allnutt et al. |
| 6,054,147 A | 4/2000 | Barclay et al. |
| 6,103,225 A | 8/2000 | Barclay et al. |
| 6,111,066 A | 8/2000 | Anderson et al. |
| 6,140,365 A | 10/2000 | Kiy et al. |
| 6,140,486 A | 10/2000 | Facciotti et al. |
| 6,166,230 A | 12/2000 | Bijl et al. |
| 6,166,231 A | 12/2000 | Hoeksema |
| 6,168,912 B1 | 1/2001 | Chen |
| 6,177,108 B1 | 1/2001 | Barclay |
| 6,180,376 B1 | 1/2001 | Liddell |
| 6,207,808 B1 | 3/2001 | Naae et al. |
| 6,255,505 B1 | 7/2001 | Bijl et al. |
| 6,335,196 B1 | 1/2002 | Anderson et al. |
| 6,340,578 B1 | 1/2002 | Anderson et al. |
| 6,350,890 B1 | 2/2002 | Kiy et al. |
| 6,372,460 B1 | 4/2002 | Gladue et al. |
| 6,372,461 B1 | 4/2002 | Frost |
| 6,376,253 B1 | 4/2002 | Anderson et al. |
| 6,395,778 B1 | 5/2002 | Luthria |
| 6,399,803 B1 | 6/2002 | Corley et al. |
| 6,410,281 B1 | 6/2002 | Barclay |
| 6,410,282 B1 | 6/2002 | Kumar et al. |
| 6,410,288 B1 | 6/2002 | Knutzon et al. |
| 6,432,468 B1 | 8/2002 | Akimoto et al. |
| 6,441,208 B2 | 8/2002 | Bijl et al. |
| 6,451,567 B1 | 9/2002 | Barclay |
| 6,461,839 B2 | 10/2002 | Yokochi et al. |
| 6,472,169 B1 | 10/2002 | Frost et al. |
| 6,472,190 B1 | 10/2002 | Frost |
| 6,509,178 B1 | 1/2003 | Tanaka et al. |
| 6,541,049 B2 | 4/2003 | Barclay |
| 6,566,123 B1 | 5/2003 | Barclay |
| 6,566,583 B1 | 5/2003 | Facciotti et al. |
| 6,568,351 B1 | 5/2003 | Barclay et al. |
| 6,582,941 B1 | 6/2003 | Yokochi et al. |
| 6,596,766 B1 | 7/2003 | Igarashi et al. |
| 6,600,077 B1 | 7/2003 | Frost et al. |
| 6,607,900 B2 | 8/2003 | Bailey et al. |
| 6,613,552 B1 | 9/2003 | Frost et al. |
| 6,620,602 B2 | 9/2003 | Frost et al. |
| 6,716,460 B2 | 4/2004 | Abril |
| 6,727,373 B2 | 4/2004 | Bijl et al. |
| 6,749,849 B2 | 6/2004 | Barclay |
| 6,750,048 B2 | 6/2004 | Ruecker et al. |
| 6,750,049 B1 | 6/2004 | Frost et al. |
| 6,783,951 B2 | 8/2004 | Long, II |
| 6,812,009 B2 | 11/2004 | Gladue et al. |
| 6,974,592 B2 | 12/2005 | Yan |
| 6,977,167 B2 | 12/2005 | Barclay |
| 7,001,772 B2 | 2/2006 | Roessler et al. |
| 7,002,047 B2 | 2/2006 | Frost et al. |
| 7,005,280 B2 | 2/2006 | Barclay |
| 7,011,962 B2 | 3/2006 | Barclay |
| 7,022,512 B2 | 4/2006 | Barclay |
| 7,033,584 B2 | 4/2006 | Barclay |
| 7,045,683 B2 | 5/2006 | Mukerji et al. |
| 7,063,855 B2 | 6/2006 | Hjaltason et al. |
| 7,067,145 B2 | 6/2006 | Place et al. |
| 7,067,285 B2 | 6/2006 | Mukerji et al. |
| 7,070,970 B2 | 7/2006 | Mukerji et al. |
| 7,087,432 B2 | 8/2006 | Qiu et al. |
| 7,172,886 B2 | 2/2007 | Keasling et al. |
| 7,183,089 B2 | 2/2007 | Keasling et al. |
| 7,192,751 B2 | 3/2007 | Keasling et al. |
| 7,214,491 B2 | 5/2007 | Yadav et al. |
| 7,214,853 B2 | 5/2007 | Facciotti et al. |
| 7,247,461 B2 | 7/2007 | Metz et al. |
| 7,259,006 B2 | 8/2007 | Komazawa et al. |
| 7,351,558 B2 | 4/2008 | Ruecker et al. |
| 7,374,908 B2 | 5/2008 | Yamaoka |
| 7,381,558 B2 | 6/2008 | Barclay |
| 7,419,596 B2 | 9/2008 | Dueppen et al. |
| 7,514,244 B2 | 4/2009 | Tanaka et al. |
| 7,642,083 B2 | 1/2010 | Frost et al. |
| 7,723,503 B2 | 5/2010 | Mukerji et al. |
| 7,842,852 B2 | 11/2010 | Cirpus et al. |
| 7,923,226 B2 | 4/2011 | Frost |
| 8,168,225 B2 | 5/2012 | Casaña Giner et al. |
| 2003/0060509 A1 | 3/2003 | Elswyk |
| 2003/0143659 A1 | 7/2003 | Bijl et al. |
| 2003/0180898 A1 | 9/2003 | Bailey et al. |
| 2004/0067574 A1 | 4/2004 | Bijl et al. |
| 2004/0209337 A1 | 10/2004 | Frost et al. |
| 2005/0181490 A1 | 8/2005 | Cheong et al. |
| 2005/0222312 A1 | 10/2005 | Frost et al. |
| 2006/0094089 A1 | 5/2006 | Barclay |
| 2006/0160203 A1 | 7/2006 | Barclay |
| 2006/0188969 A1 | 8/2006 | Barclay |
| 2006/0275904 A1 | 12/2006 | Ono et al. |
| 2008/0038800 A1 | 2/2008 | Ruecker et al. |
| 2008/0044875 A1 | 2/2008 | Ruecker et al. |
| 2008/0044876 A1 | 2/2008 | Ruecker et al. |
| 2008/0076164 A1 | 3/2008 | Cirpus et al. |
| 2008/0076166 A1 | 3/2008 | Cirpus et al. |
| 2008/0155888 A1 | 7/2008 | Vick et al. |
| 2008/0166780 A1 | 7/2008 | Barclay |
| 2008/0220515 A1 | 9/2008 | McCall |
| 2009/0029445 A1 | 1/2009 | Eckelberry et al. |
| 2009/0077863 A1 | 3/2009 | Oyler |
| 2009/0081748 A1 | 3/2009 | Oyler |
| 2010/0099901 A1 | 4/2010 | Hayashi et al. |
| 2010/0227924 A1 | 9/2010 | Cirpus et al. |
| 2011/0223641 A1 | 9/2011 | Stephanopoulos et al. |

FOREIGN PATENT DOCUMENTS

| | | |
|---|---|---|
| DE | 19832784 | 2/2000 |
| DE | 102004060340 | 2/2006 |
| EP | 568608 | 11/1993 |
| EP | 823475 | 2/1998 |
| EP | 894142 | 2/1999 |
| EP | 1305382 | 5/2003 |
| EP | 2110438 | 10/2009 |
| JP | 10072590 | 3/1998 |
| JP | 11075884 | 3/1999 |
| JP | 2976027 | 11/1999 |
| JP | 2000060587 | 2/2000 |
| JP | 2003304894 | 10/2003 |
| JP | 2003319795 | 11/2003 |
| JP | 2004168985 | 6/2004 |
| JP | 2006304686 | 11/2006 |
| WO | 8703899 | 7/1987 |
| WO | 8900606 | 1/1989 |
| WO | 9107498 | 5/1991 |
| WO | 9111918 | 8/1991 |
| WO | 9114427 | 10/1991 |
| WO | 9212711 | 8/1992 |
| WO | 9213086 | 8/1992 |
| WO | 9408467 | 4/1994 |
| WO | 9411516 A1 | 5/1994 |
| WO | 9633263 | 10/1996 |
| WO | 9704121 | 2/1997 |
| WO | 9737032 | 10/1997 |
| WO | 9743362 | 11/1997 |
| WO | 0005395 | 2/2000 |
| WO | 0054575 | 9/2000 |
| WO | 0154510 | 8/2001 |
| WO | 0210322 | 2/2002 |
| WO | 02092540 | 11/2002 |
| WO | 03033683 | 4/2003 |
| WO | 03086104 | 10/2003 |
| WO | 2004041251 | 5/2004 |
| WO | 2005058476 | 6/2005 |

(56) References Cited

FOREIGN PATENT DOCUMENTS

| WO | 2007068997 | 6/2007 |
|---|---|---|
| WO | 2007069078 | 6/2007 |
| WO | 2007074479 | 7/2007 |
| WO | 2008090989 | 7/2008 |
| WO | 2008129358 | 10/2008 |
| WO | 2009010825 | 1/2009 |
| WO | 2009034124 | 3/2009 |
| WO | 2010066703 | 6/2010 |
| WO | 2012120375 | 9/2012 |
| WO | 2014141098 | 9/2014 |

OTHER PUBLICATIONS

*Thraustochytriidae* sp. MBIC11093 gene for 18S rRNA, partial sequence, strain: MBIC11093, Primary Accession No. AB183664, Online Database EMBL-EBI, Jul. 22, 2004.
*Thraustochytriidae* sp. N1-27 gene for 18S ribosomal RNA, partial sequence, Primary Accession No. AB073308, Online Database EMBL-EBI, Apr. 20, 2002.
*Thraustochytrium* sp. CHN-1 gene for 18S rRNA, partial sequence, Primary Accession No. AB126669, Online Database EMBL-EBI, Nov. 11, 2002.
*Thraustochytrium* sp. ONC-T18 18S ribosomal RNA gene, partial sequence, Primary Accession No. DQ374149, Online Database EMBL-EBI, Oct. 20, 2006.
Thraustochytrium striatum small subunit ribosomal RNA gene, partial sequence, Primary Accession No. AF265338, Online Database EMBL-EBI, Jul. 8, 2001.
*Thraustochytriun* sp. FJN-10 18S ribosomal RNA gene, partial sequence, Primary Accession No. AY773276, Online Database EMBL-EBI, Nov. 3, 2004.
Aki et al., Thraustochytrid as a potential source of carotenoids, Journal of the American Oil Chemists' Society, vol. 80, Issue 8, 2003, pp. 789-794.
Armstrong et al., Carotenoids 2: Genetics and molecular biology of carotenoid pigment biosynthesis, Faseb Journal, vol. 10, issue 2, Feb. 1996, pp. 228-237.
Armstrong et al., Genetics of Eubacterial Carotenoid Biosynthesis: A Colorful Tale, Annual Review of Microbiology, vol. 51, 1997, pp. 629-659.
Bajpai et al., Optimization of production of docosahexaenoic acid (DHA) byThraustochytrium aureum ATCC 34304, Journal of the American Oil Chemists' Society, vol. 68, Issue 7, Jul. 1991, pp. 509-514.
Bajpai et al., Production of docosahexaenoic acid by Thraustochytrium aureum, Applied Microbiology and Biotechnology, vol. 35, Issue 6, Sep. 1991, pp. 706-710.
Baldwin, Application for the Approval of DHA-rich Oil, Omega Tech GmbH, Version No. Draft, 1997, 104 pages.
Barclay et al., Heterotrophic production of long chain omega-3 fatty acids utilizing algae and algae-like microorganisms, Journal of Applied Phycology, vol. 6, Issue 2, Apr. 1994, pp. 123-129.
Barclay et al., Nutritional Enhancement of n-3 and n-6 Fatty Acids in Rotifers and Anemia Nauplii by Feeding Spray-dried *Schizochytrium* sp., Journal of the World Aquaculture Society, vol. 27, Issue 3, Sep. 1996, pp. 314-322.
Basu et al., Nutritional and potential disease prevention properties of carotenoids, Journal of the American Oil Chemists' Society, vol. 78, Issue 7, 2001, pp. 665-675.
Bateman et al., Method for Extraction and Separation by Solid Phase Extraction of Neutral Lipid, Free Fatty Acids, and Polar Lipid from Mixed Microbial Cultures, Journal of Agricultural and Food Chemistry, Jan. 20, 1997, pp. 132-134.
Beckles et al., Omega-3 fatty acids (from fish oils) for cystic fibrosis, Cochrane Database Syst Rev., vol. 3, 2002, 12 pages.
Benson et al., GenBank, Nucleic Acids Research, vol. 33, Jan. 2005, pp. D34-D38.

Bligh et al., A Rapid Method of Total Lipid Extraction and Purification, Canadian Journal of Biochemistry and Physiology, vol. 37 No. 8, 1959, pp. 911-917.
Bowles et al., Long-chain n-3 polyunsaturated fatty acid production by members of the marine protistan group the thraustochytrids: screening of isolates and optimisation of docosahexaenoic acid production, Journal of Biotechnology, vol. 70, Issues 1-3, Apr. 1999, pp. 193-202.
Burja et al., Evaluation of fatty acid extraction methods for *Thraustochytrium* sp. ONC-T18, J. Agric. Food Chem., vol. 55, issue 12, May 12, 2007, pp. 4795-4801.
Burja et al., Isolation and characterization of polyunsaturated fatty acid producing *Thraustochytrium* species: screening of strains and optimization of omega-3 production, Appl Microbial Biotechnol., vol. 72 issue 6, Oct. 2006, pp. 1161-1169.
Carmona et al., Identification by HPLC-MS of carotenoids of the Thraustochytrium CHN-1 strain isolated from the Seto Inland Sea, Biosci Biotechnol Biochem., vol. 67, issue 4, 2003, pp. 884-888.
Caron et al., Defining DNA-Based Operational Taxonomic Units for Microbial-Eukaryote Ecology, Applied and Environmental Microbiology, vol. 75, issue 18, Sep. 2009, pp. 5797-5808.
Cartens et al., Eicosapentaenoic acid (20:5n-3) from the marine microalgaPhaeodactylum tricornutum, Journal of the American Oil Chemists' Society, vol. 73, Issue 8, Aug. 1996, pp. 1025-1031.
Clarridge, Impact of 16S rRNA Gene Sequence Analysis for Identification of Bacteria on Clinical Microbiology and Infectious Diseases, Clinical Microbiol Rev., vol. 17, issue 4, Oct. 2004, pp. 840-862.
Cleland et al., The Role of Fish Oils in the Treatment of Rheumatoid Arthritis, Drugs, vol. 63, Issue 9, May 2003, pp. 845-853.
Das et al., Beneficial effect(s) of n-3 fatty acids in cardiovascular diseases: but, why and how?, Prostaglandins Leukot Essent Fatty Acids, vol. 63, issue 6, Dec. 2000, pp. 351-362.
De Swaaf et al., Analysis of docosahexaenoic acid biosynthesis in Crypthecodinium cohnii by 13C labelling and desaturase inhibitor experiments, Journal of Biotechnology, vol. 103, Issue 1, Jun. 12, 2003, pp. 21-29.
Dongping et al., Chemical lnsdustry Press, 2006: 37-38, with translation (49 pages).
Edge et al., The carotenoids as anti-oxidants—a review, J Photochem Photobiol B., vol. 41, issue 3, Dec. 1997, pp. 189-200.
Ellenbogen et al., Polyunsaturated fatty acids of aquatic fungi: Possible phylogenetic significance, Comparative Biochemistry and Physiology, vol. 29, Issue 2, May 1969, pp. 805-811.
Felsenstein, Confidence Limits on Phylogenies: An Approach Using the Bootstrap, Evolution, vol. 39, No. 4, Jul. 1985, pp. 783-791.
Fleischhacker et al., New developments in the pharmacotherapy of schizophrenia, J. Neural Transm Suppl., vol. 64, 2003, pp. 105-117.
Franklin et al., Dietary marine algae (*Schizochytrium* sp.) increases concentrations of conjugated linoleic, docosahexaenoic and transvaccenic acids in milk of dairy cows, The American Society for Nutritional Sciences, vol. 129 No. 11, Nov. 1, 1999, pp. 2048-2054.
Fu et al., Study on Production of EPA and DHA in Microbe Fermentation, Grain Processing, No. 1, 48-51, 2004, (12 pages with translation).
Gill, Cellruptor a highly efficient biomass processing & biofuels processing platform technology, Eco-Solids International, http://w3.gre.ac.uk/cost859/Biohaste/ESICellruptor.pdf, 2008.
Haag, Essential fatty acids and the brain, Can J Psychiatry., vol. 48, issue 3, 2003, pp. 195-203.
Hauvennale et al., Fatty acid production in *Schizochytrium* sp.: Involvement of a polyunsaturated fatty acid synthase and a type I fatty acid synthase, Lipids, vol. 41, issue 8, Aug. 2006, pp. 739-747.
Honda et al., Molecular phylogeny of labyrinthulids and thraustochytrids based on the sequencing of 18S ribosomal RNA gene, Journal of Eukaryotic Microbiology, vol. 46, Issue 6, Nov. 1999, pp. 637-647.
Horrocks et al., Health Benefits of Docosahexaenoic Acid (DHA), Pharmacal Res., vol. 40, No. 3, 1999, pp. 211-225.
Huang et al., Grouping Newly Isolated Docosahexaenoic Acid-Producing Thraustochytrids Based on Their Polyunsaturated Fatty Acid Profiles and Comparative Analysis of 18S rRNA Genes, Marine Biotechnology, vol. 5, Issue 5, Oct. 2003, pp. 450-457.

(56) References Cited

OTHER PUBLICATIONS

Huang et al., Immunonutrients and neonates, Eur J Pediatr, vol. 162, issue 3, 2003, pp. 122-128.
Huang et al., Expressed sequence tag analysis of marine fungus *Schizochytrium* producing docosahexaenoic acid, J Biotechnol, 138, 1-2, 9-16, 2008.
Iida et al., Improvement of docosahexaenoic acid production in a culture of Thraustochytrium aureum by medium optimization, Journal of Fermentation and Bioengineering, vol. 81, Issue 1, 1996, pp. 76-78.
Jain et al., Docosahexaenoic acid accumulation in thraustochytrids: search for the rationale, Mar Biol, 151, 1657-1664, 2007.
Kaulmann et al., Biosynthesis of Polyunsaturated Fatty Acids by Polyketide Synthases, Angewandte Chemie International Edition, vol. 41, Issue 11, Jun. 3, 2002, pp. 1866-1869.
Kazama et al., Mineral nutrition of *Pythium marinum*, a marine facultative parasite, Canadian Journal of Botany, vol. 51, issue 4, 1973, pp. 693-699.
Khozin et al., Differential response of microalgae to the substituted pyridazinone, sandoz 9785, reveal different pathways in the biosynthesis of eicosapentaenoic acid, Phytochemistry, vol. 42, Issue 4, Jul. 1996, pp. 1025-1029.
Kowalchuk et al., Detection and characterization of fungal infections of *Ammophila arenaria* (marram grass) roots by denaturing gradient gel electrophoresis of specifically amplified 18s rDNA, Appl Environ Microbiol., vol. 63, issue 10, Oct. 1997, pp. 3858-3865.
Kumar et al., Radioprotection by antioxidant enzymes and enzyme mimetics, Pharmacol Ther., vol. 39, issue 1-3, 1988, pp. 301-309.
Leander et al., The Labyrinthulomycota Is Comprised of Three Distinct Lineages, Mycologia, vol. 93, No. 3, Botany, University of Georgia, Miller Plant Sciences, May-Jun. 2001, pp. 459-464.
Leonard et al., Elongation of long-chain fatty acids, Progress in Lipid Research, 43, 36-54, 2004.
Lewis et al., Evaluation of extraction methods for recovery of fatty acids from lipid-producing microheterotrophs, Journal of Microbiological Methods, vol. 43, Issue 2, Dec. 15, 2000, pp. 107-116.
Li et al., Production of docosahexaenoic acid by Thraustochytrium roseum, Journal of Industrial Microbiology, vol. 13, issue 4, Aug. 1994, pp. 238-241.
Liu et al, Study on Production of EPA and DHA by Microbe Fermentation, Food Science and Technology, No. 6, 13-16, 2004, (12 pages with translation).
Machlin et al., Free radical tissue damage: protective role of antioxidant nutrients, FASEB J., vol. 1, issue 6, Dec. 1987, pp. 441-445.
Mares-Perlman et al., The body of evidence to support a protective role for lutein and zeaxanthin in delaying chronic disease. Overview, The Journal of Nutrition, vol. 132 No. 3, Mar. 1, 2002, pp. 518S-524S.
Matsuda et al., "The analysis of Δ12 fatty acid desaturase function relaved that two distinct pathways are active for the synthesis of polyunsaturated fatty acids in Thraustochytrium aureum ATCC 34304", Journal of Lipid Research ASBMB, 1-47, 2012.
Metz et al., Production of polyunsaturated fatty acids by polyketide synthases in both prokaryotes and eukaryotes, Science, vol. 293, issue 5528, Jul. 2001, pp. 290-293.
Mo et al., Development of a PCR strategy for thraustochytrid identification based on 18S rDNA sequence, Marine Biology, vol. 140, Issue 5, May 2002, pp. 883-889.
Molina Grima et al., Recovery of microalgal biomass and metabolites: process options and economics, Biotechnology Advances, vol. 20, Issues 7-8, Jan. 2003, pp. 491-515.
Morita et al., Enhancement of polyunsaturated fatty acid production by cerulenin treatment in polyunsaturated fatty acid-producing bacteria, Biotechnol Lett.; vol. 27, issue 6, Mar. 2005, pp. 389-393.
Nakahara et al., Production of docosahexaenoic and docosapentaenoic acids by*Schizochytrium* sp. isolated from Yap Islands, Journal of the American Oil Chemists' Society, vol. 73, Issue 11, Nov. 1996 pp. 1421-1426.
Nakano et al., Inhibitory effects of capsaicinoids on fatty acid desaturation in a rat liver cell line, Biosci Biotechnol Biochem. vol. 65, issue 8, Aug. 2001, pp. 1859-1863.
Napier et al., The production of long chain polyunsaturated fatty acids in transgenic plants, Genetic Engineering, vol. 26, 2004, 147-148.
Pignatiello et al., An Overview of the Strategy and Tactics of Taguchi, IIE Transactions, vol. 20, Issue 3, 1988, pp. 247-254.
Pinkart et al., Rapid separation of microbial lipids using solid phase extraction columns, Journal of Microbiological Methods, vol. 34, Issue 1, Sep. 1, 1998, pp. 9-15.
Ratledge et al., Single cell oils—A coming of age, Lipid Technology, vol. 16, 2004, pp. 34-39.
Saitou et al., The Neighbor-joining Method: A New Method for Reconstructing Phylogenetic Trees, Mol. Biol. Evol., vol. 4, 1987, pp. 406-425.
Sakaguchi et al., "Versatile Transformation System That Is Applicable to both Multiple Transgene Expression and Gene Targeting for Thraustochytrids", Applied and Environmental Microbiology, 78:9, 3193-3202, 2012.
Schagerl et al., Acclimation of chlorophyll a and carotenoid levels to different irradiances in four freshwater cyanobacteria, J Plant Physiol., vol. 163, issue 7, May 2006, pp. 709-716.
Schill, OriginOil achieves rapid algae oil extraction, Biomass Magazine, retrieved from the Internet <URL:www.biomassmagazine.com/article.jsp?article id=2700>, 2009.
Shapiro, Could n-3 polyunsaturated fatty acids reduce pathological pain by direct actions on the nervous system?, Prostaglandins Leukot Essent Fatty Acids., vol. 68, issue 3, Mar. 2003, pp. 219-224.
Shimizu et al., Inhibitory effect of curcumin on fatty acid desaturation inMortierella alpina 1S-4 and rat liver microsomes, Lipids, vol. 27, Issue 7, Jul. 1992, pp. 509-512.
Shirasaka et al., Effect of Cyanocobalamin and p-toluic acid on the Fatty Acid Composition of Schizochytrium limacinum (Thraustochytriaceae, Labyrinthulomycota), Mycoscience, vol. 46, Dec. 2005, pp. 358-363.
Sijtsma et al., Recent advances in fatty acid synthesis in oleaginous yeasts and microalgae, ecent Research Developments in Microbiology, vol. 2, Jan. 1998, pp. 219-232.
Singh et al., Cancer chemoprevention. Part 1: Retinoids and carotenoids and other classic antioxidants, Oncology (Williston Park), vol. 12, issue 11, 1998, pp. 1643-1653.
Singh et al., Docosahexaenoic acid (DHA) production by *Thraustochytrium* sp. ATCC 20892, World Journal of Microbiology and Biotechnology, vol. 12, Issue 1, Jan. 1996, pp. 76-81.
Skerrett et al., Consumption of fish and fish oils and decreased risk of stroke, Prev Cardiol., vol. 6, issue 1, 2003, pp. 38-41.
Smith, Carotenoids and cancer: prevention and potential therapy, Br J Biomed Sci., vol. 55, issue 4, Dec. 1998, pp. 268-275.
Song et al., Effective Phase Separation of Biomass Pyrolysis Oils by Adding Aqueous Salt Solutions, Energy Fuels, vol. 23, Apr. 29, 2009, pp. 3307-3312.
Spector et al., Diet and asthma: has the role of dietary lipids been overlooked in the management of asthma?, Ann Allergy Asthma Immunol., vol. 90, issue 4, Apr. 2003, pp. 371-377.
Tao et al., Engineering a β-carotene ketolase for astaxanthin production, Metabolic Engineering, vol. 8, Issue 6, Nov. 2006, pp. 523-531.
Terry et al., Intakes of fish and marine fatty acids and the risks of cancers of the breast and prostate and of other hormone-related cancers: a review of the epidemiologic evidence, Am J Clin Nutr., vol. 77, issue 3, 2003, pp. 532-543.
Tian et al., Progress in understanding the origin and functions of carotenoid hydroxylases in plants, Archives of Biochemistry and Biophysics, vol. 430, Issue 1, Oct. 1, 2004, pp. 22-29.
Valadon, Carotenoids as additional taxonomic characters in fungi: A review Transactions of the British Mycological Society, vol. 67, Issue 1, 1976, pp. 1-15.
Wardencki et al., Trends in solventless sample preparation techniques for environmental analysis, Journal of Biochemical and Biophysical Methods, vol. 70, Issue 2, Mar. 10, 2007, pp. 275-288.
Yamaoka et al., Growth and carotenoid production of *Thraustochytrium* sp. CHN-1 cultured under superbright red and

(56) References Cited

OTHER PUBLICATIONS blue light-emitting diodes, Bioscience, Biotechnology, and Biochemistry, vol. 68, issue 7, 2004, pp. 1594-1597.

Yamaoka et al., Growth Characterization and Resources of Thraustochytrium CHN-1 Isolated from the Seto Inland Sea, Bulletin of the Society of Sea Water Science, Japan, vol. 59, No. 1, 2005, pp. 23-31.

Yokochi et al., Optimization of docosahexaenoic acid productions by Schizochytrium limacinum SR21, Applied Microbiology and Biotechnology, vol. 49, Issue 1, Jan. 1998, pp. 72-76.

Yokoyama et al., Taxonomic rearrangement of the genus *Schizochytrium sensu lato* based on morphology, chemotaxonomic characteristics, and 18S rRNA gene phylogeny (Thraustochytriaceae, Labyrinthulomycetes): emendation for *Schizochytrium* and erection of Aurantiochytrium and, <Oblongichytrium gen. nov.> Mycoscience, vol. 48, Issue 4, Aug. 2007, pp. 199-211.

Zhekisheva et al., Inhibition of Astaxanthin Synthesis Under High Irradiance Does Not Abolish Triacylglycerol Accumulation in the Green Alga *Haematococcus pluvialis* (Chlorophyceae), Journal of Phycology, vol. 41, Issue 4, Aug. 2005, pp. 819-826.

CN201480014547.5 , "Office Action", dated Jun. 23, 2017, 12 pages.

Office Action in related European Patent Application No. 14713925.7 dated Nov. 11, 2016, 3 pages.

Examination Report in related Australian Patent Application No. 2014229307 dated Sep. 5, 2016, 4 pages.

ENGINEERING MICROORGANISMS

CROSS REFERENCE TO RELATED APPLICATION

This application is the U.S. national phase entry of International Application No. PCT/IB2014/059687 ("the '687 application"), filed Mar. 12, 2014, which application is related to and claims priority to provisional Patent Application No. 61/779,257 ("the '257 application"), filed Mar. 13, 2013. The '687 and '257 applications are incorporated by reference herein in their entireties.

SEQUENCE LISTING

In accordance with 37 CFR §1.52(e)(5), the present specification makes reference to a Sequence Listing (entitled "Sequence_Listing.txt," created on Jul. 16, 2012 and 128 kilobytes). The entire contents of the Sequence Listing are herein incorporated by reference.

BACKGROUND

Polyunsaturated fatty acids (PUFA) have long been recognized as having beneficial effects on health. The primary source for nutritional supplements is oil from fish species that have high concentrations of PUFA, such as anchovy, sardine, salmon, menhaden, herring, and tuna. However, lack of reliability of sources, and variability in the quality and/or quantity of PUFA isolated from fish mean there remains a need for alternative sources of PUFA.

Thraustochytrids are aquatic, eukaryotic microorganisms with the capacity to produce useful products, including PUFA and antioxidants (Carmona et al., Biosci. Biotechnol. Biochem. 67(4): 884-888, 2003). These organisms are found worldwide in oceans and estuaries. Thraustochytrids are able to use a wide range of carbon and nitrogen sources for growth, indicating a potential for industrial cultivation with inexpensive nutrients.

SUMMARY

The present disclosure encompasses compositions, methods and kits to provide sources of PUFA and other useful compounds and agents. The present disclosure encompasses the recognition that genetically altered Thraustochytrids, whether by classical mutagenesis or otherwise, can provide useful sources of PUFA and other compounds and agents.

The present disclosure provides systems for genetically engineering Thraustochytrids, as well as genetically engineered Thraustochytrids that find various uses (e.g., PUFA production and/or biofuel production).

Provided herein are isolated nucleic acid molecules including a Thraustochytrid or *Thraustochytrium* gene or gene element such as a Thraustochytrid or *Thraustochytrium* promoter or terminator. Exemplary promoters in provided isolated nucleic acid molecules include, but are not limited to, a tubulin promoter (e.g., nucleic acid sequences having at least 80%, 85%, 90%, 92%, 95%, 97%, 98%, 99%, or higher sequence identity to SEQ ID NO:6 or SEQ ID NO: 10), a Δ5 elongase promoter (e.g., nucleic acid sequences having at least 80% sequence identity to SEQ ID NO: 19), a Δ4 desaturase promoter (e.g., nucleic acid sequences having at least 80%, 85%, 90%, 92%, 95%, 97%, 98%, 99%, or higher sequence identity to SEQ ID NO:24), a Δ12 desaturase promoter (e.g., nucleic acid sequences having at least 80%, 85%, 90%, 92%, 95%, 97%, 98%, 99%, or higher sequence identity to SEQ ID NO:69), and a Δ5 desaturase promoter (e.g., nucleic acid sequences having at least 80%, 85%, 90%, 92%, 95%, 97%, 98%, 99%, or higher sequence identity to SEQ ID NO:71). Exemplary terminators in provided isolated nucleic acids molecules include, but are not limited to, a tubulin terminator (e.g., nucleic acid sequences having at least 80%, 85%, 90%, 92%, 95%, 97%, 98%, 99%, or higher sequence identity to SEQ ID NO: 14 or SEQ ID NO: 18). Optionally, the isolated nucleic acid molecule is a Δ12 desaturase sequence having at least 80%, 85%, 90%, 92%, 95%, 97%, 98%, 99%, or higher sequence identity to SEQ ID NO:70. Optionally, the isolated nucleic acid molecule is a molecule that hybridizes under stringent conditions to a nucleic acid encoded by SEQ ID NO:70. Optionally, the isolated nucleic acid molecule is a Δ5 desaturase sequence having at least 80%, 85%, 90%, 92%, 95%, 97%, 98%, 99%, or higher sequence identity to SEQ ID NO:72. Optionally, the isolated nucleic acid molecule is a molecule that hybridizes under stringent conditions to a nucleic acid encoded by SEQ ID NO:72.

Provided are also isolated polypeptide molecules having amino acid sequences encoded in Thraustochytrid or *Thraustochytrium* gene elements. Optionally, the isolated polypeptide is a Δ5 elongase, Δ4 desaturase, or Δ12 desaturase. Optionally, the isolated polypeptide is a Δ12 desaturase encoded by a nucleic acid sequence having at least 80%, 85%, 90%, 92%, 95%, 97%, 98%, 99%, or higher sequence identity to SEQ ID NO:70).

Provided are isolated nucleic acid molecules including a heterologous sequence operably linked to a Thraustochytrid or *Thraustochytrium* gene promoter and a Thraustochytrid or *Thraustochytrium* gene terminator. Optionally, the heterologous sequence encodes a polypeptide. Optionally, the provided isolated nucleic acid molecules further include a zeocin resistance gene.

Thus, provided are isolated nucleic acid molecules including a Thraustochytrid or *Thraustochytrium* gene operably linked to a gene promoter. Optionally, the gene promoter is a heterologous gene promoter. Optionally, the gene promoter is a heterologous Thraustochytrid or *Thraustochytrium* gene promoter. For example, an isolated nucleic acid molecule comprising Thraustochytrid or *Thraustochytrium* Δ5 elongase, Δ5 desaturase or Δ4 desaturase can be operably linked to a Thraustochytrid or *Thraustochytrium* Δ12 desaturase promoter. Optionally, the gene promoter is exogenous to the gene to which is operably linked. Optionally, the gene promoter is endogenous to the gene to which is operably linked.

Provided are host cells including one or more provided isolated nucleic acids, recombinant nucleic acids or heterologous constructs as described herein. Optionally, the host cells are microorganisms other than Thraustochytrid or *Thraustochytrium*.

Provided are methods of mutagenizing cells of a microorganism (e.g., Thraustochytrid or *Thraustochytrium*). The methods include the steps of culturing cells of the microorganism on a medium, the medium comprising zeocin at a concentration at which zeocin kills 60-80% of the cells and isolating a subpopulation of cells that survive cultivation, thereby mutagenizing cells of a microorganism. Further provided are methods of mutagenizing cells of a microorganism (e.g., Thraustochytrid or *Thraustochytrium*) including the steps of culturing cells of the microorganism on a medium, exposing the cells to ultraviolet or microwave radiation, or combinations thereof, such that 60-80% of the cells are destroyed, and isolating a subpopulation of cells that survive cultivation, thereby mutagenizing cells of a microorganism. Optionally, the methods include multiple rounds of mutation and isolation. Mutation can be directed to specific genes through homologous recombination, inducible promoters, knockin and knockdown approaches, and other molecular means in the art.

Provided are Thraustochytrid or *Thraustochytrium* cells that contain one or more modifications to one or more genes encoding an enzyme polypeptide or part of an enzyme polypeptide complex involved in the PUFA biosynthetic pathway of Thraustochytrid or *Thraustochytrium*. Optionally, the modifications increase or decrease production of one or more PUFA by the modified cell as compared with a reference Thraustochytrid or *Thraustochytrium* cell when the modified and reference cells are cultured under comparable conditions. Optionally, the enzyme polypeptide or enzyme polypeptide complexes are selected from the group consisting of fatty acid synthase (FAS), Δ5 elongase, Δ5 desaturase, Δ12 desaturase, Δ4 desaturase, and polyketide PUFA synthase (PKS). Optionally, the one or more PUFA are selected from the group consisting of alpha-linolenic acid ("ALA"), arachidonic acid ("ARA"), docosahexaenoic acid ("DHA"), docosapentaenoic acid ("DPA"), eicosopentaenoic acid ("EPA"), gamma-linolenic acid ("GLA"), and linoleic acid ("LA"). Optionally, the enzyme or enzyme complexes are selected from the group consisting of polyketide PUFA synthase (PKS), Δ9 desaturase, elongase, and omega-3 desaturase.

Provided are methods for transforming a Thraustochytrid or *Thraustochytrium* cell. The methods include the steps of (a) providing a competent Thraustochytrid or *Thraustochytrium* cell; (b) delivering a recombinant nucleic acid into the competent Thraustochytrid or *Thraustochytrium* cell, wherein the recombinant nucleic acid comprises a selectable marker; and (c) culturing the competent Thraustochytrid or *Thraustochytrium* cell in a culturing medium containing a selection agent that reduces growth of cells without the selectable marker. Optionally, the selectable marker is an antibiotic resistance gene. Optionally, the selection agent is an antibiotic. For example, the antibiotic may be zeocin. Optionally, zeocin is present at a concentration greater than 50 µg/mL (e.g., about 100-1000 µg/mL). Optionally, zeocin is present at a concentration of approximately 500 µg/mL. Optionally, the amount of salt in the media is decreased to avoid degrading the zeocin.

In the provided methods for transforming a Thraustochytrid or *Thraustochytrium* cell, the recombinant nucleic acid further includes a gene expression cassette distinct from the selectable marker.

Optionally, the provided methods for transforming a Thraustochytrid or *Thraustochytrium* cell further includes a step of isolating a competent Thraustochytrid or *Thraustochytrium* cell containing the selectable marker.

Optionally, the step of delivering comprises biolistic delivery of particles coated with the recombinant nucleic acid. For example, particles comprising gold, tungsten or glass bead particles may be used in biolistic delivery.

Optionally, the culturing medium contains a level of salt between a lower salt concentration and an upper salt concentration. Optionally, the lower concentration is about 1, about 2, about 3, about 4, about 5, about 6, about 7, about 8, about 9, about 10, about 12, about 15, about 17, about 18, about 19, or about 20 g/L. Optionally, the upper salt concentration is about 20, about 22, about 25, about 27, about 30, about 32, about 35, about 37, about 40, about 45, about 50, about 55, about 60, about 65, or about 70 g/L. Optionally, the salt concentration is between about 3 g/L and about 70 g/L; between about 5 g/L and about 60 g/L; 10 g/L and about 40 g/L of salt (e.g., between about 15 g/L and about 35 g/L salt, or between about 18 g/L and about 35 g/L salt; or between about 9 g/L and about 18 g/L). Optionally, the salt is or comprises a salt selected from the group consisting of sodium salts (e.g., sea salt, sodium chloride, table salt, sodium sulfate, etc), potassium salts, and combinations thereof. Optionally, the salt is or comprises a non-chloride salt. Optionally, the salt is or comprises a non-chloride sodium salt.

Provided are Thraustochytrid or *Thraustochytrium* cells competent for genetic transformation.

Provided are Thraustochytrid or *Thraustochytrium* cells transformed with a recombinant nucleic acid.

Provided are methods of culturing Thraustochytrid or *Thraustochytrium* cells. The methods include growing a culture comprising Thraustochytrid or *Thraustochytrium* cells under a first set of conditions under which biomass increases (and optionally other features increase or decrease as well); shifting the first set of culture conditions to a second set of conditions in which lipid productivity increases, wherein the shifting comprises one or more of (a) decreasing oxygen concentrations from a first oxygen concentration to a second oxygen concentration; (b) increasing C:N ratio from a first C:N ratio to a second C:N ratio; (c) decreasing temperature from a first temperature to a second temperature, and combinations thereof.

Provided are methods of providing a PUFA. The methods include providing a Thraustochytrid or *Thraustochytrium* cell that is modified as compared with a reference Thraustochytrid or *Thraustochytrium* cell in that the modified cell contains one or more genetic modifications that increase production of one or more PUFA by the modified cell as compared with the reference cell when the modified and reference cells are cultured under comparable conditions; and culturing the modified Thraustochytrid or *Thraustochytrium* cell under conditions and for a time sufficient to achieve production of the one or more PUFA.

Optionally, the step of providing comprises providing a Thraustochytrid or *Thraustochytrium* cell containing at least one engineered Thraustochytrid or *Thraustochytrium* promoter.

Optionally, the step of providing comprises providing a Thraustochytrid or *Thraustochytrium* cell containing at least one engineered Thraustochytrid or *Thraustochytrium* terminator.

Optionally, the step of providing comprises providing a Thraustochytrid or *Thraustochytrium* cell that is modified with respect to a reference Thraustochytrid or *Thraustochytrium* cell in that the modified Thraustochytrid or *Thraustochytrium* cell contains at least one expressed heterologous polypeptide. Optionally, the at least one heterologous protein is expressed from a gene that is operably linked with an engineered Thraustochytrid or *Thraustochytrium* promoter, an engineered Thraustochytrid or *Thraustochytrium* terminator, or both. Optionally, the at least one heterologous polypeptide comprises at least one heterologous PUFA biosynthesis polypeptide.

The genetic modification can include at least one nucleotide mutation that increases expression or activity of PUFA biosynthesis polypeptide. Optionally, the PUFA biosynthesis polypeptide whose expression or activity is increased is an endogenous PUFA production polypeptide. Optionally, the PUFA production polypeptide whose expression or activity is increased is a heterologous PUFA biosynthesis polypeptide.

Provided are engineered Thraustochytrid or *Thraustochytrium* cells that express a heterologous PUFA production polypeptide.

Provided are engineered Thraustochytrid or *Thraustochytrium* cells that produce at least one PUFA at a level at least 36% higher than a non-engineered Thraustochytrid or *Thraustochytrium* cell when the engineered and non-engineered cells are cultured under comparable conditions.

Provided are compositions including at least one PUFA and one or more components of a Thraustochytrid or *Thraustochytrium* cell that contains an antibiotic resistance gene or is progeny of a Thraustochytrid or *Thraustochytrium* cell that contains an antibiotic resistance gene. Optionally, the antibiotic resistance gene is a zeocin resistance gene.

Provided are compositions including at least one PUFA and one or more components of (a) a Thraustochytrid or *Thraustochytrium* cell that has been cultured in or on a medium comprising zeocin at a concentration at which zeocin kills 60-80% of the cells, or (b) a progeny of a Thraustochytrid or *Thraustochytrium* cell that has been cultured in or on a medium comprising zeocin at a concentration at which zeocin kills 60-80% of the cells.

Provided are antibody polypeptides to one or more of the isolated polypeptides described herein. Optionally, antibody polypeptides are provided to an isolated polypeptide encoding a Thraustochytrid or *Thraustochytrium* Δ12 desaturase. Optionally, the antibody polypeptides have affinity constants of about $(K_A)$ of $10^9$, $10^8$, $10^7$, $10^6$, $10^5$, or $10^4$ $M^{-1}$. Optionally, the antibodies have affinity constants $(K_A)$ in the range of approximately $10^{10}$-$10^9$, $10^8$-$10^9$, $10^7$-$10^8$, $10^6$-$10^7$, $10^5$-$10^6$ or $10^4$-$10^5$ $M^{-1}$. Optionally, the antibodies are monoclonal, polyclonal, single-chain antibodies or antigen-binding fragments.

Provided herein is an isolated nucleic acid molecule including a nucleic acid sequence selected from the group consisting of (a) a nucleic acid molecule which hybridizes under stringent conditions to a molecule consisting of a nucleotide sequence set forth as SEQ ID NO:70; (b) a complement of said nucleic acid of (a) that encodes a polypeptide having Δ12 desaturase activity; (c) a nucleic acid molecule that differs from the nucleic acid molecule of (a) or (b) in codon sequence due to the degeneracy of the genetic code; (d) complements of (a) or (b) or (c); and (e) a nucleic acid molecule having a sequence that is at least 90% identical to the nucleic acid sequence of SEQ ID NO:70. Optionally, the isolated nucleic acid molecule is operatively linked to a promoter. Optionally, the promoter is heterologous to the isolated nucleic acid molecule. Optionally, the nucleic acid is derived from a microorganism. Optionally, the microorganism is selected from the group consisting of the genera *Schizochytrium, Oblongichytrium, Aurantiochytrium* and *Traustochytrium*. Optionally, the microorganism is ONC-T18.

Provided herein is an isolated nucleic acid molecule including a nucleic acid sequence selected from the group consisting of (a) a nucleic acid molecule which hybridizes under stringent conditions to a molecule consisting of a nucleotide sequence set forth as SEQ ID NO:72; (b) a complement of said nucleic acid of (a) that encodes a polypeptide having Δ5 desaturase activity; (c) a nucleic acid molecule that differs from the nucleic acid molecule of (a) or (b) in codon sequence due to the degeneracy of the genetic code; (d) complements of (a) or (b) or (c); and (e) a nucleic acid molecule having a sequence that is at least 90% identical to the nucleic acid sequence of SEQ ID NO:72. Optionally, the nucleic acid molecule is operatively linked to a promoter. Optionally, the promoter is heterologous to the isolated nucleic acid molecule. Optionally, the nucleic acid is derived from a microorganism. Optionally, the microorganism is selected from the group consisting of the genera *Schizochytrium, Oblongichytrium, Aurantiochytrium* and *Traustochytrium*. Optionally, the microorganism is ONC-T18.

Provided is an isolated nucleic acid molecule including a nucleic acid sequence selected from the group consisting of (a) a nucleic acid molecule which hybridizes under stringent conditions to a molecule consisting of a nucleotide sequence set forth as SEQ ID NO:69, (b) a complement of said nucleic acid of (a) that regulates transcription of a Δ12 desaturase; and (c) a nucleic acid molecule having a sequence that is at least 90% identical to the nucleic acid sequence of SEQ ID NO:69. Optionally, the isolated nucleic acid molecule is operatively linked to a heterologous nucleic acid sequence. Optionally, the nucleic acid molecule is operatively linked to polynucleotide encoding an enzyme polypeptide or part of an enzyme polypeptide complex with an activity selected from the group consisting of desaturase activity, elongase activity, fatty acid synthase activity and polyketide polyunsaturated fatty acid synthase (PKS) activity. Optionally, the activity is a desaturase activity. Optionally, the desaturase activity is Δ5 desaturase activity. Optionally, the nucleic acid is derived from a microorganism. Optionally, the microorganism is selected from the group consisting of the genera *Schizochytrium, Oblongichytrium, Aurantiochytrium* and *Traustochytrium*. Optionally, the microorganism is ONC-T18.

Provided herein is an isolated nucleic acid molecule comprising a nucleic acid sequence selected from the group consisting of (a) a nucleic acid molecule which hybridizes under stringent conditions to a molecule consisting of a nucleotide sequence set forth as SEQ ID NO:71; (b) a complement of said nucleic acid of (a) that regulates the transcription of a Δ5 desaturase; and (c) a nucleic acid molecule having a sequence that is at least 90% identical to the nucleic acid sequence of SEQ ID NO:71. Optionally, the isolated nucleic acid molecule is operatively linked to a heterologous nucleic acid sequence. Optionally, the nucleic acid molecule is operatively linked to polynucleotide encoding an enzyme polypeptide or part of an enzyme polypeptide complex with an activity selected from the group consisting of desaturase activity, elongase activity, fatty acid synthase activity and polyketide polyunsaturated fatty acid synthase (PKS) activity. Optionally, the activity is a desaturase activity. Optionally, the desaturase activity is Δ12 desaturase activity. Optionally, nucleic acid is derived from a microorganism. Optionally, the microorganism is selected from the group consisting of the genera *Schizochytrium, Oblongichytrium, Aurantiochytrium* and *Traustochytrium*. Optionally, the microorganism is ONC-T18.

There is provided polypeptides encoded by the nucleic acids sequences of SEQ ID NOs: 70 and 72.

There is provided vectors comprising all or part of the nucleic acid sequences of SEQ ID NOs: 69-72.

There is also provided an engineered microorganism, wherein the microorganism expresses a heterologous nucleic acid sequence selected from the group consisting of (a) a nucleic acid molecule which hybridizes under stringent conditions to a molecule consisting of a nucleotide sequence set forth as SEQ ID NO:70; (b) a complement of said nucleic acid of (a) that encodes a polypeptide having Δ12 desaturase activity; (c) a nucleic acid molecule that differs from the nucleic acid molecule of (a) or (b) in codon sequence due to the degeneracy of the genetic code; (d) complements of (a) or (b) or (c); and (e) a nucleic acid molecule having a sequence that is at least 90% identical to the nucleic acid sequence of SEQ ID NO:70. Optionally, the microorganism is selected from the group consisting of the genera *Schizochytrium, Oblongichytrium, Aurantiochytrium* and *Traustochytrium*. Optionally, the microorganism is ONC-T18. Optionally, the heterologous nucleic acid sequence is operatively linked to a heterologous promoter. Optionally, the heterologous promoter is at least 90% identical to SEQ ID NO: 71. Optionally, the heterologous promoter is selected from the group consisting of bacterial promoters, yeast promoters, eukaryotic viral promoters, or promoter elements isolated from microalgae. Optionally, the heterologous nucleic acid sequence is over-expressed. Optionally, the heterologous nucleic acid sequence is introduced into the cell by an expression vector. Optionally, the expression vector is introduced into the microorganism with at least one additional heterologous polynucleotide encoding an enzyme polypeptide or part of an enzyme polypeptide involved in polyunsaturated fatty acid biosynthesis. Optionally, the at least one additional heterologous polynucleotide encodes an enzyme polypeptide or part of an enzyme polypeptide complex selected from the group consisting of fatty acid synthase (FAS), Δ5 elongase, Δ5 desaturase, Δ12 desaturase, Δ4 desaturase, and polyketide PUFA synthase (PKS). Optionally, total fatty content of the microorganism is increased by at least 10% relative to the content in the absence of the heterologous nucleic acid sequence. Optionally, total fatty content of the microorganism is increased by at least 20% relative to the content in the absence of the heterologous nucleic acid sequence. Optionally, total fatty content of the microorganism is increased by at least 50% relative to the content in the absence of the heterologous nucleic acid sequence. Optionally, total fatty content of the microorganism is increased by at least 100% relative to the content in the absence of the heterologous nucleic acid sequence. Optionally, expression of the heterologous nucleic acid sequence reduces the content of C12-C16 saturated and mono unsaturated fatty acids by at least 10% relative to the content of said fatty acids in the absence of expression of the heterologous nucleic acid sequence. Optionally, expression of the heterologous nucleic acid sequence reduces the content of C12-C16 saturated and mono unsaturated fatty acids by at least 20% relative to the content of said fatty acids in the absence of expression of the heterologous nucleic acid sequence. Optionally, expression of the heterologous nucleic acid sequence reduces the content of C12-C16 saturated and mono unsaturated fatty acids by at least 50% relative to the content of said fatty acids in the absence of expression of the heterologous nucleic acid sequence. Optionally, expression of the heterologous nucleic acid sequence reduces the content of C12-C16 saturated and mono unsaturated fatty acids by at least 100% relative to the content of said fatty acids in the absence of expression of the heterologous nucleic acid sequence.

There is provided an engineered microorganism, wherein the microorganism expresses at least one polyunsaturated fatty acid biosynthesis polynucleotide operatively linked to a heterologous promoter selected from the group consisting of (a) a nucleic acid molecule which hybridizes under stringent conditions to a molecule consisting of a nucleotide sequence set forth as SEQ ID NO:69; (b) a complement of said nucleic acid of (a) that regulates the transcription of a Δ12 desaturase; (c) a nucleic acid molecule that differs from the nucleic acid molecule of (a) or (b) in codon sequence due to the degeneracy of the genetic code; and (d) a nucleic acid molecule having a sequence that is at least 90% identical to the nucleic acid sequence of SEQ ID NO:69. Optionally, the at least one polyunsaturated fatty acid biosynthesis polynucleotide is endogenous to the microorganism. Optionally, the at least one endogenous polyunsaturated fatty acid biosynthesis polynucleotide is operatively linked to the heterologous promoter by homologous recombination. Optionally, the at least one polyunsaturated fatty acid biosynthesis polynucleotide is exogenous to the microorganism. Optionally, the at least one polyunsaturated fatty acid biosynthesis polynucleotide encodes an enzyme polypeptide or part of an enzyme polypeptide complex selected from the group consisting of fatty acid synthase (FAS), Δ5 elongase, Δ5 desaturase, Δ12 desaturase, Δ4 desaturase, and polyketide PUFA synthase (PKS). Optionally, the engineered microorganism further over-expresses a nucleic acid sequence selected from the group consisting of (a) a nucleic acid molecule which hybridizes under stringent conditions to a molecule consisting of a nucleotide sequence set forth as SEQ ID NO:70; (b) a complement of said nucleic acid of (a) that encodes a polypeptide having Δ12 desaturase activity; (c) a nucleic acid molecule that differs from the nucleic acid molecule of (a) or (b) in codon sequence due to the degeneracy of the genetic code; (d) complements of (a) or (b) or (c); and (e) a nucleic acid molecule having a sequence that is at least 90% identical to the nucleic acid sequence of SEQ ID NO:70.

Provided are methods for producing polyunsaturated fatty acids. The methods include providing an engineered Thraustochytrid or *Thraustochytrium* cell, wherein the engineered cell expresses a heterologous nucleic acid molecule selected from the group consisting of (a) a nucleic acid molecule which hybridizes under stringent conditions to a molecule consisting of a nucleotide sequence set forth as SEQ ID NO:70, (b) a complement of said nucleic acid of (a) that encodes a polypeptide having Δ12 desaturase activity, (c) a nucleic acid molecule that differs from the nucleic acid molecule of (a) or (b) in codon sequence due to the degeneracy of the genetic code, and (d) complements of (a) or (b) or (c); and (e) a nucleic acid molecule having a sequence that is at least 90% identical to the nucleic acid sequence of SEQ ID NO:70, wherein the heterologous expression changes production of one or more polyunsaturated fatty acids by the engineered cell as compared with a reference cell when the engineered and reference cells are cultured under comparable conditions; and culturing the engineered cell under conditions and for a time sufficient to achieve production of the one or more polyunsaturated fatty acids. Optionally, the one or more polyunsaturated fatty acids is selected from the group consisting of alpha linolenic acid, arachidonic acid, docosahexanenoic acid, docosapentaenoic acid, eicosapentaenoic acid, gamma-linolenic acid, linoleic acid and/or linolenic acid. Optionally, the methods further comprise expressing at least one heterologous polynucleotide encoding an enzyme polypeptide or part of an enzyme polypeptide complex selected from the group consisting of fatty acid synthase (FAS), Δ5 elongase, Δ5 desaturase, Δ12 desaturase, Δ4 desaturase, and polyketide PUFA synthase (PKS). Optionally, the total fatty content of the cell is increased by at least 10% relative to the content in the absence of the heterologous nucleic acid sequence. Optionally, the total fatty content of the cell is increased by at least 20% relative to the content in the absence of the heterologous nucleic acid sequence. Optionally, the total fatty content of the cell is increased by at least 50% relative to the content in the absence of the heterologous nucleic acid sequence. Optionally, the total fatty content of the cell is increased by at least 100% relative to the content in the absence of the heterologous nucleic acid sequence. Optionally, expression of the heterologous nucleic acid molecule reduces the content of C12-C16 saturated and mono unsaturated fatty acids by at least 10% relative to the content of said fatty acids in the absence of expression of the heterologous nucleic acid sequence. Optionally, expression of the heterologous nucleic acid molecule reduces the content of C12-C16 saturated and mono unsaturated fatty acids by at least 20% relative to the content of said fatty acids in the absence of expression of the heterologous nucleic acid sequence. Optionally, expression of the heterologous nucleic acid molecule reduces the content of C12-C16 saturated and mono unsaturated fatty acids by at least 50% relative to the content of said fatty acids in the absence of expression of the heterologous nucleic acid sequence. Optionally, expression of the heterologous nucleic acid molecule reduces the content of C12-C16 saturated and mono unsaturated fatty acids by at least 100% relative to the content of said fatty acids in the absence of expression of the heterologous nucleic acid sequence. Optionally, the heterologous nucleic acid molecule is over-expressed.

There is also provided a method for producing polyunsaturated fatty acids including providing an engineered Thraustochytrid or *Thraustochytrium* cell, wherein the engineered cell expresses at least one polyunsaturated fatty acid biosynthesis polynucleotide operatively linked to a heterologous promoter selected from the group consisting of (a) a nucleic acid molecule which hybridizes under stringent conditions to a molecule consisting of a nucleotide sequence set forth as SEQ ID NO:69, (b) a complement of said nucleic acid of (a) that regulates transcription of a Δ12 desaturase, (c) a nucleic acid molecule having a sequence that is at least 90% identical to the nucleic acid sequence of SEQ ID NO:69, wherein the operative linkage of the heterologous promoter to at least one polyunsaturated fatty acid biosynthesis polynucleotide changes production of one or more polyunsaturated fatty acids by the engineered cell as compared with a reference cell when the engineered and reference cells are cultured under comparable conditions; and culturing the engineered cell under conditions and for a time sufficient to achieve production of the one or more polyunsaturated fatty acids. Optionally, the one or more polyunsaturated fatty acids is selected from the group consisting of alpha linolenic acid, arachidonic acid, docosahexanenoic acid, docosapentaenoic acid, eicosapentaenoic acid, gamma-linolenic acid, linoleic acid and/or linolenic acid. Optionally, the methods further comprise expressing at least one heterologous polynucleotide encoding an enzyme polypeptide or part of an enzyme polypeptide complex selected from the group consisting of fatty acid synthase (FAS), Δ5 elongase, Δ5 desaturase, Δ12 desaturase, Δ4 desaturase, and polyketide PUFA synthase (PKS). Optionally, total fatty content of the cell is increased by at least 10% relative to the content in the absence of the heterologous nucleic acid sequence. Optionally, total fatty content of the cell is increased by at least 20% relative to the content in the absence of the heterologous nucleic acid sequence. Optionally, total fatty content of the cell is increased by at least 50% relative to the content in the absence of the heterologous nucleic acid sequence. Optionally, total fatty content of the cell is increased by at least 100% relative to the content in the absence of the heterologous nucleic acid sequence. Optionally, expression of the heterologous nucleic acid molecule reduces the content of C12-C16 saturated and mono unsaturated fatty acids by at least 10% relative to the content of said fatty acids in the absence of expression of the heterologous nucleic acid sequence. Optionally, expression of the heterologous nucleic acid molecule reduces the content of C12-C16 saturated and mono unsaturated fatty acids by at least 20% relative to the content of said fatty acids in the absence of expression of the heterologous nucleic acid sequence. Optionally, expression of the heterologous nucleic acid molecule reduces the content of C12-C16 saturated and mono unsaturated fatty acids by at least 50% relative to the content of said fatty acids in the absence of expression of the heterologous nucleic acid sequence. Optionally, expression of the heterologous nucleic acid molecule reduces the content of C12-C16 saturated and mono unsaturated fatty acids by at least 100% relative to the content of said fatty acids in the absence of expression of the heterologous nucleic acid sequence. Optionally, the at least one heterologous polynucleotide encoding an enzyme polypeptide or part of an enzyme polypeptide complex is over-expressed. Optionally, the at least one polyunsaturated fatty acid biosynthesis polynucleotide encodes an enzyme polypeptide or part of an enzyme polypeptide complex selected from the group consisting of fatty acid synthase (FAS), Δ5 elongase, Δ5 desaturase, Δ4 desaturase, and polyketide PUFA synthase (PKS).

There is provided herein polyunsaturated fatty acid compositions produced by the methods disclosed herein.

There is provided an engineered microorganism, wherein the microorganism expresses a heterologous nucleic acid sequence selected from the group consisting of (a) a nucleic acid molecule which hybridizes under stringent conditions to a molecule consisting of a nucleotide sequence set forth as SEQ ID NO:72; (b) a complement of said nucleic acid of (a) that encodes a polypeptide having Δ5 desaturase activity; (c) a nucleic acid molecule that differs from the nucleic acid molecule of (a) or (b) in codon sequence due to the degeneracy of the genetic code; and (d) complements of (a) or (b) or (c); and (e) a nucleic acid molecule having a sequence that is at least 90% identical to the nucleic acid sequence of SEQ ID NO:72. Optionally, the microorganism is selected from the group consisting of the genus *Schizochytrium, Oblongichytrium, Aurantiochytrium* and *Traustochytrium*. Optionally, the microorganism is ONC-T18. Optionally, the heterologous nucleic acid sequence is operatively linked to a heterologous promoter. The heterologous promoter can be at least 90% identical to SEQ ID NO: 71. Optionally, the heterologous promoter is selected from the group consisting of bacterial promoters, yeast promoters, eukaryotic viral promoters, or promoter elements isolated from microalgae. Optionally, the heterologous nucleic acid sequence is over-expressed. Optionally, the heterologous nucleic acid sequence is introduced into the cell by an expression vector. Optionally, the expression vector is introduced into the microorganism with at least one additional heterologous polynucleotide encoding an enzyme polypeptide or part of an enzyme polypeptide involved in polyunsaturated fatty acid biosynthesis. Optionally, the at least one additional heterologous polynucleotide encodes an enzyme polypeptide or part of an enzyme polypeptide complex selected from the group consisting of fatty acid synthase (FAS). Δ5 elongase, Δ5 desaturase, Δ12 desaturase, Δ4 desaturase, and polyketide PUFA synthase (PKS). Optionally, the total fatty content of the cell is increased by at least 10% relative to the content in the absence of the heterologous nucleic acid sequence. Optionally, the total fatty content of the cell is increased by at least 20% relative to the content in the absence of the heterologous nucleic acid sequence. Optionally, the total fatty content of the cell is increased by at least 50% relative to the content in the absence of the heterologous nucleic acid sequence. Optionally, the total fatty content of the cell is increased by at least 100% relative to the content in the absence of the heterologous nucleic acid sequence. Optionally, expression of the heterologous nucleic acid sequence reduces the content of C12-C16 saturated and mono unsaturated fatty acids by at least 10% relative to the content of said fatty acids in the absence of expression of the heterologous nucleic acid sequence. Optionally, expression of the heterologous nucleic acid sequence reduces the content of C12-C16 saturated and mono unsaturated fatty acids by at least 20% relative to the content of said fatty acids in the absence of expression of the heterologous nucleic acid sequence. Optionally, expression of the heterologous nucleic acid sequence reduces the content of C12-C16 saturated and mono unsaturated fatty acids by at least 50% relative to the content of said fatty acids in the absence of expression of the heterologous nucleic acid sequence. Optionally, expression of the heterologous nucleic acid sequence reduces the content of C12-C16 saturated and mono unsaturated fatty acids by at least 100% relative to the content of said fatty acids in the absence of expression of the heterologous nucleic acid sequence.

There is provided an engineered microorganism, wherein the microorganism expresses at least one polyunsaturated fatty acid biosynthesis polynucleotide operatively linked to a heterologous promoter selected from the group consisting of (a) a nucleic acid molecule which hybridizes under stringent conditions to a molecule consisting of a nucleotide sequence set forth as SEQ ID NO:71; (b) a complement of said nucleic acid of (a) that regulates the transcription of a Δ5 desaturase; (c) a nucleic acid molecule that differs from the nucleic acid molecule of (a) or (b) in codon sequence due to the degeneracy of the genetic code; and (d) a nucleic acid molecule having a sequence that is at least 90% identical to the nucleic acid sequence of SEQ ID NO:71. Optionally, the at least one polyunsaturated fatty acid biosynthesis polynucleotide is endogenous to the microorganism. Optionally, the at least one endogenous polyunsaturated fatty acid biosynthesis polynucleotide is operatively linked to the heterologous promoter by homologous recombination. Optionally, the at least one polyunsaturated fatty acid biosynthesis polynucleotide is exogenous to the microorganism. Optionally, the at least one polyunsaturated fatty acid biosynthesis polynucleotide encodes an enzyme polypeptide or part of an enzyme polypeptide complex selected from the group consisting of fatty acid synthase (FAS), Δ5 elongase, Δ5 desaturase, Δ12 desaturase, Δ4 desaturase, and polyketide PUFA synthase (PKS). Optionally, the engineered microorganism further over-expresses a nucleic acid sequence selected from the group consisting of (a) a nucleic acid molecule which hybridizes under stringent conditions to a molecule consisting of a nucleotide sequence set forth as SEQ ID NO:70; (b) a complement of said nucleic acid of (a) that encodes a polypeptide having Δ12 desaturase activity; (c) a nucleic acid molecule that differs from the nucleic acid molecule of (a) or (b) in codon sequence due to the degeneracy of the genetic code; and (d) complements of (a) or (b) or (c); and (e) a nucleic acid molecule having a sequence that is at least 90% identical to the nucleic acid sequence of SEQ ID NO:70.

Details of one or more embodiments are set forth in the accompanying drawings and the description below. Other features, objects, and advantages will be apparent from the description and drawings, and from the claims. All cited patents, patent applications, and references (including references to public sequence database entries) are incorporated by reference in their entireties for all purposes.

This figure illustrates the stability of the ble transgene in ONC-T18 strains transformed.

Figure 18:
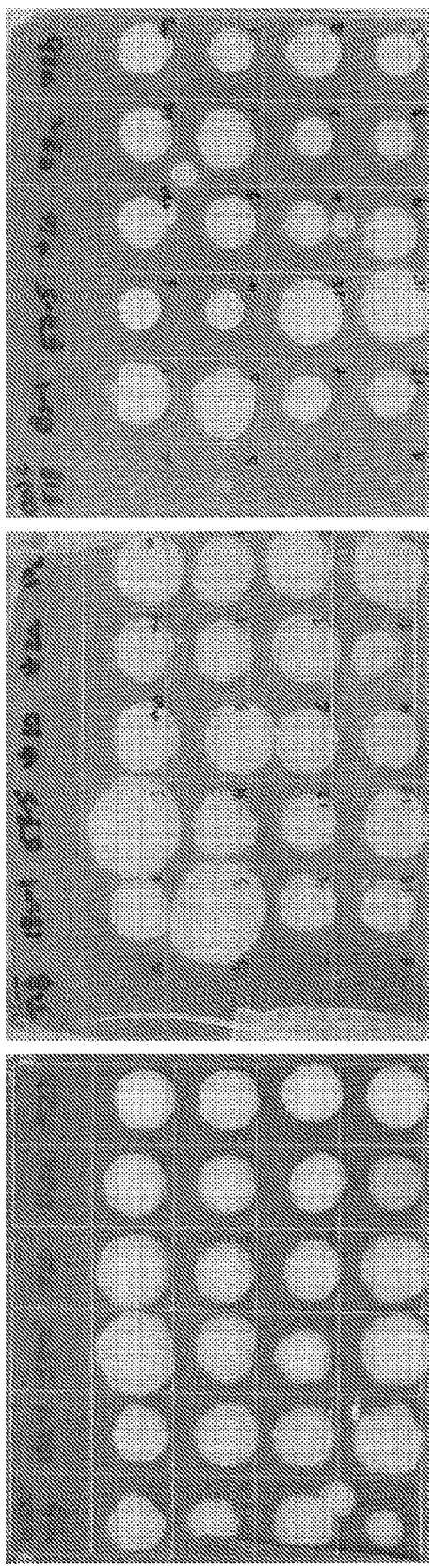

FIG. 18 shows a comparison of wild type and transformed ONC-T18 strains on agar plates either with or without zeocin.

DEFINITIONS

Affinity: As is known in the art, "affinity" is a measure of the tightness with which a particular ligand (e.g. antibody) binds to (e.g., associates non-covalently with) and/or the rate or frequency with which it dissociates from, its partner. As is known in the art, any of a variety of technologies can be utilized to determine affinity. Affinity may be used to represent a measure of specific binding.

Antibody: As used herein, the term "antibody" refers to a polypeptide consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. An antibody can be specific for a particular antigen. The antibody or its antigen can be either an analyte or a binding partner. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term "antibody," as used herein also includes antibody fragments either produced by the modification of whole antibodies or synthesized de novo using recombinant DNA methodologies.

Approximately: As used herein, the term "approximately" or "about," as applied to one or more values of interest, refers to a value that is similar to a stated reference value. The term "approximately" or "about" refers to a range of values that fall, by way of example, within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Competent: The term "competent," as used herein in reference to a cell, refers to the ability of the cell to take up extracellular genetic material. A cell may be competent naturally and/or induced artificially (e.g., in a laboratory) to be competent. Competent cells are able to take up extracellular genetic material when the extracellular genetic material is introduced by a particular method, e.g., a particular method of transformation. For example, a cell may be competent for one method of transformation, but not for another. Alternatively or additionally, a cell may be competent for more than one method of transformation. Competent cells may be obtained from any of a variety of sources. For example, they may be isolated from nature, prepared in the laboratory, and/or bought commercially. The competence of a cell can be transient or permanent.

Component: The term "component," when used herein in reference to a cell, means any part of a cell, such as a structure, part of a structure, macromolecular complex, and/or molecule contained in the cell, including, but not limited to, cell membranes, cell walls, cellular nuclei, cystosol, genetic material (e.g., chromosomes), cellular organelles, or any part of or biomolecule contained in any of the aforementioned components. Organelles typically contained in a cell may differ depending on the cell type. For example, some organelles are present only in eukaryotic cells. Some organelles are only present in plant cells, and some are only present in animal cells. Non-limiting examples of types of organelles are cellular nuclei, mitochondria, chloroplasts, peroxisomes, lysosomes, vacuoles, Golgi apparatus, endoplasmic reticulum, ribosomes, and centrosomes. Non-limiting examples of biomolecules contained in a cell include, but are not limited to, nucleic acids (e.g., DNA and/or RNA), polypeptides (e.g., proteins), nucleo-protein complexes, lipids, and phospholipids. Some cells may contain exogenous genetic material (e.g., material that has been introduced into the cell by the hand of man). Such exogenous material is included in this definition. Some cells may have extracellular components such as extracellular capsules, flagella, or fimbria (pili). These extracellular components are also included in this definition.

Concurrent Expression: As used herein, the term "concurrent expression" or "combined" refers to occurrences wherein two or more PUFA biosynthesis polynucleotides encoding a PUFA biosynthesis enzyme polypeptide or part of an enzyme polypeptide complex (e.g., a Δ12 desaturase and a Δ5 elongase) are expressed together over a time interval in not less than de minimis quantities, i.e., the polypeptides they encode are present together in non-negligible quantities. The time interval can be minutes (e.g., at least 1 minute, 1-30 minutes, 30-60 minutes), hours (e.g., at least 1 hour, 1-2 hours, 2-6 hours, 6-12 hours, 12-24 hours), days (e.g., at least 1 day, 1-2 days, 2-4 days, 4-7 days, etc.), weeks (e.g., at least 1, 2, or 3 weeks), etc. Accordingly, the two or more PUFA biosynthesis polynucleotides may, but need not be, administered simultaneously or together as part of a single expression cassette (i.e., driven by the same promoter) or simultaneously transformed into a host cell on one or more plasmids. In addition, the two or more PUFA biosynthesis polynucleotides may, but need not be, sequentially transformed into host cells within a short time of one another (e.g., less than 1 hour, less than 30 minutes, less than 10 minutes, approximately 5 minutes apart). The two or more PUFA biosynthesis polynucleotides may be administered within such time intervals as to be considered as administered at substantially the same time. When administered concurrently, the effective amounts of the enzyme polypeptides or part of an enzyme polypeptide complex encoded by the two or more PUFA biosynthesis polynucleotides needed to elicit a particular biological response may be less than the effective concentration of each when the polynucleotides are administered alone. The effects of multiple PUFA biosynthesis polynucleotides may, but need not be, additive or synergistic. The PUFA biosynthesis polynucleotides may be transformed multiple times.

Coordinated Expression: The term "coordinated expression," as used herein, refers to expression of at least two PUFA biosynthesis polynucleotides encoding a PUFA biosynthesis enzyme polypeptide or part of an enzyme polypeptide complex (e.g., a Δ12 desaturase and a Δ5 elongase) that is engineered such that the polynucleotides are expressed simultaneously, at substantially the same time, or progressively such that the expression of one PUFA biosynthesis polynucleotide follows another in a temporal manner. Coordinated expression can be achieved by operatively linking at least two PUFA biosynthesis polynucleotides to the same regulatory sequence or promoter. For example, the same exogenous promoter may be used to express at least two different polynucleotide sequences, or an endogenous promoter that naturally controls expression of one PUFA biosynthesis gene is operatively linked to control expression of another PUFA biosynthesis gene. By way of example, a promoter from a Δ12 desaturase is operatively linked to a polynucleotide (exogenous or endogenous) encoding a Δ5 desaturase, such that a host cell endogenously expresses its Δ12 desaturase and heterologously expresses Δ5 desaturase at the same time. Coordinated expression can be achieved through inducible promoter systems. Coordinated expression also includes engineered systems wherein an increase in expression of at least one first PUFA biosynthesis polynucleotide is combined with a decrease in expression of at least one second PUFA biosynthesis polynucleotide. A coordinated decrease in expression may occur simultaneously, at substantially the same time, or progressively such that the decrease follows increased expression of another polynucleotide in a temporal manner.

Engineered: In general, the term "engineered" refers to the aspect of having been manipulated by the hand of man. For example, a polynucleotide is considered to be "engineered" when two or more sequences that are not linked together in that order in nature are manipulated by the hand of man to be directly linked to one another in the engineered polynucleotide. For example, an engineered polynucleotide may include a regulatory sequence that is found in nature in operative association with a first coding sequence but not in operative association with a second coding sequence that is linked by the hand of man so that it is operatively associated with the second coding sequence. By way of example, a Thraustochytrium Δ4 or Δ5 desaturase promoter is linked to nucleic acid encoding a polypeptide other than a Thraustochytrium Δ4 or Δ5 desaturase polypeptide. Comparably, a cell or organism is considered to be "engineered" if it has been manipulated so that its genetic information is altered (e.g., new genetic material not previously present has been introduced, for example by transformation, mating, somatic hybridization, or other mechanism, or previously present genetic material is altered or removed, for example by substitution or deletion mutation, or by mating protocols). By way of example, an exogenous Thraustochytrium Δ12 desaturase gene is introduced into and expressed within a host cell. As is common practice and is understood by those in the art, progeny of an engineered polynucleotide or cell are typically still referred to as "engineered" even though the actual manipulation was performed on a prior entity.

Endogenous: The term "endogenous," as used herein, refers to a nucleic acid sequence that is native to the host cell.

Exogenous: The term "exogenous," as used herein refers to a nucleic acid sequence that is not native, i.e., from a different organism, in a host cell.

Genetic modification: The term "genetic modification," as used herein, refers to a manipulation by the hand of man through the use of genetic engineering. The term "genetic modifications" encompasses any types of changes to the genetic material of a cell, including changes to the nucleotide (e.g., DNA or RNA) sequence of the genetic material of the cell and chemical modifications to the genetic material of the cell (e.g., modifications such as methylation that may affect the expression of a genetic locus). Cells or organisms that are manipulated in such a manner are said to be "genetically modified" or "transgenic." For example, the term "transgenic cell," as used herein, refers to a cell whose DNA contains an exogenous nucleic acid not originally present in the non-transgenic cell. A transgenic cell may be derived or regenerated from a transformed cell or derived from a transgenic cell. Exemplary transgenic cells include, but are not limited to, transgenic Thraustochytrid or Thraustochytrium cells, and transgenic non-Thraustochytrid or -Thraustochytrium cells that have been engineered to express one or more Thraustochytrid or -Thraustochytrium polynucleotide sequences. Transgenic cells typically express DNA sequences that confer to the cells characteristics different from that of native, non-transgenic cells of the same strain. Progeny of transgenic cells are typically considered transgenic as well.

Heterologous: The term "heterologous," as used herein to refer to nucleic acids (e.g., nucleic acids including regulatory sequences and/or genes) or polypeptides, refers to a nucleic acid or polypeptide that is artificially introduced into a cell and/or does not naturally occur in the cell in which it is present. A heterologous nucleic acid can have a nucleotide sequence that is identical to that of a nucleic acid naturally present in the cell. For example, a Thraustochytrid host cell is engineered to include a nucleic acid having a Thraustochytrid or Thraustochytrium regulatory sequence. In a particular example, an endogenous Thraustochytrid or Thraustochytrium regulatory sequence is operably linked to a gene with which the regulatory sequence is not involved under natural conditions. Although the Thraustochytrid or Thraustochytrium regulatory sequence may naturally occur in the host cell, the introduced nucleic acid is heterologous according to the present disclosure. A heterologous nucleic acid can have a nucleotide sequence that is different from that of any nucleic acid that is naturally present in the cell. A nucleic acid that is heterologous to a particular cell has a nucleic acid sequence that is identical to that of a nucleic acid that is naturally found in a source organism that is different from the cell into which the heterologous nucleic acid is introduced. "Heterologous," as used herein, can also refer to a gene, protein, polynucleotide or polypeptide that naturally occurs in the host cell but is caused to express under conditions or at times (e.g., growth conditions, stage of development, cell cycle stage, etc.) during which the gene, protein, polynucleotide or polypeptide is not normally expressed. Likewise, "heterologous," as used herein, may also refer to the down-regulation or inhibition of expression of a gene, protein, polynucleotide or polypeptide at times or under conditions during which the gene, protein, polynucleotide or polypeptide is normally expressed.

Host cell: As used herein, the "host cell" is a cell that is manipulated according to the present disclosure. For example, a host cell is manipulated such that its production of one or more PUFA is increased (e.g., via PUFA increasing modification). A "modified host cell," as used herein, is any host cell which has been modified, engineered, or manipulated in accordance with the present disclosure as compared with an otherwise identical parental cell, and/or as compared with a particular reference cell (e.g., a wild type cell). The modified host cell has at least one (and optionally more than one) modification that results in increased production of PUFA or other cellular materials (e.g., at least one PUFA increasing modification) by the modified host cell as compared with the parent or reference cell.

Introduce: The term "introduce," as used herein with reference to introduction of a nucleic acid into a cell or organism is intended to have its broadest meaning and to encompass introduction, for example by transformation methods (e.g., calcium-chloride-mediated transformation, electroporation, particle bombardment), and also introduction by other methods including transduction, conjugation, and mating. Optionally, a vector is utilized to introduce a nucleic acid into a cell or organism.

Isolated: The term "isolated," as used herein, means substantially separated or purified with respect to sequences or polypeptides in the cell or organism in which the nucleic acid is naturally present and includes nucleic acids purified by standard purification techniques as well as nucleic acids prepared either by recombinant techniques or chemical synthesis. The term includes cDNA molecules derived from the isolated nucleic acids and other artificially produced nucleic acids derived from the isolated nucleic acids, or portions thereof, which encode substantially the same genetic information as the isolated nucleic acids. The term "substantially the same genetic information" refers to nucleic acid sequences that have at least 80% sequence identity with the nucleic acids described herein, and/or are conservatively substituted variants of the isolated nucleic acids described herein.

Microalgae: Microalgae are acknowledged in the field to represent a diverse group of organisms. For the purpose of this document, the term microalgae will be used to describe unicellular microorganisms derived from aquatic and/or terrestrial environments (some cyanobacteria are terrestrial/soil dwelling). Aquatic environments extend from oceanic environments to freshwater lakes and rivers, and also include brackish environments such as estuaries and river mouths. Microalgae can be photosynthetic; optionally, microalgae are heterotrophic. Microalgae can be of eukaryotic nature or of prokaryotic nature. Microalgae can be non-motile or motile.

Operably linked: The terms "operably linked" or "operably coupled", which may be used interchangeably, as used herein, refers to a relationship between two nucleic acid sequences wherein the expression of one of the nucleic acid sequences is controlled by, regulated by or modulated by the other nucleic acid sequence. For example, a nucleic acid sequence that is operably linked to a second nucleic acid sequence is covalently linked, either directly or indirectly, to such second sequence, although any effective three-dimensional association is acceptable. A single nucleic acid sequence can be operably linked to multiple other sequences. For example, a single promoter can direct transcription of multiple RNA species.

Polypeptide: The term "polypeptide," as used herein, generally has its art-recognized meaning of a polymer of at least three amino acids. However, the term is also used to refer to specific functional classes of polypeptides, such as, for example, desaturases, elongases, etc. For each such class, the present disclosure provides several examples of known sequences of such polypeptides. Those of ordinary skill in the art will appreciate, however, that the term "polypeptide" is intended to be sufficiently general as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreover, those in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Those in the art can determine other regions of similarity and/or identity by analysis of the sequences of various polypeptides described herein. As is known by those in the art, a variety of strategies are known, and tools are available, for performing comparisons of amino acid or nucleotide sequences in order to assess degrees of identity and/or similarity. These strategies include, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2: 482); the homology alignment algorithm of Needleman and Wunsch (J. Mol. Biol., 1970, 48: 443), the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison. Wis.). Readily available computer programs incorporating such algorithms include, for example, BLASTN, BLASTP, Gapped BLAST, PILEUP, CLUSTALW, etc. When utilizing BLAST and Gapped BLAST programs, default parameters of the respective programs may be used. Alternatively, the practitioner may use non-default parameters depending on his or her experimental and/or other requirements (see for example, the Web site having URL www.ncbi.nlm.nih.gov).

PUFA biosynthetic pathway: A "PUFA biosynthetic pathway" is a biosynthetic pathway that produces PUFA and/or PUFA precursors.

PUFA biosynthesis gene: The term "PUFA biosynthesis gene" or "polyunsaturated fatty acid biosynthesis gene." as used herein, refers to a DNA or RNA polynucleotide or nucleic acid encoding one or more PUFA biosynthesis polypeptide(s).

PUFA biosynthesis polypeptide: The term "PUFA biosynthesis polypeptide" or "polyunsaturated fatty acid polypeptide." as used herein, refers to polypeptides involved in the production of a PUFA such as, but not limited to alpha linolenic acid ("ALA"), arachidonic acid ("ARA"), docosahexanenoic acid ("DHA"), docosapentaenoic acid ("DPA"), eicosapentaenoic acid ("EPA"), gamma-linolenic acid ("GLA"), linoleic acid ("LA") and/or linolenic acid. PUFA biosynthesis polypeptides include enzymes that catalyze particular steps in a synthesis pathway that ultimately produces a PUFA. A PUFA biosynthesis polypeptide can be a fatty acid synthase. PUFA biosynthesis polypeptides can catalyze elongation of a fatty acid. PUFA biosynthesis polypeptides can catalyze desaturation of a fatty acid. The term "PUFA biosynthesis polypeptide" may also encompass polypeptides that do not themselves catalyze synthetic reactions, but that regulate expression and/or activity of other polypeptides that do so. PUFA biosynthesis polypeptides include, for example, fatty acid synthase polypeptides, elongase polypeptides, $\Delta 9$ desaturase polypeptides, $\Delta 12$ desaturase polypeptides, $\Delta 6$ desaturase polypeptides, $\Delta 8$ desaturase polypeptides, $\Delta 5$ desaturase polypeptides, $\Delta 4$ desaturase polypeptides, and $\omega 3$ desaturase polypeptides.

PUFA modification: A "PUFA modification", as used herein, refers to a modification of a host cell that increases or decreases its production of at least one PUFA. Some modifications entail PUFA increasing modifications; i.e., increased production results in a level of one or more PUFA that is at least 1%-1000% higher than wild type, e.g., about 1%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 550%, 600%, 650%, 700%, 750%, 800%, 850%, 900%, 950, 1000% higher than that of the parent cell into which the modification was introduced, and/or than that of a particular reference cell (e.g., a wild type cell). Some modifications entail PUFA decreasing modifications; i.e., decreased production results in a level of one or more PUFA that is at least 1%-1000% lower than wild type, e.g., about 1%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 550%, 600%, 650%, 700%, 750%, 800%, 850%, 900%, 950, 1000% lower than that of the parent cell into which the modification was introduced, and/or than that of a particular reference cell (e.g., a wild type cell). By way of example, production of one or more PUFA may be decreased while production of at least one other PUFA is increased. Thus, a PUFA increasing modification can increase expression or activity of one or more PUFA biosynthesis polypeptides. By way of another example, a PUFA increasing modification can decrease expression or activity of one or more polypeptides that interferes with expression or activity of a PUFA biosynthesis polypeptide, including for example, by competing with the PUFA biosynthesis polypeptide for access to a substrate. Optionally, a combination of increased expression of certain PUFA biosynthesis polypeptides and decreased expression of other PUFA biosynthesis polypeptides is engineered in order to tailor a PUFA production profile of a host cell. Optionally, a PUFA increasing modification comprises introduction of a heterologous nucleic acid into a host cell. The PUFA increasing modification can increase overall levels of fatty acid in a cell. Optionally, a PUFA increasing modification increases overall level of one or more particular PUFA in a cell, with or without increasing overall levels of fatty acid in the cell. Optionally, a PUFA increasing modification increases levels of PUFA including but not limited to ALA, ARA, DHA, DPA, EPA, GLA, and/or LA. Optionally, a PUFA increasing modification increases the level of one or more particular PUFA in a cell relative to one or more other PUFA in the cell by decreasing the levels of the other one or more PUFA relative to the particular one or more PUFA. A PUFA modification may encompass increasing and/or decreasing the levels of a plurality of PUFAs.

PUFA Production Profile: The term "PUFA Production Profile," when used herein, refers to the totality of fatty acids produced by a host cell under a given set of conditions. A PUFA production profile may consist of any combination or range of polyunsaturated fatty acids produced by the cell. The PUFA production profile may or may not comprise polyunsaturated fatty acids produced by a reference cell. A PUFA production profile results from PUFA biosynthetic pathways. Consequently, a PUFA production profile may be altered, decreased or increased by PUFA modifications. For example, a PUFA production profile may be engineered such that a host cell produces specific PUFAs to more than 0.5%, 1.0%, 2.0%, 3.0%, 4.0%, 5.0%, 10.0%, 20%, 40% or more of the total fatty acid content. General methods of modifying PUFA production profiles are known in the art (see, e.g., U.S. Pat. No. 7,247,461, incorporated by reference herein).

Progeny: The term "progeny," when used herein in reference to a cell, means a cell that arises from another cell (the "parent cell") (e.g., by cell division or budding) such that the "progeny cell" contains at least some of the genetic material of the parent cell. The progeny cell can contain all of genetic material of the parent cell. Optionally, the progeny cell does not contain all of the genetic material of the parent cell. Optionally, the progeny cell contains some genetic material in addition to the genetic material of the parent cell. The additional genetic material can be heterologous to the strain or species of the cell. The term "progeny" is meant to encompass not only direct progeny of a parent cell (e.g. cells that result from one division of or budding from a parent cell), but all indirect progeny of a parent cell (e.g., cells that result from more than one cycle of division of or budding from a parent cell). Thus, a given parent cell may have many cellular progeny, even though that cell may generate only a limited number of (e.g., two) cells in each cycle of division or budding. The term "progeny" is also meant to encompass cells that have undergone one or more manipulations by the hand of man (e.g., genetically manipulated or genetically engineered). Thus, for example, when a parent cell line is genetically manipulated or genetically engineered, all of the cells that arise therefrom are considered progeny of the cell line. All of the progeny of those progeny are also considered progeny of the parent cell line, and so on.

Promoter or Promoter element: As used herein, the terms "promoter," "promoter element" and "regulatory sequence" refer to a polynucleotide that regulates expression of a selected polynucleotide sequence operably linked to the promoter, and that effects expression of the selected polynucleotide sequence in cells. The term "*Thraustochytrium* promoter," as used herein, refers to a promoter that functions in a *Thraustochytrium* cell. The term "Thraustochytrid promoter", as used herein, refers to a promoter that functions in a Thraustochytrid cell. In some embodiments, a promoter element is or comprises untranslated regions (UTR) 5' of coding sequences. 5' UTRs form part of the mRNA transcript and so are an integral part of protein expression in eukaryotic organisms. Following transcription 5'UTRs can regulate protein expression at both the transcription and translation levels. Common 5'UTR regulatory structures include riboswitches and upstream open reading frames (uORFs). In riboswitches the mRNA secondary structure forms an aptamer, able to bind a cellular metabolite or protein. In response to binding an aptamer and/or to related mRNA secondary structure changes confirmation stimulating, suppressing, or causing alternate splicing of a related open reading frame. Known examples present in microalgae include the methionine responsive METE riboswitch and the Thiamine responsive Thi4 riboswitch.

Reference cell: The phrase "reference cell", as used herein, refers to a cell that is normal with respect to at least one characteristic for comparison purposes. For example, a reference cell for comparing against a genetically engineered cell can be a cell that is not genetically engineered. A reference cell can contain no genetic modifications or can be a cell of a wild type strain. Optionally, a reference cell contains some genetic modifications characteristic of a particular strain against which it is being compared, but does not contain one or more genetic modifications characteristic of the particular strain against which it is being compared. For example, such a reference cell would be useful for evaluating the effect of the one or more genetic modifications that it does not contain. Thus, for example, the term "reference *Thraustochytrium* cell" (or "reference Thraustochytrid cell") means a *Thraustochytrium* cell (or Thraustochytrid cell) of the same or similar strain as the cell to which it is being compared, except that the reference *Thraustochytrium* cell (or reference Thraustochytrid cell) lacks one or more characteristics (e.g., one or more genetic modifications) of a *Thraustochytrium* cell (or Thraustochytrid cell) against which the reference *Thraustochytrium* cell (or reference Thraustochytrid cell) is being compared. A reference cell may also be a host cell of any species, except that the reference host cell lacks one or more characteristics of an engineered host cell (e.g. a particular Thraustochytrid or *Thraustochytrium* gene that is transformed into the host cell).

Selectable marker: The phrase "selectable marker," as used herein, refers either to a nucleotide sequence, e.g., a gene, that encodes a product (protein) that allows for selection, or to the gene product (e.g., protein) itself. The term "selectable marker" is used herein as it is generally understood in the art and refers to a marker whose presence within a cell or organism confers a significant growth or survival advantage or disadvantage on the cell or organism under certain defined culture conditions (selective conditions). For example, the conditions may be the presence or absence of a particular compound or a particular environmental condition such as increased temperature, increased radiation, presence of a compound that is toxic in the absence of the marker, etc. The presence or absence of such compound(s) or environmental condition(s) is referred to as a "selective condition" or "selective conditions." By "growth advantage" is meant either enhanced viability (e.g., cells or organisms with the growth advantage have an increased life span, on average, relative to otherwise identical cells), increased rate of proliferation (also referred to herein as "growth rate") relative to otherwise identical cells or organisms, or both. In general, a population of cells having a growth advantage will exhibit fewer dead or nonviable cells and/or a greater rate of cell proliferation than a population of otherwise identical cells lacking the growth advantage. Although typically a selectable marker will confer a growth advantage on a cell, certain selectable markers confer a growth disadvantage on a cell, e.g., they make the cell more susceptible to the deleterious effects of certain compounds or environmental conditions than otherwise identical cells not expressing the marker. Antibiotic resistance markers are a non-limiting example of a class of selectable marker that can be used to select cells that express the marker. In the presence of an appropriate concentration of antibiotic (selective conditions), such a marker confers a growth advantage on a cell that expresses the marker. Thus, cells that express the antibiotic resistance marker are able to survive and/or proliferate in the presence of the antibiotic while cells that do not express the antibiotic resistance marker are not able to survive and/or are unable to proliferate in the presence of the antibiotic. For example, a selectable marker of this type that is commonly used in plant cells is the NPTII protein, which encodes a protein that provides resistance against the antibiotic kanamycin. More broadly, selectable markers are categorized as either selectable compounds, or antibiotics, and nutritional, or auxotrophic, markers.

Examples of selectable markers include common bacterial antibiotics, such as but not limited to ampicillin, kanamycin and chloramphenicol, as well as selective compounds known to function in microalgae; examples include rmS and AadA (Aminoglycoside 3'-adenylytranferase), which may be isolated from *E. coli* plasmid R538-1, conferring resistance to spectinomycin and streptomycin, respectively in *E. coli* and some microalgae (Hollingshead and Vapnek 1985; Meslet-Cladière and Vallon 2011). Another example is the 23S RNA protein, rrnL, which confers resistance to erythromycin (Newman, Boynton et al. 1990; Roffey, Golbeck et al. 1991). Another example is Ble, a GC rich gene isolated from *Streptoalloteichus hindustanus* that confers resistance to zeocin (Stevens, Purton et al. 1996). Aph7 is yet another example, which is a *Streptomyces hygroscopicus*-derived aminoglycoside phosphotransferase gene that confers resistance to hygromycin B (Berthold, Schmitt et al. 2002). Additional examples include: AphVIII, a *Streptomyces rimosus* derived aminoglycoside 3'-phosphotransferase type VIII that confers resistance to Paromycin in *E. coli* and some microalgae (Sizova, Lapina et al. 1996; Sizova. Fuhrmann et al. 2001); Nat & Sat-1, which encode nourseothricin acetyl transferase, from *Streptomyces noursei* and streptothricin acetyl transferase, from *E. coli*, which confer resistance to nourseothricin (Zaslavskaia. Lippmeier et al. 2000); Neo, an aminoglycoside 3'-phosphotransferase, conferring resistance to the aminoglycosides; kanamycin, neomycin, and the analog G418 (Hasnain, Manavathu et al. 1985); and Cry 1, a ribosomal protein S14 that confers resistance to emetine (Nelson, Savereide et al. 1994). Other selectable markers include nutritional markers, also referred to as auto- or auxo-trophic markers. These include photo-autotrophy markers that impose selection based on the restoration of photosynthetic activity within a photosynthetic organism. Photoautotrophic markers include; AtpB, TscA, PetB, NifH, psaA and psaB (Boynton, Gillham et al. 1988; Goldschmidt-Clermont 1991; Kindle, Richards et al. 1991; Redding, MacMillan et al. 1998; Cheng, Day et al. 2005). Alternative or additional nutritional markers include: ARG7, which encodes argininosuccinate lyase, a critical step in arginine biosynthesis (Debuchy, Purton et al. 1989); NIT1, which encodes a nitrate reductase essential to nitrogen metabolism (Fernández, Schnell et al. 1989); THI10, which is essential to thiamine biosynthesis (Ferris 1995); and NIC1, which catalyzes an essential step in nicotinamide biosynthesis (Ferris 1995). Such markers are generally enzymes that function in a biosynthetic pathway to produce a compound that is needed for cell growth or survival. In general, under nonselective conditions the required compound is present in the environment or is produced by an alternative pathway in the cell. Under selective conditions, functioning of the biosynthetic pathway, in which the marker is involved, is needed to produce the compound.

Selection agent: The phrase "selection agent." as used herein refers to an agent that introduces a selective pressure on a cell or populations of cells either in favor of or against the cell or population of cells that bear a selectable marker. For example, the selection agent is an antibiotic and the selectable marker is an antibiotic resistance gene. Optionally, zeocin is used as the selection agent.

Source organism: A "source organism," as used herein, is an organism that naturally contains or produces a polynucleotide, polypeptide, or other compound (e.g., a heterologous nucleic acid) that is to be introduced in accordance with the present disclosure into a recipient or host cell. Relevant considerations may include, for example, how closely related the potential source and host organisms are in evolution, or how related the source organism is with other source organisms from which sequences of other relevant nucleic acids and/or polypeptides have been selected. Where a plurality of different heterologous nucleic acids are to be introduced into and/or expressed by a host cell, different sequences may be from different source organisms, or from the same source organism. By way of example, individual polypeptides may represent individual subunits of a complex protein activity and/or may be required to work in concert with other polypeptides in order to achieve the goals of the present disclosure. Optionally, it may be desirable for such polypeptides to be from the same source organism, and/or to be sufficiently related to function appropriately when expressed together in a host cell. Such polypeptides may be from different, even unrelated source organisms. It will further be understood that, where a heterologous polypeptide is to be expressed in a host cell, it may be desirable to utilize nucleic acid sequences encoding the polypeptide that have been adjusted to accommodate codon preferences of the host cell and/or to link the encoding sequences with regulatory elements active in the host cell. For example, when the host cell is a *Thraustochytrium* cell, it will often be desirable to alter the gene sequence encoding a given polypeptide such that it conforms more closely to the codon preferences of such a cell. Optionally, a gene sequence encoding a given polypeptide is optimized even when such a gene sequence is derived from the host cell itself (and thus is not heterologous). For example, a gene sequence encoding a polypeptide of interest may not be codon optimized for expression in a given host cell even though such a gene sequence is isolated from the host cell strain. The gene sequence may be further optimized to account for codon preferences of the host cell. Those in the art will be aware of host cell codon preferences and will be able to employ the methods and compositions disclosed herein to optimize expression of a given polypeptide in the host cell.

Substrate: A "substrate," as used herein to describe substrates of an enzyme, refers to any entity that can be modified by activity of the enzyme.

Terminator: As used herein, the term "terminator" refers to a polynucleotide that abrogates expression of, targets for maturation (e.g., adding a polyA tail), or imparts mRNA stability to a selected polynucleotide sequence operably linked to the terminator in cells. A terminator sequence may be downstream of a stop codon in a gene. The term "*Thraustochytrium* terminator", as used herein, refers to a terminator that functions in a *Thraustochytrium* cell. The term "Thraustochytrid terminator", as used herein, refers to a terminator that functions in a Thraustochytrid cell.

Thraustochytrid: The term "thraustochytrid," as used herein, refers to any member of the order Thraustochytriales, which includes the family Thraustochytriaceae. Strains described as thraustochytrids include the following organisms: Order: Thraustochytriales; Family: Thraustochytriaceae; Genera: *Thraustochytrium* (Species: sp., *arudimentale, aureum, benthicola, globosum, kinnei, motivum, multirudimentale, pachydermum, proliferum, roseum, striatum*), *Ulkenia* (Species: sp., *amoeboidea, kerguelensis, minuta, profunda, radiata, sailens, sarkariana, schizochytrops, visurgensis, yorkensis*), *Schizochytrium* (Species: sp., *aggregatum, limnaceum, mangrovei, minutum, octosporuni*), *Japonochytrium* (Species: sp., *marinum*), *Aplanochyirium* (Species: sp., *haliotidis, kerguelensis, profunda, stocchini*), *Althornia* (Species: sp., *crouchii*), or *Elina* (Species: sp., *marisalba, sinorifica*). Species described within *Ulkenia* will be considered to be members of the genus *Thraustochytrium*. Strains described as being within the genus *Thrautochytrium* may share traits in common with and also be described as falling within the genus *Schizochytrium*. For example, in some taxonomic classifications ONC-T18 may be considered within the genus *Thrautochytrium*, while in other classifications it may be described as within the genus *Schizochytrium* because it comprises traits indicative of both genera.

Transformation: The term "transformation," as used herein refers to a process by which an exogenous or heterologous nucleic acid molecule (e.g., a vector or recombinant nucleic acid molecule) is introduced into a recipient cell or microorganism. The exogenous or heterologous nucleic acid molecule may or may not be integrated into (i.e., covalently linked to) chromosomal DNA making up the genome of the host cell or microorganism. For example, the exogenous or heterologous polynucleotide may be maintained on an episomal element, such as a plasmid. Alternatively or additionally, the exogenous or heterologous polynucleotide may become integrated into a chromosome so that it is inherited by daughter cells through chromosome replication. Methods for transformation include, but are not limited to, calcium phosphate precipitation; $Ca^{2+}$ treatment; fusion of recipient cells with bacterial protoplasts containing the recombinant nucleic acid; treatment of the recipient cells with liposomes containing the recombinant nucleic acid; DEAE dextran; fusion using polyethylene glycol (PEG); electroporation; magnetoporation; biolistic delivery; retroviral infection; lipofection; and micro-injection of DNA directly into cells. Optionally, an exogenous or heterologous nucleic acid is introduced in to a cell by mating with another cell. For example, in *S. cerevisiae*, cells mate with one another.

Transformed: The term "transformed," as used in reference to cells, refers to cells that have undergone "transformation" as described herein such that the cells carry exogenous or heterologous genetic material (e.g., a recombinant nucleic acid). The term "transformed" can also or alternatively be used to refer to microorganisms, strains of microorganisms, tissues, organisms, etc.

DETAILED DESCRIPTION

As described herein, the present disclosure provides a variety of reagents and methods related to the production of PUFA and/or to the modification of Thraustochytrids. In general, the disclosure relates to modification of Thraustochytrid host cells, and in particular to engineering Thraustochytrids, particularly to increase or tailor their production of compounds of interest (e.g., PUFA). The present disclosure encompasses identification of certain Thraustochytrid and *Thraustochytrium* sp. genetic regulatory elements and genes, as well as the development of methodologies for mutagenesis of Thraustochytrid or *Thraustochytrium*. The disclosure further provides engineered Thraustochytrid and *Thraustochytrium* sp. strains, and products produced from and with them. The disclosure also provides engineering non-Thraustochytrid host cells with Thraustochtrid genes in order to initiate, increase or tailor PUFA production in the host cells. Certain details of particular aspects of these and other aspects are discussed in more throughout.

Thraustochytrids can produce and accumulate high amounts of omega-3 (n-3) and omega-6 (n-6) PUFA within cellular lipid droplets. Some Thraustochytrids produce PUFAs through two pathways, the polyketide synthase-like (PUFA synthase) pathway (common in marine bacteria) and a desaturase/elongase (so called "standard") pathway also common in eukaryotes. Many individual genes and critical synthetic junctions in these pathways are known (see, e.g., FIG. 1). However, the effective possibilities of metabolic engineering involving these pathways to produce specific, desired end products, and total fatty acid compositions with certain ranges of particular PUFAs, remain undetermined.

Host Cells

As noted, the present disclosure provides reagents and methodologies for the manipulation of host cells.

In general, identified reagents (e.g., regulatory elements, vectors, selectable markers, mutagenic agents, etc.) and methodologies (including, for example, methods of mutagenizing) may be utilized together with any appropriate host cell. An artisan of ordinary skill, having read the present disclosure and having such reagents in hand, will readily be able to identify appropriate host cells in which such elements are active.

Host cells that may be used in the provided methods, compositions and kits include microalgae. Microalgae that may be used include, but are not limited to, *Achnanthes orientalis, Agmenellum, Amphiprora hyaline, Amphora coffeiformis, Amphora coffeiformis linea, Amphora coffeiformis punctata, Amphora coffeiformis taylori. Amphora coffeiformis tenuis, Amphora delicatissima, Amphora delicatissima capitata, Amphora* sp., *Anabaena, Anabaena variabilis, Ankistrodesmus, Ankistrodesmus falcatus, Boekelovia hooglandii, Borodinella* sp., *Botryococciis brauni, Botryococcus sudeticus, Bracteococcus minor, Bracteococcus medionucleatus, Carteria, Chaetoceros gracilis, Chaetoceros muelleri, Chaetoceros muelleri subsalsum, Chaetoceros* sp., *Chlamydomonas reinhardtii, Chlamydomonase moewusi, Chlamydomonas nivalis, Chlamydomonas caudate, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca var. vacuolata, Chlorella glucotropha, Chlorella infusionum, Chlorella infusionum var. actophila, Chlorella infusionum var. auxenophila, Chlorella kessleri, Chlorella lobophora* (strain SAG 37.88), *Chlorella luteoviridis, Chlorella luteoviridis var. aureoviridis, Chlorella luteoviidis var. lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella variabilis, Chlorella vanniellii, Chlorella vulgaris, Chlorella vulgaris f. terria, Chlorella vulgaris* var. *autotrophica, Chlorella vulgaris* var. *viridis, Chlorella vulgaris* var. *vulgaris, Chlorella vulgaris* var. *vulgarts f. tertia, Chlorella vulgaris* var. *vulgaris f. viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Coccomyxa subellipsoidea* C-169, *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella mimta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena, Franceia* sp., *Fragilaria crotonensis, Fragilaria* sp., *Gleocapsa* sp., *Gloeothamnion* sp. *Haematococcus pluvialis, Hymenomonas* sp., *Isochrysis aff galbana, Isochrysis galbana, Lepocinclis, Micractinium, Micractinium, Micromonas, Micromonas pusilla, Monoraphidium minutum, Monoraphidium* sp., *Nannochloris* sp., *Nannochloropsis salina, Nannochloropsis* sp., *Navicula acceptta, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrína, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Nostoc* sp., *Nostoc Punctiforme, Ochromonas* sp., *Oocystis parva, Oocystis pusilla, Oocystis* sp., *Oscillatoria limnetica, Oscillatoria* sp., *Oscillatoria subbrevis, Osterococcus, Osterococcus lucimarinus, Osterococcus tauri, Parachlorella kessleri, Pascheria acidophila, Pavlova* sp., *Phagus, Phaaodactylum tricornutum, Phormidium, Platymonas* sp., *Pleurochrysis carter ae. Pleurochrysis dentate, Pleurochrysis* sp., *Prochlorococcus marinus, Prototheca wickerhamii, Prototheca stagnora, Prototheca portoricensis, Prototheca monformis, Prototheca zopfii, Pseudochlorella aquatica, Pyramimonas* sp., *Pyrobotrys, Rhodococcus opacus, Sarcinoid chrysophyte, Scenedesmus armatus, Scynechocystis* sp., *Scynechococcus, Schizochytrium, Spirogyra, Spirulina platensis, Stichococcus* sp., *Synechococcus* sp., *Tetraedron, Thalassiosira pseudonana, Tetraselmis* sp., *Tetraselmis suecica, Thalassiosira weissflogii, Viridiella fridericiana,* and *Volvox carteri*.

The host cells may be fungi. Non-limiting examples of host cell fungi include yeast amenable to metabolic engineering (e.g. *Saccharomyces cerevisiae* and *Schizosaccharomyces pombe* and oleaginous yeasts (e.g., *Cryptococcus*

*curvatus, Cryptococcus terricolus, Candida* sp., *Lipomyces starkeyi, Lipomyces lipofer, Endomycopsis vernalis, Rhodotorula glutinis, Rhodotorula gracilis,* and *Yarrowia lipolytica*). Additional fungi include *Mortierella, Mortierella vinacea, Mortierella alpine, Pythium debaryanum, Mucor circinelloides, Aspergillus ochraceus, Aspergillus terreus, Pennicillium iilacinum, Hensenulo, Chaetomium, Cladosporium, Malbranchea, Rhizopus,* and *Pythium*.

Optionally, host cells for use in accordance with the present disclosure are Thraustochytrid cells. Optionally, host cells are members of the order Thraustochytriales. Optionally, host cells are members of the Thraustochytriaceae subclass. Optionally, host cells are members of a genus selected from the group consisting of *Thraustochytrium, Ulkenia, Schizochytrium, Aurantiochytrium, Aplanochytrium, Botryochytrium, Japonochytrium, Oblongichytrium, Parietichytrium,* and *Sicyoidochytrium*. Optionally, host cells are not of the genus *Schizochytrium*.

Host cells utilized in accordance with the present disclosure include members of the genus *Thraustochytrium*. Optionally, a host cell is a *Thraustochytrium* cell from one of the following species: *Thraustochytrium aggregatum, Thraustochytrium aureum, Thraustochytrium gaertnerium, Thraustochytrium kinnei, Thraustochytrium motivum, Thraustochytrium multirudimentale, Thraustochytrium pachydermum, Thraustochytrium roseum, Thraustochytrium* sp. 1.3A4.1, *Thraustochytrium* sp. ATCC 26185, *Thraustochytrium* sp. BL13, *Thraustochytrium* sp. BL14, *Thraustochytrium* sp. BL2, *Thraustochytrium* sp. BL3, *Thraustochytrium* sp. BL4, *Thraustochytrium* sp. BL5, *Thraustochytrium* sp. BL6, *Thraustochytrium* sp. BL7, *Thraustochytrium* sp. BL8, *Thraustochytrium* sp. BL9, *Thraustochytrium* sp. BP3.2.2, *Thraustochytrium* sp. BP3.3.3, *Thraustochytrium* sp. *caudivorum, Thraustochytrium* sp. CHN-1, *Thraustochytrium* sp. FJN-10, *Thraustochytrium* sp. HK1, *Thraustochytrium* sp. HK10, *Thraustochytrium* sp. HK5, *Thraustochytrium* sp. HK8, *Thraustochytrium* sp. HK8a, *Thraustochytrium* sp. KK17-3, *Thraustochytrium* sp. KL1, *Thraustochytrium* sp. KL2, *Thraustochytrium* sp. KL2a, *Thraustochytrium* sp. ONC-T18, *Thraustochytrium* sp. PJA10.2, *Thraustochytrium* sp. TR1.4, *Thraustochytrium* sp. TRR2, *Thraustochytrium striatum,* or *Thraustochytrium visurgense*.

Host cells used in accordance with the present disclosure also include members of the genus *Schizochytrium*. Optionally, a host cell is a *Thraustochytrium* cell from one of the following species: *Schizochytrium limacinum, Schizochytrium mangrovei, Schizochytrium minutum, Schizochytrium* sp. (ATCC 20111), *Schizochytrium* sp. (ATCC 20888), *Schizochytrium* sp. BR2.1.2, *Schizochytrium* sp. BUCAAA 032, *Schizochytrium* sp. BUCAAA 093, *Schizochytrium* sp. BUCACD 152, *Schizochytrium* sp. BUCARA 021, *Schizochytrium* sp. BUCHAO 113, *Schizochytrium* sp. BURABQ 133, *Schizochytrium* sp. BURARM 801, *Schizochytrium* sp. BURARM 802, *Schizochytrium* sp. FJU-512, *Schizochytrium* sp. KH105, *Schizochytrium* sp. KR-5, *Schizochytrium* sp. PJ10.4, *Schizochytrium* sp. SEK 210, *Schizochytrium* sp. SEK 345, *Schizochytrium* sp. SEK 346, *Schizochytrium* sp. SR21, or *Schizochytrium* sp. TIO01.

Optionally, the host cell is a *Thraustochytrium* sp. ONC-T18 cell. ONC-T18 is a marine *Thraustochytrium* originally isolated from the leaves of salt marsh grasses in Advocate Harbor, Bay of Fundy, Nova Scotia, Canada. ONC-T18 is described in U.S. Pat. Pub. 2009/0117194, which is herein incorporated by reference in its entirety. Optionally, a *Thraustochytrium* cell has an 18s rRNA sequence that is at least 97%, 98%, 99%, 99.1%, 99.2%, 99.3%, 99.4%, 99.5%, 99.6%, 99.7%, 99.8%, 99.9% or more (e.g., including 100%) identical to SEQ ID NO:68. Optionally, a host cell is a *Thraustochytrium* sp. ONC-T18 cell from cells deposited under ATCC strain accession number PTA-6245.

Engineering Microorganisms

The present disclosure provides, inter alia, genes, regulatory elements, nucleic acid constructs, selectable markers, methods for mutagenesis, and transformation methods for manipulation of microorganisms such as Thraustochytrids. The tools provided herein can be used alone and in various combinations to implement any desired genetic modification. For example, provided transformation methods are used to introduce nucleic acid molecules encoding one or more genes. Nucleic acid molecules can include genes encoding PUFA biosynthesis polypeptides, as well as promoter, terminator, or selectable marker sequences provided herein, or combinations thereof. Optionally, provided methods of mutagenesis are used to generate strains (e.g., Thraustochytrid strains) having desired properties. Such strains may also be transformed (e.g., with nucleic acids including one or more regulatory elements provided herein).

One or more genes encoding various enzymes in PUFA synthesis pathways can be transformed into a host cell in order to tailor the PUFA production profile of the host cell and its progeny. By selecting a desired combination of exogenous genes, endogenous genes operably linked to heterologous promoters, and exogenous genes operably linked to endogenous promoters. The synthetic pathways disclosed herein can be manipulated to achieve specific or preferential expression of one or more predetermined PUFA. For example, if a PUFA production profile optimized for biofuel is desired, then one of skill in the art could use the polynucleotides, methods and host cells disclosed herein to operably link a heterologous promoter from a Δ12 desaturase gene to drive expression of an endogenous or exogenous Δ5 desaturase, thereby tailoring PUFA production to ARA and EPA.

Any plurality of genetic modifications may be engineered to achieve a desired PUFA production or production profile. One or more nucleic acid sequences disclosed herein may be over-expressed, for example, to inhibit or prevent the synthesis of PUFA with carbon chains greater than 18 and desaturation greater than 1. Gene regulatory elements disclosed herein may be operably linked to one or heterologous or endogenous genes to tailor activation of the genes in a time- or condition-dependent manner. Non-limiting examples of genes capable of manipulation include Fatty Acid Synthase to control carbon flow into the PUFA pathway, thioesterases to catalyze termination of fatty acid biosynthesis in a chain length-specific manner, and elongation and/or desaturase controlling the terminal step synthesis of desired compounds.

In general, the polynucleotides disclosed herein function as a series of tools that allow rational engineering of PUFA biosynthetic pathways to produce a variety of products. Stated another way, the polynucleotides disclosed herein may be interchanged and their expression temporally controlled or synchronized in any one of a number of combinations. Those in the art will be able to use the tools disclosed herein accordingly, requiring only additional knowledge of the biosynthetic pathway to be manipulated (see, e.g., FIG. 1) and a means to detect, measure and/or isolate a desired end product. For example, a desaturase promoter (e.g., the Δ12 desaturase promoter of SEQ ID NO.69) or operable fragment thereof may be operably linked to a Fatty Acid Synthase (FAS) type 1 gene to increase fatty acid biosynthesis during periods of both cell growth and fatty acid production.

Optionally, a PUFA production profile (comprising all fatty acid biosynthesis pathways and the resulting products) may be tailored to produce predetermined compositions comprising at least two fatty acid products within a specified range or ranges optimized for a particular utility (e.g. biofuel production). For example, it is generally desirable to minimize long-chain polyunsaturated fatty acids ("LCPUFA"; e.g., DHA) levels in biofuels. Through manipulation of the PUFA biosynthesis polypeptides and their corresponding nucleic acid sequences disclosed herein, optionally in conjunction with particularized culture conditions, it is possible to produce a fatty acid oil composition in which LCPUFA levels are less than approximately 25% of the total fatty acids content. Optionally, fatty acid oil compositions are produced with LCPUFA levels less than approximately 20%, 15%, 10%, 5% and 1% of total fatty acid content. Optionally, LCPUFA have at least about 20, at least about 22, at least about 24, at least about 26, at least about 28 or at least about 30 carbon atoms. Optionally, the LCPUFA are docosatetraenoic acid, docosapentaenoic acid, and/or docosahexaenoic acid.

As discussed throughout, the provided organisms can encompass genetic modifications in which a gene is expressed. Optionally, however, microorganisms are engineered to reduce expression of genes that encode one more PUFA biosynthesis polypeptides. For example, a Thraustochytrid or *Thraustochytrium* can be engineered to reduce expression of an elongase or desaturases. Optionally, a Thraustochytrid or *Thraustochytrium* is engineered with reduced or ablated Δ12 desaturase expression. Methods of reducing gene expression in microorganisms are well known in the art; e.g., knockout or allele exchange constructs and anti-sense RNA.

Optionally, regulatory elements (e.g., promoter(s)) from one Thraustochytrid or *Thraustochytrium* PUFA biosynthesis gene are operably linked a heterologous PUFA biosynthesis gene in order to tailor expression of that gene. For expression, expression may be tailored to match basal expression levels of a particular gene during exponential growth or to coordinate approximately equivalent levels of gene expression.

Optionally, more than one PUFA biosynthesis gene is simultaneously or concurrently expressed within engineered microorganisms in order to tailor the PUFA production profile. The genes may be expressed from any number of expression vectors. For example, each gene may comprise an expression vector, each on an individual plasmid. Alternatively, in order to reduce the number of plasmids, the PUFA biosynthesis genes may be placed on three plasmids, two plasmids, or a single plasmid. Plasmid vectors with multiple expression cassettes are well known in the art. Genes encoding any combination of fatty acid synthase (FAS), Δ5 elongase, Δ4 desaturase, polyketide PUFA synthase (PKS), Δ5 desaturase and Δ12 desaturase may be placed on one, two, three, four, five, six or seven plasmids. Polycistronic and operon-based expression constructs may also be used.

Thus, provided are engineered microorganisms, which my derived or created from any of the aforementioned host species, including *Schizochytrium*, *Oblongichytrium*, *Aurantiochytrium* and *Thraustochytrium*. The engineered microorganisms express one or more heterologous nucleic acids that change or tailor PUFA biosynthesis in the engineered microorganism relative to a host cell or wild-type species. Optionally, ONC-T18 is engineered in a manner or manners disclosed herein. For example, a PUFA biosynthesis polynucleotide is heterologously expressed such that production of one or more PUFA is changed (i.e., increased or decreased relative to levels in the absence of heterologous polynucleotide. Optionally, the heterologous expression is over-expression. Optionally, an endogenous or exogenous polynucleotide sequence encoding an enzyme polypeptide or part of an enzyme polypeptide complex is heterologously expressed by operatively linking the polynucleotide sequence to a promoter. Optionally, the promoter is exogenous to the microorganism. Optionally, the promoter is endogenous to the microorganism, but is operatively linked a heterologous (i.e., different) PUFA biosynthesis polynucleotide. This may cause expression of the enzyme polypeptide or part of an enzyme polypeptide complex encoded by the PUFA biosynthesis polynucleotide at a time or under conditions at which the enzyme polypeptide or part of an enzyme polypeptide complex is not normally expressed. Heterologous promoters may be, for example, established promoters, known to those in the art, such as the Lac promoter of the Lactose operon of bacteria, the arabinose inducible promoter pBAD of bacteria, or the tetracycline regulated Tet promoter of bacteria. Alternatively or additionally, utilized promoters can be those found in a eukaryotic system, as known to those in the art, such as TDH3, ADH1, TPI1, ACT1, GPD or PGI or the galactose inducible promoters, GAL1, GAL7 and GAL10. Regulatory elements that may be employed by those in the art; include those found in microalgae, examples include: Rbcs2, the promoter of ribulose bisphosphate carboxylase providing constitutive high level expression (Stevens, Purton et al. 1996); PsaD, the promoter of photosystem I subunit D, that allows high level constitutive expression that can be regulated by the nuclear protein Nac2 (Fischer and Rochaix 2001); PsbA, the promoter of the photosystem II gene, PsbA, and 5' UTR. These yield high levels of recombinant protein accumulation (Manuell, Beligni et al. 2007; Surzcki, Greenham et al. 2009). Alternatively or additionally, regulatory elements include Hsp70A, the heat shock protein 70A enhancer element, which reduces gene silencing in nuclear transformants and is typically employed in combination with the Rbcs2 promoter (Schroda, Blöcker et al. 2000). Alternatively or additionally, the regulatory sequence of a native protein may be employed to drive the expression of a heterologous gene. Examples of this may include the promoters of fatty acid biosynthesis proteins, including those that are induced due to nitrogen stress. Specific examples or promoters include the regulatory sequence of a Δ12 desaturase (e.g., SEQ ID NO: 69), the regulatory sequence of a Δ5 desaturase (e.g., SEQ ID NO: 71), the regulatory sequence of a Δ4 desaturase, and the regulatory sequence of a Δ5 elongase. Alternative or additional promoters may include those that are induced in response to economically viable changes in bioprocess conditions. Such changes may include induction of an anoxic or anaerobic response by reducing agitation rate, for example, associated regulatory elements would include those driving the expression of carbonic anhydrases, a change in or depletion of organic carbon and/or nitrogen. Promoters may be constitutive or inducible.

While nucleic acid regulatory sequences or promoters can increase expression of polynucleotides to which they are operatively linked, a heterologous regulatory sequence or promoter can also decrease expression of polynucleotides to which they are linked. This effect can depend on growth stage or conditions. For example, if a regulatory sequence for a Δ5 desaturase is operatively linked to control expression of a PKS gene cluster, expression of the PKS complex will be substantially reduced during periods of exponential growth, and also during periods of fatty acid production when the microorganism is not growing or is growing at a reduced rate.

Optionally, only particular promoter elements of the regulatory sequences disclosed herein are used. For example, particular polynucleotide promoter elements of the Δ12 desaturase of SEQ ID NO:69 may be identified in silico using analysis tools known to those in the art. (see, e.g., D. J. Studholme & R. Dixon, 2003, Domain architectures of sigma54-dependent transcriptional activators, *J. Bacteriol.* 185:1757-67; R. Münch et al, 2005, *Bioinformatics* 2005 21: 4187-4189; L. Gordon et al., 2003, *Bioinformatics* 19:1964-71; J. M. Carlson et al., 2007, *Nucl. Acids Res.* 35: W259-W264; the Transcription Regulatory Element Database of Cold Spring Harbor Laboratory; the Eukaryotic Promoter Database of the Swiss Institute of Bioinformatics.) These promoter elements can then be isolated and rearranged, and expression accordingly optimized, using standard genetic engineering techniques (e.g., PCR, restriction digestion/ligation, and arranging the elements in a report construction to evaluate impact on expression of the report gene under various conditions, growth phase, etc.) Optionally, polynucleotide promoter elements from different regulatory sequences (e.g., Δ5 and Δ12 desaturases) may be combined into hybrid promoter elements in order to drive gene expression in unexpected, but determinable, ways.

Some engineered microorganisms can include multiple combinations of heterologous promoters operatively linked different PUFA biosynthesis polynucleotides. Optionally, at least additional heterologous polynucleotides encoding an enzyme polypeptide or part of an enzyme polypeptide complex involved in PUFA biosynthesis are transformed into the microorganism. Optionally, additional heterologous polynucleotides include fatty acid synthase (FAS), Δ5 elongase, Δ5 desaturase, Δ12 desaturase, Δ4 desaturase, and polyketide PUFA synthase (PKS).

Heterologous nucleic acid sequence and promoters may be introduced into host cells or engineered microorganisms according to methods known in the art. The sequences may be placed in one or more expression cassettes or expression vectors, and introduced into the cells on one or more plasmids. The heterologous sequences can be transformed into the cells using conventional techniques (e.g., electroporation and cationic lipid based techniques). Additional techniques of transforming heterologous sequences into host cells include lithium acetate transformation, spheroplasting, protoplast fusion, lipofection, transfection, transduction, conjugation, infection, and the like. Expression vectors may be constructed as disclosed in the examples herein.

Heterologous (exogenous or endogenous) promoter sequence(s) may be introduced into cells and operatively linked to an endogenous PUFA biosynthesis polynucleotide of choice by homologous recombination. The endogenous PUFA biosynthesis polynucleotide may be located extrachromosomally on a plasmid, or integrated into (i.e., covalently linked to) chromosomal DNA making up the genome of the host cell.

As a result of the modifications discussed above, the PUFA production profile and total fatty acid content of an engineered microorganism is affected in a predetermined manner. Thus, engineered microorganisms can have the total fatty acid content of the cell increased by at least 10%, 20%, 50%, 100% or more relative to the content in the absence of the heterologous nucleic acid sequence or promoter. Optionally, expression of the heterologous nucleic acid sequence reduces the content of C12-C16 saturated and mono unsaturated fatty acids relative to the content of said fatty acids in the absence of expression of the heterologous nucleic acid sequence. Levels of C12-C16 saturated and mono unsaturated fatty acids may be reduced by at least 10%, 20%, 50%, 100% or more relative to the content of said fatty acids in the absence of expression of the heterologous nucleic acid sequence or promoter.

Heterologous expression of PUFA biosynthesis polynucleotides can affect the overall PUFA production profile in an engineered host cell. For example, heterologous expression of any one of the PUFA biosynthesis polynucleotides disclosed herein can increase the total fatty acid content of a host cell, and particularly increase the content of PUFAs with four or more double bonds. For example, over-expression, and optionally concurrent and coordinated expression, of the polynucleotides disclosed herein can increase production of PUFA with four or more double bonds (e.g., DHA, DPA, ARA) such that a host cell produces PUFAs with more than four double bonds to more than 0.5%, 1.0%, 2.0%, 3.0%, 4.0%, 5.0%, 10.0%, 20%, 40% or more of the total fatty acid content.

Gene Expression

The present disclosure encompasses compositions and methods for engineering microorganisms. Optionally, the present disclosure provides compositions and methods for engineering Thraustochytrids (e.g., *Thraustochytrium*). "Engineered" cells include cells that have been modified (e.g., by introduction of an exogenous nucleic acid) and progeny thereof that retain the modification.

The present disclosure also provides nucleic acids that include regulatory sequences from Thraustochytrid or *Thraustochytrium*. Gene expression in eukaryotes often requires regulatory sequences that are species-specific, or that function in organisms that are closely related. The availability of regulatory sequences from Thraustochytrid or *Thraustochytrium* allows genes of interest to be expressed in Thraustochytrids. Optionally, regulatory sequences include promoter sequences and terminator sequences.

The PUFA biosynthesis peptides and their corresponding polynucleotides may be transformed and expressed in any host cell. For example, a Thraustochytrid or *Thraustochytrium* desaturase (e.g., the Δ12 desaturase of SEQ ID NO:70) and/or elongase (e.g., a Δ5 elongase) may be expressed in *Saccharomyces cerevisiae* to increase conversion of oleic acid to linoleic acid (see, e.g., FIG. 1) and/or EPA to Docosapentaenoic acid, thereby tailoring PUFA production. Optionally, a dominant-negative Thraustochytrid or *Thraustochytrium* desaturase may be transformed into a non-Thraustochytrid or -*Thraustochytrium* host cell to cause accumulation of oleic acid. Dominant-negative PUFA biosynthesis peptides may be generated through mutagenesis methods disclosed herein.

Provided are isolated nucleic acids including a Thraustochytrid or *Thraustochytrium* promoter. Optionally, a nucleic acid provided herein includes a *Thraustochytrium* Δ4 desaturase gene promoter. A sequence of an exemplary Δ4 desaturase gene promoter is shown in SEQ ID NO:24. Optionally, a nucleic acid provided herein includes a *Thraustochytrium* Δ5 elongase gene promoter. A sequence of an exemplary Δ5 elongase gene promoter is shown in SEQ ID NO: 19. A *Thraustochytrium* Δ5 elongase gene promoter is a strong promoter in Thraustochytrids (e.g., *Thraustochytrium*). Optionally, a nucleic acid provided herein includes a Thraustochytrid or *Thraustochytrium* tubulin gene promoter. Sequences of exemplary *Thraustochytrium* tubulin gene promoters are shown in SEQ ID NOs:6 and 10. Optionally, a nucleic acid provided herein includes a *Thraustochytrium* Δ12 desaturase gene promoter. A sequence of an exemplary Δ12 desaturase gene promoter is shown in SEQ ID NO:69. Optionally, a nucleic acid provided herein includes a *Thraustochytrium* Δ5 desaturase gene promoter. A sequence of an exemplary Δ5 desaturase gene promoter is shown in SEQ ID NO:71. Nucleic acids provided herein for use may have at least 80%, 85%, 90%, 92%, 95%, 97%, 98%, 99%, or higher sequence identity to the SEQ IDs above.

The present application also provides an isolated nucleic acid including a Thraustochytrid or *Thraustochytrium* gene. Optionally, the gene provided herein includes a *Thraustochytrium* Δ12 desaturase gene. A sequence of an exemplary Δ12 desaturase gene is shown in SEQ ID NO:70. Optionally, a Δ12 desaturase gene may have at least 80%, 85%, 90%, 92%, 95%, 97%, 98%, 99%, or higher sequence identity to the SEQ ID NO:70. Optionally, the Δ12 desaturase gene is a *Thraustochytrium* sp. ONC-T18 Δ12 desaturase. Optionally, the gene provided herein includes a *Thraustochytrium* Δ5 desaturase gene. A sequence of an exemplary Δ5 desaturase gene is shown in SEQ ID NO:72. Optionally, a Δ5 desaturase gene may have at least 80%, 85%, 90%, 92%, 95%, 97%, 98%, 99%, or higher sequence identity to the SEQ ID NO:72. Optionally, the Δ5 desaturase gene is a *Thraustochytrium* sp. ONC-T18 Δ5 desaturase.

An isolated nucleic acid molecule may be described by the conditions upon which it hybridizes to a corresponding nucleic acid sequence. For example, an isolated nucleic acid molecule is provided that hybridizes to a nucleic acid sequence corresponding to SEQ ID NOs: 70 or 72 under stringent conditions. Stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is approximately 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory. Cold Spring Harbor, N.Y., 1989; Kunkel et al. Methods Enzymol. 1987:154: 367, 1987). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as desired homology is increased, and further, depending upon the G-C or A-T richness of any area wherein high homology is desired, as known in the art.

Optionally, an isolated nucleic acid including a Thraustochytrid or *Thraustochytrium* promoter provided herein is a cassette, e.g., an expression cassette. Optionally, an isolated nucleic acid including a Thraustochytrid or *Thraustochytrium* promoter provided herein is a vector, e.g., an expression vector.

Provided herein are cells engineered to include a Thraustochytrid or *Thraustochytrium* gene or gene promoter. Optionally, a Thraustochytrid or *Thraustochytrium* cell is engineered to include a Thraustochytrid or *Thraustochytrium* promoter, e.g., a *Thraustochytrium* Δ4 desaturase gene promoter, a *Thraustochytrium* Δ5 elongase gene promoter, a *Thraustochytrium* Δ12 desaturase gene promoter, a *Thraustochytrium* Δ5 desaturase gene promoter or a *Thraustochytrium* tubulin gene promoter.

Provided herein are host cells engineered to express one or more Thraustochytrid or *Thraustochytrium* genes encoding PUFA biosynthesis polypeptides. Optionally, only a single gene is expressed to affect PUFA biosynthesis in a host cell. The gene may be a master regulator (e.g., Δ12 desaturase), over-expression of which increases total fatty acid levels and, in particular, polyunsaturated fatty acid levels. Optionally, genes encoding one or more PUFA biosynthesis peptides are over-expressed by approximately 2-fold. 3-fold, 4-fold, 5-fold, 10-fold. 15-fold, 20-fold, 25-fold. 30-fold, 40-fold, 50-fold, 75-fold, 100-fold or more relative to expression levels in a reference cell. Expression levels may be determined by methods well known to those of skill in the art, including Western blot, Northern blot, rtPCR and real-time PCR. Optionally, expression of a plurality of genes is coordinated to manipulate carbon flow through PUFA biosynthesis pathway(s). Genes that may be manipulated include: Δ12-desaturase, Δ9-desaturase, Δ8-desaturase, Δ5-desaturase, Δ4-desaturase, Δ9-elongase, Δ6-elongase, 6-elongase, Δ5-elongase, fatty acid synthase and polyketide PUFA synthase (PKS).

As a result of the modifications discussed herein, the PUFA production profile and total fatty acid content of host cells or engineered microorganism is affected in a predetermined manner. These effects may be achieved through over-expression of one or more PUFA biosynthesis genes or polynucleotides (e.g., nucleic acid sequences disclosed herein). Optionally, PUFA production is tailored by over-expressing at least one polynucleotide encoding a PUFA biosynthesis enzyme or enzyme polypeptide (e.g., Δ12 desaturase) while concurrently decreasing expression of a different polynucleotide encoding a PUFA biosynthesis enzyme or enzyme polypeptide (e.g., PKS). As discussed herein, these affects are achieved in some embodiments by over-expression using endogenous or exogenous promoters, and/or by coordinately or temporally expressing a group of PUFA biosynthesis polynucleotides to channel carbon flow through the biosynthesis pathway to a desired outcome. Thus, provided herein are expression cassettes and vectors capable of increasing the total fatty acid content of a host cell by at least 10%, 20%, 50%, 100% or more relative to the content in the absence of the heterologous nucleic acid sequence or promoter. Optionally, expression of the heterologous nucleic acid sequence reduces the content of C12-C16 saturated and mono unsaturated fatty acids relative to the content of said fatty acids in the absence of expression of the heterologous nucleic acid sequence. Thus, provided herein are expression cassettes and vectors capable of reducing levels of C12-C16 saturated and mono unsaturated fatty acids by at least 10%, 20%, 50%, 100% or more relative to the content of said fatty acids in the absence of expression of the heterologous nucleic acid sequence or promoter.

Provided are isolated nucleic acids including a Thraustochytrid or *Thraustochytrium* gene terminator. Optionally, a nucleic acid provided herein includes a Thraustochytrid or *Thraustochytrium* tubulin gene terminator. Sequences of exemplary *Thraustochytrium* tubulin gene terminators are shown in SEQ ID NOs: 14 and 18.

Optionally, an isolated nucleic acid including Thraustochytrid or *Thraustochytrium* genes and regulatory sequences provided herein includes a cassette, e.g., an expression cassette. Optionally, an isolated nucleic acid including a Thraustochytrid or *Thraustochytrium* gene provided herein is a vector, e.g., an expression vector. Recombinant expression vectors for use include vectors capable of expression in prokaryotic and eukaryotic cells. For example, the Thraustochytrid or *Thraustochytrium* genes disclosed herein can be expressed in bacterial cells (e.g., *E. coli*), insect cells (e.g., baculovirus), and yeast (see, e.g., Romanos, M. A., et al. (1992) "Foreign gene expression in yeast: a review", Yeast 8:423-488; van den Hondel, C. A. M. J. J., et al. (1991) "Heterologous gene expression in filamentous fungi", in: *More Gene Manipulations in Fungi*. J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: *Applied Molecular Genetics of Fungi*. Peberdy, J. F., et al., Ed., pp. 1-28, Cambridge University Press: Cambridge). Methods of gene expression in various host cells and appropriate vectors for such expression are known in the art. (see, e.g., *Gene Expression Systems*, Fernandez, J. and Hoeffler, J. P. Ed., Academic Press: San Diego, $1^{st}$ Ed. (1998)) Multiple expression cassettes, each comprising a different gene disclosed herein or the same gene under control of different regulatory elements, can be introduced into a host cell by simultaneous transformation of a plurality of expression vectors. Additionally or alternatively, multiple expression cassettes may be positioned within a single expression vector or vector.

Provided are isolated nucleic acids including one or more gene regulatory elements. Optionally, included gene regulatory elements facilitate inducible gene regulation. Non-limiting examples of inducible systems that may be employed in combination with provided nucleic acids include tetracycline-inducible systems, ethanol inducible systems, and chemically inducible gene expressions systems. (See, e.g. Park and Morschhäuser (2005), Li et al. (2005), and Jepson et al. (1998), the entire contents of each of which are incorporated by reference herein).

Nucleic acids having regulatory sequences provided herein may be operably linked to a heterologous sequence, such as a gene encoding a heterologous polypeptide. For example, provided are gene expression cassettes that typically comprise a Thraustochytrid or *Thraustochytrium* gene promoter operably linked to heterologous nucleic acid sequence, which is operably linked to a Thraustochytrid or *Thraustochytrium* gene terminator. In one non-limiting example, a gene cassette comprises a *Thraustochytrium* Δ12 desaturase gene promoter operable linked to a polynucleotide encoding a *Thraustochytrium* Δ5 desaturase. Optionally, the heterologous nucleic acid sequence comprises at least part of a coding sequence in a gene, e.g., the heterologous nucleic acid sequence encodes a gene product such as a polypeptide or RNA. Optionally, the provided gene expression cassettes further include a selection marker (e.g., a zeocin resistance gene such as Sh ble, or any other selection marker discussed herein). Optionally, provided gene expression cassettes further include a reporter gene (e.g., fluorescent proteins (GFP, YFP, RFP), luciferase, mCherry, GUS (β-glucuronidase and β-galactosidase).

Nucleic acid sequences disclosed herein can be operably linked to non-Thraustochytrid promoter sequences. Examples may include promoters found in bacteria, such as Lac, pBAD, Tet, yeast promoters such as TDH3, ADH1, TPI1, ACT1, GPD, PGI, GAL1, GAL7 and GAL10. Eukaryotic viral promoters such as SV40, or additionally, promoter elements may be isolated from microalgae, for example, Rbcs2, PsaD, Nac2. PsbA, PspD, FcpA and Hsp70A. Many regulatory control elements, including various promoters, are active in diverse species. Thus, the gene promoters disclosed herein may be used to drive expression of fatty acid biosynthesis genes from or in any of the host cells described herein. Likewise, specific and constitutively actively promoters isolated from host cells described herein may be used to drive expression of any of the Thraustochytrid or *Thraustochytrium* genes disclosed herein.

As described herein, Thraustochytrid or *Thraustochytrium* gene promoters can be operably linked to heterologous nucleic acid sequences to drive expression of the sequences. Optionally, the gene promoters are operable coupled or linked to nucleic acid sequences within an expression cassette or gene expression vector. Optionally, the gene promoters are inserted (e.g. by homologous recombination) into an appropriate location within the genome of a host cell to drive expression of a PUFA biosynthesis gene within the host cell. Homologous recombination has been demonstrated previously in microalgae, for example, *Chlorella vulgaris* (Dawson, Burlingame et al. 1997) and *Nannochloropsis* sp., both demonstrate efficient homologous recombination (Kilian, Benemann et al. 2011). Optionally, operably coupling may be achieved through non-homologous recombination. Non-homologous recombination is common among microalgae and differs from homologous recombination in that integration into the host cell genomic DNA is independent of DNA sequence similarity. Non-homologous recombination offers the advantage of a range of gene expression properties within a transformed population of cells, allowing tailored and optimized gene expression. Non-homologous recombination in microalgae has been described previously in, for example, *Chlamydomonas reinhardtii* (Kindle 1990). *Volvox carteri* (Hallmann and Sumper 1994: Schiedlmeier, Schmitt et al. 1994). *Phaeodactylum tricornutum* (Apt, Grossman et al. 1996), *Thalassiosira pseudonana* (Poulsen, Chesley et al. 2006), which are incorporated by reference herein.

Optionally, both the gene promoter and the nucleic acid sequence are isolated from Thraustochytrids or *Thraustochytrium*. Optionally, the nucleic acid sequences encode PUFA biosynthesis peptides. Optionally, the Thraustochytrid or *Thraustochytrium* gene promoters and nucleic acid sequences to which they are operably coupled are transformed into a Thraustochytrid or *Thraustochytrium* host cell. The gene promoter and/or the nucleic acid sequences to which it is operably coupled or linked may be exogenous to a host cell. Expression of a Thraustochytrid or *Thraustochytrium* desaturase gene can be affected by placing the gene under the control of a heterologous promoter. Heterologous promoters cause the gene to be expressed differentially from its normal temporal or sequential expression patterns within PUFA biosynthesis pathways. Thus, one can optimize or coordinate expression of any PUFA biosynthesis polypeptide to manipulate carbon flow through the biosynthesis pathways and direct the carbon to a specified end product (e.g., ARA, DHA or EPA).

Thraustochytrid or *Thraustochytrium* gene promoters may be operably linked to isolated Thraustochytrid or *Thraustochytrium* PUFA biosynthetic pathway genes. PUFA biosynthesis gene promoters can be influenced by growth stage, culture conditions, and substrate availability. In general, each promoter and/or gene can function independently, allowing each to be removed or included using standard molecular biology techniques; thus providing for engineered Thraustochytrid or *Thraustochytrium* strains optimized for production of a particular PUFA or production of total fatty acid with optimized ranges of components. For example, engineered strains are provided that produce oil compositions that contain less than 25%, less than 20%, less than 15%, less than 10% and less than 5% long-chain PUFA components.

Optionally, a Δ12 desaturase promoter is used to drive expression of a Δ5 desaturase. Optionally, a Δ12 desaturase promoter is used to drive expression of fatty acid synthase (FAS), Δ5 elongase, Δ4 desaturase and polyketide PUFA synthase (PKS). Optionally, a Δ5 desaturase promoter is used to drive expression of a gene or gene cluster responsible for DHA production. For example, a Δ5 desaturase promoter is used to drive expression of fatty acid synthase (FAS), Δ5 elongase, Δ4 desaturase, Δ12 desaturase and polyketide PUFA synthase (PKS).

Optionally, genetic modification reduces expression of one or more PUFA biosynthesis polypeptides. This reduction in expression may be accomplished through any means known in the art, including reducing transcription, translation, activation or availability of desired PUFA polypeptides. For example, placing the gene under the control of heterologous promoters reduces expression of a Thraustochytrid or *Thraustochytrium* desaturase gene. As discussed herein, heterologous promoters cause the gene to be expressed differentially from its normal temporal or sequential expression patterns within PUFA biosynthesis pathways. When a genetic modification reduces expression of one or more PUFA biosynthesis peptides, the reduced expression may stop or slow carbon flow to undesired end products. For example, expression of a Thraustochytrid or *Thraustochytrium* desaturase gene is reduced to prevent or inhibit the synthesis of long-chain polyunsaturated fatty acids. Optionally, expression of a Thraustochytrid or *Thraustochytrium* Δ12 desaturase gene (e.g., SEQ ID NO.:70) is reduced to inhibit the synthesis of fatty acids with a carbon chain greater than 18 (C18) and a desaturation level greater than 1 (C18:1) in the standard elongation/desaturation pathway. The effect of this modification is a PUFA production profile in which C18:2 and C:22 PUFA are reduced. Such modifications may be useful for the production of biofuels where a low percentage of C18:2 and C:22 PUFA are desired.

Any of the genetic manipulations disclosed herein may also be combined with engineering of secondary effectors of PUFA synthesis. For example, regulatory genes such as genes for inductors, repressors, transcription factors, stabilizers, transporters or any gene that regulates expression of one or more genes of the PUFA biosynthesis pathway can be introduced into a host cell to affect PUFA synthesis in a predetermined manner.

Any of the genetic modifications described herein may be combined with any other modification now known or later developed. For example, overexpression or reduced expression of a Thraustochytrid or *Thraustochytrium* desaturase gene (e.g., Δ12 desaturase) may be combined with modifications to the PKS pathway or thioesterases. Non-limiting examples of additional genetic modifications include: acyl-CoA dehydrogenase(s), acyl-ACP (acyl carrier protein) desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) or combinations thereof.

Molecular biology and DNA manipulation procedures can generally be performed according to Sambrook et al. or Ausubel et al. (Sambrook J. Fritsch E F, Maniatis T (eds). 1989. Molecular Cloning. A Laboratory Manual. Cold Spring Harbor Laboratory Press: New York; Ausubel F M, Brent R, Kingston R E, Moore D D, Seidman J G, Smith J A, Struhl K (eds). 1998. Current Protocols in Molecular Biology. Wiley: New York).

Mutagenesis

The present disclosure provides agents and/or methods for mutagenizing microorganisms, as well as strains and/or cells produced by mutagenesis. For example, as described herein, it has been discovered that antibiotics such as bleomycins, phleomycins, and/or tallysomycins can be used to mutagenize microorganisms. The availability of such effective mutagens for microorganisms such as Thraustochytrids (e.g., *Thraustochytrium*) allows for the development of strains having desired features. In particular, the present disclosure demonstrates that zeocin (phleomycin D1) can be used to mutagenize microorganisms such as Thraustochytrids (e.g., *Thraustochytrium*).

The antibiotic zeocin is a basic, water soluble, copper-chelated glycopeptide from culture broth of a *Streptomyces verticillus* mutant (InvivoGen, San Diego, Calif. USA). Zeocin is a member of the phleomycin group of antibiotics, which are glycopeptides that have been widely used as potent antitumor agents against lymphomas, head and neck cancers and testicular cancer (Umezawa et al., New antibiotics, bleomycin A and B, *Journal of Antibiot.*, (1966) 19:200-209; Sikic et al., *Bleomycin Chemotherapy*, Academic Press, Orlando, Fla., (1985)). It is generally believed that the molecular mode of action of these antibiotics is related to their ability to bind DNA by intercalation of their planar bithiazole-containing moiety and cleave DNA resulting single strand break or double strand break that causes cell death (Povirk et al., *Nucleic Acids Research*, (1977) 4:3573-3580). Because of their toxicity toward a broad spectrum of cell types, this group of antibiotics is employed as drugs for positive selection. The present disclosure encompasses the discovery that zeocin is a useful mutagen for industrial microbial strain improvement. Additionally, it is shown herein that at certain concentrations at which zeocin kills most treated cells, surviving cells have increased mutation frequency. The ability to produce cells with increased mutation frequency allows for easier selection and isolation of mutagenized strains.

Provided are also systems and/or methods for mutagenizing Thraustochytrid cells. Optionally, provided are systems and methods for mutagenizing cells selected from the group consisting of *Thraustochytrium* cells, *Ulkenia* cells, *Schizochytrium* cells, *Aurantiochytrium* cells, *Aplanochytrium* cells, *Botryochytrium* cells, *Japanochytrium* cells, *Oblongichytrium* cells, *Parietichytrium* cells. *Sicyoidochytrium* cells, fungi of *Mortierella*, heterotrophically grown algae (e.g., a species of the genus *Crypthecodinium*). Optionally, provided are systems and/or reagents for mutagenesis of ONC-T18.

Optionally, a microorganism is mutagenized by application to a suitable solid medium (e.g., agar medium) comprising a relevant antibiotic (e.g., zeocin), wherein the antibiotic is present at a concentration below the concentration at which it exhibits complete or nearly complete inhibition of cell growth. Microorganisms used for these methods do not carry a zeocin resistance gene (e.g., Sh ble). Optionally, the antibiotic (e.g., zeocin) is used for mutagenesis at a concentration below the concentration at which it kills at least 85%, 90%, 95%, or 100% of cells of that type. Optionally, antibiotic (e.g., zeocin) is used for mutagenesis at a concentration above the concentration at which it kills 30%, 40%, 50%, or 60% of cells of that type. Optionally, antibiotic (e.g., zeocin) is used for mutation. Optionally, antibiotic is used at a concentration and under conditions at which it increases mutation frequency in cells exposed to it above that of spontaneous mutation observed for the cells. Optionally, antibiotic is used at a concentration and under conditions at which it inhibits growth or kills 60-80% of cells of that type.

ONC-T18 cells are highly sensitive to zeocin at a concentration of 100 µg/mL (see Example 3). Thus, zeocin can be used for mutagenesis at a concentration below 100 g/mL (e.g., at 90, 85, 80, 75, 70, 65, 60, 55, 50, 45, 40, 35, or 30 g/mL). Optionally, zeocin is used for mutagenesis at a concentration of about 50 g/mL. Optionally, medium in which cells are mutagenized with zeocin has a salt concentration of 18 g/L or less. Mutagenized cells may show morphology changes relative to cells grown at lower concentrations or in the absence of the mutagen. By way of example, mutagenized cells can show altered growth rate, color, and/or total or specific lipid amount.

Optionally, cells (e.g., Thraustochytrid or *Thraustochytrium* cells) are spread onto a solid medium containing antibiotic (e.g., zeocin) at a concentration of 1-1000 µg/mL. Optionally, cells are spread onto a solid medium comprising antibiotic (e.g., zeocin) at a concentration of about 100 µg/mL, 200 µg/mL, 300 µg/mL, 400 µg/mL, 500 µg/mL, 1 g/mL, 5 g/mL or more. Colonies emerging under these conditions after at least 4 days (e.g., 5, 6, 7, 8, 9, or 10 days) are isolated. Isolated cells can be tested for a desired feature resulting from mutagenesis. For example, cells from mutagenized colonies can be compared to reference cells (e.g., parental cells) to detect a change in a feature, such as biomass and/or lipid productivity.

Provided are microorganisms (e.g., Thraustochytrid or *Thraustochytrium* isolated by antibiotic (e.g., zeocin) mutagenesis. Optionally, a microbial strain (e.g., a *Thraustochytrium* strain) isolated by antibiotic (e.g., zeocin) mutagenesis produces at least 10%, 20%, 30%, 40%, 50% more total lipids than a parental or reference strain. Optionally, a Thraustochytrid strain isolated by zeocin mutagenesis produces at least 10%, 20%, 30%, 40%, 50% more ALA, ARA, DHA, DPA, EPA, GLA, and/or LA, or a combination thereof, than a parental strain. Optionally, a Thraustochytrid strain isolated by zeocin mutagenesis produces at least 10%, 20%, 30%, 40%, 50% more ARA, DHA, EPA, or a combination thereof, than a parental strain.

One particular strain of ONC-T18 isolated by zeocin mutagenesis produces about 36% more DHA than its parental strain.

Selection

Provided are methods for selecting microorganisms such as Thraustochytrids (e.g., *Thraustochytrium*). Such methods may be used in conjunction with and/or as a part of, for example, transformation methods as described herein in order genetically manipulate the microorganisms.

Generally, in the provided selection methods, a selection agent is used to favor growth of microorganisms bearing a selectable marker suitable for the selection agent over microorganisms that do not bear the selectable marker. Typically the selection agent inhibits, reduces, and/or slows growth of microorganisms that do not bear the selection marker. During selection, microorganisms are typically cultivated in growth medium as described herein, except that the growth medium is supplemented with the selection agent ("selection medium").

Optionally, microorganisms are cultivated in selection medium for a period of time sufficient to allow the culture to become comprised predominantly of cells that bear the selection marker. That is, during the period of growth in selection medium, cells that do not bear the selection marker do not grow and are overtaken in the culture by cells that do bear the selection marker. Optionally, microorganisms are cultivated in selection medium for between 1 to 15 days, 1 to 12 days, or 1 to 9 days. Optionally, microorganisms are cultivated in selection medium for a period of time longer than 1, 2, 3, 4, 5, 6, 7, 8, 9, or 10 days and/or shorter than 50, 45, 40, 35, 30, 25, 20, 15, 14, 13, 12, 11, or 10 days. Optionally, microorganisms are cultivated in selection medium for between about 3 and about 5 days, or between about 5 and about 10 days. Optionally, microorganisms are kept in selection medium after selection. Optionally, microorganisms are transferred to a medium without a selection agent for at least a period of time. e.g., during a recovery phase.

Optionally, the selectable marker is removed after the cells have been grown for a period of time in selection medium. Removal of the selectable marker may be performed immediately after the period of time the cells are grown in selection medium, after a "recovery period" during which the cells are grown in medium without a selection agent, or later (e.g., after the cells have been stored for a period of time, after the cells have been frozen and then thawed). Methods of genetically engineering cells such that introduced genetic elements (e.g., selectable markers) can later be removed are well known in the art. Such methods typically employ the use of recombinase polypeptides, which typically recognize particular nucleotide sequences ("recognition sites" or "recognition sequences"). For example, a selectable marker can be engineered into a Thraustochytrid or *Thraustochytrium* cell with recognition sites for a particular recombinase flanking the selectable marker. When deletion of the selectable marker is desired, the cells can be exposed to an appropriate recombinase (that is, a recombinase that recognizes the recognition sites flanking the selectable marker), which perform a homologous recombination reaction on the recognition sites, resulting in deletion or inversion of the nucleic acid sequence between the recognition sites.

Optionally, the selection agent is or comprises an antibiotic and the selection marker is or comprises a resistance gene for the antibiotic.

Optionally, a combination of selection agents is used and/or a combination of selection markers is used.

Optionally, a microorganism undergoes selection by application to a suitable medium comprising zeocin, wherein the zeocin is present at a concentration above a threshold concentration.

The threshold concentration may correspond approximately to a concentration at which zeocin exhibits complete or nearly complete inhibition of growth of cells that do not contain a zeocin resistance gene. Optionally, the threshold concentration is at or above the concentration at which zeocin kills at least 85%/o, 90%, or 100% of cells of that type that do not contain a zeocin resistance gene. Optionally, the threshold concentration may vary depending on culture conditions (e.g., salt concentration, type of culture medium, culture temperature, liquid or solid culture, etc.). Optionally, the threshold concentration is above 50 µg/mL. Optionally, the threshold concentration is at or above 60, 65, 70, 75, 80, 85, 90, 95, 100, 110, 120, 130, 140, 150, 160, 170, 180, 190, or 200 µg/mL. Optionally, the threshold concentration is at or about 100 µg/mL.

The antibiotic resistance gene can be or can include a phleomycin, bleomycin and/or tallysomycin resistance gene. Optionally, the antibiotic resistance gene is or comprises a gene (e.g., the ble gene) from *S. hidustanus*.

The salt concentration of the medium used during selection can differ from a salt concentration typically used in medium used for cultivation of the microorganism without selection. Optionally, the salt concentration in the medium used during selection is approximately the same as a salt concentration typically used in medium used for cultivation of the microorganism without selection. Optionally, the salt concentration is between about 10 g/L and about 40 g/L, between about 15 g/L and about 35 g/L, and/or between about 18 g/L and about 35 g/L. Optionally, the salt concentration is about 18 g/L. Optionally, the salt concentration is about 35 g/L.

Optionally, a zeocin concentration at or above 30 µg/mL is used when the culture medium has a salt concentration of about 18 g/L. Optionally, a zeocin concentration at or above 100 µg/mL is used when the culture medium has a salt concentration of about 35 g/L.

The suitable medium used during selection can be a solid medium. When a solid medium is used, microorganisms may be spread out (e.g., using an inoculation loop, a cell spreader, beads, or other mechanisms for spreading) on a planar surface of the solid medium such that single-cell colonies may be allowed to grow.

Single-cell colonies may be picked and cultivated to obtain larger and/or sufficient quantities for analysis (e.g., transgene analysis, analysis of growth characteristics, analysis of lipid profile, etc.) and/or production of compounds as described herein. Alternatively or additionally, single-cell colonies and/or cultures obtained therefrom may be stored (e.g., by freezing in an appropriate freezing medium) for later use.

Transformation

Provided are methods for transforming Thraustochytrid (e.g., *Thraustochytrium*) cells. Such methods generally include steps of providing a competent Thraustochytrid cell; delivering a heterologous (e.g., recombinant or engineered) nucleic acid into the competent cell, wherein the recombinant nucleic acid comprises a selectable marker; and culturing the competent cell in a culturing medium containing a selection agent that reduces growth of cells without the selectable marker.

Thraustochytrid cells competent for genetic transformation are provided by the present disclosure. Optionally, competent cells are of the strain ONC-T18. Such competent cells may be provided by any of a variety of methods, a non-limiting example of which is described in greater detail in Example 5. In methods of preparing competent cells such as the one described in Example 5, competent cells are obtained by inoculating solid or liquid medium with inoculum from a desired strain of Thraustochytrid or *Thraustochytrium* and allowing the cells to grow, supplying fresh culture media as necessary. Preparation of competent cells typically involves one or more phases of growth in a liquid medium followed by centrifugation of the cells and resuspension of the cells in sterile liquid to a desired cell density. Competent cells may be prepared fresh as needed for experiments, and/or they may be prepared and then stored (e.g., frozen) for future use.

Optionally, cells are grown in flasks (e.g., of volumes of 250 mL, 500 mL, or 1 L).

Optionally, cells are grown in a nitrogen-source-rich medium. By way of example, cells are grown in a medium with high levels of peptone. Optionally, cells are grown in a medium comprising at least 5-25 g/L of peptone (or other nitrogen source).

Optionally, cells are grown in high levels of dissolved oxygen. Optionally, cells are agitated during growth, e.g., at about 100 to about 500, or about 125 to about 400, or at about 150 to about 300 rpm.

Optionally, cells are mutagenized during vegetative propagation or during vigorous vegetative propagation. Optionally, cells are not mutagenized during the zoospore stages.

The heterologous (e.g., recombinant, synthesized (whether chemically or biologically), and/or engineered in that its nucleic acid sequence was selected by the hand of man) nucleic acid may be a DNA, an RNA, an RNA:DNA hybrid, or any suitable derivative thereof. Optionally, the recombinant nucleic acid is delivered as part of a vector. Any of a variety of vectors may be suitable for use in accordance with methods of the disclosure including, but not limited to, plasmids, cosmids. BACs (bacterial artificial chromosomes), YACs (yeast artificial chromosomes), and viral vectors. The heterologous DNA may be or may include chemically synthesized polynucleotides. Optionally, the heterologous DNA may comprise enzymatically synthesized polynucleotides. Optionally, heterologous DNA is or comprises a polymerase chain reaction ("PCR") product.

Recombinant or engineered nucleic acids typically comprise a selection marker for use in selection methods as described herein. Typically, the selection marker comprises a gene expression cassette that allows expression of a gene product that, when present in a cell, allows growth of the cell in selection medium containing a selection agent at or above a threshold concentration as described herein. For example, when an antibiotic is used as a selection agent, the selection marker can include a gene expression cassette for expressing a corresponding antibiotic resistance gene.

Recombinant or engineered nucleic acids may further include one or more additional gene expression cassettes for expression one or more desirable gene products. Representative one or more desirable gene products may include, for example, a polypeptide that has commercial value, and/or may be a polypeptide (e.g., an enzyme polypeptide or other biosynthetic pathway component) that is important for the synthesis of one or more downstream products (e.g., compounds such as PUFA) that have commercial value. Alternatively or additionally, a desirable gene product may confer certain desirable characteristics to the microorganism (e.g., suitability for growth in a particular set of conditions, suitability for growth in large-scale production methods, etc.). Alternatively or additionally, a desirable gene product may be one that allows labeling of cells that have been transformed. Alternatively or additionally, cells are engineered to produce elevated levels of one or more biofuels, drugs, vaccines, antibodies, lipids, resolvins, neuroprotectins, pharmaceutical compounds, polypeptides, etc.

Elements that are typically contained in a gene expression cassette have been described herein, e.g., a promoter or other gene regulatory element that drives expression of the gene, the gene to be expressed, and a terminator sequence that works in the microorganism to be transformed. The gene to be expressed may be referred to as a "transgene." The transgene may be a heterologous gene, e.g., one that is not normally present in the microorganism. Either or both the selection marker and the additional gene expression cassette may include such a heterologous gene.

Accordingly, vectors suitable for use in accordance with methods of the disclosure include gene expression vectors.

Optionally, one recombinant nucleic acid is delivered into a microorganism. For example, a microorganism may be transformed with one plasmid construct comprising a recombinant nucleic acid.

Optionally, more than one recombinant nucleic acid is delivered into a microorganism. For example, a combination of plasmid constructs (each plasmid construct comprising a recombinant nucleic acid) may be delivered into a microorganism. Optionally, a combination of selection agents and selection markers is used to select for presence of the combination of desired recombinant nucleic acids.

Any of a variety of methods for introducing genetic material (e.g., genetic material comprising a recombinant nucleic acid) into a cell may be suitable for use in accordance with transformation methods of the present disclosure. Introduction methods include, but are not limited to, calcium phosphate precipitation; $Ca^{2+}$ treatment; fusion of recipient cells with bacterial protoplasts containing the recombinant nucleic acid; treatment of the recipient cells with liposomes containing the recombinant nucleic acid; DEAE dextran; fusion using polyethylene glycol (PEG); electroporation; magnetoporation; biolistic delivery; retroviral infection; lipofection; and micro-injection of DNA directly into cells.

A biolistic delivery method (also known as "gene cannon," "particle bombardment," and "micro-projectile" method) can be used. A biolistic device accelerates particles coated with the recombinant nucleic acid to speeds sufficient to penetrate cell membranes (and/or cell walls, if present). Optionally, the particles comprise or consist of gold particles. Methods for biolistic delivery of genetic material are known in the art, and equipment and reagents for performing such biolistic deliveries are commercially available. See, e.g., Sanford et al., Part. Sci. Technol. 5:27 (1987), Sanford, J. C., Trends Biotech. 6:299 (1988), Sanford, J. C., Physiol. Plant 79:206 (1990), and Klein et al., Biotechnology 10:268 (1992), the entire contents of each of which is incorporated herein by reference.

Optionally, nucleic acids are delivered using a method such as *Agrobacterium*-mediated transformation, protoplast transformation, etc, as would be known and understood by those of ordinary skill in the art.

After delivery of a heterologous (e.g., recombinant or engineered) nucleic acid, cells are cultured in a medium containing a selection agent that reduces growth of cells without the selectable marker, as described herein in the "Selection" section. Cells that are selected (e.g., exhibit presence of the selectable marker and therefore of the recombinant nucleic acid) can be stored, analyzed, and/or grown in larger quantities as desired.

Optionally, transformed cells are subject to one or more analyses to confirm presence of the recombinant nucleic acid. For example, a PCR analysis may be used to confirm presence of a genetic element, e.g., a transgene and/or a selectable marker, that is part of the recombinant nucleic acid.

Engineered Strains

The present disclosure provides, inter alia, genes, regulatory sequences, nucleic acid constructs, transformation methods, methods of mutagenesis, and genetic selection methods that enable manipulation of certain microorganisms such as Thraustochytrids. The compositions and methods provided herein can be used to engineer microorganisms (e.g., Thraustochytrids) for any of a number of applications. As noted herein, genes, regulatory sequences, nucleic acid constructs and selectable markers provided herein can be used to express any polypeptide of interest in an organism in which the sequences and/or selectable markers are operable (e.g., in Thraustochytrids). Optionally, a polypeptide from a different organism is expressed. Optionally, a polypeptide from the host cell is expressed (e.g., overexpressed).

Microorganisms can be engineered to have increased production of a compound of interest. Optionally, microorganisms are engineered to have increased production of a fatty acid, an antioxidant, resolvins and/or protectins. Alternatively or additionally, cells are engineered to produce elevated levels of one or more biofuels, drugs, vaccines, antibodies, lipids, resolvins, neuroprotectins, pharmaceutical compounds, polypeptides, etc.

The present disclosure provides Thraustochytrid microorganisms (e.g., *Thraustochytrium*) that are engineered to have tailored PUFA production profiles. That is, provided are engineered Thraustochytrid cells including at least one PUFA increasing modification, and/or at least one PUFA decreasing modification, combinations thereof, and PUFA compositions with specific ranges of particular fatty acids. Optionally, such microorganisms are engineered to have altered (e.g., increased or decreased) expression of at least one PUFA biosynthesis polypeptide.

Figure 1:
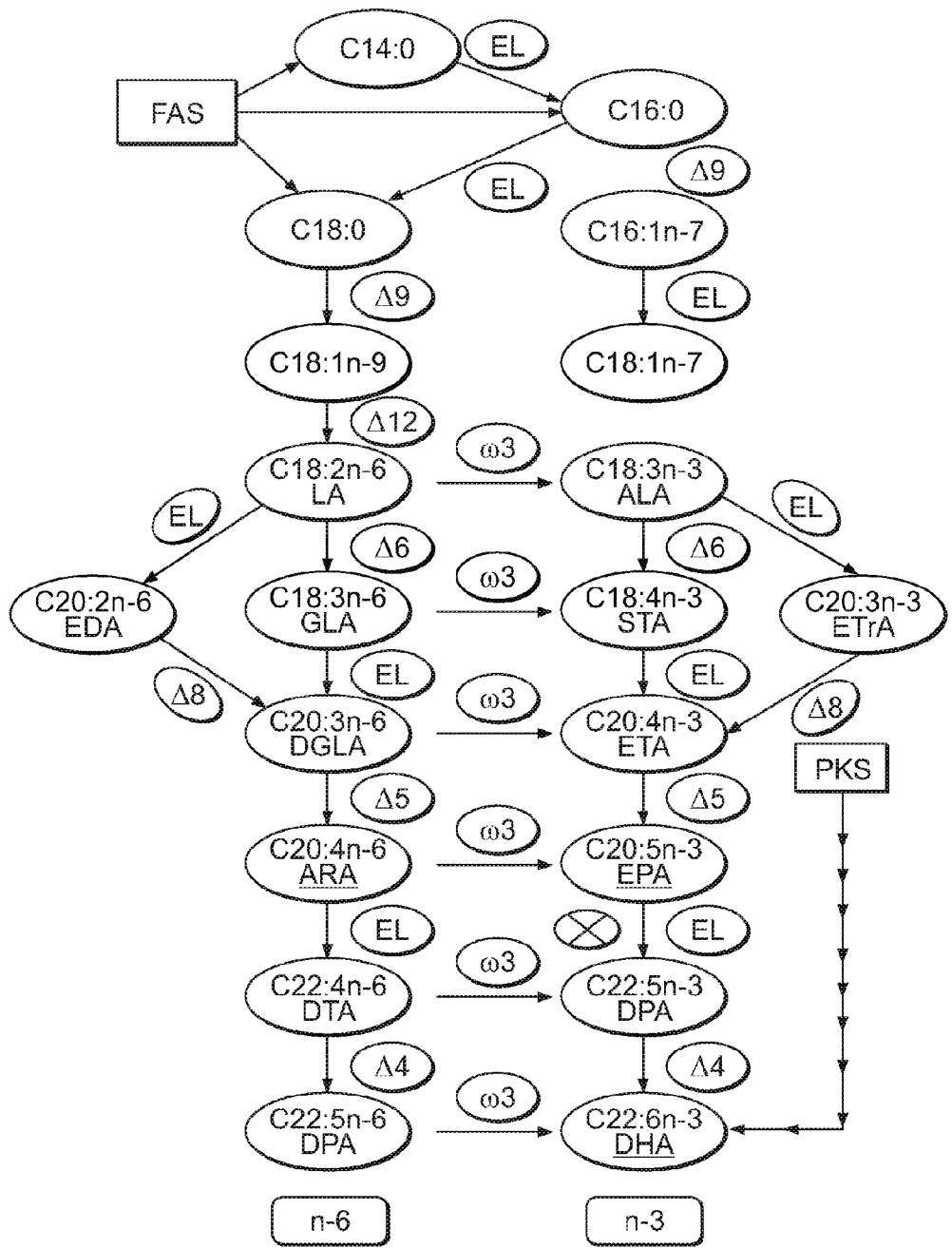
FIG. 1 shows a representation of the biosynthetic pathways of PUFA in *Thraustochytrium* sp. ONC-T18 ("ONC-T18", ATCC accession no.: PTA-6245; International Patent Application No. PCT/IB2006/003977, the entire contents of which are herein incorporated by reference). FAS, fatty acid synthase; EL, elongase; Δ12, Δ12 desaturase; Δ9, Δ9 desaturase; Δ8, Δ8 desaturase; Δ6, Δ6 desaturase; Δ5, Δ5 desaturase; Δ4, Δ4 desaturase; ω3, omega-3 desaturase; C14:0, myristic acid; C16:0, palmitic acid; C16:1n-7, palmitoleic acid; C18:0, stearic acid; C18:1n-7, cis-vaccenic acid; C18:1n-9, oleic acid; C18:2n-6 (LA), linoleic acid; C18:3n-3 (ALA), ω-linolenic acid; C18:3n-6 (GLA), γ-linolenic acid; C18:4n-3 (STA), stearidonic acid; C20:2n-6 (EDA), eicosadienoic acid; C20:3n-6 (DGLA), dihomo-γ-linolenic acid; C20:4n-3 (ETA), eicosatetraenoic acid; C20:3n-3 (ETE), eicosatetraenoic acid; C20:4n-6 (ARA), arachidonic acid; C20:5n-3 (EPA), eicosapentaenoic acid; C22:4n-6 (DTA), docosatetraenoic acid; C22:5n-3 (DPA), docosapentaenoic acid; C22:5n-6, docosapentaenoic acid; C22:6n-3 (DHA), docosahexaenoic acid; and PKS, polyketide PUFA synthase, n-6 denotes the omega-6 PUFA biosynthetic pathway and n-3 denotes the omega-3 PUFA biosynthetic pathway.

As depicted in FIG. 1, PUFA biosynthesis in ONC-T18 involves generation of fatty acids such as myristic acid (C14:0) and stearic acid (C18:0) by the fatty acid synthase (FAS) enzyme complex, followed by a series of enzymatic reactions on such fatty acids. Each of these reactions is typically catalyzed by either a desaturase (which removes hydrogen atoms to create a carbon-carbon double bond) or an elongase (which lengthen fatty acids by adding two carbon atoms to the fatty acid's carboxylic acid end). The polyketide PUFA synthase (PKS) complex also generates DHA in ONC-T18. PUFA biosynthesis in ONC-T18 appears to have at least two intersecting biosynthetic pathways: the omega-6 and the omega-3 PUFA biosynthetic pathways. Conversion of omega-6 fatty acids to omega-3 fatty acids can be catalyzed by omega-3 desaturase. Thus, as depicted in FIG. 1, a variety of fatty acids are produced at various points in the pathway. Any and all combinations of these points may be manipulated through the genes, regulatory sequences and selectable markers provided herein.

Expression of one or more genes encoding enzyme polypeptides in the pathway can be regulated to increase production of particular PUFA and/or other fatty acids as desired. For example, expression of the FAS gene may be downregulated to increase PUFA production. Downregulation of expression of the Δ5 elongase, Δ4 desaturase, Δ12 desaturase and/or any of the PKS genes may increase EPA production and/or PUFA production. Downregulation of expression of any one of the PKS genes may increase ARA production. Upregulation of expression of any of the PKS genes may increase DHA production. Upregulation of expression the Δ5 desaturase gene may increase ARA and EPA production. Upregulation of the Δ12 desaturase gene may reduce C12-C18 saturated or mono-unsaturated fatty acids, (e.g., palmitic acid, stearic acid, and oleic acid), thereby increasing total fat. Correspondingly, reducing or eliminating expression would increase the concentration of C12-C18 saturated and mono-unsaturated fatty acids, while dramatically decreasing levels of C18-C22 multi-saturated fatty acids (e.g., linoleic acid, arachidonic acid, and eicosapentaenoic acid) and downstream n-3 and n-6 PUFAs.

Optionally, expression of one or more genes encoding enzyme polypeptides in the pathway is regulated to produce biofuels. For example, downregulation of expression of any of the PKS, Δ9 desaturase, Δ12 desaturase, elongase, and omega-3 desaturase genes, and/or upregulation of FAS gene expression may increase production of short chain lipids for use as biofuel stocks. If a PUFA production profile optimized for biofuel is desired, then one in the art could use the polynucleotides, methods and host cells disclosed herein to operably link a heterologous promoter from a Δ12 desaturase gene to drive expression of an endogenous or exogenous Δ5 desaturase, thereby tailoring PUFA production to ARA and EPA. Optionally, a PUFA production profile (comprising all fatty acid biosynthesis pathways and the resulting products) may be tailored to produce predetermined compositions comprising at least two fatty acid products within a specified range or ranges optimized for a particular utility (e.g. biofuel production). For example, it is generally desirable to minimize long-chain polyunsaturated fatty acids ("LCPUFA"; e.g., DHA) levels in biofuels. Through manipulation of the PUFA biosynthesis polypeptides and their corresponding nucleic acid sequences disclosed herein, optionally in conjunction with particularized culture conditions, it is possible to produce a fatty acid oil composition in which LCPUFA levels are less than approximately 25% of the total fatty acids content. Optionally, fatty acid oil compositions are produced with LCPUFA levels less than approximately 20%, 15%, 10%, 5% and 1% of total fatty acid content. Optionally, LCPUFA have at least about 20, at least about 22, at least about 24, at least about 26, at least about 28 or at least about 30 carbon atoms. Optionally, the LCPUFA are docosatetraenoic acid, docosapentaenoic acid, and/or docosahexaenoic acid.

Alteration (e.g., downregulation or upregulation) of gene expression of a pathway component can be accomplished by generating a gene knockout by, e.g., homologous or non-homologous recombination. Typically, a linearized DNA construct is introduced into cells using any of a variety of techniques including, but not limited to, biolistic projectile DNA delivery. Optionally, the frequency of homologous recombination in ONC-T18 is greater than about 30%, 40%, 50%, or more.

Optionally, alteration (e.g., downregulation or upregulation) of gene expression of a pathway component is accomplished by mutagenesis of one or more gene targets. Mutagenesis can be performed by chemical treatment (e.g., neomycin treatment), microwave or UV irradiation, site-directed mutagenesis, error-prone PCR gene replacement (e.g., by homologous recombination), or other means known to those of skill in the art.

Engineered microorganisms provided herein can produce a lipid fraction comprising n-3 DHA, EPA and n-6 DPA at greater than about 4.0 g/L of medium. Optionally, microorganisms provided herein can produce a lipid composition comprising n-3 DHA, EPA and n-6 DPA at greater than about 20.0 g/L of medium. Optionally, microorganisms can produce a lipid composition comprising n-3 DHA, EPA and n-6 DPA at greater than about 14.0 g/L of medium. Optionally, microorganisms can produce from about 1.5 g/L to about 5.0 g/L (e.g., about 4.6 g/L) of the n-3 DHA, from about 0.5 g/L to about 1.5 g/L (e.g., about 0.22 g/L) of the n-3 EPA, and from about 0.5 g/L to about 1.5 g/L of the n-6 DPA. Optionally, engineered microorganisms provided herein can produce a lipid composition comprising n-3 DHA, EPA, n-6 DPA, or ARA at a yield up to about 120 g/L, which corresponds to more than about 75% of total lipids. Optionally, engineered microorganisms provided herein can produce a lipid composition comprising short chain fatty acids (typically C12-C18 fatty acids) at a yield up to about 128 g/L, which corresponds to more than about 80% of total lipids. Furthermore, the microorganism can produce a lipid fraction comprising myristic, myristoleic, pentadecanoic, palmitic, palmitoleic, stearic oleic, linoleic, alpha-linolenic, gamma-linolenic, eicosadienoic, arachidonic, eicosapentaenoic, docosahexanoic, and docosapentaenoic acids greater than 300 mg/g or even 800 mg/g of cellular biomass. Optionally, the microorganism can also produce a fraction comprising between 44.3 and 57 mg/g myristic acid (equal to 1134.5 to 1458.1 mg/L), 0.5 to 0.65 mg/g myristoleic acid (equal to 13.3 to 16.63 mg/L), 33.5 to 34.6 mg/g, pentadecanoic acid (equal to 856.9 to 885.1 mg/L), 121.9 and 165.1 mg/g palmitic acid (equal to 3118.2 to 4923.3 mg/L), 7.9 to 28.5 mg/g palmitoleic acid (equal to 202.1 to 729 mg/L), 4.38 to 5.9 mg/g stearic acid (equal to 112 to 151 mg/L), 6.94 to 9.9 mg/g oleic acid (equal to 177.5 to 253.2 mg/L), 0.4 to 1.3 mg/g linoleic acid (equal to 11.26 to 33.3 mg/L), 0.5 to 1.0 mg/g eicosadienoic acid (equal to 12.8 to 25.6 mg/L), 0.4 to 0.5 mg/g arachidonic acid (equal to 10.2 to 13 mg/L), 75 to 100 mg/g docosahexanoic acid (equal to 1918 to 2560 mg/L), 1.9 to 6 mg/g eicosapentaenoic acid (equal to 48.6 to 153.5 mg/L) and 17.1 to 33.7 mg/g docosapentaenoic acid (equal to 437.4 to 862.1 mg/L), having a total fatty acid content within the cellular biomass of between 301 to 800 mg/g (equal to 7700 to 20,209 mg/L).

Fermentation and Production

The provided methods include or can be used in conjunction with steps of culturing a microorganism (e.g., a Thraustochytrid, e.g., a *Thraustochytrium* sp.). Cultivation methods for Thraustochytrids have been described, e.g., in U.S. Patent Publication US2009/0117194A1, the entire contents of which are herein incorporated by reference. Typically, microorganisms are grown in a growth medium (also known as "culture medium"). Any of a variety of media may be suitable for use in accordance with selection methods provided herein. Typically the medium supplies various nutritional components, including a carbon source and a nitrogen source, for the microorganism.

Microorganisms provided herein can be cultivated under conditions that increase biomass and/or production of a compound of interest. Thraustochytrids are typically cultured in saline media. For example, Thraustochytrids can be cultured in medium having a salt concentration between about 2.0-50.0 g/L. Optionally, Thraustochytrids are cultured in media having a salt concentration between about 2-35 g/L. Optionally, Thraustochytrids are cultured in a medium having a salt concentration between about 18-35 g/L. It has been found under certain circumstances that Thraustochytrids grow well in low salt conditions. Optionally, Thraustochytrids are cultured in a medium having a salt concentration between about 5-20 g/L. Optionally. Thraustochytrids are cultured in a medium having a salt concentration between about 5-15 g/L. Culture media may or may not include NaCl. Culture media may or may not include addition of NaCl. Optionally, a medium contains artificial sea salt, e.g., INSTANT OCEAN™, Aquaria, Inc. Culture media may or may not include natural or artificial seawater. Optionally, a medium contains natural or artificial seawater, e.g., from about 2% to 100% seawater.

Chloride ions may cause corrosion of the fermenter or other downstream processing equipment. Optionally, the chloride concentration in culture media is reduced. Optionally, culture media include non-chloride-containing sodium salts (e.g., sodium sulfate) as a source of sodium. For example, a significant portion of the total sodium may be supplied by non-chloride salts such that less than about 100%, 75%, 50%, or 25% of the total sodium in culture media is supplied by sodium chloride.

Optionally, culture media have chloride concentrations of less than about 3 g/L, 500 mg/L, 250 mg/L, or 120 mg/L. Optionally, culture media have chloride concentrations of between about 60 mg/L and 120 mg/L.

Examples of non-chloride sodium salts suitable for use in accordance with the present disclosure include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein.

Media for Thraustochytrid culture can include any of a variety of carbon sources. Examples of carbon sources include fatty acids; lipids; glycerols triglycerols; carbohydrates such as glucose, starch, celluloses, hemicelluloses, fructose, dextrose, xylose, lactulose, galactose, maltotriose, maltose, lactose, glycogen, gelatin, starch (corn or wheat), acetate, m-inositol (derived from corn steep liquor), galacturonic acid (derived from pectin), L-fucose (derived from galactose), gentiobiose, glucosamine, alpha-D-glucose-1-phosphate (derived from glucose), cellobiose, dextrin, and alpha-cyclodextrin (derived from starch); sucrose (from molasses); polyols such as maltitol, erythritol, adonitol and oleic acids such as glycerol and tween 80; amino sugars such as N-acetyl-D-galactosamine. N-acetyl-D-glucosamine and N-acetyl-beta-D-mannosamine; and any kind of biomass or waste stream.

Optionally, media include carbon sources at a concentration of about 5 g/L to about 200 g/L. Optionally, media have a C:N (carbon to nitrogen ratio) ratio between about 1:1 and about 40:1. If two-phase cultures are used, media can have a C:N ratio of between about 1:1 to about 5:1 for the first phase, then about 1:1 to about 1:~0 (i.e., no or nearly no nitrogen) in the second phase.

Media for Thraustochytrids culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$), peptone, tryptone, yeast extract, malt extract, fish meal, sodium glutamate, soy extract, casamino acids and distiller grains. Concentrations of nitrogen sources in suitable media typically range between about 1 g/L and about 25 g/L.

Optionally, media include a phosphate, such as potassium phosphate or sodium phosphate. Inorganic salts and trace nutrients in media can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

For example, a suitable medium might be comprised of between about 11 and about 13 g/L (e.g., about 12 g/L) sodium sulfate, between about 0.45 and about 0.55 g/L (e.g., about 0.5 g/L) KCl, between about 1.8 and about 2.2 g/L (e.g., about 2 g/L) $MgSO_4.7H_2O$, between about 0.3 and about 0.4 g/L (e.g., about 0.35 g/L) Hodag K-60 antifoam, between about 0.60 and about 0.70 g/L (e.g. about 0.65 g/L) $K_2SO_4$, between about 0.9 and about 1.1 g/L (e.g., about 1.0 g/L) $KH_2PO_4$, between about 0.95 and about 1.1 g/L (e.g., about 1 g/L) $(NH_4)_2SO_4$, between about 0.15 and about 0.19 (e.g., about 0.17 g/L) $CaCl_2.H_2O$, between about 2 and about 10 g/L (e.g., about 4.5 g/L) 95 DE corn syrup (solids basis), between about 2.7 and about 3.3 mg/L (e.g., about 3 mg/mL) $MnCl_2.4H_2O$, between about 2.7 and about 3.3 mg/L (e.g., about 3 mg/mL) $ZnSO_4.7H_2O$, between about 0.035 and about 0.045 mg/L (e.g., about 0.04 mg/L) $CoCl_2.6H_2O$, between about 0 and about 0.045 mg/L (e.g., about 0.04 mg/L) $Na_2MoO_4.2H_2O$), between about 1.8 and about 2.2 mg/L (e.g., about 2 mg/L) $CuSO_4.5H_2O$, between about 1.8 and about 2.2 mg/L (e.g., about 2 mg/L) $NiSO_4.6H_2O$, between about 9 and about 11 mg/L (e.g., about 10 mg/L) $FeSO_4.7H_2O$, between about 4 and about 15 mg/L (e.g., about 9.5 mg/L) thiamine, between about 0.05 and about 0.25 mg/L (e.g., about 0.15 mg/L) vitamin $B_{12}$, between about 1.3 and about 5.1 (e.g., about 3.2 mg/L) calcium pantothenate, and about 28% $NH_4OH$ solution.

The pH of medium is adjusted to between 3.0 and 10.0 using acid or base where appropriate, and/or using the nitrogen source. Optionally, medium is adjusted to have a between pH 4.0 and 6.5. Medium can be sterilized.

Optionally, a medium used for culture of a microorganism is a liquid medium. Optionally, a medium used for culture of a microorganism is a solid medium. In addition to carbon and nitrogen sources as discussed herein, a solid medium may contain one or more components (e.g., agar or agarose) that provide structural support and/or allow the medium to be in solid form.

Cells can be cultivated for anywhere from 1-60 days. Optionally, cultivation is carried out for 14, 13, 12, 11, 10, 9, 8, 7, 6, 5, 4, 3, 2, or 1 days, or less. Optionally, cultivation is carried out at temperatures between 4 to 30° C., e.g., 18 to 28° C. Optionally, cultivation includes aeration-shaking culture, shaking culture, stationary culture, batch culture, semi-continuous culture, continuous culture, rolling batch culture, or wave culture, or the like. Cultivation can be carried out using a conventional agitation-fermenter, a bubble column fermenter (batch or continuous cultures), a wave fermenter, etc.

Optionally, cultures are aerated by shaking. Optionally, shaking ranges from 100 to 1000 rpm, e.g., from 350 to 600 rpm, from 1000 and 450 rpm. Optionally, cultures are aerated differently (e.g., using different shaking speeds) during biomass-producing phases as they are during lipid-producing phases. For example, cultures are aerated by shaking at a speed between about 150 and about 350 rpm during biomass phases and at a speed between about 30 and about 120 rpm during lipid-producing phases. Alternatively or additionally, shaking speeds may vary depending on the type of culture vessel (e.g., shape or size of flask).

Optionally, the level of dissolved oxygen (DO) is higher during the biomass production phase than it is during the lipid production phase, e.g., DO levels are reduced during the lipid production phase. Optionally, the level of dissolved oxygen is reduced below saturation; for example, the level of dissolved oxygen is reduced to a very low, or even undetectable, level.

It has been discovered that production of desirable lipids can be enhanced by culturing cells in according to methods that involve a shift of one or more culture conditions in order to obtain higher quantities of desirable compounds. Optionally, cells are cultured first under conditions that maximize biomass, followed by a shift of one or more culture conditions to conditions that favor lipid productivity. Conditions that are shifted can include oxygen concentration, C:N ratio, temperature, and combinations thereof. Optionally, a two-stage culture is performed in which a first stage favors biomass production (e.g., using conditions of high oxygen (e.g., generally or relative to the second stage), low C:N ratio, and ambient temperature), followed by a second stage that favors lipid production (e.g., in which oxygen is decreased, C:N ratio is increased, and temperature is decreased). That is, the provided methods may involve culturing cells under a first set of conditions that includes one or more conditions selected from the group consisting of a first oxygen concentration, a first C:N ratio, a first temperature, and combinations thereof. Culturing under this first set of conditions continues for a first time period, the duration of which may vary. At the end of the first time period (which is not necessarily a discrete point in time), one or more conditions are altered so that cells are cultured under a second set of conditions that includes one or more conditions selected from the group consisting of a second oxygen concentration, a second C:N ratio, a second temperature, and combinations thereof. Optionally, some conditions are changed at the end of the first time period, and some are maintained until the end of a second time period at which time one or more conditions may be changed again, and/or one or more conditions may be changed for a first time. Optionally, the first C:N ratio in within the range of about 2:1 to about 1:1; and the first temperature is within the range of about 10 to about 30° C. Optionally, the second C:N ratio is about 1:~0; and the second temperature is within the range of about 15 to about 30° C.

Optionally, a shift from a first condition to a second condition is performed and/or occurs gradually. Optionally, the shift from a first condition to a second condition is performed and/or occurs abruptly.

Optionally, oxygen concentration is shifted (e.g., decreased) during cultivation in a number of possible ways including, for example, by shifting the intensity of aeration.

Optionally, temperature is shifted (e.g., decreased) during cultivation by at least 2° C. Optionally, temperature is shifted by 3° C., 4° C., 5° C. 6° C., 7° C., 8° C., 9° C., or 10° C. Optionally, temperature is shifted from about 25° C. to about 20° C.

Cells' productivity for compounds of interest can be evaluated by any available method(s).

Products

PUFA and other compounds produced can be utilized in any of a variety of applications, for example exploiting their biological or nutritional properties. For example, compounds can be used in biofuels, pharmaceuticals, food supplements, animal feed additives, cosmetics, and the like. Compounds produced in accordance with the present disclosure may also be used as intermediates in the production of other compounds.

It will be appreciated that PUFA and/or other compounds produced by manipulated cells as described herein are incorporated into a final product (e.g., food or feed supplement, infant formula, pharmaceutical, etc.) in the context of the host cell. For example, host cells may be lyophilized, freeze dried, frozen, pasteurized, or otherwise inactivated, and then whole cells may be incorporated into or used as the final product. Optionally, a host cell (whether or not dried) may be further processed prior to incorporation in the product (e.g., via lysis, sonication, bead milling, pressure treatment, freeze-thawing, pulsed field electrophoresis (PFE) to separate components, and/or enzyme treatment, or combinations thereof; optionally, at least two or more such processes are utilized). Lysed cells can be extracted into an oil using an appropriate solvent and refined using well known processes. Optionally, a final product incorporates only a portion of the host cell (e.g., fractionated by size, solubility), separated from the whole. For example, lipids can be isolated from the host cells and are incorporated into or used as the final product. Lipids containing PUFA can be extracted using supercritical fluid extraction, or extraction with one or more solvents (e.g., acetone, chloroform, isopropanol, hexane, methylene chloride, or methanol). Optionally, lipids are concentrated by any of a variety of methods, such as urea complexation, column chromatography, and/or supercritical fluid fractionation. Techniques for concentration of solvent-extracted lipids include hydrolysis (e.g., using base, acid, or enzymatic hydrolysis), further extraction, acidification, crystallization, filtration, and combinations thereof (see, e.g., U.S. Pat. Pub. 2009/0117194, which is incorporated by reference herein in its entirety).

Optionally, one or more produced PUFA and/or other compounds are incorporated into a component of food or feed (e.g., a food supplement). Types of food products into which compounds can be incorporated according to the present disclosure are not particularly limited, and include beverages such as milk, water, sports drinks, energy drinks, teas, and juices; confections such as jellies and biscuits; fat-containing foods and beverages such as dairy products; processed food products such as soft rice (or porridge); infant formulae; breakfast cereals; or the like. Optionally, one or more produced compounds are incorporated into a dietary supplement, such as for example a multivitamin. Optionally, a PUFA compound produced according to the provided methods is included in a dietary supplement and may be directly incorporated into a component of food or feed (e.g., a food supplement).

Examples of feedstuffs into which compounds produced in accordance with the provided methods may be incorporated include, for instance, pet foods such as cat foods, dog foods and the like, feeds for aquarium fish, cultured fish or crustaceans, etc., feed for farm-raised animals (including livestock and fish or crustaceans raised in aquaculture). Food or feed material into which the compound(s) produced in accordance with the provided methods is incorporated is preferably palatable to the organism that is the intended recipient. This food or feed material may have any physical properties currently known for a food material (e.g., solid, liquid, soft).

Optionally, one or more produced compounds (e.g., PUFA) is incorporated into a pharmaceutical. Examples of such pharmaceuticals include, for instance, various types of tablets, capsules, drinkable agents, etc. Optionally, the pharmaceutical is suitable for topical application. Dosage forms are not particularly limited, and include capsules, oils, granula, granula subtilae, pulveres, tabellae, pilulae, trochisci, or the like. Oils and oil-filled capsules may provide additional advantages both because of their lack of ingredient decomposition during manufacturing, and because PUFA-containing lipid droplets may be readily incorporated into oil-based formulations.

Pharmaceuticals according to the present disclosure may be prepared according to techniques established in the art including, for example, the common procedure as described in the United States Pharmacopoeia, for example.

Compounds produced according to the present disclosure (whether isolated or in the context of cells) may be incorporated into products as described herein by combinations with any of a variety of agents. For instance, such compounds may be combined with one or more binders or fillers. Optionally, products will include one or more chelating agents, pigments, salts, surfactants, moisturizers, viscosity modifiers, thickeners, emollients, fragrances, preservatives, etc., and combinations thereof.

Antibodies

Antibodies and antibody polypeptides binding to the isolated Thraustochytrid polypeptides disclosed herein are also provided. Antibody polypeptides that specifically bind to the isolated Thraustochytrid polypeptides, may be generated by methods well known to those in the art. For example, isolated polypeptides or fragments thereof may be used as antigens to induce antibody production in various hosts such as goats, rabbits, rats, mice, etc. The hosts may be immunized by injection with any portion or fragment that possesses immunogenic properties. Depending on the host species, various adjuvants may be used to increase the immunological response. Such adjuvants include, but are not limited to, Freund's, mineral gels such as alumina hydroxide, and surface-active substances such as lysolecithin, pluronic polyols, polyanions, peptides, oil emulsions, keyhole limpet hemocyanin, and dinitrophenol.

To generate polyclonal antibodies, isolated polypeptides may be conjugated to a conventional carrier in order to increase its immunogenicity, and an antiserum to the isolated polypeptide-carrier conjugate raised. Coupling of a peptide to a carrier protein and immunizations may be performed as described in Dymecki et al., 1992, J. Biol. Chem., 267:4815. The serum can be titered against isolate polypeptide antigen by methods known to those of skill in the art (e.g., ELISA or alternatively by dot or spot blotting (Boersma & Van Leeuwen, 1994, J. Neurosci. Methods, 51:317)). A useful serum will react strongly with the isolated polypeptide by ELISA, for example, following the procedures of Green et al., 1982, Cell, 28:477.

Techniques for preparing monoclonal antibodies are well known, and are described, for example, by Amheiter et al., 1981, Nature. 294:278. Monoclonal antibodies are typically obtained from hybridoma tissue cultures or from ascites fluid obtained from animals into which the hybridoma tissue was introduced. Monoclonal antibody-producing hybridomas (or polyclonal sera) can be screened for antibody binding to isolated peptides according to methods known in the art.

The disclosure will be more fully understood by reference to the following examples. They should not, however, be construed as limiting the scope of the disclosure. All literature citations are incorporated by reference.

EXAMPLES

Example 1: Isolation and Identification of Genes, Promoter and Terminator Sequences This example describes identification and isolation of certain exemplary gene expression promoter and terminator nucleic acid sequences from ONC-T18.

The applicant has largely sequenced the genome of ONC-T18 using both shotgun sequencing and pyrosequencing (GS-20; 454) techniques. Among other things, the present disclosure provides analysis of such sequence information, for example utilizing publicly available EST (expressed sequence tag) collection information (Huang et al., 2008), the functional annotation of and/or bioinformatics software (e.g., Kodon package available from Applied Maths and/or one or more algorithms such as BLAST). To provide tools for expression of homologous and heterologous genes (e.g., genes involved in lipid and fatty acid biosynthesis within Thraustochytrid microbes), house-keeping tubulin gene promoters and terminators and desaturase and elongase genes and promoters were cloned from genomic DNA of *Thraustochytrium* sp. ONC-T18 using polymerase chain reaction (PCR) techniques.

The ONC-T18 strain was grow in supplemented seawater medium. DNA was extracted using a modified FastPrep (MP Biomedicals) protocol and sent to The Centre for Applied Genomics (TCAG, The Hospital for Sick Children, Toronto) for one plate of 454 sequencing and one lane of Illumina 2.5 kb mate-pair sequencing (76 base reads). RNA was extracted from cells sampled during the rapid growth phase of the cell culture and during the high lipid production through the RNeasy procedure (Qiagen). Total RNA was shipped to TCAG for RNA-Seq analysis of one Illumina lane (76 base reads) for each condition.

Bioinformatic analyses were carried out on the IMB Research Informatics servers using open source software. Genome assembly was done with Mira (Chevreux et al., 1999) and potential scaffolds were generated with Bambus (Pop et al., 2004). Genome annotation was carried out with MAKER (Cantarel et al., 2008), using gene models from Snap (Korf, 2004) and Augustus (Stanke and Waack, 2003). RNA encoding genes were identified by Infernal (Eddy, 2006) analysis of the Rfam database (Griffiths-Jones et al., 2003). PASA and Inchworm (Haas et al., 2003) were used to identify 5' and 3' untranslated regions. Protein encoding genes were analyzed with AutoFact (Koski et al., 2005), which employs Blast and rpsblast (Altschul et al., 1990) to query the non-redundant, uniref90, Kegg (Ogata et al., 1999), COG (Tatusov et al., 2003) and pfam (Finn et al., 2008) databases. Analysis of RNA-Seq data used Tophat (Trapnell et al., 2009) and Cufflinks (Trapnell et al., 2010) to map reads to the draft genome, estimate transcript abundance and determine differential expression. Custom Perl scripts were used to reformat, assemble and analyze data.

The ONC-T18 draft genome was assembled from one plate of 454 reads (1,131,145 reads, 302 Mb total), one lane of Illumina mate-pair sequences (21,570,704 reads, 1.47 Gb total) and Sanger sequences (34,261 reads, 30 Mb total) that had been generated previously from plasmid and cosmid libraries. Mira was the only assembler capable of handling this assortment of read types. Information on the assembly is presented in Table 1.

TABLE 1

| ONC-T18 genome assembly information | |
|---|---|
| Number of contigs | 2471 |
| Total consensus | 34,463,560 bp |
| Average coverage | 40.63x (8x 454, 32x Illumina, 0.63x Sanger) |
| Mean contig size | 13,974.62 bp |
| Median contig size | 7555 bp |
| Largest contig | 164,938 bp |
| Smallest contig | 490 bp |

While the number of contigs in the assembly was fairly high, this is typical for draft genomes. The N50 contig size, which was the contig length above which half the genome is represented, was 29,352 bp. This compared favorably to many draft genomes, which often have N50<10,000 bp. The N95 was 4931 indicating that 95% of the genome was in contigs greater than about 5 kb.

During the annotation phase, 12 contigs were noted as containing mitochondrial genes. These were removed from the assembly and reassembled separately. This resulted in 5 contigs with the largest being 30965 bp, while the other four were all less than 1800 bp and appear to be variants of regions in the large contig. The large contig has complex repeat regions at each end that aren't easily joined into a circular genome. This situation has been noted previously for thraustochytrid mitochondrial genomes (GenBank accession AF288091).

Finding genes in the ONC-T18 sequence was not completely straightforward. While the majority of genes were encoded in a single exon, there were a substantial number of multi-exon genes, requiring the use of gene modeling software to sort out single vs. multi-exon genes and for the latter, to identify proper intron/exon boundaries. MAKER coordinates the analysis of the genome by several methods: inputs from gene modeling software (Snap and Augustus), alignments to RNA reads and alignments to proteins. The predicted genes were further analyzed by PASA which uses assembled transcripts (from Inchworm) to identify 5' and 3' untranslated regions, a number of which include introns. RNA encoding genes (rRNA, tRNA and other non-coding RNA such as small nuclear DNA, (snoRNA/snRNA)) were identified by Infernal searches of the Rfam database. Annotation data are presented in Table 2.

TABLE 2

| ONC-T18b annotation data | |
|---|---|
| Protein encoding genes | 13,022 |
| Single exon | 10,272 |
| Two exons | 2,136 |
| Three exons | 425 |
| More than three exons | 161 |
| No Genbank hits | 3258 |
| Hypothetical/conserved proteins | 841 |
| rRNA genes | 79 |
| tRNA genes | 131 |
| other RNA genes | 8 |

Running the predicted proteins through AutoFACT analyzed protein coding genes. This software coordinates blast searches against the uniref90, non-redundant. Kegg, COG and pfam databases and outputs a consensus of the expected protein function. Also, COG functions and KEGG pathways were identified and, if possible, EC numbers. Gene ontology classifications are also identified where possible. These data are essential to identifying the biochemical pathways present in ONC-T18b.

Genes for all of the enzymes in the classical elongation/desaturation pathway from 18:1 fatty acids to DHA were identified in the genome. Genes for the three subunits of the PUFA polyketide synthase, which directly synthesizes DPA and DHA from malonyl-CoA, were also identified, though two of them were split among contigs due to the repetitive nature of the proteins. Also, several genes for poorly defined enzymes, generally described as "elongation of very long chain fatty acids protein" were identified, suggesting that these genes are either divergent variants of the enzymes in the C18-C22 pathway or are involved in the synthesis of fatty acids with chain lengths greater than C22.

1. Isolation and Identification of a Tubulin Gene Promoter #701.

Oligonucleotide primers #52 (SEQ ID NO: 1) and #53 (SEQ ID NO: 2) were designed based on the *Thraustochytrium* sp. ONC-T18 genomic sequence data using the bioinformatics software package Kodon (Applied Maths). Oligonucleotide primers were synthesized and purchased from Invitrogen (California, USA).

Genomic DNA of ONC-T18 was extracted from cells cultured in the growth medium (ONC-T18-GM0) at 25° C. for 36 hours in a shaker incubator with constant agitation at 150 rpm. Cells of 50 mL cultures were harvested by centrifugation for 5 min at room temperature at 4300 rpm in a Sorvall Super T21 centrifuge with the rotor ST-H750 with the adapter Sorvall #00436. Genomic DNA was isolated from the cells using the Ultraclean Microbial DNA Isolation kit (MO BIO Laboratories, Inc, Solana Beach, Calif.) following the manufacturer's protocol.

The components of the growth medium ONC-T18-GM0 are: 5 g/L yeast extract (RM668, HiMedia labs), 5 g/L soy peptone (RM007, HiMedia labs), 10 g/L D(+)-glucose (CERELOSE™ Dextrose 020010. Corn Products International), 35 g/L artificial sea salt (INSTANT OCEAN™, Aquaria, Inc.), 1.25 mg/L trace elements (5 g/L $NaH_2PO_4.H_2O$. 3.15 g/L $FeCl_3.6H_2O$, 4.36 g/L $Na_2EDTA-2H_2O$, 0.6125 mg/L $CuSO_4.5H_2O$, 0.0597 g/L $Na_2MoO_4.2H_2O$, 0.022 g/L $ZnSO_4.7H_2O$, 0.01 g/L $CoCl_2.6H_2O$, 0.18 g/L $MnCl_2.4H_2O$, 13 µg/L $H_2SeO_3$, 2.7 mg/L $NiSO_4.6H_2O$, 1.84 mg/L $Na_3VO_4$ and 1.94 mg/L $K_2CrO_4$) and 1.25 mg/L vitamins (1 mg/L vitamin B12, 1 mg/L biotin, 0.20 g/L thiamine HCl).

The tubulin gene promoter #701 including the partial open reading frame sequence was amplified from genomic DNA of ONC-T18 using the following PCR conditions: 94° C. for 1 minute, 94° C. for 30 seconds and 68° C. for 6 minutes and repeated for 30 cycles, and 72° C. for 10 minutes. PCR was carried out in a 50 µL reaction mixture containing 2.5 units TaKaRa LA Taq™ DNA Polymerase (TAKARA BIO INC., Shiga, Japan), 1×LA PCR Buffer II, dNTP Mixture (0.40 mM each), 225 ng of the template genomic DNA, 0.20 µM primer #52 and 0.20 µM primer #53.

PCR products were resolved in 0.8% agarose gel for electrophoresis at 65 voltages for 60 minutes. Bands with the expected sizes were cut out with a razor blade and DNAs were extracted and purified with QIAquick Gel Extraction Kit (Qiagen, Valencia, Calif.) as per manufacturer's protocol.

The purified DNA fragments were cloned into pT7Blue-3 vector using Perfectly Blunt® Cloning Kits (Novagen, San Diego, Calif.) as per manufacturer's protocol. Positive clones were screened using direct colony PCR method. Briefly, transformed *Escherichia coli* colonies were picked with toothpicks and swirled in a 20 µL PCR reaction mixture containing following components: Taq DNA polymerase (Sigma), 1×PCR buffer, 2.5 mM $MgCl_2$, dNTPs mixture (0.20 mM each), 0.25 µM primer #62 (SEQ ID NO: 3) and 0.25 µM primer #63 (SEQ ID NO:4) in a 200 µL PCR tube, respectively. Meanwhile colonies were also streaked on a reference plate for the isolation of plasmid DNAs.

The PCR was carried out under the following conditions: 94° C. for 3 minute for one cycle; 94° C. for 1 minute. 53° C. for 2 minutes and 72° C. for 4 minutes, and repeated for 30 cycles; and 72° C. for 10 minutes. PCR products were differentiated in 0.8% agarose gel. Colonies from which a PCR product of the expected size was amplified were considered to be positive colonies.

Plasmid DNA of the positive clone JZ2-17-10 was isolated from the bacterial *E. coli* cells of 3 mL culture using ZYPPY™ Plasmid Miniprep Kit (Zymo Research Corp., Orange, Calif.). Its insert was sequenced using the forward primer #62 (SEQ ID NO:3) and the reverse primer #63 (SEQ ID NO: 4). The resulting sequences were assembled and analyzed using bioinformatics software package Kodon (Applied Maths) and algorithms BLAST. The nucleotide sequence of the insert from the clone JZ2-17-10 is 724 base pairs long (SEQ ID NO: 5). The 498 nucleotides upstream of the putative translation start code ATG of a partial putative tubulin gene open-reading frame (ORF) was determined to be a putative gene expression promoter (sequence

701; SEQ ID NO: 6) based on analyses using various bioinformatics software. Typical gene promoter elements were identified within this sequence. A search for sequences homologous to this putative promoter sequence #701 (SEQ ID NO: 6) was performed in various databases of the GenBank including the database of the patent sequences using The Basic Local Alignment Search Tool (BLAST) (Altschul et al., 1990). No homologous sequence was found to this unique promoter sequence #701. The 5'-end partial sequence of the ORF has the greatest homology to *Chlamydomonas reinhardtii* beta tubulin 2 (TUB2) gene (GenBank accession No.: XM_001693945) in a BLAST search.

The identified promoter sequence is 498 nucleotides long and contains a −10 Pribnow-Schaller box (AGGAAGACT) at the position 444, and a −35 box at position 424 (CTGACG), a putative transcription start site at position 459, and a putative transcription factor binding site AAGGTAGA at position 468.

2. Isolation and Identification of a Tubulin Gene Promoter #341.

Oligonucleotide primers #54 (SEQ ID NO: 7) and #55 (SEQ ID NO: 8) were designed based on *Thraustochytrium* sp. ONC-T18 genomic sequence data using the bioinformatics software package Kodon (Applied Maths). Oligonucleotide primers were synthesized and purchased from Invitrogen (California, USA).

The tubulin gene promoter #341, including the downstream partial open reading sequence, was amplified from the genomic DNA of ONC-T18 by PCR using the same conditions as described for the isolation of the tubulin gene promoter #701. The purified DNA fragment amplified was cloned into pT7Blue-3 vector using Perfectly Blunt® Cloning Kits (Novagen, San Diego, Calif.) as per manufacturer's protocol. The plasmid DNA of the positive clone JZ2-17-14 was isolated from *E. coli* cells of 3 mL culture using ZYPPY™ Plasmid Miniprep Kit (Zymo Research Corp., Orange, Calif.).

The insert of the recombinant plasmid DNA was sequenced using the forward primer #62 (SEQ ID NO: 3) and the reverse primer #63 (SEQ ID NO: 4). The resulting sequences were assembled and analyzed using bioinformatics software package Kodon (Applied Maths) and algorithms BLAST. The insert nucleotide sequence of the clone JZ2-17-14 is 1115 base pairs long (SEQ ID NO: 9). A partial ORF of a tubulin gene located at the 3'-nd sequence of the insert, has been identified. The upstream sequence of the putative translation start code ATG of the ORF is considered as the putative promoter #341 (SEQ ID NO: 10).

A search for sequences homologous to the tubulin gene promoter #341 (SEQ ID NO: 10) was performed in various Genbank databases including the database of patent sequences using The Basic Local Alignment Search Tool (BLAST) (Altschul et al., 1990). No sequence homologous to this unique tubulin gene promoter #341 sequence was found. The 5'-end sequence of the putative partial ORF has the greatest homology to *Chlamydomonas reinhardtii* alpha tubulin 2 (TUA2) gene (GenBank accession No.: 5728641) in a BLAST search.

This 1004 nucleotide long promoter sequence contains a −10 box (CGCTAAAAT) at position 542, and −35 box (TTCACG) at position 518, the putative transcription start site at position 557 and the putative transcription factor binding site GCTAAAAT at position 543 as well as a −10 box (TAGTAGATT) at position 143, and −35 box (TTGCTC) at position 125, the putative transcription start site at position 158 and the putative transcription factor binding sites ATTTTGTA at position 149 and TTTTGTAA at position 150.

3. Isolation and Identification of a Tubulin Gene Terminator #347.

Oligonucleotide primers #58 (SEQ ID NO: 11) and #59 (SEQ ID NO: 12) were designed based on genomic sequence data of ONC-T18 using bioinformatics software package Kodon (Applied Maths). The oligonucleotide primers were synthesized and purchased from the company Invitrogen (California, USA).

The tubulin gene terminator #347 was amplified from genomic DNA of ONC-T18 with PCR using the same conditions as described for the isolation of the tubulin gene promoter #341. The purified DNA fragment was cloned into pT7Blue-3 vector using Perfectly Blunt® Cloning Kits (Novagen, San Diego, Calif.) as per manufacturer's protocol. The plasmid DNA of the positive clone JZ2-17-22 was isolated from the bacterial *E. coli* cells of 3 mL culture using the ZYPPY™ Plasmid Miniprep Kit (Zymo Research Corp., Orange, Calif.).

The insert of the recombinant plasmid DNA was sequenced using the forward primer #62 (SEQ ID NO: 3) and the reverse primer #63 (SEQ ID NO: 4). The resulting sequences were assembled and analyzed using bioinformatics software package Kodon (Applied Maths) and algorithms BLAST. The insert of the nucleotide sequence of the clone JZ2-17-22 is 727 base pairs long (SEQ ID NO: 13). The 5'-end sequence of the insert has been identified as a putative partial ORF that contains a putative gene translational stop codon TAA. The downstream sequence of the stop codon TAA is considered as the putative tubulin gene terminator #347 (SEQ ID NO: 14).

A search for sequences homologous to the tubulin gene terminator #347 sequence (SEQ ID NO: 14) was performed in various databases of the Genbank including the database of the patent sequences using The Basic Local Alignment Search Tool (BLAST) (Altschul et al., 1990). No homologous sequence of this unique tubulin gene terminator #347 sequence was found. The partial sequence of the putative ORF has the greatest homologue to *Ceratopteris richardii* alpha tubulin gene (GenBank accession No.: XM_001691824) in a BLAST search.

The 590 nucleotide long terminator sequence contains a putative polyadenalytion signal sequence AAAACAAAAA functioning for the termination of transcription by RNA polymerase.

4. Isolation and Identification of a Tubulin Gene Terminator #713.

Oligonucleotide primers #60 (SEQ ID NO: 15) and #61 (SEQ ID NO: 16) were designed based on genomic sequence data of ONC-T18 using bioinformatics software package Kodon (Applied Maths). The oligonucleotide primers were synthesized and purchased from Invitrogen (California, USA).

The tubulin gene terminator #713 was amplified from the genomic DNA of ONC-T18 with PCR using the same conditions as described for the isolation of the tubulin gene promoter #341. The purified DNA fragment was cloned into pT7Blue-3 vector using Perfectly Blunt® Cloning Kits (Novagen, San Diego, Calif.) as per manufacturer's protocol. The plasmid DNA of the positive clone JZ2-22-9 was isolated from the bacterial *E. coli* cells of 3 mL culture using ZYPPY™ Plasmid Miniprep Kit (Zymo Research Corp., Orange, Calif.).

The insert of the recombinant plasmid DNA was sequenced using the forward primer #62 (SEQ ID NO: 3)

and the reverse primer #63 (SEQ ID NO: 4). The resulting sequences were assembled and analyzed using bioinformatics software package Kodon (Applied Maths) and algorithms BLAST. The insert of the nucleotide sequence of the clone JZ2-22-9 is 869 base pairs long (SEQ ID NO:17). The 5'-end sequence of the insert has been identified as a putative partial ORF that contains a putative gene translational stop codon TAA. The downstream sequence of the stop codon TAA is considered as the putative tubulin gene terminator #347 (SEQ ID NO:18).

A search for a sequence homologous to the tubulin gene terminator #713 sequence (SEQ ID NO:18) was performed in various databases of the Genbank including the database of the patent sequences using The Basic Local Alignment Search Tool (BLAST) (Altschul et al., 1990). No sequence homologous to this unique tubulin gene terminator #713 sequence was found. The partial sequence of the putative ORF has the greatest homology to *Cyanophora paradoxa* beta 1 tubulin (tubB1) gene (GenBank accession No.: AF092952) in a BLAST search.

The 640 nucleotide long terminator sequence (SEQ ID NO: 14) contains a putative polyadenalytion signal sequence CATAAA functioning for the termination of transcription by message RNA polymerases.

5. Isolation and Identification of a Δ5 Elongase Gene (PCT/IB2007/004553; WO/2009/010825) Promoter Sequence (SEQ ID NO: 19).

Based on the genomic sequence data of ONC-T18 using bioinformatics software package Kodon (Applied Maths), the oligonucleotide primer #3 (SEQ ID NO: 20) in which a restriction enzyme site XbaI was added at its 5'-end for the convenience of downstream molecular cloning, and primer #4 (SEQ ID NO: 21) in which a restriction enzyme site NcoI was added at its 5'-end, were designed. The oligonucleotide primers were synthesized and purchased from Invitrogen (California, USA). The Δ5 elongase gene promoter was amplified from the genomic DNA of ONC-T18 with PCR, precipitated, digested with the restriction enzymes XhoI and NcoI, agarose-gel-purified and cloned into the corresponding restriction sites of the vector pSV40/Zeo2 (Invitrogen Corporation, California). The insert of the positive clone JZ1-57-7 was sequenced using primer #14 (SEQ ID NO: 22) and primer #15 (SEQ ID NO:23). The resulting sequences were assembled and analyzed using bioinformatics software package Kodon (Applied Maths) and algorithms BLAST. The insert of the nucleotide sequence of the clone JZ1-57-7 is 950 base pair long (SEQ ID NO: 19) and has been identified as the Δ5 elongase gene promoter (SEQ ID NO: 19) of ONC-T18.

This 950 nucleotide long promoter sequence (SEQ ID NO: 19) contains a −10 box (TGCCAGACT) at position 113, −35 box (TTTTCT) at position 91, a putative transcription start site at position 128 and putative transcription factor binding sites CTCCTTTT, TTTCTTTT, TTCTTTTT and TTGCTCCT at position 87, 92, 93 and 131 as well as a −10 box (AGTTCTGAT) at position 444, a −35 box (TTTCCG) at position 419, and a putative transcription start site at position 459.

A search for sequences homologous to the A5 elongase gene promoter sequence (SEQ ID NO: 19) was performed in various databases of the Genbank including the database of the patent sequences using the Basic Local Alignment Search Tool (BLAST) (Altschul et al., 1990). No sequence homologous to the Δ5 elongase gene promoter sequence (SEQ ID NO: 19) was found.

6. Isolation and Identification of a Δ4 Desaturase Gene (PCT/IB2007/004553; WO/2009/010825) Promoter Sequence (SEQ ID NO: 24).

The oligonucleotide primer #1 (SEQ ID NO: 25) in which an restriction enzyme site XhoI was added at its 5'-end for the convenience of downstream molecular cloning and primer #2 (SEQ ID NO: 26) in which an restriction enzyme site NcoI was added at its 5'-end, were employed for the isolation of the Δ4 desaturase gene promoter sequence (SEQ ID NO: 24). The DNA fragment of Δ4 desaturase gene promoter was amplified using PCR, precipitated, digested with the restriction enzymes XhoI and NcoI, agarose-gel-purified and cloned into the corresponding restriction sites of the vector pSV40/Zeo2 (Invitrogen Corporation, California) digested with the same restriction enzymes and gel-purified. The insert of a positive clone JZ1-57-1 was sequenced using the primer #14 (SEQ ID NO:22) and primer #15 (SEQ ID NO:23). The resulting sequences were assembled and analyzed using bioinformatics software package Kodon (Applied Maths) and algorithms BLAST. The insert of the nucleotide sequence of the clone JZ1-57-1 is 1216 base pairs long (SEQ ID NO: 24) and has been identified as the Δ4 desaturase gene promoter (SEQ ID NO:24) of ONC-T18.

This 1216 nucleotide long promoter sequence (SEQ ID NO: 24) contains a −10 box (GCGTATTAT) at position 58, −35 box (CTACAG) at position 34, the putative transcription start site at position 73 and a putative transcription factor binding sites TTATATTT and TTTTCGCA at positions 63 and 69 as well as a −10 box (CGTCATCCT) at the position 1038, −35 box (TGGACG) at position 1014, and a putative transcription start site at position 1053.

A search for sequences homologous to the Δ4 desaturase gene promoter sequence (SEQ ID NO: 24) was performed in various databases of the Genbank including the database of the patent sequences using the Basic Local Alignment Search Tool (BLAST) (Altschul et al., 1990). No sequence homologous to the Δ4 desaturase gene promoter (SEQ ID NO: 15) was found.

7. Identification and Isolation of Δ12 Desaturase Gene (SEQ ID NO: 70).

RNA-Seq analysis of RNA from rapidly growing cells and cells producing high amounts of lipid provided a number of insights into the biology of ONC-T18. RNA reads from both conditions were mapped to 11,407 genes (87.6%). The 1613 genes with no apparent expression were either not real genes, were only expressed at very low levels or were only expressed under very specific conditions (e.g., sporulation). Comparisons between the two growth conditions identified 1519 genes that were expressed only under the rapid growth condition while 442 genes were expressed only under the high lipid production condition (Table 3). The analysis allows the identification of genes that are highly expressed in either condition as well as those that show the greatest change. The expression data clearly identified a number of genes with regulated and/or strong promoters. These promoter regions can be used to drive the expression of genes introduced into ONC-T18.

TABLE 3

Genes most highly expressed in the high lipid production condition, comparison of exponential growth (A expr) and fatty acid biosynthesis (B expr).

| Description | A expr. | B expr. | ratio B/A |
|---|---|---|---|
| Delta 12 fatty acid desaturase | 1540.39 | 66133.1 | 42.9327 |
| 60S ribosomal protein L40 | 20680.2 | 33016.5 | 1.596527 |

TABLE 3-continued

Genes most highly expressed in the high lipid production condition, comparison of exponential growth (A expr) and fatty acid biosynthesis (B expr).

| Description | A expr. | B expr. | ratio B/A |
|---|---|---|---|
| Fructose-bisphosphate aldolase | 8584.79 | 26817.6 | 3.12385 |
| No hits | 23667.6 | 20419.4 | 0.862758 |
| No hits | 4648.85 | 18867 | 4.058423 |
| Sperm flagellar energy carrier protein | 15761 | 17993.1 | 1.141622 |
| Elongation factor 1-alpha | 31931.4 | 16981.2 | 0.531803 |
| Glyceraldehyde-3-phosphate dehydrogenase, type I | 4794.26 | 15752.3 | 3.285658 |
| ATPase 4, plasma membrane-type | 5823.11 | 13852.5 | 2.378883 |
| No hits | 10563.6 | 12461.5 | 1.179664 |
| Pyruvate kinase | 2248.7 | 12195.4 | 5.423311 |
| ATP synthase subunit alpha | 12958.5 | 11405.6 | 0.880164 |

Particularly notable is the greater than 40-fold increase in expression in Δ12 desaturase, a key enzyme early in the pathway for synthesis of polyunsaturated fatty acids (desaturation of 18:1 to 18:2). Standard bioinformatic analysis confirmed the highest upregulated gene as a putative Δ12 Desaturase. In brief. BLASTn analysis revealed low level homology to regions of *Micromonas* sp. PCC299 chromosome 5 as a top hit. The BLASTn results also showed a portion of the target sequence to be 96.9% similar to the Δ12 Desaturase of *Verticillium albo-atrum* VaMS.102. BLASTx identified the target sequence as a protein with a substantial portion (46%) that was 92% similar to the Δ12 Desaturase of *Pheodactylum tricornutum*. A BLASTp analysis to identify conserved domains identified two conserved Δ12 fatty acid desaturase motifs. A SIB:myhits motif scan (available at http://myhits.isb-sib.ch/cgi-bin/motif_scan) to analyze the protein sequence for the presence of motifs revealed two fatty acid desaturase motifs within the sequence, further suggesting function as a fatty acid desaturase. Confirmatory analysis with EMBL-EBI InterProScan also revealed the presence of motifs characteristic of fatty acid desaturase proteins.

Among other things, this example demonstrates that expression of Δ12 desaturase of *Thraustochytrium* sp. ONC-T18 is upregulated by over 40-fold during fatty acid production. This unexpected and dramatic increase in expression identifies the Δ12 desaturase as a master regulator of PUFA biosynthesis in Thraustochytrids or *Thraustochytrium*, particularly in ONC-T18. Manipulation levels of this master regulator through over-expression, down-regulation or inhibition can tailor PUFA biosynthesis along particular pathways as shown in FIG. 1. The proximal and distal regulatory elements (e.g., promoter(s), 5' UTRs, introns, terminators and 3' UTRs of the Δ12 desaturase may be operably linked to one or more additional PUFA biosynthesis genes in order to increase expression levels of those genes to similar orders of magnitude during fatty acid production. In essence, the regulatory elements of Δ12 desaturase are switches to drive PUFA biosynthesis pathways in one or more predetermined directions.

To isolate this gene, the highest upregulated gene described above, PCR amplification was carried out in a 50 µl volume containing: 200 ng *Thraustochytrium* sp. ONC-T18 genomic DNA, 10 µl betaine, 10 mM Tris-HCl, pH 8.3, 50 mM KCl. 1.5 mM MgCl$_2$, 0.001% gelatin, 200 µM each deoxyribonucleotide triphosphate, 1 µM of each primer and 0.2 unit of high fidelity polymerase. Thermocycling was carried out at an annealing temperature of 55.7° C., the PCR reaction was resolved on a 0.8% low melt agarose gel, and the band of about 600 bp was gel purified. The PCR product was eluted from agarose with water and then purified with QIAquick PCR Purification kit (Qiagen, Valencia, Calif.). These DNA fragments were cloned into the pT7Blue-3 Perfectly Blunt Cloning kit (Novagen, San Diego. Calif.) as per manufacturer's specifications. The recombinant plasmids were transformed into NovaBlue competent cells (Novagen, San Diego, Calif.), and clones were sequenced. One clone was thus isolated and sequenced.

The Δ12 Desaturase full-length gene insert is 1239 bp (SEQ ID NO:70) in length and, beginning with the first ATG, contains 1238 bp open reading frame encoding 412 amino acids.

TABLE 4

Δ12 Desaturase from ONC-T18 (SEQ ID NO: 70)

ATGTGCAAGGTGGAGCCCACGCGGCACGAGCAGACGGCTGCGGCCAAGCC

GCAAGAGCAGCAGCAGCAGCGTCAGAGTCCCATCATCCATGGCAAGCACA

ACCCGGACCTGCCGACGCTCGGCGAGATTCGCGCCGTGGTGCCGAAGCAC

TGCTTTGAGCGCTCGCTCGTGACGAGCTCGCTTTACCTGGGCCGCGACCT

TCTCATGGCAGCCACCCTCTTCTTCCTCGCCAGACAATTCCTTCCCGTTT

ACGACATGGGCCTCTCGGGCGCGCTCGCCTGGACTGTCTACGTCTGTGTG

CAGGGTACCGTCGGTGCCGGCCTTTGGGTGCTTGGGCATGAATGCGGTCA

CCAGGCCTTTTCCAACTACAGGATCGTCAACGACGGCGTCGGCTTTCTGG

TCCACACGAGCCTGTTGGTGCCTTATTTCAGCTGGGCGTACACGCACGGC

TTGCACCATGCCCGCGTCAACCACATGCTCGACGGCGAGTCGCACACGCC

GAACCTGAAGAAGAAGGTGGCCGCCAACTTTCAAAAGTTCTGCGACATGA

TGGGCGATGAGGCGTTTGCCGTTCTTCACGTCTTCGTCTACCTTCTCCTG

GCCTGGCCGCTTTACATCATCAACGGGAGCGGCGCGTCCAAGCGCAACCA

CGAGGGAAAGCGCTGGTCGAAGGATTTCTGGAAGCGCCCCAACCACTTTT

TGCCCACCTCGGAGCTCTTTCCGGACAAGATGCGCCTCAAGGCCGCCGTC

TCCACGATCGGCGTCCTTACCGTCATTGCCGGCCTCTGCTACTGGGGCTC

TATCGAGGGCGGGCGCACCGTGCTGCTCCAGTACTTTCTGCCCTACCTGG

TGGTCAATGCCTATCTCATTGGGTTTACCTGGATGCAACACACCCACCCG

GACGTCCCGCACCTCGGCGAGGACGAGTGGTCCTGGGTCGCGGGCACTGT

GCTCACCGTCGATCGCCCCTACCCGCCTTTTATCGACGTTCTGACCCACC

GCATCGGGTCTACGCACGTGGCGCATCACCTCTTCTCCAAGATGCCGTGG

TACCACGCGCGCGAGGCTACGACCCACATCCGGACCCTCCTCGAGCCCAA

GGGCGTCTACAACTATGACCCGATGCCCTTTTACAAGGCCTTGTTTCACA

CTGCTAAGTACTGCCACTACATGGAGGGCGTCGACGGTATTCAGTTCTTC

AAACATGCCGCTGCCCAGCCCAAGGCCAAGGAGCTCTAA

8. Isolation and Amplification of Δ5 Desaturase Gene (SEQ ID NO: 72).

The sequence of a Δ5 Desaturase from *Thraustochytrium* sp. ONC-T18 was isolated and identified in a manner similar to that of the Δ12 Desaturase. The complete sequence is:

TABLE 5

Δ5 Desaturase from ONC-T18 (SEQ ID NO: 72)

ATGGGCAAGGGAAGCGAGGGCCGCAGCGCGGAGCGCGAGATGTCGGCCGA

GGCGAGCGGCGACAAGCGGAAAACAATTTTGATCGAGGGCGTCCTGTATG

ACGTGACGAACTTTAAGCACCCGGGCGGTTCGATCATCAACTTTTTGACC

GAGGGCGAGGCCGGCGTGGACGCGACACAGGCGTACCGCGAGTTCCATCA

GCGGTCCGGCAAGGCTGACAAGTACCTCAAGTCGCTGCCGAAACTGGATG

CGTCCAAGGTGGAGTCGCGGTTCTCGGCCAAGGAGCAGGCGCGGCGCGAC

GCCATGACGCGCGACTATGCGGCCTTTCGCGAGGAGCTCATCGCCGAGGG

GTACTTTGACCCGTCGATCCCACACATGATTTTCCGCGTCGTCGAGATTG

TGGCGCTCTTTGCGCTCTCGTTCTGGCTCATGAGCAAGGCCTCGCCCAGC

TCGCTCGTGCTGGGCGTGGTGATGAACGGCATTGCGCAGGGCCGGTGCGG

CTGGGTCATGCACGAGATGGGCCACGGGTCGTTCACGGGCGTCATTTGGC

TCGACGACCGGCTGTGCGAGTTCTTTTACGGAGCCGGCTGCGGCATGAGC

GGGCACTACTGGAAGAACCAGCACAGCAAGCACCACGCCGCGCCCAACCG

CCTCGAGCACGATGTCGATCTCAACACGTTGCCCCTGGTCGCCTTTAACG

AGCGCGTTGTGCGCAAGGTCAAGCCGGGGTCTCTGCTTGCGCTCTGGCTG

CGTGTGCAGGCGTACCTCTTTGCGCCCGTCTCGTGCCTGCTCATTGGCCT

CGGCTGGACGCTGTACCTGCACCCGCGCTACATGCTGCGCACCAAGCGGC

ACATGGAGTTTGTCTGGATCTTTGCGCGCTATCTTGGTTGGTTCTCGCTC

ATGGGCGCTCTCGGTTACACGCCGGGCCGCTCGATCGGGATGTACCTGTG

CTCGTTTGGCCTCGGCTGCATTTACATTTTCCTGCAGTTCGCCGTCAGCC

ACACGCACCTGCCGGTGACTAACCCAGAGGACCAGCTGCACTGGCTCGAG

TACGCGGCGGACCACACGGTGAACATTAGCACCAAGTCCTGGTTCGTCAC

ATGGTGGATGTCGAACCTGAACTTTCAGATCGAGCACCACCTTTTCCCCA

CGGCGCCGCAGTTTCGCTTCATGGAAATCAGCCCTCGCGTCGAGGCCCTC

TTCAAGCGCCACAACCTCCCATACTACGACCTGCCCTACACGAGCGCGGT

CTCGACCACCTTTGCCAACCTTTATTCCGTCGGCCACTCGGTCGGCGACT

CGGTCGGCGCCGACACCGACGCCAAGAAGCAAGACTAG

The predicted amino acid sequence is:

TABLE 6

Predicted Amino Acid Sequence of Δ5 Desaturase from ONC-T18 (SEQ ID NO: 73)

MGKGSEGRSAEREMSAEASGDKRKTILIEGVLYDVTNFKHPGGSIINFLT

EGEAGVDATQAYREFHQRSGKADYLKSLPKLDASKVESRFSAKEQARRD

AMTRDYAAFREELIAEGYFDPSIPHMIFRVVEIVALFALSFWLMSKASPS

SLVLGVVMNGIAQGRCGWVMHEMGHGSFTGVIWLDDRLCEFFYGAGCGMS

GHYWKNQHSKHHAAPNRLEHDVDLNTLPLVAFNERVVRKVKPGSLLALWL

RVQAYLFAPVSCLLIGLGWTLYLHPRYMLRTKRHMEFVWIFARYLGWFSL

MGALGYTPGRSIGMYLCSFGLGCIYIFLQFAVSHTHLPVTNPEDQLHWLE

TABLE 6-continued

Predicted Amino Acid Sequence of Δ5 Desaturase from ONC-T18 (SEQ ID NO: 73)

YAADHTVNISTKSWFVTWWMSNLNFQIEHHLFPTAPQFRFMEISPRVEAL

FKRHNLPYYDLPYTSAVSTTFANLYSVGHSVGDSVGADTDAKKQD*

9. Isolation and Identification of a Δ12 Desaturase Gene Promoter Sequence (SEQ ID NO: 69).

Based on the genomic sequence data of ONC-T18 using bioinformatics software package Kodon (Applied Maths), oligonucleotide primers were designed to flank the upstream regulatory region of the Δ12 desaturase gene. The primers were designed to include restriction enzyme sites for the convenience of downstream molecular cloning. The oligonucleotide primers were synthesized and purchased from Invitrogen (California, USA). The Δ12 desaturase gene promoter was amplified from the genomic DNA of ONC-TI 8 with PCR, precipitated, digested with the appropriate restriction enzymes, agarose-gel-purified and cloned into the corresponding restriction sites of the vector pSV40/Zeo2 (Invitrogen Corporation, California). Following transformation in to a suitable bacteria host cell and selection, several transformed bacteria were selected, cultured in 3.5 ml columns and plasmid DNA extracted using Zyppy plasmid DNA extraction kit. Purified plasmid DNA was digested with appropriate restriction enzymes to confirm presence of the desired DNA fragment. The insert of a positive clone was sequenced using appropriate primers of 25 bp sequences spaced about 500 bp apart, from the 5' (forward) and 3' (reverse) end. The resulting sequences were assembled and analyzed using bioinformatics software package Kodon (Applied Maths) and algorithms BLAST. The insert of the nucleotide sequence of the clone was 3247 base pair long (SEQ ID NO: 69) and has been identified as the Δ12 desaturase gene promoter (SEQ ID NO: 69) of ONC-T18.

TABLE 7

Proximal Promoter of ONC-T18 Δ12 Desaturase (SEQ ID NO: 69)

CGGACGGCGTGCTTAGTAACTGAATGAATAATTATACCAGCTGGGGATTC

TGCGAATGCGAACGACGCTTCCAGAGCCTCACCTTTTGCAGCGACAGCGT

GCCGCGCGCGATACTTGCTTCTATTCTAGCAAAGCCCAACGCAAGGCTTG

CCTACTCCTTGTCGAGCTTGTACATGTCCTTGGAGGTGTACCCATTCGCG

ATGAGGCTCTCGTACGCGGCTTCGACCTGCTCCTTGTAGGAGCGGTACTC

GCCGAGGCCGAGGCCGCCCTCGCTGGTCGGTTTGAGGGACTTTTCGACGT

TGTAGCGAGTGCGGTGTGGCGGCGGCGCCCCGAGCCGGGTGCGGGAAGC

TTCGGGTCCACCTCGGTAGGAAGCTCTTTTTTCCGGTCCCTCAGAAACCT

TGTTAGACTCGCGCAAAACCTGGACAATTTCTTCGCGCATGGGGGCACCG

CCAATAAGAAGGAAGCGCTCGCCCCAGCCCTTCCAGTCAAAGTCCATCTG

TGCGGCGTTGACGTGGGCGCGCGCCACATCGCGCACGTCCGTGATGCAGG

CGTTGGCCTGTTGAACCTTGGAGGCGCCAAAGTATGCTAGCACGGAGACC

GAGCTGGTGTTGAGCTCGGGGAGGCCGGGAAGCATGGGGCCGTAGATGAA

GCTCGGGTTGAGCGCAGCAAGCTTGAAAGAGCTCTCCTTGGCGATCTCCC

TABLE 7-continued

Proximal Promoter of ONC-T18 Δ12 Desaturase
(SEQ ID NO: 69)

AGGCCGTTTTCTCGGCGAGGAGCTTGGAAAGGCCATAGTAGTTCTTTTTC

TCCTCGAGGACCTTGTCGTCGGTCCAGTCCTCTTCGCTGTAGACGTACTC

GGGGGGCTTCGCGCCGTACGTGATGTAGATGTTGGCGATCGAGGCGGTAA

GCACGACCTTTTCCACACCGAGCTTCTCGCAGGACTCAAGCACGTTGCGC

GTGCCCTTCACGGCCGGCTCGACGAGTTTCTGGCGCGCCGACTCGTCGTT

TATGCGGATAAAGGGCGACGCCGAGTGGATCACCGTGGGGCATCCCTTGA

TGGCCTCATCGAAGCTGCCCTGCTCCAGGAGATCGCAGCCAGTGAAAAGC

TTGAGCCGCTCCTGGGCGCCATCGAGCTTTTGCAGAAAGTCCACCTTTTT

GCCGGACCGCGTCGTTCCGTGCACCTCGAAGCCGGCCTCCAGCGCGTACT

TGACTACCCACGAGCCCAGGAAACCGGTACACCCCGTCACGCACACGCGT

TTCGCCTCCGGCACCGACATGCTGCTTGTTTGTCCACCTCCTCGGCTCTT

GCTCCGCTCGCGTATAGGCCAGGCGGCTGGCTAGCTGCTCGGGCTCGGGA

CCAAAACGTTTCTGCAAGTTTCGAGACTGCGGCTTCAGCTGGGATTTTGT

GGCGTTTGCCTCGGCCTCACCGTCATCGCCTCATCCCGTGCGCGCAGATG

ACGACGATGCCGCCGACCTCGCACGACCTCAAGCGGTTCAGGAGTCGTTC

GCTGCGCCAAGAAATGGGCAGCGCAACGCACGCCGCTCGAGGTGGGCTGT

GAGCGCCTCGGGCACGCGACTAATAAGCCCCAGGGCGCTCGGGATGCCCT

CCTTCCGCCGCACGCGTTGCATTCTTGCTTGCTTGCTTGCTTGCTTGCTT

GCTTGCTTGCTTGCCTGCGCGGAGAAGTGTTGGTTTTTCCGATCGACGGC

AAAGATAACGCGCGTGTACTAGCGTCGATCGCGAGTCCCTTGACCTGCCT

GCCTCCGTCAGCATGCTGCCAAGGGTTGATGCGAGTAGCGCGGCGCCGCG

TTGCTGCGAGATGCGCGCGCGGAGTGGTCCGCGTCCTTGCTGCCTGCAT

CGACACGACGCTGATGAGGGTCGAGCTTCCTTCTTCCCTTCCGGCGCCGT

TGAACCCGCCCACCCATGTTGGCGAGGTGAATCTGGAGCCCGTGCCGGCG

GCCGGCGGCACCGTGGGCCACCCGCACGCGGGCTACCAAGCACGCTTTGC

GGCGGCGGGCACCGCCCGCGAAACGCGTTGCGCAGACACCCATTTCCAG

CATTTCGAGGTACTGAGGCTAACCGACGACGCGACGCAGCGACGGCGCCC

CCGGCATGACGCGGCTCGGGAGCGTTTGTTTTGGCGTGCGTTGCTCGCGC

GGCGGACGTTCACGAAACCCGTGTCGGGCCGGGATCCGCGCTGGTCCGGG

CGCTCGACATCGATTTCCTTTCGAGCGCGCTGCCGCGTCGAAGGGGCTCC

GGGTCGCGCTAGGTCTTCTGGCCTAGGAAAGGAAAGAAAACGGGAAGGAG

GATCAAAGTCATACTATGCGTACACGCCGCGTTCGGAAACCCTAGCTGGT

TCAACCAGTTCCCTCTTCTGATTCCCTCGCTGGGTTCTGCGGGCCACGCT

CAAGCCGTCCGGGACGTCATGGACGTCGCGCTGCCCTGCGTCGTTCTTCT

ACGCGTACGCACAAGAAGGCGTCACCGCCGCGCCCGCGCCGAAGACCTCC

CTCCCGATCGAAGGTCCTGGTTCTCGGGAGGCGCTGTGCGTGGTATGTCG

ACGCGCTCGGCTCTGCGCTGGAGAGCGCAAGGCGGCTTTTTGACCAGGTT

GCCTGCCTCCTACCACGTGCCCGTAGGGAGGGGGAATGTACCGCAGTGCG

GTGGTCCGCCAAGCAAGAAACCCCGCAGAGAAGGCGTAAAGTGGAAGAAA

AACAGCGTCGTATGCCGCCGTCGTCGCAGGTGCTCGTCGTCGCCTCGTCG

ATGGGACCCATCATGCGCTGAGAGTCTGCTGCAAAAGAGGTAGGGACTCG

GGAAGGACCTGGTTCGCGCTGGCTGGGGAATCAGTAATCGCATTTCGGAC

ATGGATGCGGAGACGCTCCCCGATGACGATGCTCCAGGAATCGCGCGGCA

CGTTTTACGGCGGCGAGAGAGAAAGTCTCAGCTTCTTTTCGAGGGTATAC

TCCGTGGCGGGTTATCATCATGTGAGAGATGTATCGACGCGATGGAGAAG

CATCGGGTCTTCGTCGAACATCCGGGGTCGCCGGTTCGTCACGAAGCCAG

CTCATGCCTCCACATGTCTCACAAGACCACCGAAAAACTGTCGAACTTGA

TTCTTTAGGTCTCTCGGACGCAAATAAAAAGCATCGGCGCGCTCGCGTTC

ACCAGCAAGCAGACAAAACCAATATCAGCCTATTGGCCGACCAAAACCAA

GCAGCAGTTCCTCAACTCGGCTCTGCTCAACTCAGCAAACTGCCAACGCG

TACTAGCAGACAAGGATTCACCCCAGCTTCGGTTGAAACTACAAGATC

Analysis of the Δ12 desaturase sequence revealed the presence of twenty-four putative open reading frames (ORFs), greater than 100 bp in length, within the 3247 bp region. BLASTP analysis of these identified several with potential relevance to control mechanisms, and this application. Examples include those with homology to NADPH-dependent cinnamyl alcohol dehydrogenases (E=2e-55), with conserved NADB rossmann and Epimerase domains, bifunctional protease/dUTPase-like proteins (E=2.2), Flavin-containing monooxygenase (E=0.48), putative thiamine biosynthesis lipoprotein precursor (E=0.17), nucleotidyl transferase (E=0.99) and putative periplasmic maltose-binding protein (0.5). It is known in the field that upstream ORFs (uORFs) can impact a regulatory function on protein expression (Child, Miller et al. 1999), as can alternative splicing and riboswitch mechanisms (Epshtein, Mironov et al. 2003, Croft, Moulin et al. 2007). Online promoter/transcription start site bioinformatic analysis with Fruitfly identified the following putative promoter/transcription start sites:

Promoter Predictions Forward Strand

| Start | End | Score | Promoter Sequence | SEQ ID NO: |
|-------|-----|-------|-------------------|------------|
| 444 | 494 | 0.89 | GCACCGCCAATAAGAAGGAAGCGCTCGC CCCAGCCCTTCCAGTCAAAGTC | 74 |
| 947 | 997 | 0.95 | GTTTATGCGGATAAAGGGCGACGCCGAGT GGATCACCGTGGGGCATCCCT | 75 |
| 1509 | 1559 | 0.96 | GGGCACGCGACTAATAAGCCCCAGGGCG CTCGGGATGCCCTCCTTCCGCC | 76 |
| 2637 | 2687 | 0.83 | AAAGTGGAAGAAAAACAGCGTCGTATGC CGCCGTCGTCGCAGGTGCTCGT | 77 |
| 3060 | 3110 | 0.99 | CTCTCGGACGCAAATAAAAAGCATCGGCG CGCTCGCGTTCACCAGCAAGC | 78 |

Promoter Predictions Reverse Strand

| Start | End | Score | Promoter Sequence | SEQ ID NO: |
|---|---|---|---|---|
| 2866 | 2816 | 0.98 | CTCGCCGCCGTAAAACGTGCCGCGCGATT CCTGGAGCATCGTCATCGGGG | 79 |
| 2551 | 2501 | 0.99 | GCAACCTGGTCAAAAAGCCGCCTTGCGCT CTCCAGCGCAGAGCCGAGCGC | 80 |
| 2410 | 2360 | 0.87 | TGCGTACGCGTAGAAGAACGACGCAGGG CAGCGCGACGTCCATGACGTCC | 81 |
| 1537 | 1487 | 0.88 | GCGCCCTGGGGCTTATTAGTCGCGTGCCC GAGGCGCTCACAGCCCACCTC | 82 |
| 305 | 255 | 0.93 | CTACAACGTCGAAAAGTCCCTCAAACCGA CCAGCGAGGCGGCCTCGGCC | 83 |

A search for sequences homologous to the Δ12 desaturase gene promoter sequence (SEQ ID NO:69) was performed in various databases of the Genbank including the database of the patent sequences using the Basic Local Alignment Search Tool (BLAST) (Altschul et al., 1990). No significant sequence homologous to the Δ12 desaturase gene promoter sequence (SEQ ID NO:69) was found.

10. Isolation and Identification of a Δ5 Desaturase Gene Promoter Sequence (SEQ ID NO:71).

Oligonucleotide primers were designed to flank the upstream regulatory region of the Δ5 desaturase gene. The primers were designed to include restriction enzyme sites for the convenience of downstream molecular cloning. The DNA fragment of Δ5 desaturase gene promoter was amplified using PCR, precipitated, digested with the restriction enzymes XhoI and NcoI, agarose-gel-purified and cloned into the corresponding restriction sites of the vector pSV40/Zeo2 (Invitrogen Corporation, California) digested with the same restriction enzymes and gel-purified. The insert of a positive clone was sequenced using appropriate primers. The resulting sequences were assembled and analyzed using bioinformatics software package Kodon (Applied Maths) and algorithms BLAST. The insert of the nucleotide sequence of the clone is 1066 base pairs long (SEQ ID NO: 71) and has been identified as the Δ5 desaturase gene promoter (SEQ ID NO:71) of ONC-T18.

TABLE 8

Proximal Promoter of ONC-T18 Δ5 Desaturase (SEQ ID NO: 71)

GATATGTATTTACGTGATCAACAACCAATCAGCCACGACGTTATCGTCGT

TGTCGGCCTTGTCGTCGTTGTCGAAGCAGAGGTTGGAGAACGACAGCAAC

AACGCGACGGGGAGAATGTTGATTACGCCCCGTCAATCTCGGAAGGGCCG

ACCTAGCCCAGAAGTCCTCGGCAGCCTTTGGTTAACTTCGGAGCCCGCAA

CGTTCTGGGACTGTCTTTGCTCTAATGTAATGCGATGCCGCGCCTTGCGA

CCAAGGTTCTGCCCCGTCGGCGTTGAAGTCTTCGCTCGAGGGCTTCTGGA

TGTTGGAGAACTGATTGCACCCAATGCGATCGCCAATCGATCGATGCGCG

CTCCGGGCGACCTTCTTCTCGCCGTGCCGCTTTTGCCTCCTTTGCAGCCA

GGTACGTAGCCTCGCACCTGGGGCTGTCCTCGACCATGGTCTCGTGGCCC

ATCTCGAAGCAAACGAAAAGCAGCGCACCACCTTCGTTTTCGGCCCTTTT

TABLE 8-continued

Proximal Promoter of ONC-T18 Δ5 Desaturase (SEQ ID NO: 71)

CGCCGCATTCCCCCGGCATCGTGAAACTTGCGCGCCGGCCCCGGCTAAAG

TGCGCGTGACACATTGATCGCCCAGGACCAGGCTGCACATTGGGGGTAGA

AAACTTAGTGTCGGCGCGGCCCTGCGTGCGTCAGCAGCATACGTAAGCCA

GCATCCTCGCCCTAAGTGTGCACTGAAAACGCACACTCCTTGGTCATGTG

TGGGGACACCCGACGGGGACTCAGCGAGGACGGTGTCCCCACCTCCGCGT

ACCGGCAACGTAGAGGGCAAGGCAAAATCGTTGGATCCTCACGACAACAG

GCCACGCCCAGGTCACCCTCCATTCCATTGTACCGTCCGTTTCGACTGGC

GGCTAACGAAAAGCCTATAGCCGTTCTCGTTTGCCATTTATTGACGACTC

TGCCCGGATGAATCCCAAACACGATTCATATGCGCGGTCTGCTCCGTCTT

ATGGATGACGCTGGATGGATGGGAAAAGGTAAAATAGGCGTTCTTTACTG

TCAGGGTCTTGCAGTCGTCTTGTGTTGCTTGGCCGAGTAATCGTCACGCG

CAAACGATCGGCGCCT

Online ORF prediction tool, ORF finder (http://www.ncbi.nlm.nih.gov/projects/gorf/) identified 12 putative ORFs of greater than 100 bases, within the 1066 bp promoter. Of these, homology to the non-redundant database at NCBI (as identified by BLASTP analysis) was found for several ORFs; however homology was low and so not deemed relevant to this work. Regardless, as discussed previously, uORFs and riboswitches may impact the function of the promoter in previously undetermined ways. Online promoter/transcription start site bioinformatic analysis with Fruitfly identified the following putative promoter/transcription start sites.

| Start | End | Score | Promoter Sequence | SEQ ID NO: |
|---|---|---|---|---|
| | | | Promoter Predictions Forward Strand | |
| 534 | 584 | 0.83 | GCCGGCCCCGGCTAAAGTGCGCGTGACACAT TGATCGCCCAGGACCAGGC | 84 |
| 973 | 1023 | 0.85 | GAAAAGGTAAAATAGGCGTTCTTTACTGTCA GGGTCTTGCAGTCGTCTTG | 85 |
| | | | Promoter Predictions Reverse Strand | |
| 902 | 852 | 0.86 | CAGAGTCGTCAATAAATGGCAAACGAGAACG GCTATAGGCTTTTCGTTAG | 86 |

A search for sequences homologous to the Δ5 desaturase gene promoter sequence (SEQ ID NO:71) was performed in various databases of the Genbank including the database of the patent sequences using the Basic Local Alignment Search Tool (BLAST) (Altschul et al., 1990). No sequence homologous to the Δ5 desaturase gene promoter (SEQ ID NO:71) was found.

Example 2: Identification of an Antibiotic that can be Used for Genetic Manipulation of *Thraustochytrium* sp. ONC-T18

The present Example describes experiments identifying an antibiotic for which resistance can be used as a selectable marker for genetic manipulation of ONC-TI 8.

*Thraustochytrium* sp. ONC-T18 was grown on agar plates (20 g agar per liter ONC-T18-GM0). One loop of inoculum of ONC-T18 was inoculated into 50 mL of liquid ONC-T18-GM0, and the culture was incubated in a shaker incubator at 25° C. at 250 rpm for 36 hours. Half a milliliter of the culture was transferred into a 1.5 mL tube and vortexed at full speed for 30 seconds to break down cell clusters, then diluted in 50 mL sterilized water. One hundred microliters of the resulting solution was spread onto each ONC-T18-GM0 medium plate. Each plate contained one of various antibiotics at one of various concentrations. Plates were incubated at 25° C. and emergence and development of colonies were observed daily. As can be seen in Table 9, growth of ONC-T18 was insensitive to most of the antibiotics tested. However, zeocin significantly inhibited the growth of ONC-T18 in ONC-T18-GM0 agar plates.

Thus, the present Example identifies zeocin as an antibiotic that can be used for selection in genetic manipulation experiments.

TABLE 9

Effects of antibiotics on the growth of Thraustochytrium sp. ONC-T18

| Antibiotics | Concentration (µg/mL medium) | | | | |
|---|---|---|---|---|---|
| | 0 | 1 | 10 | 50 | 100 |
| Nourseothricin | ++++ | ++++ | ++++ | ++++ | ++++ |
| Bialophos | ++++ | ++++ | ++++ | ++++ | ++++ |
| | 0 | 100 | 200 | 500 | |
| Kanamycin | ++++ | ++++ | ++++ | ++++ | |
| | 0 | 10 | 30 | 50 | 100 |
| Zeocin | ++++ | +++ | ++ | + | --- |

Example 3: Mutagenic Agent

This Example describes, among other things, the discovery of an effective mutagenic agent. This agent is particularly useful for mutagenesis in Thraustochytrids.

Zeocin breaks chromosomal DNA in cells. It was hypothesized that antibiotic zeocin would be a useful mutagenic agent for thaustochytrid strains for strain improvement. At certain concentrations, zeocin can kill most treated cells, but some cells still survived. Treatment of cells at high concentration increases the mutation frequency, which can facilitate selection and isolation of mutated strains.

The marine protist wild type strain of ONC-T18 was chosen as a model system to test if zeocin would be effective to induce mutagenesis in this strain. One full loop of the inocula of ONC-T18, growing in the agar plates containing ONC-T18-GM0 medium [5 g/L yeast extract, 5 g/L peptone, 10 g/L D(+)-glucose. 35 g/L artificial sea salt, 1.25 mg/L trace elements (5 g/L $NaH_2PO_4.H_2O$, 3.15 g/L $FeCl_3.6H_2O$, 4.36 g/L $Na_2EDTA.2H_2O$, 0.6125 mg/L $CuSO_4.5H_2O$, 0.0597 g/L $Na_2MoO_4.2H_2O$, 0.022 g/L $ZnSO_4.7H_2O$, 0.01 g/L $CoCl_2.6H_2O$, 0.18 g/L $MnCl_2.4H_2O$, 13 µg/L $H_2SeO_3$, 2.7 mg/L $NiSO_4.6H_2O$, 1.84 mg/L $Na_3VO_4$ and 1.94 mg/L $K_2CrO_4$). 1.25 mg/L vitamins (1 mg/L vitamin B12, 1 mg/L biotin, 0.20 g/L thiamine HCl) and 20 g agar per liter], was inoculated into 50 mL liquid ONC-T18-GM0 medium, and incubated in a shaker incubator at 25° C. at 250 rpm for 36 hours. Half a milliliter of culture was transferred into a 1.5 mL tube and vortexed at full speed for 30 seconds, and then diluted in 50 mL sterilized water. One hundred microliters of the diluted inocula were respectively spread on the agar plates containing zeocin at various concentrations (0, 10, 30, 50, and 100 µg/mL). Plates were incubated at 25° C. incubator. The emergence and development of the colonies were observed daily. Six days post inoculation, the sizes of the colonies growing at 10 µg/mL zeocin were similar to that at 0 g/mL zeocin, and gradually decreased at 30 to 50 µg/mL zeocin. The colony numbers per plate also were gradually reduced at 10, 30, and 50 µg/mL zeocin. Only a few of colonies were seen at 50 µg/mL zeocin. Remarkably, colony sectors with various visible colony-morphology changes were observed in some of the colonies growing at 50 µg/mL zeocin, but were not observed in the colonies growing at lower concentration or without zeocin, indicating that zeocin indeed is an effective mutagen agent for Thraustochytrid stains. Under these conditions, zeocin was effective within the range of at least 10-200 µg/mL; higher concentrations may well also be effective. For example, concentrations in the range of 200-500 µg/mL or higher could work. In some cases, higher concentrations of zeocin are used when salt concentrations are also increased to counteract possible degradation of zeocin from salt. Under the particular conditions utilized in the present Example, zeocin worked best at 50 µg/mL.

Example 4: Nucleic Acid Constructs

This example describes the construction of the Thraustochytrid-specific gene expression vectors. The present disclosure therefore provides, among other things, vectors comprising *Thraustochytrium* genes, promoters and/or terminators operatively linked to a heterologous gene (e.g., so that the promoter is upstream of the gene and the terminator is downstream). Such vectors include, for example, one or more replication origins, and one or more detectable or selectable markers. The present disclosure therefore provides, among other things, vectors comprising a *Thraustochytrium* promoter operatively linked to a heterologous gene. In some embodiments, such vectors include, for example, a terminator, one or more replication origins, and one or more detectable or selectable markers.

Figure 2:
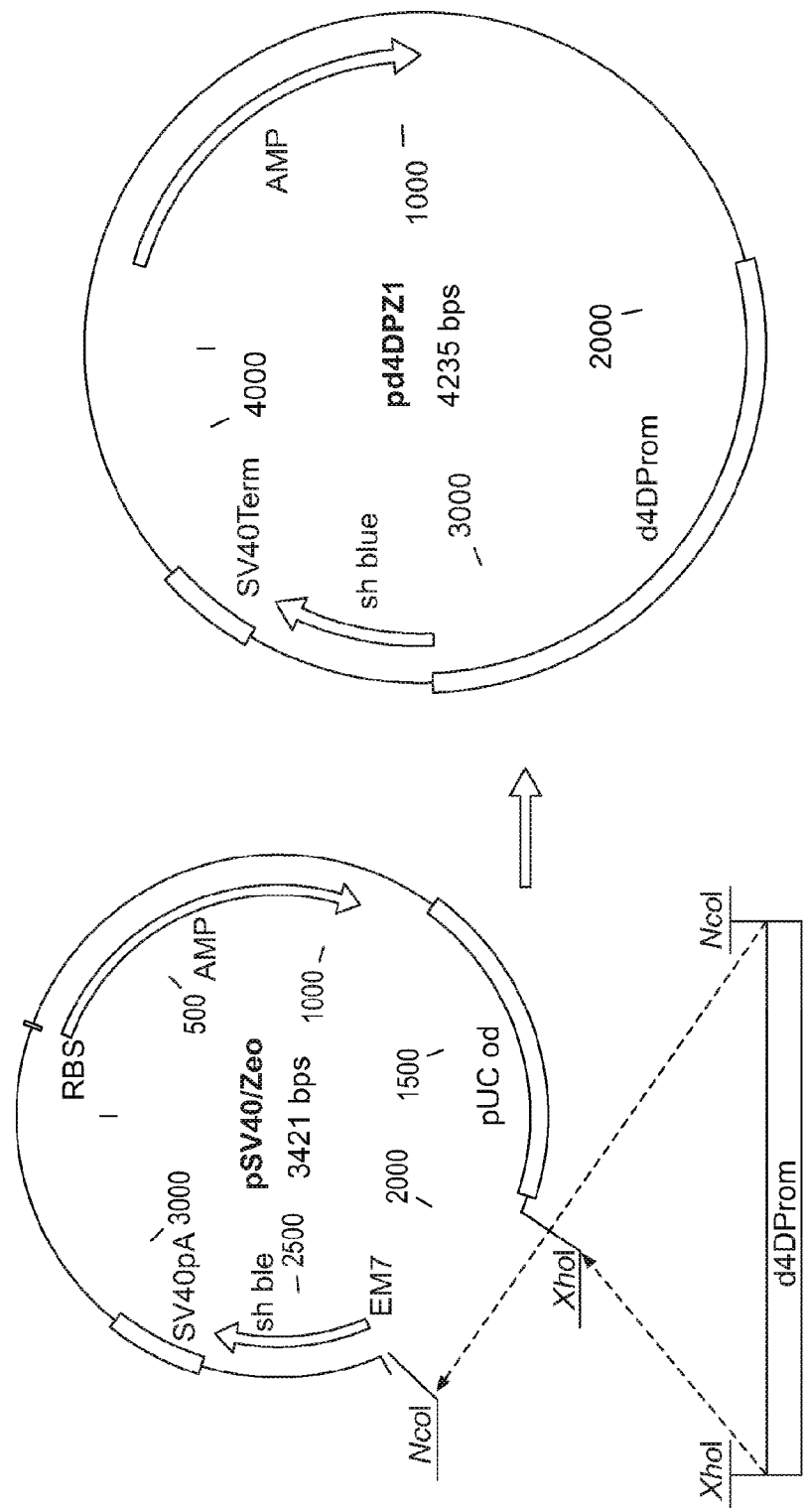
FIG. 2 is a schematic representation of the generation of the gene expression vector pd4DPZ1.
Figure 3:
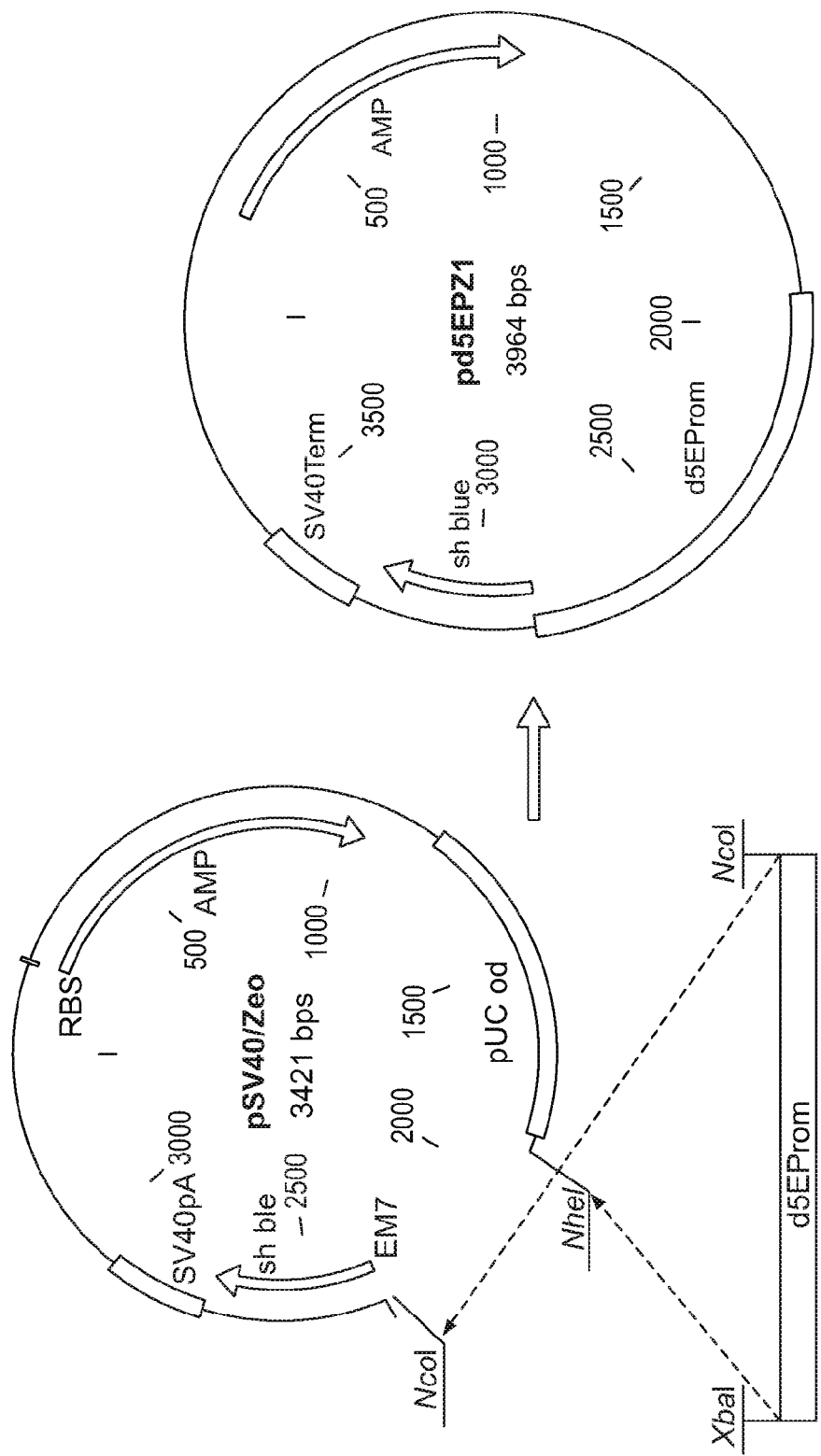
FIG. 3 is a schematic representation of the generation of the gene expression vector pd5EPZ1.

1. Generation of the Recombinant Plasmid Vectors pD4DPZ1 (SEQ ID NO:30; FIG. 2) and pE5PZ1 (SEQ ID NO:31; FIG. 3).

Promoter DNA fragments of the Δ4 desaturase and Δ5 elongase genes of ONC-T18 were amplified with PCR using the genomic DNA of ONC-T18 as the template and TaKaRa LA Taq™ DNA polymerase (Takara Bio Inc., Shiga, Japan). Primer #1 (SEQ ID NO: 25) bearing the restriction enzyme site XhoI at its 5'-end, and primer #2 (SEQ ID NO: 26) embracing the restriction enzyme site NcoI at its 5'-end were utilized for the amplification of the Δ4 desaturase gene promoter (SEQ ID NO:24). Primer #3 (SEQ ID NO: 20) bearing the restriction enzyme site XbaI at its 5'-end and primer #4 (SEQ ID NO: 21) containing the restriction enzyme site NcoI at its 5'-end were employed for the amplification of the Δ5 elongase promoter (SEQ ID NO:19). PCR reactions were carried out in a volume of 50 µL reaction mix containing 2.5 units TaKaRa LA Taq™ DNA Polymerase (Takara Bio Inc., Shiga, Japan), 1×LA PCR Buffer II. dNTP Mixture (0.40 mM each), 225 ηg of the genomic DNA template, 0.20 µM primers [primer pairs, #1 (SEQ ID NO: 25) and #2 (SEQ ID NO: 26) for amplification of the Δ4 desaturase gene promoter, and #3 (SEQ ID NO: 20) and #4 (SEQ ID NO: 21) for amplification of the Δ5 elongase promoter] under the following conditions: 94° C.

for 30 seconds for one cycle, 98° C. for 10 seconds and 55° C. for 5 seconds, 72° C. for 2 minutes for 30 cycles.

The PCR products were precipitated following these procedures: added nuclease-free ddH$_2$O to a total volume 200 µL, then added 20 µL 3M NaAc (pH 5.2) and 440 µL 100% ethanol and mixed by briefly vortexing, incubated in ice for 1 hours, centrifuged at full speed with a desktop centrifuge for 10 minutes, discarded the supernatant, added 500 µL 75% ethanol and centrifuged for 2 minutes at full speed, discarded the supernatant and vacuum-dried the DNA pellets for about 10 minutes. The PCR products of the Δ4 desaturase gene promoter were digested with restriction enzymes NcoI (10 units) and XhoI (10 units) in a volume of 25 µL reaction mixture containing 1× NEBuffer 2 and 1×BSA; (New England Biolabs, Ipswich, Mass., USA) at 37° C. for 2 hours. PCR products of the Δ5 elongase gene promoter were digested with restriction enzymes NcoI (10 units) and XbaI (10 units) in the same conditions. The digested PCR products were resolved in 0.8% agarose gel for electrophoresis at 88 voltages for 45 minutes. The DNA bands of the PCR products were cut out with a razor blade from the agarose gel and the DNAs were extracted and purified with QIAquick Gel Extraction Kit (Qiagen, Valencia, Calif.) as per the manufacturer's protocol. The resulting 0.4 desaturase gene promoter DNA fragment with the enzyme-specific sticky ends was ligated into the corresponding restriction sites NcoI and XhoI of the vector pSV40/Zeo2 digested with the same restriction enzymes and agarose-gel-purified, to yield the vector pD4DPZ1 (SEQ ID NO:30; FIG. 2). The resulting Δ5 elongase gene promoter DNA fragment with the enzyme-specific sticky ends, was ligated into the restriction sites of the vector pSV40/Zeo2 (Invitrogen Corporation, California) digested with NcoI and NheI restriction enzymes and agarose-gel-purified, to yield the vector pE5PZ1 (SEQ ID NO:31; FIG. 3). The ligation reactions were carried out in a volume of 10 µL reaction mix containing 1× ligation buffer, the insert and vector DNAs (3:1 molar ratio) and 0.5 unit T4 DNA ligase (Invitrogen, California) at the ambient temperature for 12 hours. Then the ligated DNAs were transformed into the *E. coli* Top10 competent cells (Invitrogen Corporation, California). The plasmid DNAs of three colonies of the transformants were isolated from 3 mL bacterial cultures using Zyppy™ Plasmid Miniprep Kit (Zymo Research Corp., Orange, Calif.). The integrity of the clones was preliminarily tested with restriction enzyme digestions using enzymes XhoI and NotI for Δ5 elongase gene promoter construct, and enzymes NcoI and XhoI for Δ4 desaturase gene promoter construct. The inserts of the preliminarily identified positive clones JZ1-57-1 of Δ4 desaturase gene promoter vector, and JZ1-57-7 of Δ5 elongase gene promoter vector were thoroughly sequenced using the primer #14 (SEQ ID NO:22) and primer #15 (SEQ ID NO:23). The resulting vector pD4DPZ1 (SEQ ID NO: 30; FIG. 2) contains the ble gene from *Streptoalloteichus hidustanus*, flanked by Δ4 desaturase gene promoter of ONC-T18 and the SV40 terminator. The resulting vector pE5PZ1 (SEQ ID NO:31; FIG. 3) also contains the ble gene flanked by Δ5 elongase gene promoter of ONC-T18 and the SV40 terminator.

The present disclosure therefore provides, among other things, vectors comprising a *Thraustochytrium* promoter operatively linked to a heterologous gene. Such vectors include, for example, a terminator, one or more replication origins, and one or more detectable or selectable markers.

Figure 4:
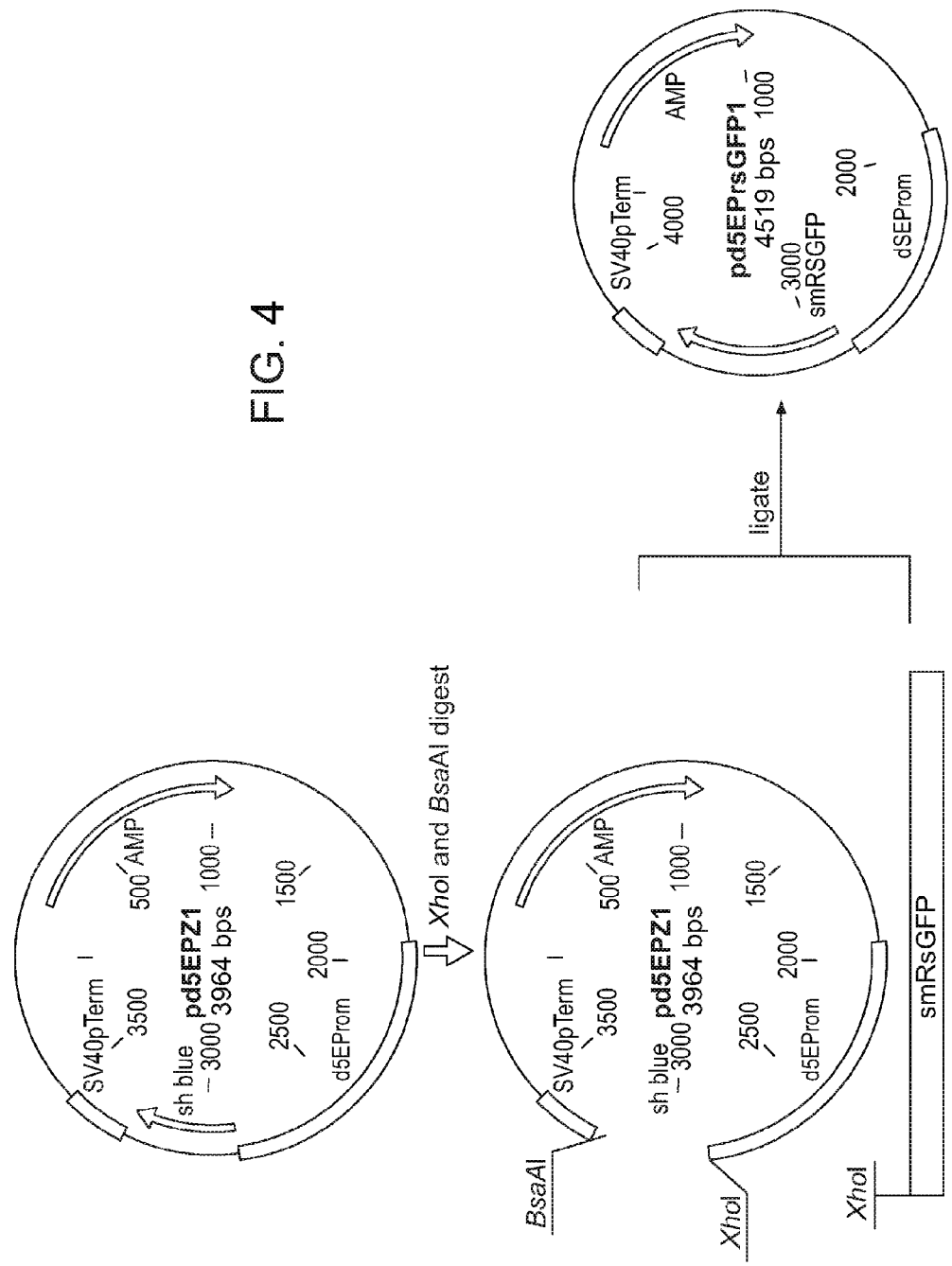
FIG. 4 is a schematic representation of the generation of the gene expression vector pd5EPrsGFP1 as well as the constructs of the intermediate plasmid produced by the processes.

2. Generation of Green Fluorescent Protein (GFP) Marker Gene Expression Vector (SEQ ID NO:32; FIG. 4).

For preparing the template plasmid DNA of GFP gene, the bacterial stock of *E. coli* containing the plasmid pCD3-327 [GenBank accession No. U70496; (Davis and Vierstra, 1998)] was purchased from the *Arabidopsis* Deposit Center (Ohio, USA). The bacteria were streaked in the LB agar plate containing 100 µg/mL ampicillin. A single colony was inoculated in 3 mL LB medium containing 100 µg/mL ampicillin and grown overnight. The plasmid DNA from the cultured bacteria was isolated using Ultraclean Microbial Miniprep DNA Isolation kit (MO BIO Laboratories, Inc, Solana Beach, Calif.) as per the manufacturer's protocol.

The GFP gene DNA fragment was amplified with PCR using TaKaRa PrimeStar Taq™ DNA Polymerase (Takara Bio Inc., Shiga, Japan), the template plasmid pCD3-327 DNA and primer pairs #5 (SEQ ID NO:33) bearing the restriction enzyme site XhoI at its 5'-end and #6 (SEQ ID NO:34). Then the PCR products were precipitated with ethanol and digested with restriction enzyme XhoI and gel-purified. The gel-purified DNA was ligated into the restriction enzyme sites XhoI and BsaAI of the backbone of the vector pE5PZ1 plasmid DNA (SEQ ID NO:31; FIG. 3) digested with XhoI and BsaAI enzymes and gel purified, to replace the ble gene with the green fluorescent protein (GFP) marker gene and yield the expression vector pE5PRsGFP1 (SEQ ID NO:32; FIG. 4) in which the GFP gene is flanked by Δ5 elongase gene promoter of ONC-T18 and the SV40 terminator. As shown in FIG. 4, an AMP resistance gene provided positive selection of transformed clones.

The present disclosure therefore provides, among other things, vectors comprising a *Thraustochytrium* promoter operatively linked to a heterologous gene. In some embodiments, such vectors include, for example, a terminator, one or more replication origins, and one or more detectable or selectable markers. In light of the description provided herein of a plurality of such vectors, and sequence information with regard to certain elements such as promoters and/or terminators sufficient to permit linkage of elements (e.g., promoters, terminators) having such sequences to other elements, those of ordinary skill in the art, reading the present disclosure, would be well enabled to make and use a wide range of different individual vector constructs, for example by combining provided sequences with any of a variety of known other elements, often according to known techniques.

Figure 5:
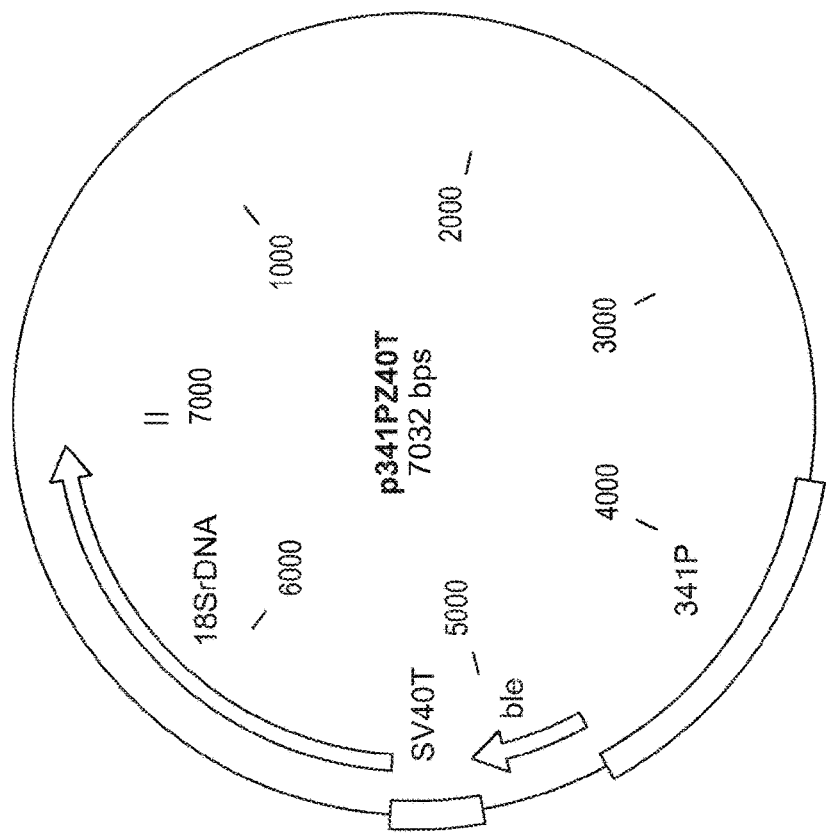
FIG. 5 is a schematic illustration of the generation of the gene expression vector p341PZ40T.

3. Generation of the Recombinant Plasmid Vectors p341PZ40T (SEQ ID NO:35; FIG. 5).

To construct the vector p341PZ40T (SEQ ID NO:35; FIG. 5) which contains the ble gene from *Streptoalloteichus hidustanus*, flanked by the tubulin gene promoter #341 of ONC-T18 and SV40 terminator, the DNA fragment of the tubulin gene promoter #341 was amplified with PCR using the primer pairs #66 (SEQ ID NO:36) and #67 (SEQ ID NO:37), and the template plasmid DNA of the clone JZ2-17-14 described in Example 1. The 5'-end sequence of primer #66 (SEQ ID NO:36) is complementary to a small region of an intermediate vector derived from vector pT7Blue-3 (Novagen, Gibbstown, N.J., USA), and its 3'-end is complementary to the minus-strand of the 5'-end of the tubulin gene promoter #341 of ONC-T18. The 5'-end sequence of primer #67 (SEQ ID NO:37) is complementary to the plus-strand of the 5'-end sequence of the open reading frame of the ble gene and its 3'-end is complementary to the plus-strand of the 3'-end of the tubulin gene promoter #341 of ONC-T18.

The DNA fragment of the ble gene ORF including SV40 terminator located at its 3'-end was also amplified with PCR using the primer pairs #68 (SEQ ID NO:38) and #71 (SEQ ID NO:39), and the plasmid template DNA of the vector pSV40/Zeo2 (Invitrogen, California). The 5'-end sequence of primer #68 (SEQ ID NO:38) is complementary to the minus-strand of the 3'-end sequence of the tubulin gene promoter #341 of ONC-T18 and its 3'-end sequence is complementary to the minus-strand of the 5'-end of the ble gene ORF. The 5'-end sequence of primer #71 (SEQ ID NO:39) is complementary to a small region of an intermediate vector derived from vector pT7Blue-3 and its 3'-end sequence is complementary to the plus-strand of the 3'-end sequence of SV40 terminator.

The PCR reactions were carried out in a volume of 50 μL reaction mix containing 2.5 units TaKaRa PrimeStar Taq™ DNA Polymerase (Takara Bio Inc., Shiga, Japan). 1× PrimerStar PCR Buffer, dNTP Mixture (0.40 mM each), 1 ηg of the template plasmid DNA, 0.20 μM of each primer of the primer pairs. The PCR conditions, 98° C. for 10 seconds and 55° C. for 5 seconds and 72° C. for 2 minutes, for 30 cycles, were employed. The PCR products of the tubulin gene promoter #341 and ble gene ORF were resolved in 0.8% agarose gel for electrophoresis at 65 voltages for 60 minutes. The bands with the right sizes were cut out with a razor blade and their DNAs were extracted and purified with QIAquick Gel Extraction Kit (Qiagen, Valencia, Calif.) as per manufacturer's protocol. Then the gel-purified PCR products were mixed in similar molar ratios, which were used as the DNA templates for the extension PCR to fuse the tubulin gene promoter #341, the ble gene ORF including SV40 terminator together (Higuchi, Krummel, and Saiki, 1988, Zhang, Wege, and Jeske, 2001). The extension PCR was carried out in a volume of 50 μL reaction mix using TaKaRa PrimeStar Taq™ DNA Polymerase (Takara Bio Inc., Shiga, Japan), ~100 ng of the template DNA of the mixed PCR products, and the primer pairs #66 (SEQ ID NO:36) and #71 (SEQ ID NO:39) (0.20 μM each). The PCR conditions, 98° C. for 10 seconds, 50° C. for 5 minutes and 72° C. for 3 minutes for 6 cycles; and 98° C. for 10 seconds, 50° C. for 5 seconds and 72° C. for 3 and a half minutes for 25 cycles, were employed. The PCR product containing ONC-T18-specific ble gene expression cassette was gel purified with QIAquick Gel Extraction Kit (Qiagen, Valencia, Calif.) as per manufacturer's protocol, and cloned into an intermediate vector derived from vector pT7Blue-3 (Novagen, Gibbstown, N.J., USA) using extension PCR (Higuchi, Krummel, and Saiki, 1988; Zhang, Wege, and Jeske, 2001). The extension PCR was carried out in a volume of 50 μL PCR reaction mix containing 2.5 units TaKaRa PrimeStar Taq™ DNA Polymerase (Takara Bio Inc., Shiga, Japan). 1× PrimerStar PCR Buffer, dNTP Mixture (0.40 mM each), 200 ng DNA of the gel purified PCR product containing the ONC-T18-specific ble gene expression cassette and 600 ng plasmid DNA of an intermediate vector linearized with the restriction enzyme HindIII. The PCR conditions, 98° C. for 10 seconds, 60° C. for 5 seconds and 72° C. for 5 and a half minutes for 30 cycles, were employed. Afterward the template plasmid DNA was destroyed by the restriction enzyme digestion of DpnI which specifically digested the methylated plasmid DNA isolated from some bacterial strains. This digestion was carried out in a reaction volume of 150 μL containing 50 μL extension PCR products, 30 unit DpnI and 1× restriction enzyme reaction buffer 4 (New England Biolabs, Ipswich, Mass., USA) at 37° C. for 2 hours. After digestion, the DpnI enzyme was inactivated by incubation at 80° C. for 20 minutes. Then added sterilized water in the digestion mixture up to 350 μL and further desalted and concentrated the DNA to ~100 ng/μL using the column Microcon (YM-100, Millipore Corporate, Billerica, Mass.).

One μL of the desalted DNA was used to transform the Top10 E. coli competent cells (Invitrogen, California, USA) using the electroporator (Eppendorf 5210) set up at 1890 voltages as well as the electroporation cuvettes of 1 mm gap (Eppendorf, NY, USA). Positive colonies were preliminarily screened with the direct colony PCR as described in Example 1 using the primer pairs #64 (SEQ ID NO:40) and #65 (SEQ ID NO:41). The insert of the positive clone JZ2-53-10 was completely sequenced using forward and reverse primers as well as internal primers #15 (SEQ ID NO:23), #16 (SEQ ID NO:42), #54 (SEQ ID NO: 7). #64 (SEQ ID NO:40). #65 (SEQ ID NO:41) and #85 (SEQ ID NO:43). The resulting sequences were assembled and analyzed using bioinformatics software package Kodon (Applied Maths) and the integrity of the cloned insert was confirmed. The resulting ble gene expression vector was named p341PZST (SEQ ID NO:35; FIG. 5), in which the ble gene is flanked by the tubulin gene promoter #341 of ONC-T18 and SV40 terminator.

Figure 6:
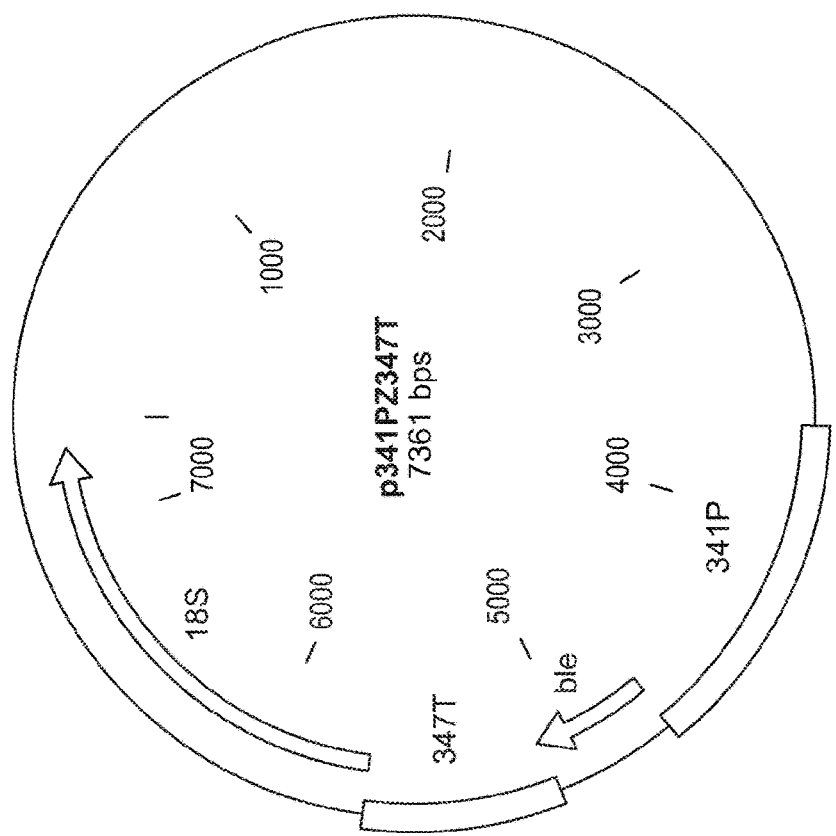
FIG. 6 is a schematic illustration of the generation of the gene expression vector p341PZ347T.

4. Generation of the Recombinant Plasmid Vectors p341PZ347T (SEQ ID NO:44; FIG. 6).

To construct the vector p341PZ347T (SEQ ID NO:44; FIG. 6) which contains the ble gene from Streptoalloteichus hidustanus, flanked by the tubulin gene promoter #341 and a tubulin gene terminator #347 of ONC-T18, the DNA fragment of the tubulin gene promoter #341 was amplified with PCR using the primer pairs #66 (SEQ ID NO:36) and #67 (SEQ ID NO:37), and the template plasmid DNA of the clone JZ2-17-14 described in Example 1.

The DNA fragment of the ble gene ORF was also amplified with PCR using primer pairs #68 (SEQ ID NO:38) and #72 (SEQ ID NO:45), and the plasmid template DNA of vector pSV40/Zeo2 (Invitrogen, California). The 5'-end sequence of primer #72 (SEQ ID NO:45) is complementary to the plus-strand of the 5'-end sequence of the tubulin gene terminator #347.

The DNA fragment of the tubulin gene terminator #347 was amplified with PCR using primer pairs #73 (SEQ ID NO:46) and #74 (SEQ ID NO:47), and the template plasmid DNA of clone JZ2-17-22, described in Example 1. The 5'-end sequence of the primer #73 (SEQ ID NO:46) is complementary to the minus-strand of the 3'-end sequence of the open reading frame of the ble gene and its 3'-end is complementary to the minus-strand of the 5'-end of the tubulin gene terminator #347 of ONC-T18. The 5'-end sequence of the primer #74 (SEQ ID NO:47) is complementary to a small region of an intermediate vector derived from the vector pT7Blue-3 and its 3'-end is complementary to the plus-strand of the 3'-end of the Thraustochytrium sp. tubulin gene terminator #347.

The PCRs were carried out exactly as described in Example 2, section 3. The PCR products were gel purified with QIAquick Gel Extraction Kit (Qiagen. Valencia, Calif.) as per manufacturer's protocol. The gel-purified PCR products of the tubulin gene promoter #341, ble gene ORF and tubulin gene terminator #347, were mixed in similar molar ratios, which were used as DNA templates for the extension PCR to fuse the tubulin gene promoter #341, the ble gene ORF and the tubulin gene terminator #347 together. The extension PCR was carried out using primer pairs #66 (SEQ ID NO: 36) and #74 (SEQ ID NO: 47), 0.20 μM each, as described in Example 2, section 3. The fusion PCR product was gel purified with the QIAquick Gel Extraction Kit (Qiagen, Valencia, Calif.) as per manufacturer's protocol, and cloned into an intermediate vector derived from vector pT7blue-3 using extension PCR as described in Example 2, section 3. The extension PCR products were transformed into Top10 *E. coli* competent cells (Invitrogen, California, USA) with electroporation. The positive colonies were initially screened with colony PCR method using primer pairs #64 (SEQ ID NO: 40) and #65 (SEQ ID NO:41), primer pairs #16 (SEQ ID NO:42) and #59 (SEQ ID NO:12), and primer pairs #54 (SEQ ID NO:7) and #15 (SEQ ID NO:23). The insert of the positive clone JZ2-69-2a was completely sequenced using forward and reverse primers as well as internal primers #15 (SEQ ID NO:23), #16 (SEQ ID NO:42), #54 (SEQ ID NO: 7), #59 (SEQ ID NO:12), #63 (SEQ ID NO:4), #64 (SEQ ID NO:40), #65 (SEQ ID NO:41), and #85 (SEQ ID NO: 43). The resulting sequences were assembled and analyzed using bioinformatics software package Kodon (Applied Maths) and the integrity of the cloned insert was confirmed. The resulting ble gene expression vector was named to p341PZ347T (SEQ ID NO:44; FIG. 6) in which the ble gene is flanked by the tubulin gene promoter #341 of ONC-T18 and terminator #347.

The present disclosure therefore provides, among other things, vectors comprising *Thraustochytrium* promoters and terminators operatively linked to a heterologous gene (e.g., so that the promoter is upstream of the gene and the terminator is downstream). In some embodiments, such vectors include, for example, one or more replication origins, and one or more detectable or selectable markers. The present disclosure therefore provides, among other things, vectors comprising a *Thraustochytrium* promoter operatively linked to a heterologous gene. In some embodiments, such vectors include, for example, a terminator, one or more replication origins, and one or more detectable or selectable markers.

Figure 7:
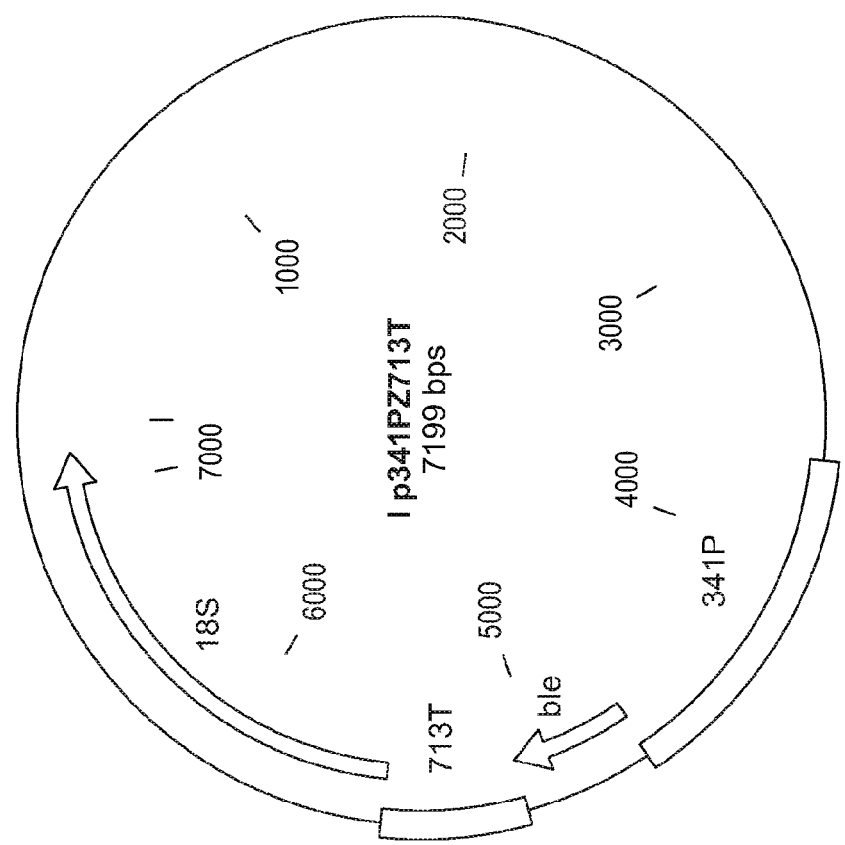
FIG. 7 is a schematic illustration of the generation of the gene expression vector p341PZ713T.

5. Generation of the Recombinant Plasmid Vector p341P713T (SEQ ID NO:48; FIG. 7).

To construct vector p341PZ713T (SEQ ID NO:48; FIG. 7) which contains the ble gene from *S. hidustanus*, flanked by tubulin gene promoter #341 and tubulin gene terminator #713 of ONC-T18, the DNA fragment of tubulin gene promoter #341 was amplified with PCR using primer pair #66 (SEQ ID NO:36) and #67 (SEQ ID NO:37), and the template plasmid DNA of the clone JZ2-17-14 described in Example 1.

The DNA fragment of the ble gene ORF was amplified with PCR using primer pair #68 (SEQ ID NO:38) and #75 (SEQ ID NO:49), and the plasmid template DNA of the vector pSV40/Zeo2 (Invitrogen, California). The 5'-end sequence of the primer #75 (SEQ ID NO:49) is complementary to the plus-strand of the 5'-end sequence of the tubulin gene terminator #713.

The DNA fragment of tubulin gene terminator #713 was amplified with PCR using the primer pair #76 (SEQ ID NO:50) and #77 (SEQ ID NO:51), and the template plasmid DNA of the clone JZ2-22-9 described in Example 1. The 5'-end sequence of the primer #76 (SEQ ID NO:50) is complementary to the minus-strand of the 3'-end sequence of the ble gene ORF and its 3'-end complementary to the minus-strand of the 5'-end of tubulin gene terminator #713 ONC-T18. The 5'-end sequence of the primer #77 (SEQ ID NO:51) is complementary to a small region of an intermediate vector derived from vector pT7blue-3 and its 3'-end complementary to the plus-strand of the 3'-end of the tubulin gene terminator #713 of ONC-T18.

The PCR products of the tubulin gene promoter #341, ble gene ORF and tubulin gene terminator #713, were gel-purified, mixed in similar molar ratios, and used as the DNA template for extension PCR using the primer pairs #66 (SEQ ID NO:36) and #77 (SEQ ID NO:51) to fuse the tubulin gene promoter #341, the ble gene ORF and tubulin gene terminator #713 together. The fused PCR product was gel purified with QIAquick Gel Extraction Kit (Qiagen, Valencia, Calif.), and cloned into an HindIII-linearized intermediate vector derived from vector pT7blue-3 using a second extension PCR. One microliter (~100 ηg) extension PCR product DNAs were used to transform Top10 *E. coli* competent cells (Invitrogen, California, USA) with electroporation. Positive colonies were initially screened with colony PCR using primer pair #64 (SEQ ID NO:40) and #65 (SEQ ID NO.41), primer pair #16 (SEQ ID NO:42) and #77 (SEQ ID NO:51), and primer pair #54 (SEQ ID NO:7) and #15 (SEQ ID NO:23). The insert of the positive clone JZ2-69-2b was completely sequenced using forward and reverse primers as well as internal primers #15 (SEQ ID NO:23), #16 (SEQ ID NO:42), #54 (SEQ ID NO: 7), #63 (SEQ ID NO:4), #64 (SEQ ID NO:40), #65 (SEQ ID NO:41), and #85 (SEQ ID NO:43). The resulting sequences were assembled and analyzed using bioinformatics software package Kodon (Applied Maths), and the integrity of the cloned insert was confirmed. Resulting ble gene expression vector was named to p341PZ713T (SEQ ID NO: 48; FIG. 7), in which the ble gene is flanked by the tubulin gene promoter #341 and terminator #713 of ONC-T18.

The present disclosure therefore provides, among other things, vectors comprising *Thraustochytrium* promoters and terminators operatively linked to a heterologous gene (e.g., so that the promoter is upstream of the gene and the terminator is downstream). In some embodiments, such vectors include, for example, one or more replication origins, and one or more detectable or selectable markers. The present disclosure therefore provides, among other things, vectors comprising a *Thraustochytrium* promoter operatively linked to a heterologous gene. In some embodiments, such vectors include, for example, a terminator, one or more replication origins, and one or more detectable or selectable markers. In light of the description provided herein of a plurality of such vectors, and sequence information with regard to certain elements such as promoters and/or terminators sufficient to permit linkage of elements (e.g., promoters, terminators) having such sequences to other elements, those of ordinary skill in the art, reading the present disclosure, would be well enabled to make and use a wide range of different individual vector constructs, for example by combining provided sequences with any of a variety of known other elements, often according to known techniques.

Figure 8:
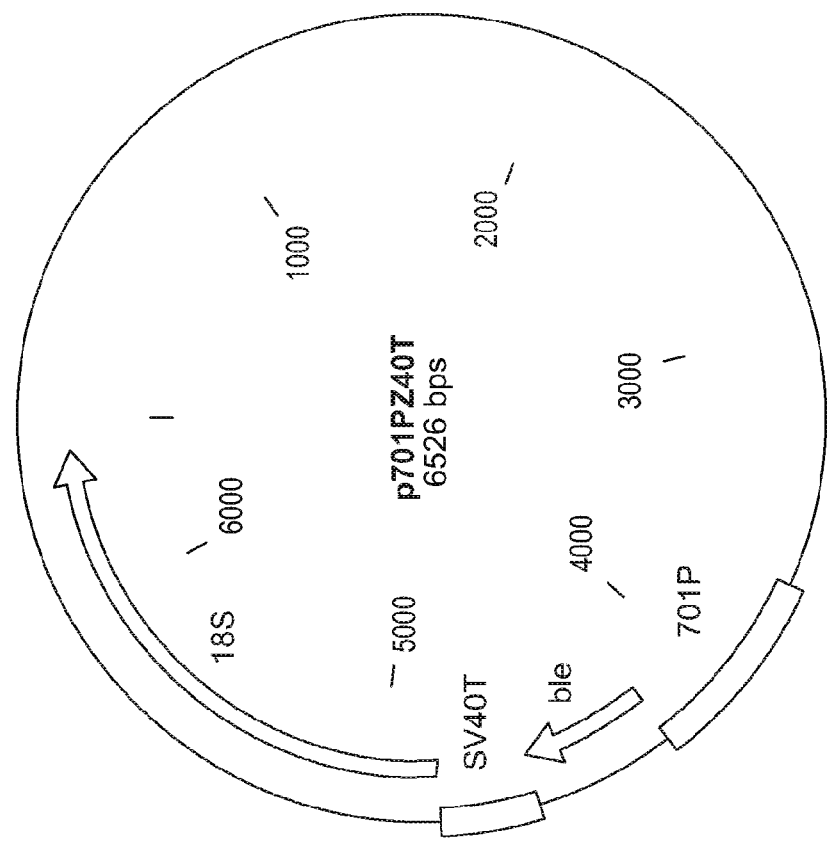
FIG. 8 is a schematic illustration of the generation of the gene expression vector p701PZ40T.

6. Generation of the Recombinant Plasmid Vector p701PZ40T (SEQ ID NO:52; FIG. 8).

To construct the vector p701PZ40T (SEQ ID NO:52; FIG. 8) which contains the ble gene from *S. hidustanus*, flanked by the tubulin gene promoter #701 of ONC-T18 and SV40 terminator, the DNA fragment of tubulin gene promoter #701 was amplified with PCR using the primer pair #87 (SEQ ID NO:53) and #88 (SEQ ID NO:54), and the template plasmid DNA of the clone JZ2-17-10 described in Example 1. The 5'-end sequence of primer #87 (SEQ ID NO: 48) is complementary to a small region of vector p341PZ40T and its 3'-end complements to the minus-strand of the 5'-end sequence of the tubulin gene promoter #701. The 5'-end sequence of primer #88 (SEQ ID NO: 54), is complementary to the plus-strand of the 5'-end sequence of the ble gene ORF and its 3'-end matches the plus-strand of the 3'-end of the tubulin gene terminator #701. The PCR product was gel purified and cloned into the vector of p341 PZ40T to replace the tubulin gene promoter #341 using extension PCR (Higuchi et al., 1988; Zhang et al., 2001). TaKaRa PrimeStar Taq™ DNA polymerase, 200 ng DNA of the gel purified PCR products and 600 ng BglII-linearized plasmid DNA of vector p341PZ40T, were used in the extension PCR. One microliter (~100 ηg) extension PCR product DNAs were used to transform Top10 *E. coli* competent cells (Invitrogen, California, USA) with electroporation. Positive colonies were initially screened with colony PCR method using primer pair #52 (SEQ ID NO: 51) and #53 (SEQ ID NO: 52). The insert of the positive clone was completely sequenced using forward and reverse primers as well as internal primers #52 (SEQ ID NO: 1) and #53 (SEQ ID NO: 2), #15 (SEQ ID NO:23), #16 (SEQ ID NO:42), #63 (SEQ ID NO:4), #64 (SEQ ID NO:40), #65 (SEQ ID NO: 41), and #85 (SEQ ID NO: 43). Resulting sequences were assembled and analyzed using bioinformatics software package Kodon (Applied Maths) and the integrity of the cloned insert was confirmed. The resulting ble gene expression vector was named to p701PZ40T (SEQ ID NO: 52; FIG. 7), in which the ble gene is flanked by the tubulin gene promoter #701 of ONC-TI 8 and SV40 terminator.

Figure 9:
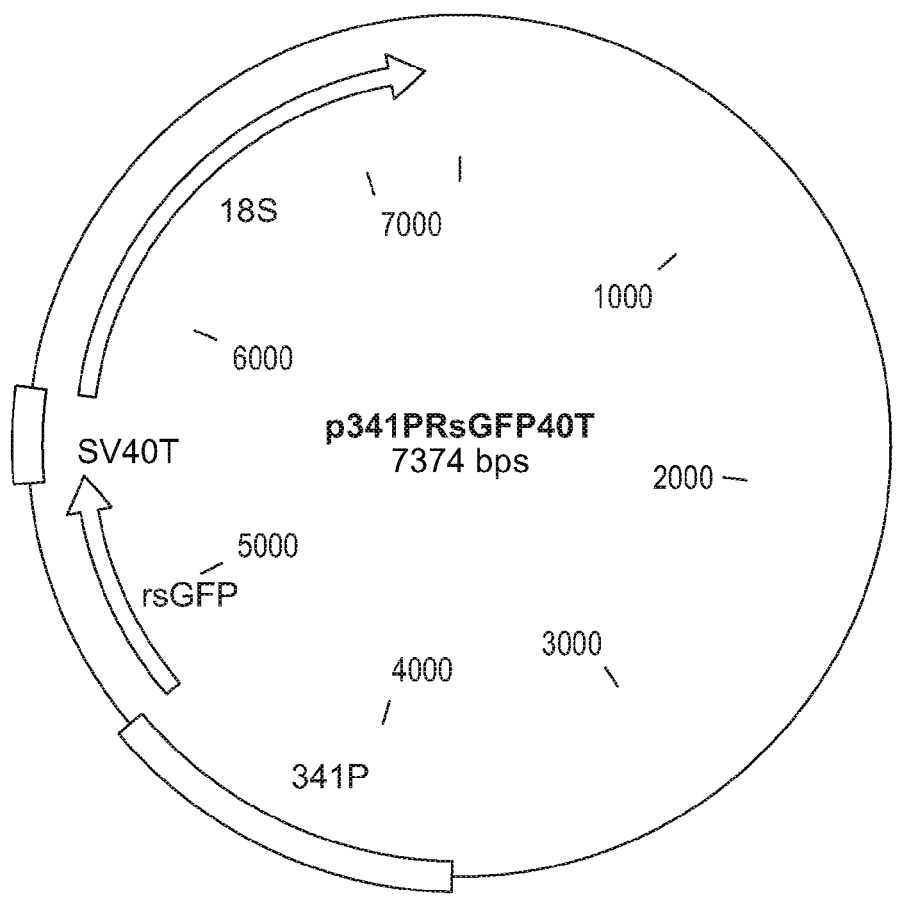
FIG. 9 is a schematic illustration of the generation of the gene expression vector p341PsmRsGFP40T.

7. Generation of the Recombinant Plasmid Vector p341PRsGP40T (SEQ ID NO: 55; FIG. 9).

To construct the vector p341PRsGFP40T (SEQ ID NO:55; FIG. 9) which contains the GFP gene from *Aequorea victoria*, flanked by the tubulin gene promoter #341 of ONC-T18 and SV40 terminator, the DNA fragment of the tubulin gene promoter #341 was amplified with PCR using primer pair #66 (SEQ ID NO: 36) and #78 (SEQ ID NO: 56), and the template plasmid DNA of the clone JZ2-17-14 described in Example 1. The 5'-end sequence of primer #78 (SEQ ID NO: 56) is complementary to the plus-strand of the 5'-end sequence of the GFP gene ORF and its 3'-end matches the plus-strand of the 3'-end of the tubulin gene promoter #341 of ONC-T18.

The DNA fragment of the GFP gene ORF was also amplified with PCR using primer pair #79 (SEQ ID NO: 57) and #80 (SEQ ID NO: 58), and the template plasmid DNA of vector pCD3-327. The 5'-end sequence of the primer #79 (SEQ ID NO: 57) is complementary to the plus-strand of the 3'-end sequence of the tubulin gene promoter #341 of ONC-T18 and its 3'-end sequence matches the minus-strand of the 5'-end of the GFP gene ORF. The 5'-end sequence of the primer #80 (SEQ ID NO: 58) is complementary to the plus-strand of the 5'-end sequence of the SV40 terminator, and its 3'-end matches the plus-strand of the 3'-end sequence of the GFP gene ORF.

The DNA fragment of the SV40 terminator was also amplified with PCR using primer pair #81 (SEQ ID NO: 59) and #71 (SEQ ID NO: 39), and the template plasmid DNA of vector pSV40/Zeo2 (Invitrogen, California). The 5'-end sequence of the primer #81 (SEQ ID NO: 59) is complementary to the minus-strand of the 3'-end sequence of the GFP gene ORF, and its 3'-end sequence matches the 5'-end of SV40 terminator.

The above three PCR products were gel purified, mixed in similar molar ratios, and used as the DNA template for the extension PCR using primer pair #66 (SEQ ID NO:36) and #71 (SEQ ID NO:39) to fuse the tubulin gene promoter #341, GFP gene ORF and SV40 terminator together (Higuchi. Krummel, and Saiki, 1988). The extension PCR product containing the ONC-T18-specific GFP gene expression cassette was gel purified, and cloned into vector p341PZ40T linearized with restriction enzyme HindIII in a second round extension PCR. The second round PCR products were cleaned, desalted, and transformed into Top10 *E. coli* competent cells with electroporation. The positive colonies were screened using direct colony PCR and the primer pair #54 (SEQ ID NO:7) and #86 (SEQ ID NO:60). The insert of the positive clone JZ2-53-20 was completely sequenced using forward and reverse primers as well as internal primers #15 (SEQ ID NO:23), #16 (SEQ ID NO:42), #54 (SEQ ID NO:7), #63 (SEQ ID NO:4), #64 (SEQ ID NO:40), #65 (SEQ ID NO:41), #85 (SEQ ID NO:43), and #86 (SEQ ID NO:60). The resulting sequences were assembled and analyzed using bioinformatics software package Kodon (Applied Maths) and the integrity of the cloned insert was confirmed. The resulting GFP gene expression vector was named to p341PRsGFP40T (SEQ ID NO:55; FIG. 8) in which the GFP gene is flanked by the tubulin gene promoter #341 of ONC-TI 8 and SV40 terminator.

Figure 10:
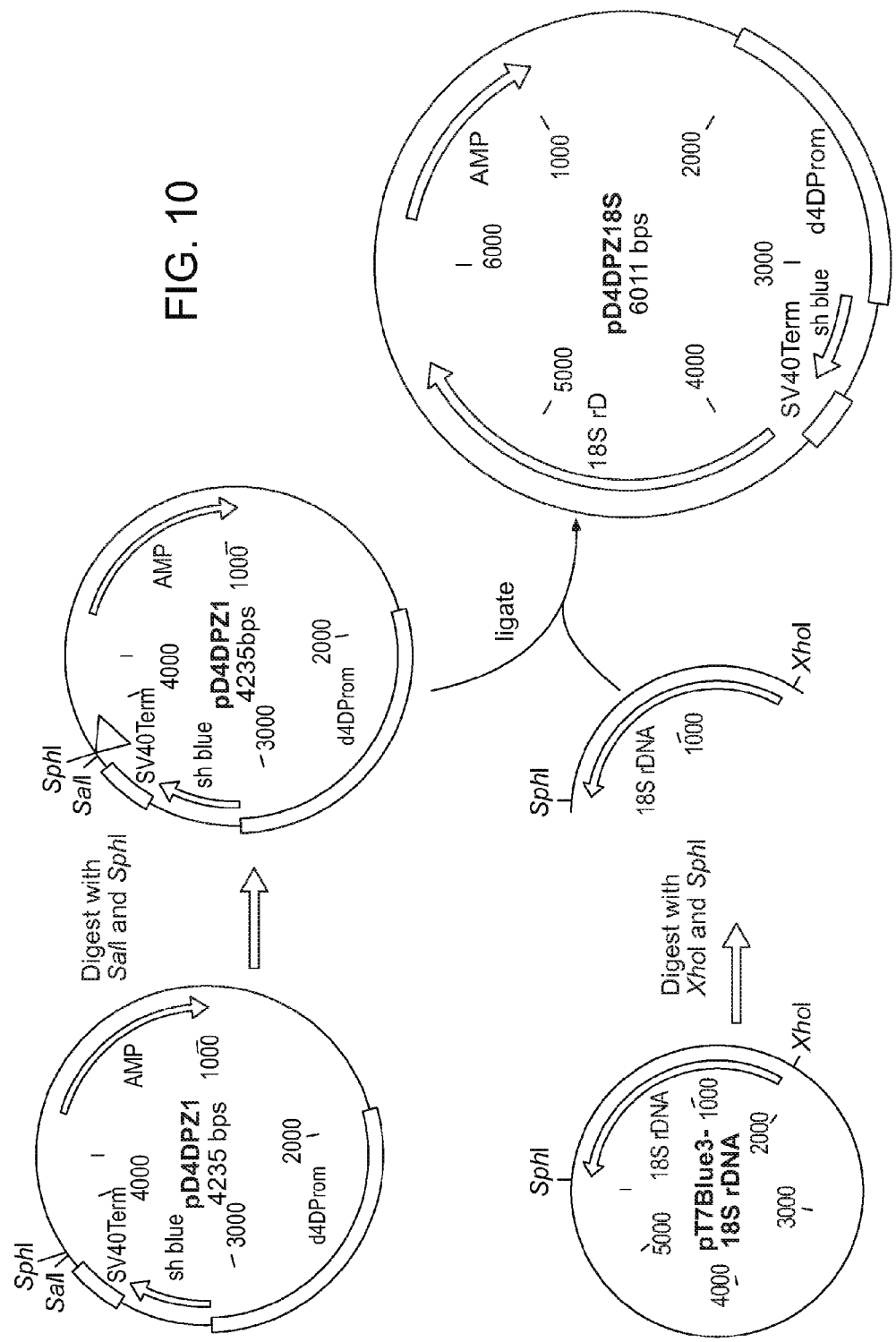
FIG. 10 is a schematic illustration of the generation of the gene expression vector pD4DPZ18S as well as the constructs of the intermediate plasmid produced by the processes.

8. Generation of the Recombinant Plasmid Vector pD4DPZ118S (SEQ ID NO:61; FIG. 10).

To construct pD4DPZ18S (SEQ ID NO:61; FIG. 10) vector, the plasmid DNA of vector pD4DPZ1 was digested with restriction enzymes SalI and SphI to linearize the vector and then gel purified with QIAquick Gel Extraction Kit (Qiagen, Valencia, Calif.) as per manufacturer's protocol. The 18S rDNA fragment (SEQ ID NO: 29) that was amplified from the genomic DNA of ONC-TI 8 with PCR using primer pair 18SrRNAf (SEQ ID NO: 27) and 18SrRNAr (SEQ ID NO: 28) and cloned into vector pT7Blue-3, was released from the plasmid DNA of the clone JZ2-3-1 by restriction digestion with enzymes XhoI and SphI, then gel purified and ligated into the restriction sites SalI and SphI of the linearized vector of pD4DPZ1, to yield the pD4DPZ18S (SEQ ID NO: 61; FIG. 10) which bears a DNA fragment of the 18S ribosome RNA gene.

Figure 11:
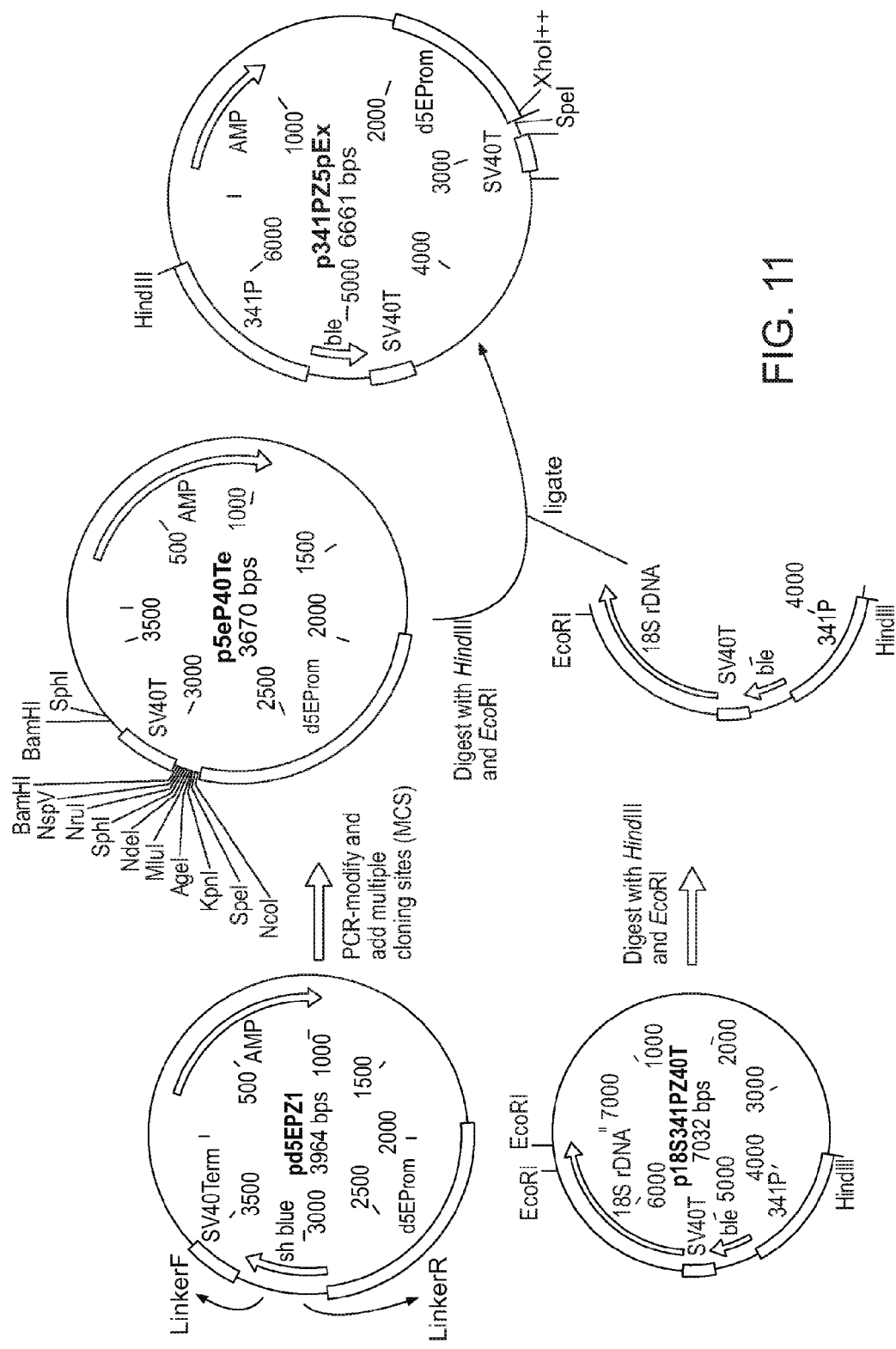
FIG. 11 is a schematic representation of the generation of the gene expression vector p341PZSEpEx and the constructs of the intermediate plasmids produced by the processes.

9. Generation of the Recombinant Plasmid Vector p341PZ5pEx (SEQ ID NO:62; FIG. 11).

To construct the vector p341PZ5pEx for the over-expression of homologous and heterogenous genes (e.g., Δ12 desaturase), the zeocin resistance gene expression vector pd5EPPZ1 was modified with PCR using primers LinkerF (SEQ ID NO:63) and LinkerR (SEQ ID NO:64) to replace the zeocin resistance gene ORF with multiple cloning sites including endonuclease restriction sites (NcoI, SpeI, KpnI, MluI, NdeI, SphI, NruI, BstBI and BamHI). After PCR, the template plasmid DNA was destroyed using the endonuclease restriction enzyme DpnI. The PCR product was precipitated and digested with endonuclease restriction enzyme MluI, gel-purified, re-ligated together with T4 DNA ligase (Invitrogen, California) and then transformed into Top10 *E. coli* cells. The preliminary screening of the positive clones was carried out using restriction digestions. The integrity of positive clones was confirmed with DNA sequencing and named as the plasmid p5eEP40T (SEQ ID NO: 65). The plasmid DNA of the positive clone was digested with the endonuclease restriction enzymes HindIII and EcoRI and the backbone plasmid DNA was gel purified. The zeocin resistance gene expression cassette in which the zeocin gene ORF is flanked by the tubulin gene promoter #341P and SV40 terminator, was also isolated and gel-purified from vector p18S341PZ40t digested with the same endonuclease restriction enzymes HindIII and EcoRI. The zeocin resistance gene expression cassette was then ligated into the corresponding endonuclease restriction sites HindIII and EcoRI of the plasmid p5eEP40T, resulting in the gene expression vector p341 PZ5pEx.

10. Generation of the Recombinant Plasmid Vectors pD12DPZ1 and pD5DPZ1.

Promoter DNA fragments (approximately 2 kilobases 5-prime of the gene ORFs) of the Δ12 and Δ5 desaturase genes of ONC-T18 are amplified with PCR using the genomic DNA of ONC-T18 as the template and TaKaRa LA Taq™ DNA polymerase (TAKARA BIO INC., Shiga, Japan). An appropriately designed forward PCR primer bearing the restriction enzyme site XhoI at its 5'-end, and a reverse primer embracing the restriction enzyme site NcoI at its 5'-end are utilized for the amplification of the Δ12 desaturase gene promoter. Likewise, an appropriately designed forward bearing the restriction enzyme site XhoI at its 5'-end, and a reverse primer comprising the restriction enzyme site NcoI at its 5'-end are utilized for the amplification of the Δ5 desaturase gene promoter. PCR reactions are carried out in a volume of 50 μL reaction mix containing 2.5 units TaKaRa LA Taq™ DNA Polymerase (Takara Bio Inc., Shiga, Japan), 1×LA PCR Buffer II, dNTP Mixture (0.40 mM each), 225 ng of the genomic DNA template, 0.20 μM primers, under the following conditions: 94° C. for 3 minutes for one cycle, 98° C. for 30 seconds and 55° C. for 30 seconds, 72° C. for 2 minutes for 30 cycles.

The PCR products are precipitated following these procedures: add nuclease-free ddH$_2$O to a total volume 200 μL, then added 20 μL, 3M NaAc (pH 5.2) and 440 μL 100% ethanol and mixed by briefly vortexing, incubated in ice for 1 hours, centrifuged at full speed with a desktop centrifuge for 10 minutes, discarded the supernatant, added 500 μL 75% ethanol and centrifuged for 2 minutes at full speed, discarded the supernatant and vacuum-dried the DNA pellets for about 10 minutes. The PCR products of the Δ12 desaturase gene promoter are digested with restriction enzymes NcoI (10 units) and XhoI (10 units), and the PCR products of the Δ5 desaturase gene promoter are digested with restriction enzymes NcoI (10 units) and XhoI (10 units), in a volume of 25 μL reaction mixture containing 1× NEBuffer 2 and 1×BSA; (New England Biolabs, Ipswich, Mass., USA) at 37° C. for 2 hours. The digested PCR products are resolved in 0.8% agarose gel for electrophoresis at 88 voltages for 45 minutes. The DNA bands of the PCR products are cut out with a razor blade from the agarose gel and the DNAs are extracted and purified with QIAquick Gel Extraction Kit (Qiagen. Valencia, Calif.) as per the manufacturer's protocol. The resulting Δ12 desaturase gene promoter DNA fragment with the enzyme-specific sticky ends is ligated into the corresponding restriction sites NcoI and XhoI of the vector pSV40/Zeo2 digested with the same restriction enzymes and agarose-gel-purified, to yield the vector pD12DPZ1. Likewise, the resulting Δ5 desaturase gene promoter DNA fragment with the enzyme-specific sticky ends is ligated into the corresponding restriction sites NcoI and XhoI of the vector pSV40/Zeo2 digested with the same restriction enzymes and agarose-gel-purified, to yield the vector pD5DPZ1. The ligation reactions are carried out in a volume of 10 μL reaction mix containing 1× ligation buffer, the insert and vector DNAs (3:1 molar ratio) and 0.5 unit T4 DNA ligase (Invitrogen, Calif.) at the ambient temperature for 12 hours. Then the ligated DNAs are transformed into the *E. coli* Top10 competent cells (Invitrogen Corporation. California). The plasmid DNAs of 1-10 colonies of the transformants are isolated from 3 mL bacterial cultures using Zyppy™ Plasmid Miniprep Kit (Zymo Research Corp., Orange, Calif.). The integrity of the clones is preliminarily tested with restriction enzyme digestions using appropriately corresponding enzymes. The resulting vectors, pD12DPZ1 and pD5DPZ1, contain the ble gene from *Streptoalloteichus hidustanus*, flanked by the Δ12 or Δ5 desaturase gene promoter, respectively, of ONC-T18 and the SV40 terminator.

The present disclosure therefore provides, among other things, vectors comprising the *Thraustochytrium* Δ12 and/or Δ5 desaturase promoters operatively linked to a heterologous gene (e.g., Fatty Acid Synthase (FAS) type 1). In some embodiments, such vectors include, for example, a terminator, one or more replication origins, and one or more detectable or selectable markers.

11. Generation of Recombinant Plasmid Vector with Δ12 Desaturase Gene Promoter to Drive Δ5 Desaturase Gene Expression.

The first 2 kilobases of the Δ5 desaturase gene of ONC-T18 plus the promoter region (approximately 2 kilobases 5-prime of the gene ORF) are amplified via PCR using appropriately selected and designed primers to both amplify the sequence and insert restriction digestion sites on the end the amplified sequence. The resulting PCR product is isolated, and purified, then a second round of PCR is conduct with appropriately designed primers to insert a restriction site between the start of the ORF and the promoter. The resulting construct is cloned into a bacterial expression vector using standard techniques.

The isolated sequence of the Δ12 desaturase gene promoter (SEQ ID NO: 69) is then cloned 5-prime to the ORF of the Δ5 desaturase gene using the engineered restriction sites and standard molecular biology techniques. Then the ligated DNAs are transformed into the *E. coli* Top10 competent cells (Invitrogen Corporation, California). The plasmid DNAs of 1-10 colonies of the transformants are isolated from 3 mL bacterial cultures using Zyppy™ Plasmid Miniprep Kit (Zymo Research Corp., Orange, Calif.). The integrity of the clones is preliminarily tested with restriction enzyme digestions using enzymes specific to the engineered restriction sites.

12. Generation of Recombinant Δ12 Desaturase Yeast Expression Vector.

Plasmid DNA from Example 1.7 was purified using UltraClean 6 Minute Mini Plasmid Prep kit (MO BIO Laboratories, Inc, Solana Beach, Calif.). The plasmid thus obtained is digested with BamHI/NotI and cloned into the yeast expression vector pYES2 (Invitrogen, Carlsbad, Calif.) to generate clone pYΔ12Desat which was then used for expression studies in yeast.

13. Generation of a Δ12 Desaturase Knockout Vector pT7-ΔΔ12Desat.

To demonstrate the function of the Δ12 desaturase gene within the host organism, the pT7-ΔΔ12desat vector is made. 1000 bp of the 5' sequence immediately flanking the Δ12 desaturase ORF is amplified along with the Δ12 desaturase ORF and part of the 3' UTR sequence via PCR. This provides both 5' and 3' sequence for homologous recombination. Primers used are Δ12RegF1—GGATCAAAGTCAT-ACTATGCGTACACG (SEQ ID NO: 87) and Δ12RegR1—GGTACCGTGAATACAGTCGAGGTAGC (SEQ ID NO: 88), producing a 2368 bp DNA fragment. This DNA fragment is cloned into plasmid pT7-Blue3 (Novagen) via standard TA cloning methods, according to the manufacturer's instructions. Positive clones are identified via digest analysis of extracted plasmid DNA, and sequenced to confirm construct fidelity, producing plasmid pT7-Δ12desat. The Ble-SV40 DNA fragment is isolated and amplified via PCR from a suitable template DNA. Primers Δ12delMW-F-
(SEQ ID NO: 89)
GACAAGGATTCACCCCAGCTTCGGTTGAAACTACAAGATCATGGCCAAGT
TGACCAGTGC and Δ12delMW_R-
(SEQ ID NO: 90)
CGAATCTCGCCGAGCGTCGGCAGGTCCGGGTTGTGCTTGCCATGCAGACA
TGATAAGATACATTG are employed for this. Primers are designed to include 5' extensions that introduced homology to the Δ12 desaturase DNA fragment (bold and underlined in primers D12delMW F and D12delMW R). PCR is performed with Phusion DNA polymerase using standard reaction conditions. To increase insertion efficiency, plasmid pT7-D12desat is digested with a restriction enzyme that cleaves at a unique site between base 1 and 95 of the Δ12 desaturase ORF, such as NcoI. Linear plasmid DNA is gel purified and employed along with the gel purified product of the Ble-SV40 PCR generated, from primers D12DelMW F and D12delMW R, in a second PCR reaction that designed to insert the Ble-SV40 DNA fragment into pT7-D12desat in a site specific fashion, denerating plasmid pT7-ΔΔ12desat. This PCR method is called MEGAWHOMP PCR, and has been described previously (Miyazaki 2011), and is completed according to standard protocols with Phusion DNA polymerase. Following amplification the PCR reaction is digested with DpnI via the addition of 5 µl 10×NEB buffer 4 and 2 µl DpnI restriction endonuclease. Reactions are digested at 37° C. for 16 hours. Following digestion DNA samples are precipitated via SureClean reagent (Bioline), as per the manufacturer's instructions, resuspended in 10 µl nuclease free water and 3 µl used to transform electrocompetent E. coli cells. Transformation is achieved according to standard protocols, and cells are immediately resuspended in 750 µl SOC media and incubated at 37° C. for 1 hour. Selection is subsequently achieved by spreading cells on LB agar plates containing ampicillin and incubating 37° C. for >16 hours. Several resultant colonies are selected, cultured in 3.5 Ml LB broth, supplemented with ampicillin, and plasmid DNA extracted via zippy plasmid DNA extraction kit according to the manufacturer's instructions. Digestion is completed to confirm the presence of the Ble-SV40 DNA fragment within pT7-D12desaturase, and positive plasmids are sequenced to confirm fidelity and accuracy of insertion. Thereby creating plasmid pT7-ΔΔ12desat.

Example 5: A Novel Fermentation Procedure

This Example describes a two-stage fermentation method for obtaining high biomass, total lipids and PUFA production in Thraustochytrid strains.

The life cycle of the strain ONC-T18 was studied in detail through microscopic observations of the cells from cultures growing under various conditions such as ratios of X:N sources, dissolved oxygen level and temperatures. It was discovered that at low oxygen concentration with a high carbon to nitrogen ratio (C:N) (e.g., within the range of 40:1 to 1:~0, and specifically at 1:1 to 1:~0 and ambient temperature, the strain ONC-T18 grew vigorously and propagated mainly through production of zoospores, resulting in large numbers of small vegetative cells that contains relative small and less subcellular oil bodies. In contrast, at high C:N ratio, low oxygen level and relative low temperature (e.g., within the range of 10-30° C. and specifically at 20-25° C.), the strain ONC-T18 mainly propagated through directly vegetative cell dividing, resulting in a large population of giant cells that contain remarkably bulky subcellular oil bodies. Hence, a two-stage fermentation method was developed to maximize biomass, total lipid and PUFA productivity. This is one optimal method for growing and screening high lipid and PUFA thraustochytrid strains. The following three assays were conducted:

Assay I:
The wild type strain ONC-T18 was inoculated in 10 mL liquid ONC-T18-GM0 medium. Cultures were grown at 25° C. in a shaker incubator set at 250 rpm for 2 days. Then the inocula ($OD_{660}$=12) was inoculated in 100 mL ONC-T18-GM0 medium in 250 mL flasks. Three cultures were inoculated for each strain. Cultures were grown in a shaker incubator set at 250 rpm at 25° C. for 2 days, then switched to 150 rpm and 20° C., and grown for another 4 days. Biomasses of the cultures were harvested by transferring the cell cultures into a 50 mL falcon tube and centrifuging at 4000 rpm using a SORVALL LEGEND RT+ centrifuge (Thermo Fisher Scientific Inc., MA, USA). The biomass floated on the surface of the liquid medium as a compacted layer. The liquid medium was released by punching a very small hole at the bottom of the falcon tube using an 18 G 1½ syringe needle. The pellet of the biomass in the tube was frozen in a -80° C. freezer overnight and then freeze dried using a freeze dryer for three days. The biomass of each sample was weighed.

Assay II:
The inocula were prepared as described in the Assay I. Next, the inocula ($OD_{660}$=6) was inoculated in 50 mL ONC-TI 8-GM0 medium in 250 mL flasks. Three cultures were inoculated for each strain. Cultures were grown in a shaker incubator set at 250 rpm at 25° C. for 2 days, then switched to 150 rpm and 20° C. At 2 days post inoculation, 5 mL of autoclaved 50% glucose was added into each culture flask, then at 4 days post inoculation, 6 mL of glucose were added. After 6 days post inoculation, biomasses of the cultures were harvested as described in Assay I.

Assay III:
The inocula were prepared as described in Assay I. Then the inocula ($OD_{660}$=6) was inoculated in 50 mL ONC-T18-GM0 medium in 250 mL baffled flasks. Cultures were grown in a shaker incubator set at 250 rpm at 25° C. At 2 and 4 days post inoculation, 5 and 6 mL of autoclaved 50% glucose were added into each culture flasks, respectively, as was done in Assay II. At day 6 post inoculation, biomasses of cultures were harvested as described in Assay I.

Total lipid and DHA contents of each sample were analyzed using direct transesterification method. Approximately 20 mg of freeze dried cell biomass and 3 mL of transesterification reaction buffer (methanol:hydrochloric acid:chloroform) were mixed by vortexing for 10 seconds and then incubated in a 90° C. water bath for two hours. After the completion of transesterification, the samples were removed and cooled down to ambient temperature. One mL of water was added and mixed via vortexing for 10 seconds. Fatty acid methyl esters (FAME) were then extracted by adding 3×2 mL of the solvent of hexane:chloroform (v/v, 4:1) and vortexing for 10 seconds, and allowed to sit until phase separations were completed.

Gas chromatographic (GC) analysis of the FAMEs was carried out using two internal standards (200 µL). One hexacosaenoic acid (C23:0) was added before transesterification and the other one, nonadecaenoic acid (C19:0) was added directly before analysis. Analyses were performed in an Agilent 6890 GC (Agilent Technologies, Palo Alto, Calif., USA) installed with a 30 m×0.32 mm internal diameter (0.25 µm film thickness) OMEGAWAX 320 fused-silica capillary column (Sigma-Aldrich, St. Louis, Mo., USA) and flame ionization detector set at 250° C., split ratio 50:1 to FID detector at 275° C. The injection volume was 1 µL. The carrier gas was $H_2$ with a constant flow of 5.0 mL per minute. Confirmation of the FAME identity was carried out using a Trace GC-DSQ mass spectrometer (Thermo Electron, Boston, USA) and comparison of the retention times for laboratory standards.

Results (Table 10) indicated that the fermentation conditions used in Assay II were the best for high lipid and DHA production in ONC-T18: levels within the range of about 50 to about 70% of dry biomass were observed; levels as high as about 70% to about 90% can be expected based on these findings. Observed DHA yields were within the range of about 5 to about 7.5 g/L culture. Based on these findings, DHA yields as high as about 45 to about 95 g/L can be expected.

TABLE 10

Biomass, total lipids and DHA productivities of *Thraustochytrium* sp. ONC-T18 under various fermentation conditions

| Assay | Biomass (g/L) | Total Lipid (mg/g) | Total Lipid (g/L) | DHA (g/L) | DHA % |
|---|---|---|---|---|---|
| I | 7.10 | 211.20 | 1.499 | 0.45 | 30.02 |
| II | 41.32 | 671.09 | 27.729 | 5.94 | 21.42 |
| III | 46.50 | 661.07 | 30.740 | 3.06 | 9.96 |

Increasing dissolved oxygen for example by using baffled flask and high shaking speed in Assay III can significantly enhance the biomass productivity, but DHA productivity was considerable lower than that in Assay II. Therefore, optimization of fermentation parameters such as C:N ratio, glucose concentration, dissolved oxygen and temperature as well as the dynamics of these parameters during fermentation processes, impact cost effective production of lipids and PUFA in thraustochytrid strains. Without wishing to be bound by any particular theory, the inventors propose that the increased yields observed in Assay II as compared to Assay I may be attributed at least in part to the higher glucose concentration and/or lower levels of dissolved oxygen in Assay II.

Example 6: Optimization of Salinity in ONC-T18-GM0 Medium for Effective Selection of *Thraustochytrium* sp. ONC-T18 Transformants As is known in the art, zeocin is unstable at high salt concentrations (Invitrogen, CA, USA). It has also been shown that ONC-T18 prefers to grow under conditions of relatively high salinity because of its natural inhabiting environments (PCT/IB2006/003977). The present Example describes the determination of optimal zeocin concentrations and salinities for efficient selection of ONC-T18 transformants using a zeocin resistance gene as the selectable marker.

Figure 12:
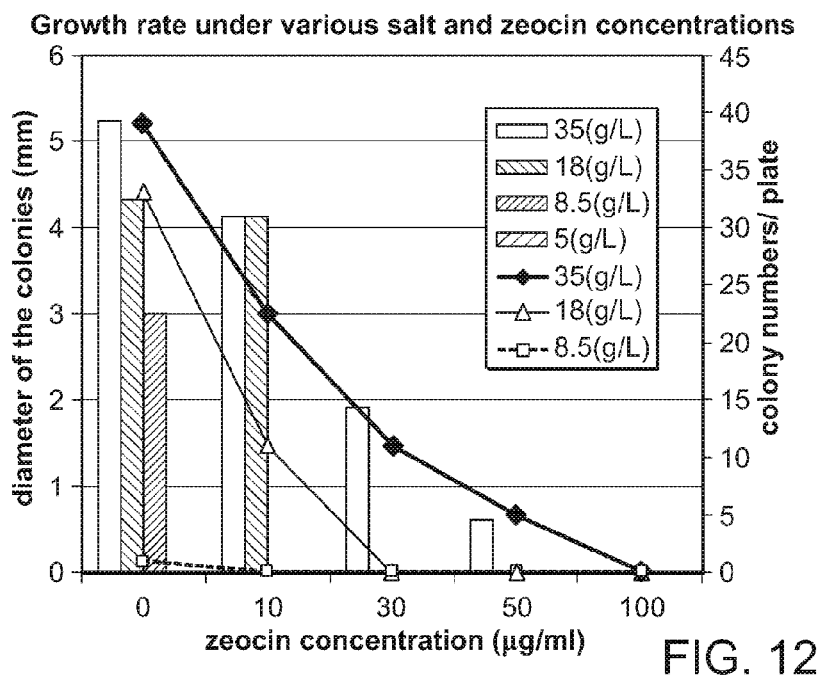
FIG. 12 illustrates effects of antibiotic zeocin on the growth and colony numbers of ONC-T18 at various salinities in the growth medium ONC-T18-GM0 plates. Results indicate that ONC-T18 grew faster and produced more colonies under higher salinity (e.g. 35 g/L artificial sea salt) in ONC-T18-GM0 medium than under lower salinity (e.g., 8.5 g/L artificial sea salt). At the median salinity (e.g., 18 g/L artificial sea salt), zeocin, at the concentration 30 μg/mL, could completely inhibit the growth of ONC-T18 in ONC-T18-GM0 agar plates.

One hundred μL of ONC-T18 cell suspension diluted at 1:500 from a 2-day culture were spread onto ONC-T18-GM0 plates containing various concentrations of antibiotic zeocin and sea salt. Inoculated plates were incubated in a 25° C. incubator for 10 days. The numbers of the colonies on each plate were counted. Means of colony numbers from two duplicate plates are presented in Table 2. After 10 days post-inoculation, no colonies were observed in ONC-T18-GM0 agar plates containing 5 g/L sea salt and various concentrations of zeocin. In plates containing 8.5 g/L sea salt without zeocin, only one colony was observed. In plates containing 18 g/L sea salt without zeocin, colony numbers were similar to that of plates containing 35 g/L sea salt without zeocin. However, zeocin at a concentration of 30 μg/mL completely inhibited growth of ONC-T18 in ONC-T18-GM0 agar plates containing 18 g/L sea salt, whereas 100 μg/mL zeocin was needed for complete inhibition of ONC-T18 in ONC-T18-GM0 agar plates containing 35 g/L sea salt. The diameters of single colonies in two duplicate plates were measured and their means are shown in Table 3. Salinities between 18 g/L and 35 g/L did not affect the sizes of the colonies significantly (FIG. 12). The present Example therefore demonstrates, among other things, that better growth is observed in the presence of sea salt at a concentration above about 8.5 g/L. Concentrations in the range of 8.5 g/L to more than 35 g/L (e.g., to about 36 g/L, 37 g/L, 38 g/L, 39 g/L, 40 g/L, 41 g/L, 42 g/L, 43 g/L, 44 g/L, 45 g/L. 46 g/L. 47 g/L, 48 g/L, 49 g/L, 50 g/L or more, even possibly as much as 55 g/L, 60 g/L, 65 g/L, 70 g/L, 75 g/L, 80 g/L, 85 g/L, 90 g/L, 95 g/L, 100 g/L or more may be suitable for growth. For selection of transformants using zeocin, of course, it is desirable to achieve robust growth with maintained sensitivity to zeocin. Therefore, for this work, 18 g/L sea salt was used to make ONC-T18-GM0 for selection of ONC-T18 transformants transformed with constructs bearing a zeocin-resistant gene expression cassette.

TABLE 11

Effects of zeocin and salinity on the colony numbers of *Thraustochytrium* sp. ONC-T18

| Salt concentration (g/L) | Zeocin concentration (μg/mL) | | | | |
|---|---|---|---|---|---|
| | 0 | 10 | 30 | 50 | 100 |
| 5 | 0 | 0 | 0 | 0 | 0 |
| 8.5 | 1 | 0 | 0 | 0 | 0 |
| 18 | 33 | 11 | 0 | 0 | 0 |
| 35 | 39 | 22.5 | 11 | 5 | 0 |

TABLE 12

Effects of zeocin and salinity on the colony growth rates (diameter in mm) of *Thraustochytrium* sp. ONC-T18

| Salt concentration (g/L) | Zeocin concentration (μg/mL) | | | | |
|---|---|---|---|---|---|
| | 0 | 10 | 30 | 50 | 100 |
| 5 | 0 | 0 | 0 | 0 | 0 |
| 8.5 | 3 | 0 | 0 | 0 | 0 |
| 18 | 4.3 | 4.1 | 0 | 0 | 0 |
| 35 | 5.2 | 4.1 | 1.9 | 0.6 | 0 |

Transformation efficiencies were tested at various pressure conditions. In the present Example, it was found that a pressure condition of about 1100 psi resulted in a better transformation efficiency than did other pressure conditions tested.

Example 7: Transformation of *Thraustochytrium* sp. ONC-T18

This Example describes a biolistic transformation method of ONC-T18.
Materials and Methods.
Generating Competent Cells.
ONC-T18 was maintained on ONC-T18-GM0 agar plates in a 25° C. incubator and transferred to fresh plates every 3-4 weeks. One loop of inoculum of ONC-T18, taken from vigorously growing cells, was inoculated in 50 mL ONC-T18-GM0 in a 250 mL Erlenmeyer flask, then cultured in a shaker incubator at 25° C. at 150 rpm for about 46 hours. Half a milliliter of the culture was transferred into a sterilized 1.5 mL centrifuge tube in a laminar flow hood under sterile conditions, then centrifuged in a desktop centrifuge at 3,000 rpm for 1 minute. The supernatant was discarded, the cell pellet was re-suspended in 0.5 mL sterilized water, and 100 μL of the cell suspension was spread onto the central area (approximately 28 cm²) of an ONC-T18-GM0 agar plate. Petri dishes were left opened in a laminar flow hood under sterile conditions for 10 to 15 minutes to let cells settle down and to evaporate liquid water.

Biolistic Transformation.

Plasmids pd5EPZ1, p341PZ40T, p341PZ347T, p341PZ713T, and pD4DPZ18S (constructed as described in Example 2, see also FIGS. 3, 5, 6, 7, and 10) were isolated from bacterial cultures of strains containing the respective plasmids using the ZYPPY™ Plasmid Maxiprep Kit (Zymo Research Corp., Orange, Calif.) per manufacturer's protocol. As discussed in Example 2, each of these plasmids contains a ble transgene, which confers resistance to zeocin, phleomycin, and bleomycin. (See, e.g., Gatignol et al. (1988) and Dumas et al. (1994), the entire contents of each of which are incorporated by reference herein.) In the present Example, a Sh ble (*Streptoalloteichus hindustanus*) transgene was employed. Other ble transgenes are also suitable, such as the Tn5 ble and Sa ble (*Staphylococcus aureus*) transgenes.

For each plasmid, five μL (~1 μg/μL) of plasmid DNA was mixed with 25 μL of gold particle suspension (60 mg/mL in 50% glycerol) by vortexing for 3 minutes and incubating on ice for 10 minutes. Ten μL of 0.1 M spermidine and 25 μL of 2.5 M $CaCl_2$ were added into the mixture and immediately vortexed for 4 minutes, then centrifuged for 10 seconds at full speed in a desktop centrifuge. The supernatant was discarded. Plasmid DNA-coated gold particles were washed twice with 70% ethanol and re-suspended in 36 μL 98% ethanol. Six μL of the gold particle suspension was spread on each macrocarrier disc and discs were air-dried (Zhang et al. 2001).

The PSD-1000/He particle delivery system (Bio-Rad Laboratories, Inc., California) was used for delivery of plasmid DNAs bearing zeocin resistant gene expression cassettes into ONC-T18 competent cells under sterilized conditions in a laminar flow hood according to the manufacturer's protocol. Parts of the particle delivery system, including macrocarrier holders, macrocarriers, stopping screens, were autoclaved. The chamber of the particle delivery system was disinfected by wiping with 70% ethanol. After bombardment, petri dishes containing transformed cells were incubated at 25° C. incubator in darkness for 6 to 16 hours. Transformed cells were then washed out of the dishes using 1 mL sterilized culture media, transferred into a 1.5 mL autoclaved micro-centrifuge tube, and centrifuged at 3,000 rpm for 2 minutes. The supernatant was discarded and the pellet was re-suspended in 0.5 mL autoclaved culture media. Fifty to one-hundred fifty μL of the cell suspension was spread on agar ONC-T18-GM0 plates containing ~50-500 μg/mL zeocin. After the liquid in the plates had been evaporated, plates were sealed with PARAFILM® M and incubated at 25° C. incubator for 6-10 days. Zeocin-resistant colonies were picked using 10 μL pipette tips and suspended in 50 μL sterilized water in a 200 μL PCR tube. One μL of the cell suspension was spotted onto ONC-T18-GM0 agar plates containing 150-200 μg/mL zeocin. After 3-5 day incubation at 25° C., vigorously growing colonies were chosen for further analysis.

Zeocin-resistant colonies were grown on ONC-T18-GM0 agar plates containing 50-500 μg/mL zeocin 4-6 days after biolistic transformation. Zeocin-resistant strains were generated with various constructs derived from combinations of various promoters and terminators isolated from ONC-T18. The numbers of the transformants generated per transformation using different constructs were variable. (See, for example, Table 13.). In some embodiments, the number of transformation is approximately 10-500 per 5 g of plasmid DNA.

TABLE 13

Number of transformants per transformation

| Constructs | Number of transformants/5 μg plasmid DNAs |
|---|---|
| pd5EPZ1 | 11 |
| p341PZ40T | 9 |
| p341PZ347T | 4 |
| p341PZ713T | 7 |
| pD4DPZ18S | 5 |

Example 8: PCR Analysis of Transformants of *Thraustochytrium* sp. ONC-T18

This Example describes confirmation of the presence of transgene in transformed ONC-T18. A PCR assay was used to assess presence of the ble transgene, which is present in each of the plasmid constructs used to transform ONC-T18.

Figure 13:
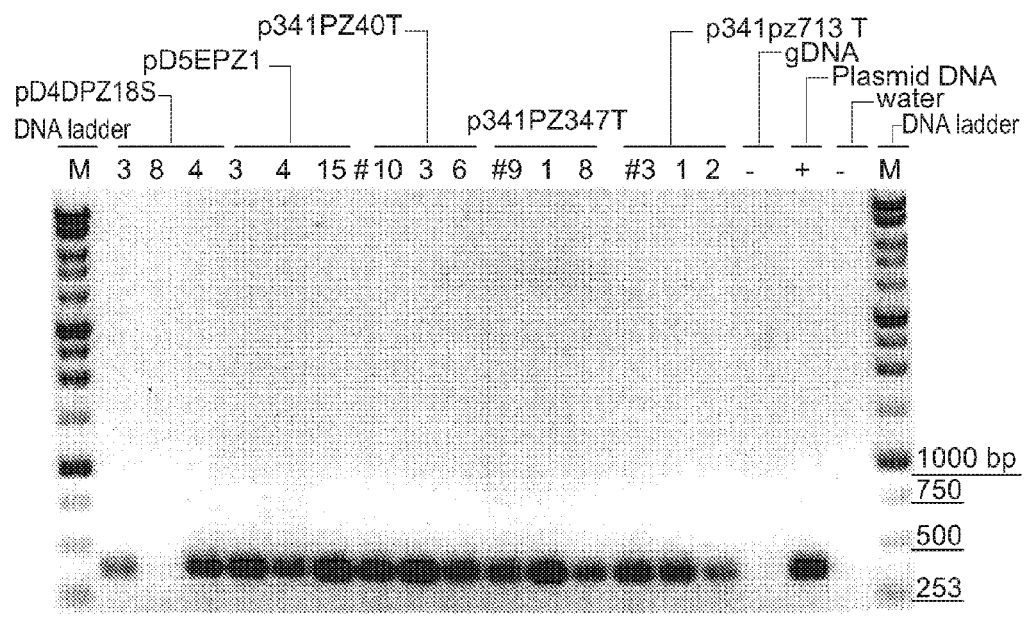
FIG. 13 illustrates the detection of the transgene of the zeocin resistance gene in the zeocin-resistant strains transformed. The zeocin gene specific DNA fragments were amplified from the genomic DNA of each transformant strain with PCR technique using zeocin resistant gene specific primers.

One loop of inoculum of each potentially transformed strain growing on zeocin-ONC-T18-GM0 agar plates was inoculated in 10 mL liquid ONC-TI 8-GM0 medium in a 50 mL flask and grown in a shaker incubator at 25° C. and at 250 rpm for 2 days. Two-mL cultures were used for isolation of the genomic DNA of each strain using an Ultraclean Microbial Mini-prep DNA Isolation kit (MO BIO Laboratories, Inc, Solana Beach, Calif.) following the manufacturer's protocol. Genomic DNA concentrations were measured using spectrum photometer Spectro 2000RSP (Lebomed, Inc., Culver City, Calif., U.S.A). A half μL of genomic DNA was used for a 20 μL PCR reaction containing the following components: Taq DNA polymerase (Sigma), 1×PRC buffer, 2.5 mM $MgCl_2$, dNTPs mixture (0.20 mM each), 0.25 μM primer #64 (SEQ ID NO:66), and 0.25 μM primer #65 (SEQ ID NO:67) in a 200 μL PCR tube. PCR reactions were carried out using the following thermal cycle program: 94° C. for 3 minutes, 94° C. for 1 minute, 55° C. for 2 minutes, and 72° C. for 2 minutes for 30 cycles. Primer #64 anneals to the 5'-end and primer #65 anneals to the 3'-end of the ble gene of each plasmid used for transforming ONC-T18. A ~350 base pair DNA fragment was amplified from the genomic DNAs of positive transformants and from plasmid DNA of the positive control, but not from genomic DNA of the negative control isolated from the cells of the wild type ONC-T18. These results confirm that most zeocin-resistant strains are true transformants (FIG. 13).

Example 9: Growth Rates of Transformants

This Example describes the determination of growth rates of transformed single cell-derived strains. Inocula of zeocin-resistant strains that had been transferred three times on zeocin ONC-T18-GM0 agar plates were picked from each colony using a 10 μL pipette tip and re-suspended in 50 μL sterilized water in a 200 μL PCR tube. One μL of the cell suspension was spotted on ONC-T18-GM0 agar plates (15 g/L agar) containing either 18 g/L or 35 g/L sea salt. The diameters of the spotted colonies were measured on day 1, day 3, day 5, day 7, and day 9 post-inoculation.

Most tested strains grew faster than the wild type strain ONC-T18 on ONC-T18-GM0 agar plates, whether they were grown on plates containing 18 g/L or 35 g/L sea salt.

Figure 14:
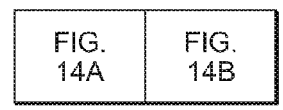
FIGS. 14A and 14B illustrate the growth rates of transformed single cell-derived strains. Inocula of zeocin-resistant strains that had been transferred three times on zeocin ONC-T18-GM0 agar plates was picked from each colony using a 10 μL pipette tip and re-suspended in 50 μL sterilized water in a 200 μL PCR tube. One μL of the cell suspension was spotted on ONC-T18-GM0 agar plates (15 g/L agar) containing either 18 g/L or 35 g/L sea salt. The diameters of the spotted colonies were measured on day 1, day 3, day 5, day 7, and day 9 post-inoculation.
Figure 14A:
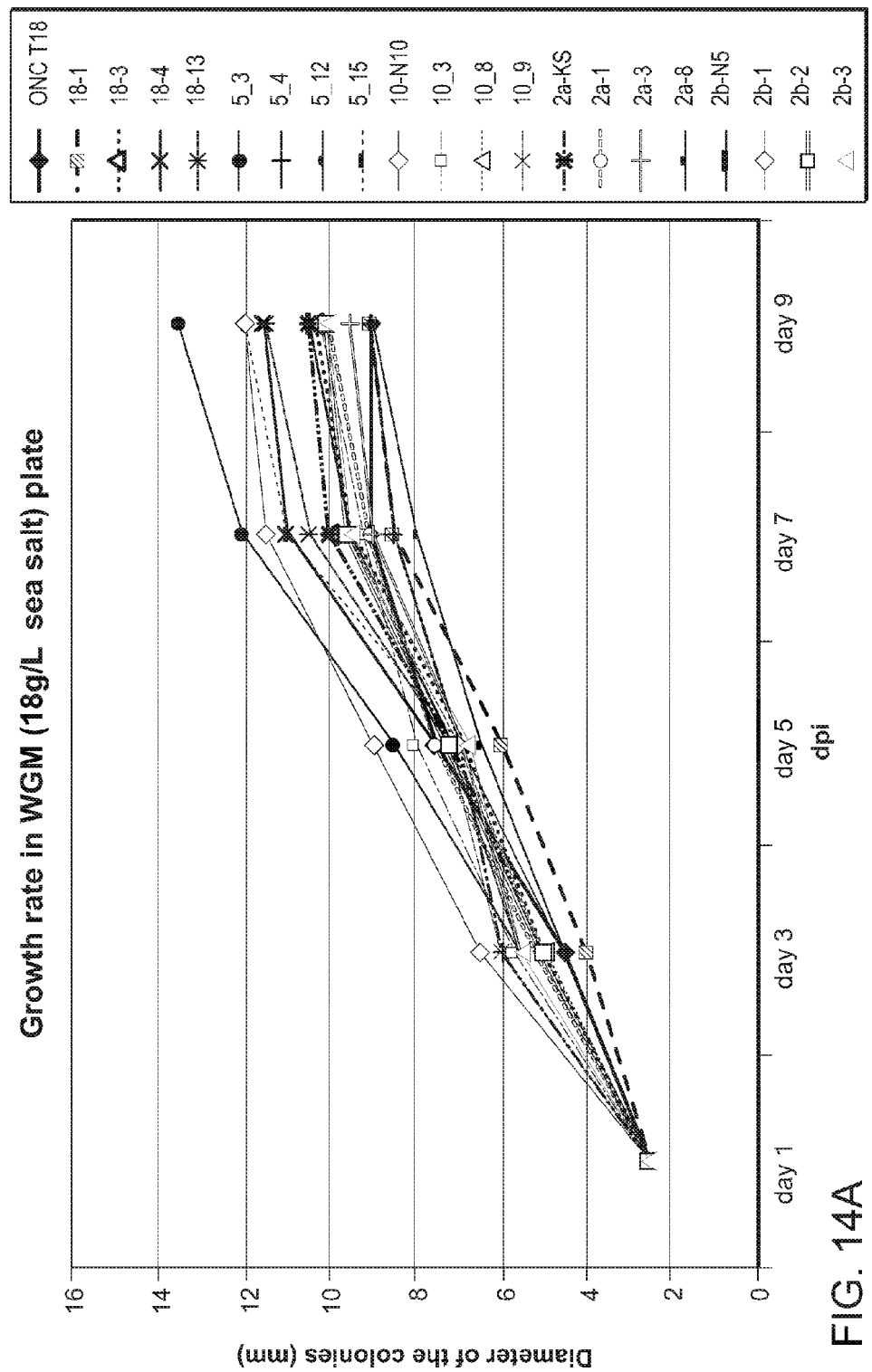
Figure 14B:
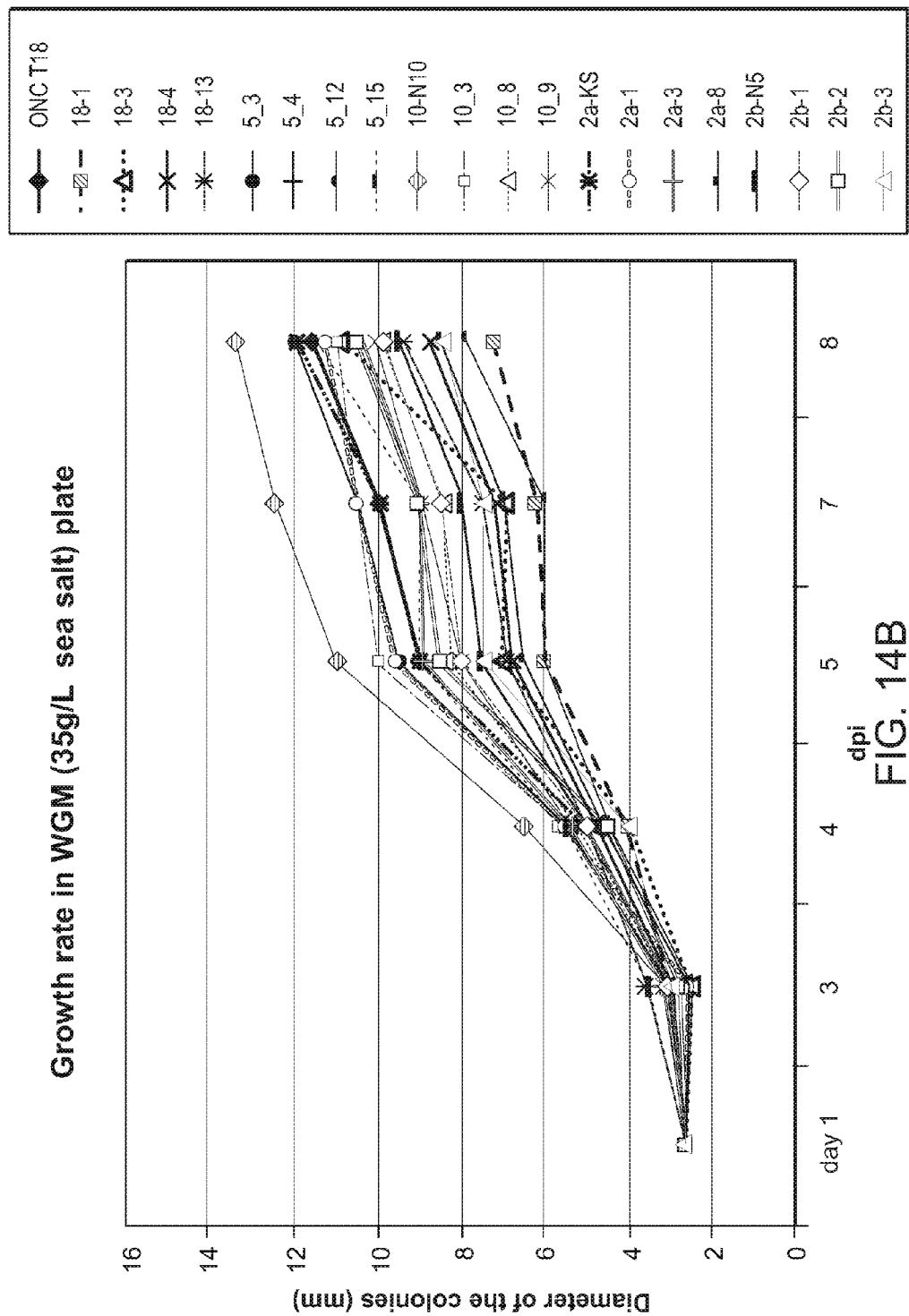

Among the tested strains, most grew faster on plates containing 18 g/L than on plates containing 35 g/L sea salt. Some strains that grew fastest on ONC-T18-GM0 agar plates containing 18 g/L sea salt (such as strain 5-3) grew slower than other strains on plates containing 35 g/L sea salt. It appears that most transformed strains prefer to grow on media containing lower salinity, for example 18 g/L sea salt (FIG. 14).

Example 10: Zeocin Sensitivity of Transformed Strains

This Example describes assays of the zeocin sensitivity of single-cell derived transformed strains.

A very small amount of inoculum of zeocin-resistant strains that had been transferred three times via colony passages on zeocin/ONC-T18-GM0 agar plates (as well as their parental strain or the wild type strain) was picked from colonies using a 10 µL pipette tip and re-suspended in 50 µL sterilized water in a 200 µL PCR tube. One µL of the cell suspension was spotted on ONC-T18-GM0 agar plates containing 18 g/L sea salt (15 g/L agar) and zeocin at a concentration ranging from 0 to 5000 µg/mL (Invitrogen, CA, USA). The diameters of the spotted colonies were measured on day 1, day 3, day 5, day 7, and day 8.

Figure 15:
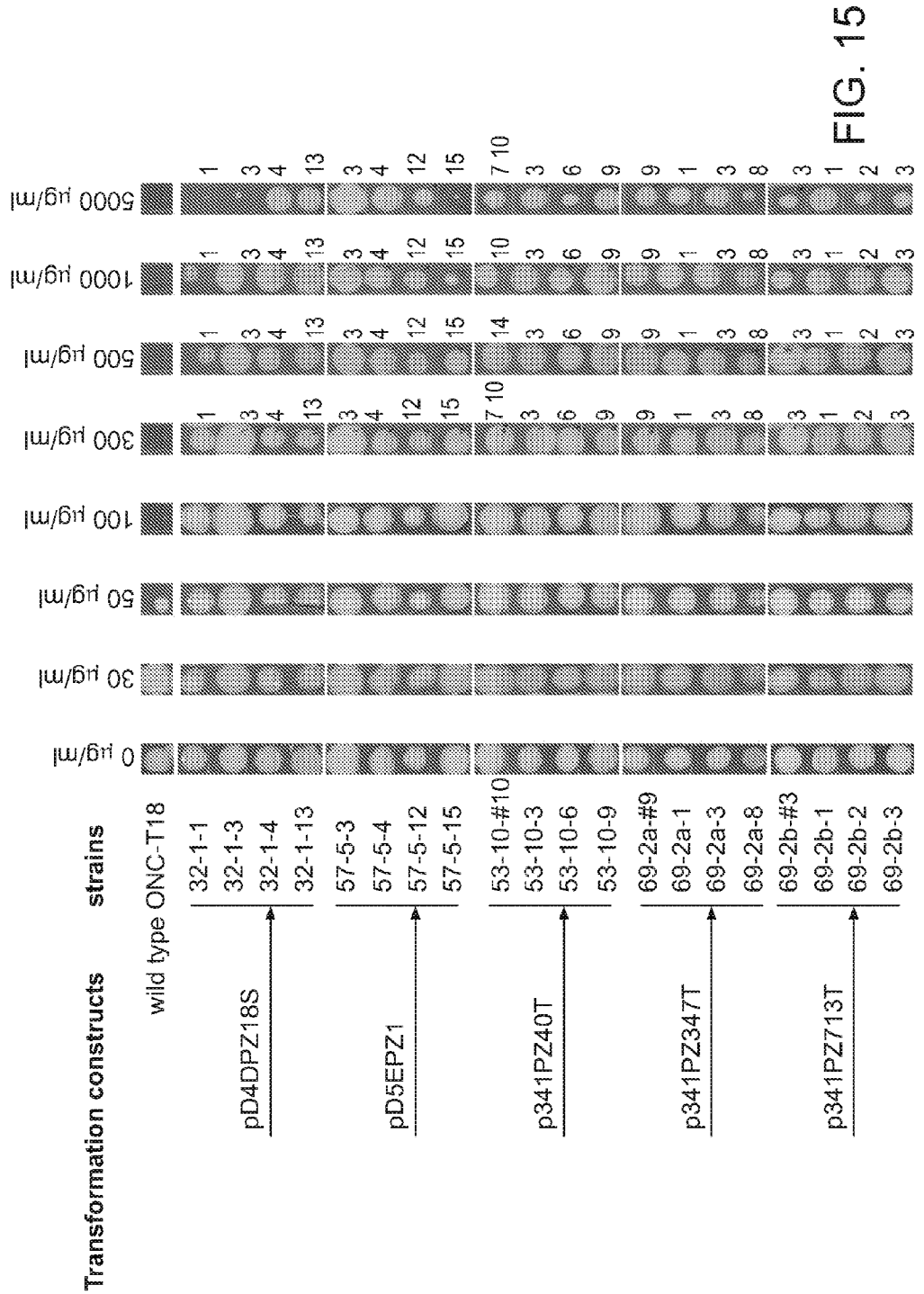
FIG. 15 illustrates the growth rates of the wild type and various transformed ONC-T18 strains in the agar plates of the growth medium (ONC-T18-GM0) containing zeocin at concentrations from 0 µg/ml to 5000 µg/ml. One µL of the cell suspensions was spotted on the ONC-T18-GM0 agar plates and the diameters of the colonies were measured daily.

All strains tested grew well on ONC-T18-GM0 agar plates in the absence of zeocin, but their growth rates differed. The parental strain (the wild type strain) ONC-T18 only grew on ONC-T18-GM0 agar plates that had 30 µg/mL or less zeocin. For all of the five different plasmid constructs, all transformed strains bearing the zeocin-resistance gene (from *S. hidustanus*) expression cassette grew well on ONC-T18-GM0 agar plates having zeocin at concentrations ranging from 30 to 1000 µg/mL (FIG. 15). However, at a concentration of 5000 µg/mL zeocin, most strains grew remarkably slower than that they did on media with 1000 µg/mL or less zeocin, and some of the strains could not grow at all on 5000 µg/mL zeocin (FIG. 15). Several strains, especially those transformed with a plasmid construct bearing zeocin-resistance gene expression cassette driven by the Δ5 elongase gene promoter, however grew very well (FIG. 15), suggesting that expression of the zeocin resistance gene was elevated in these strains compared to others, reasons for this could include, (i) the Δ5 elongase promoter allowing accumulation of more recombinant protein in the cell, due to strong expression, stable mRNA, suppression of gene silencing, for example, (ii) transgene insertion was within an actively transcribed region of the genome, again increasing recombinant protein level in the cell, or (iii) the Δ5 elongase construct could preferentially induce multiple insertion events from a single transformation, increasing expression level and recombinant protein level in the cell.

These results are consistent with DHA being the major energy storage fatty acid in the group of Thraustochytrid microalgae (Jain et al. 2007) and with the Δ5 elongase elongation step being the rate-limiting step during DHA biosynthesis in DHA omega-3 fatty acid producing microbes (Leonard et al. 2004). Growth rate variability among strains transformed with the same plasmid construct either reflects variability in expression level due to variability in insertion location (as discussed previously), or variation in copy number of the ble transgene (as discussed previously) within the chromosomes of the host strain ONC-T18.

These results demonstrate that various promoter and terminator sequences isolated from ONC-T18 can effectively drive transgene expression in PUFA-producing microorganisms. In addition, these results indicate that the ble transgene from *S. hidustanus* is a very effective selection marker gene for industrial strain improvement programs and genetic manipulation of *Thraustochytrium* sp. strains, as described previously (Hou and Shaw 2010; Sakaguchi, Matsuda et al. 2012).

Example 11: Comparisons of Biomass Productivities Between Transformed Strains and Wild Type Strain *Thraustochytrium* sp. ONC-T18

The present Example describes comparisons of biomass productivities of transformants to that of the wild type strain *Thraustochytrium* sp. ONC-T18, 10 mL ONC-T18-GM0 (18 g/L sea salt) cultures were each inoculated with a transformed strain (i.e., carrying a zeocin resistance gene) or with the wild type strain ONC-T18. Cultures inoculated with a transformed strain contained 200 µg/mL zeocin in the medium. Cultures inoculated with wild type strain ONC-T18 were grown in media without zeocin. Cultures were grown at 25° C. in a shaker incubator set at 250 rpm for 3 days until the $OD_{600}$ reached about 1.979-2.369 grams. Then 50 mL ONC-T18-GM0 cultures containing either 18 g/L or 35 g/L sea salt in 250 mL flasks were inoculated with 6 $OD_{600}$ of the inocula of each strain, including the wild type strain ($OD_{600}$ was measured for 1 mL of culture and then the volume of culture was scaled up to correspond to an $OD_{600}$ value of 6; e.g., if the $OD_{600}$ measurement were 2, then (1 mL×(6/2.0))=3 mL was used as inoculate). Cultures were grown in a shaker incubator set at 250 rpm at 25° C. for 2 days. Five mL of autoclaved 50% glucose were then added into each culture flask. Cultures were continually grown in a shaker incubator set at 150 rpm and at 20° C. for another 2 days. Six mL of autoclaved 50% glucose were then added into each culture flask and the cultures were constantly grown in a shaker incubator set at 150 rpm and at 20° C. for 3 more days. The biomasses of cultures of each strain in the two types of ONC-TI 8-GM0 media (with 18 g/L or with 35 g/L sea salt) were harvested by transferring cell cultures into a 50 mL falcon tube and centrifuging at 4000 rpm using the SORVALL LEGEND RT+ centrifuge (Thermo Fisher Scientific Inc., MA, USA). Biomass floated on the surface of the liquid medium as a compacted layer. Liquid medium was released by punching a very small hole at the bottom of the falcon tube using an 18 G 1½ syringe needle. The pellet of the biomass in the tube was frozen in a −80° C. freezer overnight and then freeze-dried using a freeze dryer for three days. The biomass of each sample was weighed. Nine strains including the wild type were tested.

Figure 16:
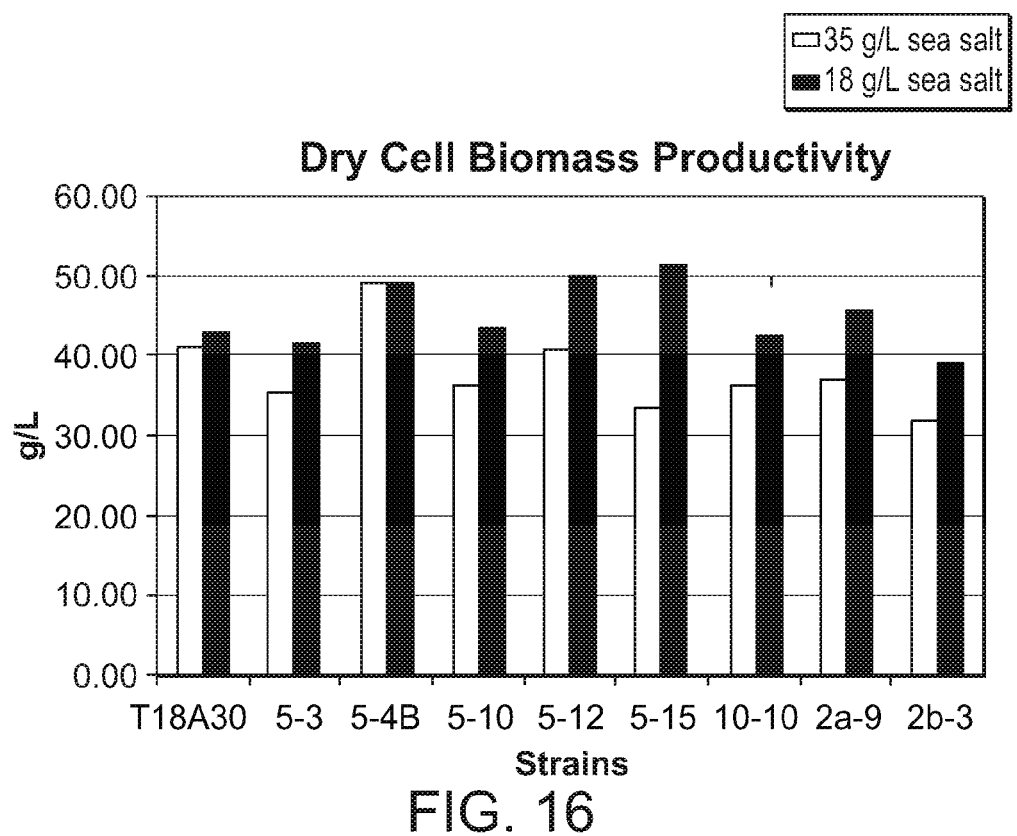
FIG. 16 illustrates the biomass productivity of the wild type and various transformed ONC-T18 strains in liquid growth medium (ONC-T18-GM0) containing artificial sea salt at the concentration of 18 g/L or 35 g/L. Results shows that at the lower salinity, all strains tested produced more biomass than at a higher salinity.

As expected, most transformants produced similar amounts of dry cell biomass to that of the wild type strain ONC-T18 when grown in ONC-T18-GM0 containing 35 g/L artificial sea salt. However, one out of 8 transformed strains produced about 22% more dry cell biomass than that of the wild type strain ONC-T18 (FIG. 16) when grown under the same conditions. Similarly, in the ONC-T18-GM0 containing 18 g/L sea salt, 7 out of 8 transformed strains produced similar amounts or more biomass than that of the wild type strain ONC-T18. One out of 8 tested strains produced 19.5% more biomass than that of the wild type strain ONC-T18 (FIG. 16). This demonstrates that transformation and transgene expression does not negatively impact biomass production by ONC-T18. Therefore it is assumed that ONC-T18 biology is robust enough to withstand the stress associated with transformation and heterologous protein biosynthesis.

Example 12: Comparisons of DHA Productivity Between Transformed Strains and the Wild Type Strain of *Thraustochytrium* sp. ONC-T18

The present Example describes DHA productivity in the various strains transformed with expression vectors comprising Δ5 desaturase, Δ12 desaturase, Δ4 desaturase, Δ5 elongase, and combinations thereof in either multi-plasmid or polycistronic expression systems. Elevated levels of DHA are observed when compared to the wild type strain and strains transformed with empty vector controls. The present Example demonstrates, among other things, that levels within the range of at least 1%-36% higher than wild type (e.g., 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, etc.) can be achieved. Based on these findings, one of ordinary skill in the art will appreciate that further elevation can be achieved (e.g., to levels within the range of 1%-1000% higher than wild type, e.g., about 1%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 550%, 600%, 650%, 700%, 750%, 800%, 850%, 900%, 950, 1000% or more higher than wild type). The present Example further demonstrates achievement of DHA:biomass ratios within the range of about 1:4 to about 1:2, at least about 40% higher than those typically observed with wild type strains. (See, e.g., Table 2 in Raghukumar (2008), the entire contents of which are incorporated by reference herein.) Based on these findings, those in the art would appreciate that at least ratios of about 1:5 can be achieved. We have achieved DHA to biomass ratios (DHA:biomass) of about 1:8 to 1:4 and expect to achieve ratios of about 1:3. Examples in literature (such as the review published by Raghukumar, 2008) indicate achievements that have not reduced this ratio below 1:5.

Cultures of 256 strains (transformed with every combination of expression vectors comprising Δ5 desaturase, Δ12 desaturase, Δ4 desaturase, Δ5 elongase) are transformed individually with their parental strain (wild type) are grown, and the biomass is harvested and freeze-dried under the same conditions as described. Fatty acid methyl ester (FAME) extraction is performed via the direct transesterification method. Approximately 20 mg of freeze dried cell biomass and 3 mL of transesterification reaction buffer (methanol:hydrochloric acid:chloroform) is mixed by vortexing for 10 seconds and then incubated in a 90° C. water bath for two hours. After completion of transesterification, the samples are removed and cooled down to ambient temperature. One mL of water is added and mixed by vortexing for 10 seconds. FAMEs are then extracted by adding 3×2 mL of a hexane:chloroform (v/v, 4:1) solvent and vortexing for 10 seconds; samples are then allowed to sit until phase separations were completed.

Gas chromatographic (GC) analysis of the FAMEs is carried out using two internal standards (200 μL). One hexacosaenoic acid (C23:0) is added before transesterification and the other one, nonadecaenoic acid (C19:0) is added directly before analysis. Analyses is performed in an Agilent 6890 GC (Agilent Technologies. Palo Alto, Calif., USA) installed with a 30 m×0.32 mm internal diameter (0.25 μm film thickness) OMEGAWAX 320 fused-silica capillary column (Sigma-Aldrich, St. Louis, Mo., USA) and flame ionization detector set at 250° C., split ratio 50:1 to FID detector at 275° C. The injection volume is 1 μL. The carrier gas is $H_2$ with a constant flow of 5.0 mL per minute. Confirmation of FAME identity is carried out using a Trace GC-DSQ mass spectrometer (Thermo Electron, Boston, USA) and comparison of the retention times for laboratory standards.

Many of the transformed strains produce about 6.337 g/L DHA. This yield is about 16% more than that of the wild type strain ONC-T18 when grown in ONC-T18-GM0 containing 35 g/L artificial sea salt. Some transformed strains produce DHA, ranging from 1 to 13% more, than that of the wild type strain ONC-T18 when grown in ONC-T18-GM0 containing 18 g/L artificial sea salt under the same conditions.

Some of the transformed strains produce 7.445 g/L and 7.871 g/L DHA, which represent 25% and 36%, respectively, more than their parental strain (5.935 g/L) grew in ONC-T18-GM0 containing 35 g/L artificial sea salt. Use of lower salinity ONC-T18-GM0 not only directly reduces DHA production costs, but also slows down the erosion of the fermenters caused by high concentrations of sodium chloride salt in growth medium for culturing Thraustochytrid microbes.

The ratio of DHA to total lipids from high level DHA-producing transformed strains is higher than that of their parental strain. The DHA to total lipids factor can influence downstream processing of DHA extracted from the cells of transformed strains. DHA:total lipid ratios achieved with strains and methods provided herein may vary according to fermentation conditions. For example, for cultures grown in flasks, a DHA percentage of about 15% to about 50% of total lipids (corresponding to DHA:total lipids ratios of about 0.15:1 to about 0.50:1) can typically be achieved with transformed strains. For cultures grown in a fermenter, a DHA percentage of about 30% to about 75% of total lipids (corresponding to DHA:total lipids ratios of about 0.3:1 to about 0.75:1) can typically be achieved with transformed strains. Much greater DHA yields are obtained from transformed strains disclosed herein than can be obtained with wild type strains. For example, DHA yields from transformed strains typically range from about 7 (based on above data) to about 50 g/L (grams DHA per liter of media), whereas DHA yields from wild type ONC-T18 strains typically range from about 0.5 to about 6 g/L. (See, e.g., Table 2 in Raghukumar (2008)). The ratio of DHA to biomass from high level DHA production transformed strains is also higher than that of their parental strain. This higher ratio of DHA to biomass benefits the downstream extraction of DHA from the cell biomass of the transformed strains.

All of the cultures in this Example are grown under the same conditions (wild type ONC-T18 was cultured in the absence of zeocin). The higher level of DHA production by the transformed strains indicate that those strains have a higher efficiency of converting carbon sources into DHA, which can reduce the cost of DHA production from those transformed strains.

Example 13: Comparison of Total Lipid Productivity Between Transformed Strains and the Wild Type Strain *Thraustochytrium* sp. ONC-T18

As amply described and demonstrated herein, ONC-T18 has great potential for use as an efficient biofactory not only for PUFA and its derivatives of pharmaceutical and nutraceutical biomolecule productions, but also for biofuel production. In order to assess and characterize the ability of ONC-T18 to be employed for biofuel production, total lipid productivities and fatty acid profiles of transformed strains of ONC-T18 were analyzed for potential use in methods for changing fatty acid profiles for specialty product applications. For example, it may be desirable to increase production of short chain fatty acids (i.e. fatty acids with less than 16 carbons) or of particular PUFA, as mentioned herein in the discussion of the PUFA biosynthetic pathway. It may, for example, be desirable to increase production of EPA (e.g., by mutating or knocking out the PKS genes and Δ5 elongase genes) or of ARA (e.g., by downregulating any of the PKS genes and/or upregulation of the Δ12 desaturase gene).

Cultures of 8 ONC-T18 strains transformed with vectors comprising zeocin resistance transgenes and compared to a negative control parental strain (wild type; T18A30). The cells were grown, and the biomass was harvested and freeze-dried under the same conditions as described in Example 9. FAME extraction and GC analysis were carried out as described above.

Figure 17A:
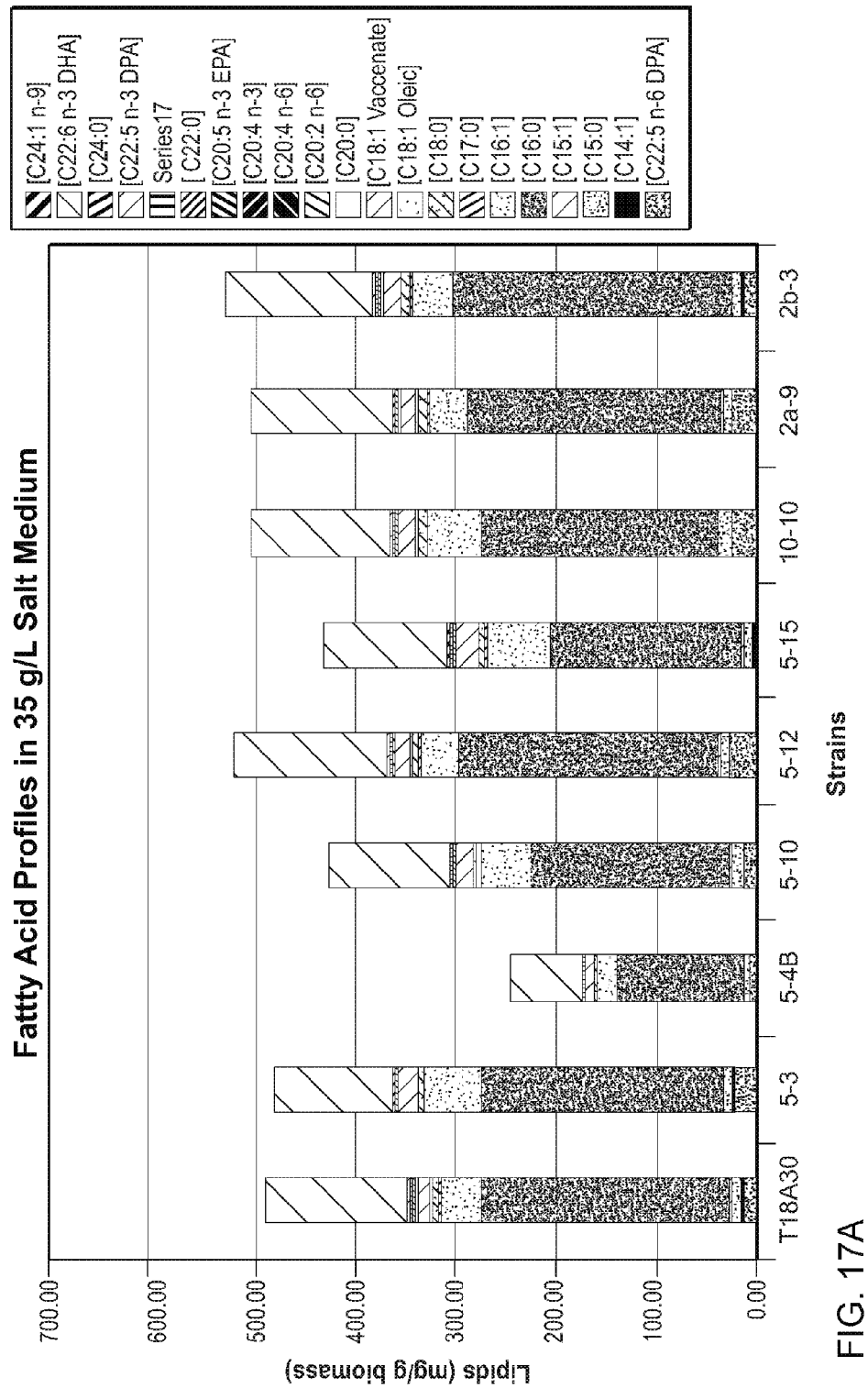
FIGS. 17A, 17B, 17C and 17D illustrate the fatty acid profiles and total lipid productivities of the transformed strains that grew in liquid ONC-T18-GM0 media having various salinities.

We found that fatty acid profiles, i.e. the composition of the fatty acid extract with respect to DHA, EPA, ARA, for example, of the transformed strains were very similar to that of their parental strains when grown in ONC-T18-GM0 containing 35 g/L artificial sea salt. Four out of eight transformed strains produced more total lipids than that of their parental strain, further demonstrating that the transformation process itself and the presence and/or expression of the transgene did not significantly affect fatty acid profiles in these strains, nor it did interrupt genes potentially involved in lipid metabolic pathways of most derivative strains. Thus, it appears that strains retain the genetic integrity of the parental strains after the transformation process (FIG. 17A).

Figure 17B:
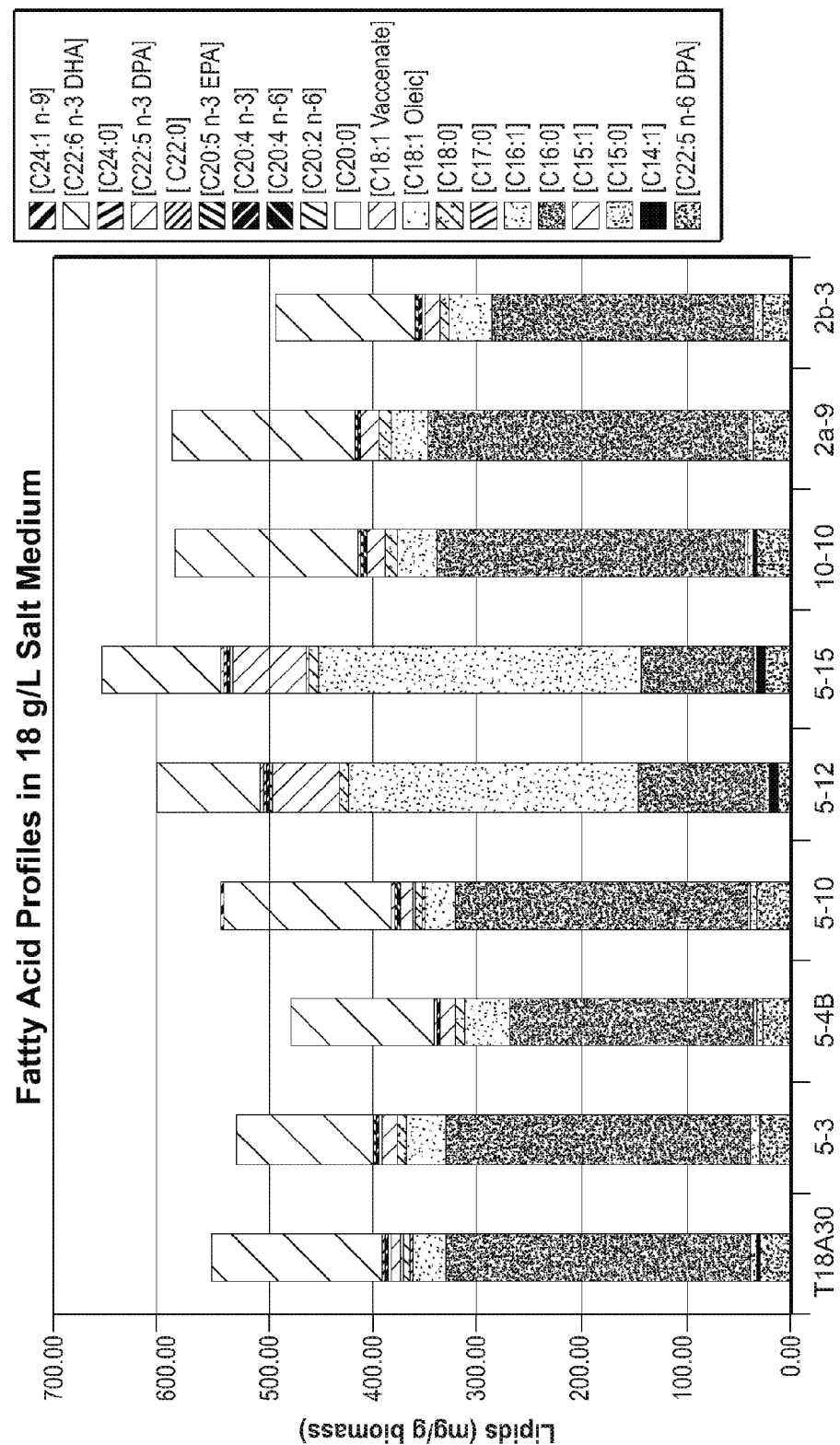

The ability to transform *Thraustochytrium* strains provides enormous opportunity to genetically modify these microbes and to channel metabolic pathways. Remarkably, when the transformed strains were grown in ONC-T18-GM0 containing 18 g/L sea salt, two strains showed significantly higher level of C16 fatty acid production than that of their parental strain. These results are useful in the development of this strain ONC-T18 into a platform for short chain fatty acid biofuel production. These results demonstrate that during the selection process of zeocin-resistant transformants, mutagenesis occurred in the cells with relatively high frequency. This high frequency of mutagenesis can be used in strain improvement programs (FIG. 17B).

Figure 17C:
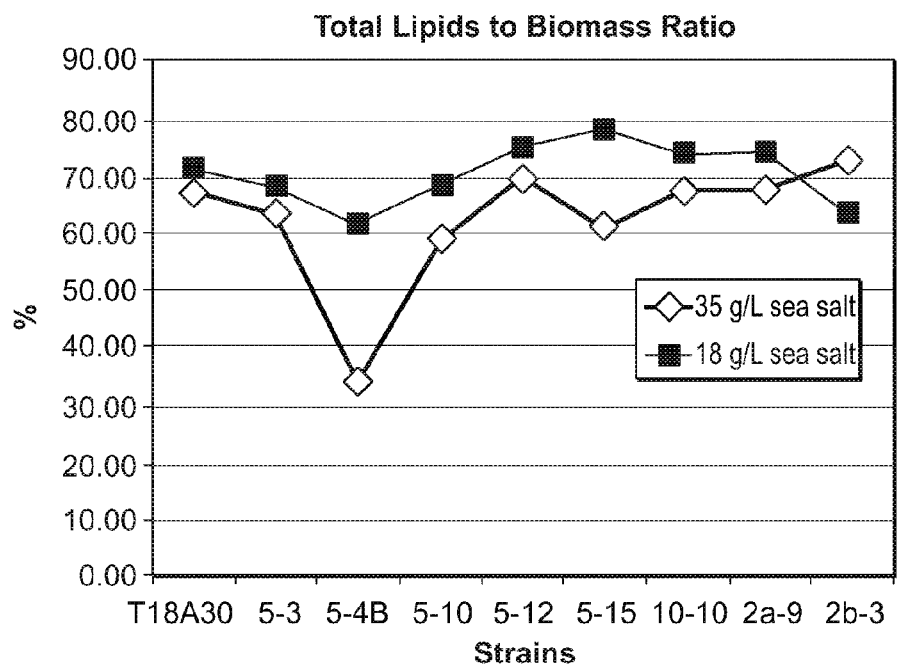

Ratios of total lipid to biomass were higher in strains that produce high levels of short chain fatty acids than in low-level production strains (FIG. 17C); such higher ratios may be beneficial to downstream oil extraction and the reduction of processing costs.

Figure 17D:
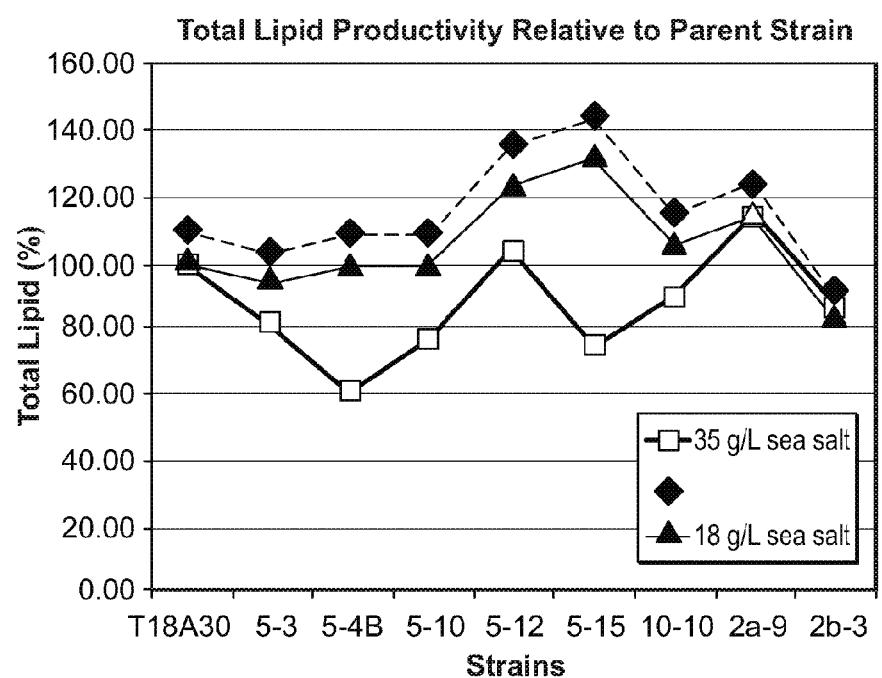

Growing in low sea salt ONC-T18-GM0 (18 g/L) enhanced overall total lipid productivity for most strains tested (FIG. 17D).

Example 14: Stability of the Ble Transgene in the Transformed Strains of *Thraustochytrium* sp. ONC-T18

The present Example confirms transgene stability in transformed *Thraustochytrium* sp. strains as described herein.

Transgene stability is important for certain applications of genetic engineering in industrial microbial strain improvement programs where microorganisms are used in pharmaceutical or industrial processes, and where product quantity and quality are paramount. We therefore carried out transgene stability estimate assays of transformed ONC-T18 strains. As for the growth rate assays described in above, inocula of four strains of each transformation as well as their ancestor wild type strains were spotted on ONC-T18-GM0 agar plates in the absence of zeocin and incubated at 25° C. for seven days. (Each transformation had been performed using one of the five different plasmid constructs, each of which bears various zeocin-resistant gene expression cassettes driven by a combination of different promoters and terminators). Then, using the same method, strains were transferred on a new fresh ONC-T18-GM0 agar plate and incubated at 25° C. for 7 days; colony passages were carried out 6 times. Finally, strains were transferred back onto ONC-T18-GM0 agar plates either without or with zeocin at a concentration of 200 μg/mL media.

Results indicate that after six colony passages, all strains can grow well on ONC-T18-GM0 agar plates either with or without zeocin (FIG. 18). However, on ONC-T18-GM0 agar plates having zeocin at a concentration at 200 μg/mL media, only the transformed strains grew well, whereas none of the wild type strains were able to grow.

These results demonstrate that there were no observed losses of the transgene in the strains examined. Furthermore, no resistance was observed in wild type strains, indicating that there was no spontaneous mutation for these traits and there was no detectable contamination. Presence of the ble transgene in the transformed strains after six time colony-passages was further confirmed using the PCR as described in herein. All transformed strains retained the ble transgene even after 6 colony passages. Thus, the ble transgene showed stability in transformed ONC-T18 strains.

Example 15: Application of a Mutagenic Agent

This Example describes the application of the mutagenic agent, zeocin, for strain improvement of Thraustochytrids.

Inocula from colony sectors were transferred into new fresh plates and developed into new strains. Four new strains, 1a, 1b, 3a and 3b were chosen for further study (results are shown in table 2). These four strains and their wild type parent strain ONC-T18 were inoculated in 10 mL liquid medium of ONC-T18-GM0. The cultures were grown at 25° C. in a shaker incubator set at 250 rpm for 3 days till the $OD_{660}$ was greater than 2. Then the inocula ($OD_{660}$=6) of each strain, including the wild type strain, were respectively inoculated in 50 mL ONC-T18-GM0 medium in 250 mL flasks. The following experimental conditions and procedures used were the same as in Example 14, assay II.

TABLE 14

Biomass, total lipids and DHA productivities of four selected strains and their wild type parent strain Thraustochytrium sp. ONC-T18

| Strains | Biomass (g/L) | Total Lipid (mg/g) | DHA (g/L) |
| --- | --- | --- | --- |
| ONC-T18 (parent strain) | 37.78 | 648.03 | 4.904 |
| 1a | 36.29 | 592.06 | 3.774 |
| 1b | 36.33 | 574.74 | 3.330 |
| 3a | 43.91 | 670.38 | 5.135 |
| 3b | 32.58 | 612.60 | 3.988 |

Experimental results indicated that three out of four selected strains produced significantly less biomass, total lipids and DHA compared to that of their wild type parent strain (Table 6). However, strain 3a produced more biomass, more lipids and DHA than that of its wild type strain. The high DHA productivity of strain 3a is due to not only its high biomass productivity, but high ratio of DHA to biomass. This result indicated that the mutagenic agent discovered can be used to improve a microbial strain's fitness (such as, e.g., capability of using cheaper carbon sources such as waste stream, glycerol, starch, cellulose, and hemicellulose), product quality and quantity such as ARA. DHA, and/or EPA productivity of PUFA, and fatty acid and/or lipid profiles favorable for biofuel applications.

Produced materials may be separated from production strains and/or media components by any of a variety of means. Extraction of produced materials is facilitated, for example, by taking one or more steps that alter fatty acid secretion and/or that weaken the cell wall.

Example 16: A Novel Strain of *Thraustochytrium* sp.

This Example describes the discovery of a novel strain of *Thraustochytrium* sp. with high productivity levels of lipids and DHA.

Single cells of ONC-T18 were spread on the agar plates containing ONC-T18-GM0 medium and 50 µg/mL zeocin. Ten to 15 days post inoculation, the colonies were screened visually. Large colonies without visible morphology changes were randomly isolated and developed into new strains. The biomass, total lipid and DHA productivity of new strains were compared. One strain ONC-T18/35/Z50 was initially found to be able to produce significantly more biomass, total lipids and DHA, which have been confirmed repeatedly with optimized fermentation conditions, methods and procedures described in Example 5, Assay II. In the two stage fermentation assays using ONC-T18-GM0 medium containing 35 g/L sea salt, the new strain ONC-T18/35/Z50 produced 5% more biomass, 7% more total lipids and 14% more DHA than that of its parent strain ONC-T18. Using the same medium, but containing 18 g/L sea salt, the new strain ONC-T18/35/Z50 produced about 10% more biomass, 20% more total lipids and 36% more DHA than that of its parent strain ONC-T18. Moreover, the ratios of DHA and total lipid to biomass, in high level DHA producing new strain ONC-T18/35/Z50, are higher than that of its parent strain, demonstrating that the new strain has a more robust capacity in converting carbon resources such as glucose to lipids and DHA. This novel strain is useful not only in improvement of yields, but also in reducing fermentation and downstream processing costs for biological lipid and PUFA production such as DHA from microalgae.

Example 17: Expression of *Thraustochytrium* ONC-T18 Δ12 Desaturase in Yeast

Clone pYΔ12desat, which consists of the full-length Δ12 Desaturase cloned into pYES2 (Invitrogen, Carlsbad, Calif.), as described in Example 4. pYΔ12desat, is transformed into competent *Saccharomyces cerevisiae* INVSc1. Yeast transformation is carried out using the S. c. EasyComp Transformation kit (Invitrogen, Carlsbad, Calif.) according to conditions specified by the manufacturer. Transformants are selected for uracil auxotrophy on media lacking uracil (SC-Ura). To detect the specific desaturase activity of these clones, transformants are cultured under conditions conducive to fatty acid biosynthesis. The negative control strain is INVSc1 containing the unaltered pYES2 vector, which is grown simultaneously. The cultures are vigorously agitated (150 rpm) and grown for 96 hours at 30° C. The cells are pelleted and washed in 100 mM phosphate buffer, pH 7.0, cell pellets were freeze dried. The lipids are then extracted and derivatized to fatty acid methyl esters (FAME) for gas chromatography analysis (GC). Transesterification and extraction are done using 100 mg freeze dried cells, with C19:0 as internal standard, add transesterification reaction mix (methanol:hydrochloric acid:chloroform, 10:1:1) mix and heat at 90° C. for 2 hours, then cooling at room temperature. FAMEs are extracted by adding 1 ml water, and 2 ml hexane:chloroform (4:1), and allow organic and aqueous phases to separate. The organic layer is extracted and treated with 0.5 g of anhydrous sodium sulfate to remove particulates and residual water. The organic solvents are evaporated under a stream of argon. The FAMEs are resuspended in iso-octane and analyzed by GC-FID. Comparison of FAMEs profiles for D12 desaturase over expressing mutants and the control strain demonstrated an enhanced accumulation of linoleic acid, and reduced oleic acid content.

To investigate the substrate specificity of the Δ12 desaturase, yeast cells transformed to express the Δ12 desaturase gene, via plasmid pYΔ12desat, are compared to a wild type yeast control transformed with an empty vector, and thus not containing the experimental Δ12 desaturase. The fatty acid compositions of these transformants are analyzed by GC using their corresponding FAMEs. The peak corresponding to the C18:2$^{9,12}$ methyl ester standard is found in the GC spectra of Δ12 desaturase transformants, but not in those of the mock transformants. GC-MS analysis of the newly generated peak from the Δ12 desaturase transformants subsequently confirms that the peak corresponding to C18:2$^{9,12}$ is indeed linoleic acid, based on ion fragmentation spectra, demonstrating that endogenous oleic acid is converted into linoleic acid the Δ12 desaturase transformed yeast strain. Between 1-50% of oleic acid was converted to linoelic acid. This result demonstrates that the ONC-T18 derived Δ12 desaturase is a 12-fatty acid desaturase. Subsequent analysis demonstrates that the Δ12 desaturase is not able to introduce double bonds into myristoleic acid (14:1$^9$), palmitoleic acid (16:1$^9$), heptadecenoic acid (17:1$^{10}$), elaidic acid (18:1$^9$ trans), linolenic acid (C18:3$^{6,9,12}$), dihomo-γ-linolenic acid (C20:3$^{8,11,14}$), arachidonic acid (C20:4$^{5,8,11,14}$) or docosatetraenoic acid (C22:4$^{7,10,13,16}$) when fatty acids were added to the culture media externally. Taken together, these data further demonstrate that the identified Δ12 desaturase encodes a 12-fatty acid desaturase.

Example 18: Heterologous Expression of *Thraustochytrium* ONC-T18 Δ12 Desaturase in ONC-T18

The isolated Δ12 desaturase of ONC-T18 (SEQ ID NO:70) is cloned into the p341PZ5pEx vectors as described in Example 4.9 for the constitutive over-expression, resulting in vector p341PZ5pD12Ex. The heterologous overexpression vector is transformed into ONC-T18 as described above in Example 7. The PUFA production profile of transformants can then be assessed as above and compared to negative controls (empty vectors transformants). Changes in copy number and expression level of PUFA biosynthesis genes are confirmed by quantitative real time PCR.

The present Example describes PUFA productivity in the various transformed strains, and demonstrates elevated levels as compared to the wild type. The present Example demonstrates, among other things, that over-expression of ONC-T18 Δ12 desaturase increases total fatty acid content, but reduces levels of C12 and C16 saturated and mono unsaturated fatty acids. Total fatty acid levels within the range of at least 1%-50% higher than wild type (e.g., 1%, 2%, 3%, 4%, 5%, 6%, 7%, 8%, 9%, 10%, 11%, 12%, 13%, 14%, 15%, 16%, 17%, 18%, 19%, 20% . . . 30%, 31%, 32% . . . 41%, 42%, 43%, etc.) may be achieved. Based on these findings, one in the art will appreciate that further elevation can be achieved (e.g., to levels within the range of 1%-1000% higher than wild type, e.g., about 1%, 5%, 10%, 15%, 20%, 25%, 30%, 35%, 40%, 45%, 50%, 55%, 60%, 65%, 70%, 75%, 80%, 85%, 90%, 95%, 100%, 1100% 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 4600%, 470%, 480%, 490%, 500%, 550%, 600%, 650%, 700%, 750%, 800%, 850%, 900%, 950%, 1000% or more higher than wild type), particularly when manipulation of Δ12 desaturase levels is combined with ideal culture conditions and/or co-manipulation of other PUFA biosynthesis genes. C12 and C16 saturated and mono unsaturated fatty acids may be reduced by levels of approximately 1% to 50% compared to wild-type (e.g., about 1%, 5%, 10%, 15%, 20%, 25%, 30%, 35%, 40%, 45%, 50%, etc).

The present Example further demonstrates achievement of PUFA production profiles of specified fatty acid content. Over-expression of Δ12 desaturase increases ARA, EPA and/or DHA levels relative to controls. The present Example further demonstrates achievement of DHA:biomass ratios within the range of about 1:8 to about 1:2, at least about 40% higher than those typically observed with wild-type strains.

Example 19: Deletion of the Δ12Desaturase within ONC-T18

To further demonstrate the function of the Δ12 desaturase protein of ONC-TI 8, and the impact of its deletion, this coding region is truncated and replaced via the use of plasmid pT7-ΔΔ12desat. This plasmid contains 1000 bases of 5' immediately upstream of the Δ12 desaturase ORF, and 1000 bp of 3' sequence homology that corresponds to part of the Δ12 desaturase ORF and proceeding into the 3' UTR. This provides substantial homology to the ONC-T18 genome at the Δ12 desaturase loci, allowing insertion of the Ble-SV40 cassette via homologous recombination. Insertion via homologous recombination places the zeocin resistance gene and SV40 terminator into the Δ12 desaturase ORF and in frame with the Δ12 desaturase start codon (ATG). As a result Ble expression is under the control of the Δ12 desaturase promoter and the SV40 terminator prevents transcription of the Δ12 desaturase gene. Moreover, insertion of the Ble-SV40 construct produces an 87 bp 5' truncation of the Δ12 desaturase ORF and also introduces a frame shift mutation into the ORF. Therefore, insertion of the pT7-ΔΔ12 desaturase construct via homologous recombination into the Δ12 desaturase loci eliminates expression of the native Δ12 desaturase. Competent ONC-T18 cells and transformation are prepared and performed as described in the materials and methods section of Example 7. Selection is performed on GM0-agar plates with 18 and 35 g/L salt, separately. Due to the unknown impact of the Δ12 desaturase promoter on Ble expression and subsequent zeocin resistance, selection is performed with zeocin supplementation of the agar plates at 20-2000 μg/L. Following incubation at 25° C. for 7 days, colonies are picked, replicated on zeocin containing GMO agar plates, and used to inoculate 10 mL of GMO broth culture media. Cultures are incubated at 25° C., 150 rpm for 3 days, harvested via centrifugation and genomic DNA extracted using the MoBio DNA extraction kit as per the manufacturer's instructions. To confirm the presence of the Ble-SV40 construct within the Δ12 desaturase genomic loci PCR is employed with primers that flank the insertion site. PCR primers 5'FlankRegionF—CCTCCACATGTCTCA-CAAGACCACCG (SEQ ID NO: 91) and 3'FlankRegionR—GCAAGCAATGCTCGATTTCCTACC (SEQ ID NO: 92) were designed and employed for this purpose. In the wild type strain, amplification produced a 1587 bp DNA fragment; while in the mutant strain, in which the D12 desaturase ORF was deleted, a PCR product of 2185 bp was produced. Positive strains were labeled ONC-T18-ΔΔ12desaturase.

The compositions of the fatty acids in the wild-type and ΔΔ12 desaturase ONC-T18 strains are analyzed by GC-MS using their FAMEs. In contrast to the wild-type, the ONC-T18-ΔΔ12 desaturase mutants have no linoleic acid (C18:$2^{\Delta 9,12}$), the major product of the Δ12 desaturase; instead they accumulate a significant amount of OA (C18:$1^{\Delta 9}$), the major substrate for the Δ12 desaturase. Importantly, the downstream derivatives of linoleic acid in the standard elongation/desaturation pathway also decrease drastically in ONC-T18-ΔΔ12 desaturase mutants, except for DHA. DHA actually increases in ONC-T18-ΔΔ12 desaturase mutants by approximately 5%, 10%, 15%, 20%, 25%, 30%, 35% or more relative to wild type strains. This increases DHA within the total fatty acid content of the cell from by approximately 2-fold, 3-fold, 4-fold, 5-fold, 10-fold, 15-fold, 20-fold or more relative to wild type.

Furthermore, the C17:$1^{\Delta 9}$ and C19:$1^{\Delta 9}$ contents also increases in the ONC-T18-ΔΔ12 desaturase mutants, suggesting that these odd-chain fatty acids may be substrates for the Δ12 desaturase. The accumulation of OA and the decrease of LA and its downstream PUFAs in the standard pathway are observed not only in the total fatty acid fraction but also in each lipid class (i.e., neutral lipids, phospholipids, and glycolipids) of the ONC-T18-ΔΔ12 desaturase mutants. Despite the significant changes in the fatty acid profiles in the total fatty acid and complex lipid fractions, no difference is observed in cell growth between the wild-type strain and ONC-T18-ΔΔ12 desaturase disruption mutants, nor in total fatty acids, under experimental conditions employed.

Example 20: Application of the ONC-T18 Δ12 Desaturase Gene Promoter to Drive Δ5 Desaturase Gene Expression The heterologous Δ12 desaturase promoter and Δ5 desaturase gene, described above, are combined for heterologous expression of the Δ5 desaturase gene following transformation of ONC-T18 as described above in Example 7. Briefly, plasmid pP Δ12-Δ5Desat-Δ12UTR-Zeo is created via isolation and amplification, and 3' extension of the Δ12 desaturase 5' flanking sequence, encompassing the putative promoter region, using PCR primers 5' Δ12FlankF: GGATCAAAGTCATACTATGCGTACACG (SEQ ID NO: 93) and 5' Δ12FlankR: ATCTATGTTAACCGAATGCAAT-TGCGTCCGAGACCTAAAGAATCAAGTCG (SEQ ID NO: 94). The 5' Δ12FlankR primer extends the promoter sequence and introduces a unique MfeI restriction enzyme site into the produced PCR fragment. PCR produces a DNA fragment of 845 bp. The Δ12desaturase 3'UTR sequence is isolated, amplified and extended at the 5' end via PCR in a similar fashion, which is achieved via PCR with primers 3' Δ12FlankF: TATCATCAATTGATGTAGGTTAACGC-CATTTCTAGCTCGAGCTGC (SEQ ID NO: 95) and 3' Δ12FlankR: ATGTGCCAATTTGGTACCGTGAATACA-GTCG (SEQ ID NO: 96). PCR amplification of the 3' Δ12 desaturase DNA fragment produces a 165 bp product. Primer 3' Δ12FlankF introduces a unique MfeI restriction enzyme site into the 5' end of the 3' Δ12 desaturase PCR product. PCR products are purified via precipitation, digested with restriction enzyme MfeI and gel purified. Digested DNA fragments are then employed in an overnight ligation reaction. Ligation is performed with 200 ng of each DNA fragment, 10 U of T4 DNA ligase and 4 μl of 5×T4 DNA ligase buffer, in a 20 μl reaction volume. Ligation is performed at 16° C. Ligation of the 5' and 3' Δ12 desaturase DNA fragments is confirmed via agarose gel electrophoresis, based on migration distance compared to a size standard, and the desired product is extracted from the agarose gel using the Qiagen Minielute Gel extraction kit, as per the manufacturer's instructions. DNA products are subsequently 3' adenylated via the addition of 2 U Taq DNA polymerase, 2 μl 10×PCR buffer, 0.5 μl 10 mM dATP, 0.4 μl 50 mM magnesium chloride, and nuclease free water to 20 μl. 3' adenylation is completed at 68° C. for 10 minutes. DNA products of this reaction are then cloned into plasmid pT7-Blue3 via standard protocols, producing plasmid pT7-5-3 Δ12desat.

The Δ5 desaturase is amplified via PCR using primers Δ5 desatF: ATGGGCAAGGGAAGCGAGGG (SEQ ID NO: 97) and Δ5 desat R: CTAGTCTTGCTTCTTGGCGTC (SEQ ID NO: 98). PCR produces a product of the size and sequence of SEQ ID: 72. Plasmid pT7-5-3 Δ12deat is digested with restriction enzyme HpaI and dephosphorylated. Dephosphorylated and linear plasmid pT7-5-3 Δ12desat is subsequently employed in an overnight ligation reaction along with the Δ5 desaturase PCR product' reaction conditions are identical to those described previously, with the exception of a vector to insert molar ratio of 6:1 being employed. Digestion with restriction enzyme HpaI and ligation of the described Δ5 desaturase PCR product retains exact spacing at the nucleotide level for the Δ12 desaturase promoter. Thus, no additional nucleotides or spare sequence is incorporated into the final construct between the Δ12 desaturase promoter and the Δ5 desaturase gene. Ligation products are transformed into E. coli. The produced library is screened for the desired construct via standard PCR and digestion methods. Plasmids with the Δ5 desaturase ORF ligated into plasmid pT7-5-3 Δ12desat are sequenced to confirm fidelity and labeled pP Δ12-Δ5Desat-Δ12UTR. The expression cassette of plasmid pP Δ12-Δ5Desat-Δ12UTR is removed from this vector and ligated into plasmid pD4DPZ1 using respective unique restriction sites, which allows transformation and selection for resistance to zeocin, as described previously. The produced plasmid was labeled pP Δ12-Δ5Desat-Δ12UTR-Zeo.

Following transformation of plasmid pPΔ12-Δ5Desat-Δ12UTR-Zeo into ONC-T18 the presence of the transgene is confirmed using PCR, with appropriate combinations of the previously described primers. The PUFA production profile of transformants can then be assessed as above and compared to negative controls (empty vectors transformants). Changes in expression of PUFA biosynthesis genes are confirmed by quantitative real time PCR.

Δ5 desaturase catalyzes the final step in the synthesis of ARA and EPA. Application of the Δ12 desaturase promoter to drive expression of the Δ5 desaturase gene significantly increases production of Δ5 desaturase protein; approximately 20-fold during exponential growth and approximately 40-100 fold in fatty acid biosynthesis. Provided fatty acid precursors are available, the over-expressed Δ5 desaturase protein drastically impacts ARA and/or EPA biosynthesis through the elongation/desaturation pathway.

Example 21: Application of the ONC-T18 Δ5 Desaturase Gene Promoter to Drive PKSAGene Cluster The PKSA gene cluster is responsible for DHA production in ONC-T18. The PKSA sequence and part of its promoter region are shown below in Table 15:

TABLE 15

| PKSA Sequence (SEQ ID NO: 99) |
| --- |
| GCCGTGCGGCACGACGGTCCGTGAGTCGTGGGAGACAATCCGTGCTGGCA |
| TCGACTGCCTGTCGGACCTCCCCGAGGACCGCGTCGACGTGACGGCCTAC |
| TTTGACCCGGTCAAGACGACCAAGGACAAGATCTACTGCAAGCGCGGCGG |
| CTTCATCCCCGACTACGACTTTGACGCTCGGGAGTTCGGCCTTAACATGT |
| TCCAGATGGAGGACTCGGACGCAAACCAGACCATTTCGCTCCTCAAGGTC |
| AAGGAGGCCCTCCAGGATGCCGGCATCGACGCCCTCTCCAAGGAGAAGAA |
| GAACATCGGCTGCGTCCTCGGCATTGGCGGCGGCCAGAAGTCGAGCCACG |
| AGTTCTATTCGCGCCTTAATTATGTTGTCGTCGAGAAGGTCCTCCGCAAA |
| ATGGGCATGCCCGAGAAGGACGTGAAGGTGGCCGTCGAAAAGTACAAGGC |
| CAACTTTCCCGAGTGGCGCCTCGACTCCTTCCCCGGCTTCCTCGGCAATG |
| TTACCGCCGGACGCTGCACCAACACCTTTAACCTCGACGGCATGAACTGC |
| GTCGTCGACGCCGCCTGCGCCTCGTCACTCATCGCCGTCAAGGTCGCCAT |
| CGACGAGCTCCTACACGGCGACTGCGACATGATGGTGACTGGCGCCACCT |
| GCACGGACAACTCCATCGGCATGTACATGGCCTTCTCCAAGACGCCGGTG |
| TTCTCCACCGACCCCAGCGTCCGCGCCTACGACGAGAAGACAAAGGGTAT |
| GCTTATCGGCGAGGGCTCGGCCATGCTCGTCCTCAAGCGCTACGCCGACG |
| CCGTACGCGACGGCGACGAGATCCACGCCGTCATCCGTGGCTGCGCCTCC |
| TCGAGCGATGGTAAGGCCGCCGGCATCTACACGCCCACCATCTCGGGGCA |
| GGAGGAGGCCCTCCGCCGCGCCTACAACC |

Operably linking control of this gene cluster to the Δ5 desaturase promoter reduces expression of the PKS protein complex from 1189 units to 71 units during exponential growth, and from 5102 units to 62 during fatty acid production. To achieve this, the 5' flanking sequence of PKSA is isolated and amplified via PCR, using primers XhoI-PPKSA F: ATA<u>CTCGAG</u>CCGTGCGGCACGACGGTC-CGTGAGT (SEQ ID NO: 100) and PPKSA-NcoI: TAT<u>CCATGG</u>CCGTCGAGGTTAAAGGTGTTGGTGCAG (SEQ ID NO: 101). Restriction enzyme motifs are in italics and underlined. The produced PCR product is digested with restriction enzymes XhoI and NcoI. Plasmid pD4DPZ1 is similarly digested with restriction enzymes XhoI and NcoI. Both DNA fragments are gel extracted and combined in an overnight ligation, as described previously. Digestion of plasmid pD4DPZ1 results in the removal of the Δ4 desaturase promoter sequence, while ligation results in the insertion of the PKSA 5' flanking sequence in place of the Δ4 desaturase. This provides 541 bp of homology to the 5' sequence of the PKSA gene within ONC-T18, producing plasmid pPKSA-PZ1. Δ5 desaturase promoter sequence (SEQ ID: 71) is amplified via PCR using primers EcoRI-Δ5desatF: ATA<u>GAATTC</u>GATATGTATTTACGTGAT-CAAC (SEQ ID NO: 102) and Δ5desat-PKSA R: GGCG- GCGTCGACGACGCAGTTCATAGGCGCCGATCGTTT-GCGCGT (SEQ ID NO: 103). The EcoRI site is underlined and in italics in the forward primer, while the homology for subsequent fusion PCR is highlighted in bold in the reverse primer. PCR results in the introduction of homology towards the first 24 bp of the PKSA gene. The first 388 bp of the PKSA gene is isolated and amplified via PCR using primers PKSA F: ACGCGCAAACGATCGGCGCCTATGAACT-GCGTCGTCGACGCCGCC (SEQ ID NO: 104) and PKSA-PstI R: TATCTGCAGGTTGTAGGCGCGGCGGAG-GGCCTCCTCCT (SEQ ID NO: 105). The PstI site is highlighted in italic and underlined in the reverse primer, while homology for subsequent fusion PCR is highlighted in bold in the forward primer. DNA products are precipitated via standard protocols and employed in a subsequent fusion PCR using standard protocols. Template DNA for this fusion PCR is 100 ng of each of the Δ5 desaturase promoter PCR product and the PKSA first 388 bp PCR product. Primers used are EcoRI-Δ5desatF and PKSA-PstI R. Following amplification, DNA is separated via agarose gel electrophoresis and the DNA product corresponding to the fusion of Δ5desaturase promoter and the PKSA DNA fragment, based on size, is purified using the QIAGEN minielute gel extraction kit. The resulting DNA fragment is digested with EcoRI and PstI overnight, and ligated into plasmid pPPKS-PZ1, previously digested, with EcoRI and PstI overnight, and gel purified, to produce pPPKS-PZ1-PΔ5desatPKSA. Plasmid pPPKS-PZ1-PΔ5desatPKSA therefore contains a zeocin selectable marker, that following correct integration is expressed from the native PKSA promoter, and a Δ5 promoter, which following correct integration will drive expression of the PKSA, within the ONC-T18 genome. Only correct integration can achieve selection based on zeocin selection. Correct integration is confirmed via genomic DNA extraction and PCR analysis using primers described previously.

The change in expression of the PKS protein complex reduces the DHA composition of the produced oil by approximately 1% to 50% or more compared to wild-type and negative controls (e.g., about 1%, 5%, 10%, 15%, 20%, 25%, 30%, 35%, 40%, 450/%, 50%, etc.). Thraustochytrid or *Thraustochytrium* gene promoters may be operably linked to isolated Thraustochytrid or *Thraustochytrium* PUFA biosynthetic pathway genes. PUFA biosynthesis gene promoters are activated by growth stage, culture conditions, and substrate availability. In general, each promoter and/or gene can function independently, allowing each to be removed or included using standard molecular biology techniques; thus providing for engineered Thraustochytrid or *Thraustochytrium* strains optimized for production of a particular PUFA or production of total fatty acid with optimized ranges of components. The present disclosure thus provides engineered strains that produce oil compositions that contain less than 25%, less than 20%, less than 15%, less than 10% and less than 5% long-chain PUFA components.

EQUIVALENTS

Those skilled in the art will recognize, or be able to ascertain using no more than routine experimentation, many equivalents to the specific embodiments described herein. The scope is not intended to be limited to the above Description. Alternative methods and materials and additional applications will be apparent to one of skill in the art, and are intended to be included within the following claims.

REFERENCES

Altschul, S. F., Gish, W., Miller, W., Myers, E. W., and Lipman, D. J. (1990). Basic local alignment search tool. *J Mol Biol* 215(3), 403-10.

Apt, K., A. Grossman, et al. (1996). "Stable nuclear transformation of the diatom<i>Phacodactylum tricornutum</i>." *Molecular and General Genetics MGG* 252(5): 572-579.

Berthold, P., R. Schmitt, et al. (2002). "An Engineered *Streptomyces hygroscopicus* aph 7" Gene Mediates Dominant Resistance against Hygromycin B in *Chlamydomonas reinhardtii*." *Protist* 153(4): 401-412.

Boynton, J. N. Gillham, et al. (1988). "Chloroplast transformation in *Chlamydomonas* with high velocity microprojectiles." *Science* 240(4858): 1534-1538.

Cheng, Q., A. Day, et al. (2005). "The *Klebsiella pneumoniae* nitrogenase Fe protein gene (nifH) functionally substitutes for the chlL gene in *Chlamydomonas reinhardtii*." *Biochemical and Biophysical Research Communications* 329(3): 966-975.

Child, S. J., M. K. Miller, et al. (1999). "Translational Control by an Upstream Open Reading Frame in the HER-2/neu Transcript." *Journal of Biological Chemistry* 274(34): 24335-24341.

Croft, M. T., M. Moulin, et al. (2007). "Thiamine biosynthesis in algae is regulated by riboswitches." *Proceedings of the National Academy of Sciences* 104(52): 20770-20775.

Davis, S. J., and Vierstra, R. D. (1998). Soluble, highly fluorescent variants of green fluorescent protein (GFP) for use in higher plants. *Plant Mol Biol* 36(4), 521-8.

Dawson. H. N., R. Burlingame, et al. (1997). "Stable Transformation of <i>Chlorella</i>: Rescue of Nitrate Reductase-Deficient Mutants with the Nitrate Reductase Gene." *Current Microbiology* 35(6): 356-362.

Debuchy, R., S. Purton, et al. (1989). "The argininosuccinate lyase gene of *Chlamydomonas reinhardtii*: an important tool for nuclear transformation and for correlating the genetic and molecular maps of the ARG7 locus." *EMBO J* 8(10): 2803-2809.

Dumas et al. (1994) The three-dimensional structure of a bleomycin resistance protein. *EMBO J.* 242(5), 595-601.

Epshtein, V., A. S. Mironov, et al. (2003). "The riboswitch-mediated control of sulfur metabolism in bacteria." *Proceedings of the National Academy of Sciences* 100(9): 5052-5056.

Fernández, E. R. Schnell, et al. (1989). "Isolation and characterization of the nitrate reductase structural gene of *Chlamydomonas reinhardtii*." *Proceedings of the National Academy of Sciences* 86(17): 6449-6453.

Ferris, P. J. (1995). "Localization of the nic-7, ac-29 and thi-10 Genes Within the Mating-Type Locus of *Chlamydomonas reinhardtii*." *Genetics* 141(2): 543-549.

Fischer, N. F. and J. D. R. Rochaix (2001). "The flanking regions of PsaD drive efficient gene expression in the nucleus of the green alga *Chlamydomonas reinhardtii*." *Molecular Genetics and Genomics* 265(5): 888-894.

Gatignol et al. (1988) Bleomycin resistance conferred by a drug-binding protein. *FEBS Letters,* 230:171-175.

Goldschmidt-Clermont, M. (1991). "Transgenic expression of aminoglycoside adenine transferase in the chloroplast: a selectable marker for site-directed transformation of *Chlamydomonas*." *Nucleic Acids Research* 19(15): 4083-4089.

Hallmann, A. and M. Sumper (1994). "Reporter genes and highly regulated promoters as tools for transformation experiments in *Volvox carteri*." *Proceedings of the National Academy of Sciences* 91(24): 11562-11566.

Hasnain, S. E., E. K. Manavathu, et al. (1985). "DNA-mediated transformation of *Chlamydomonas reinhardtii* cells: use of aminoglycoside 3'-phosphotransferase as a selectable marker." *Molecular and Cellular Biology* 5(12): 3647-3650.

Higuchi, R., Krummel. B., and Saiki, R. K. (1988). A general method of in vitro preparation and specific mutagenesis of DNA fragments: study of protein and DNA interactions. *Nucleic Acids Res* 16(15), 7351-67.

Hollingshead, S. and D. Vapnek (1985). "Nucleotide sequence analysis of a gene encoding a streptomycin/spectinomycin adenyltransferase." *Plasmid* 13(1): 17-30.

Hou, C. T. and J.-F. Shaw (2010). *Biocatalysis and Biomolecular Engineering*. Hoboken, N.J., John Wiley & Sons, Inc.

Huang. J., Jiang, X., Zhang, X., Chen, W., Tian, B., Shu, Z., and Hu, S. (2008). Expressed sequence tag analysis of marine fungus *Schizochytrium* producing docosahexaenoic acid. *J Biotechnol* 138(1-2), 9-16.

Jain, R., Raghukumar, S., Sambaiah, K., Kumon, Y., and Nakahara, T. (2007). Docosahexaenoic acid accumulation in thraustochytrids: search for the rationale. *Mar Biol* 151, 1657-1664.

Jepson et al. (1998) *Pesticide Science*, 54(4), 360-367.

Kilian. O., C. S. E. Benemann, et al. (2011). "High-efficiency homologous recombination in the oil-producing alga *Nannochloropsis* sp." *Proceedings of the National Academy of Sciences*.

Kindle, K. L. (1990). "High-frequency nuclear transformation of *Chlamydomonas reinhardtii*." *Proceedings of the National Academy of Sciences* 87(3): 1228-1232.

Kindle, K. L., K. L. Richards, et al. (1991). "Engineering the chloroplast genome: techniques and capabilities for chloroplast transformation in *Chlamydomonas reinhardtii*." *Proceedings of the National Academy of Sciences* 88(5): 1721-1725.

Leonard, A., Pereira. S., Sprecher, H., and Huang, Y.-S. (2004). Elongation of long-chain fatty acids. *Progress in Lipid Research* 43, 36-54.

Li et al. (2005) *Plant Sciences,* 169(3). 463-469.

Manuell, A. L., M. V. Beligni, et al. (2007). "Robust expression of a bioactive mammalian protein in *Chlamydomonas* chloroplast." *Plant Biotechnology Journal* 5(3): 402-412.

Meslet-Cladière, L. and O. Vallon (2011). "Novel Shuttle Markers for Nuclear Transformation of the Green Alga *Chlamydomonas reinhardtii*." *Eukaryotic Cell* 10(12): 1670-1678.

Miyazaki, K. (2011). MEGAWHOP cloning: a method of creating random mutagenesis libraries via megaprimer PCR of whole plasmids. *Methods in Enzymology*. 498: 399-406.

Nelson, J. A., P. B. Savereide, et al. (1994). "The CRY1 gene in *Chlamydomonas reinhardtii*: structure and use as a dominant selectable marker for nuclear transformation." *Molecular and Cellular Biology* 14(6): 4011-4019.

Newman, S. M., J. E. Boynton, et al. (1990). "Transformation of chloroplast ribosomal RNA genes in *Chlamydomonas*: molecular and genetic characterization of integration events." *Genetics* 126(4): 875-888.

Park and Morschhäuser (2005) *Eukaryotic cell* 4(8), 1328-1342.

Poulsen, N., P. M. Chesley, et al. (2006). "MOLECULAR GENETIC MANIPULATION OF THE DIATOM *THALASSIOSIRA PSEUDONANA* (BACILLARIOPHYCEAE) 1." *Journal of Phycology* 42(5): 1059-1065.

Raghukumar S. (2008) Thraustochytrid Marine Protists: Production of PUFAs and Other Emerging Technologies. *Mar. Biotech.* 10:631-640.

Redding, K., F. MacMillan, et al. (1998). "A systematic survey of conserved histidines in the core subunits of Photosystem I by site-directed mutagenesis reveals the likely axial ligands of P700." *EMBO J* 17(1): 50-60.

Roffey, R. A., J. H. Golbeck, et al. (1991). "Photosynthetic electron transport in genetically altered photosystem II reaction centers of chloroplasts." *Proceedings of the National Academy of Sciences* 88(20): 9122-9126.

Sakaguchi, K., T. Matsuda, et al. (2012). "Versatile Transformation System That Is Applicable to both Multiple Transgene Expression and Gene Targeting for Thraustochytrids." *Applied and Environmental Microbiology* 78(9): 3193-3202.

Schiedlmeier, B., R. Schmitt, et al. (1994). "Nuclear transformation of *Volvox carteri*." *Proceedings of the National Academy of Sciences* 91(11): 5080-5084.

Schroda, M., D. Blöcker, et al. (2000). "The HSP70A promoter as a tool for the improved expression of transgenes in *Chlamydomonas*." *The Plant Journal* 21(2): 121-131.

Sizova, I., M. Fuhrmann, et al. (2001). "A *Streptomyces rimosus* AphVII gene coding for a new type phosphotransferase provides stable antibiotic resistance to *Chlamydomonas reinhardtii*." *Gene* 277(1-2): 221-229.

Sizova, A., T. V. Lapina, et al. (1996). "Stable nuclear transformation of *Chlamydomonas reinhardtii* with a *Streptomyces rimosus* gene as the selective marker." *Gene* 181(1-2): 13-18.

Stevens, D., S. Purton, et al. (1996). "The bacterial phleomycin resistance gene ble as a dominant selectable marker in *Chlamydomonas*." *Molecular and General Genetics* 251(1): 23-30.

Surzycki, R., K. Greenham, et al. (2009). "Factors effecting expression of vaccines in microalgae." *Biologicals* 37(3): 133-138.

Zaslavskaia, L. A., J. C. Lippmeier, et al. (2000). "Transformation of the diatom *Phaeodactlum tricornutum* (Bacillariophyceae) with a variety of selectable marker and reporter genes." *Journal of Phycology* 36(2): 379-386.

Zhang, S. C., Wege, C., and Jeske, H. (2001). Movement proteins (BC1 and BV1) of Abutilon mosaic geminivirus are cotransported in and between cells of sink but not of source leaves as detected by green fluorescent protein tagging. Virology 290(2), 249-60.

We claim:

1. A vector comprising a first nucleic acid molecule and a second nucleic acid molecule, wherein the first nucleic acid molecule is heterologous and wherein the second nucleic acid molecule (a) has a sequence that is at least 90% identical to the nucleic acid sequence of SEQ ID NO: 70 and encodes a polypeptide having Δ12 desaturase activity.

2. The vector of claim 1, wherein the second nucleic acid molecule is operatively linked to a promoter.

3. The vector of claim 2, wherein the promoter is heterologous to the second nucleic acid molecule.

4. The vector of claim 1, wherein the second nucleic acid is derived from a microorganism selected from the group consisting of the genus *Schizochytrium, Oblongichytrium, Aurantiochytrium* and *Thraustochytrium*.

5. The vector of claim 4, wherein the microorganism is ONC-T18.

6. A vector comprising a first nucleic acid molecule and a second nucleic acid molecule, wherein the first nucleic acid molecule is heterologous and the second nucleic acid molecule (a) has a sequence that is at least 90% identical to the nucleic acid sequence of SEQ ID NO:69 or (b) has a sequence that is at least 90% identical to the nucleic acid sequence of SEQ ID NO:71.

7. The vector of claim 6, wherein the second nucleic acid molecule is operatively linked to a third nucleic acid sequence.

8. The vector of claim 7, wherein the third nucleic acid sequence is a heterologous nucleic acid sequence.

9. The vector of claim 7, wherein the third nucleic acid sequence encodes an enzyme polypeptide with an activity selected from the group consisting of desaturase activity, elongase activity, fatty acid synthase activity and polyketide polyunsaturated fatty acid synthase (PKS) activity.

10. The vector of claim 9, wherein the activity is a desaturase activity and wherein the desaturase activity is Δ5 desaturase activity or Δ12 desaturase activity.

11. The vector of 6, wherein the second nucleic acid is derived from a microorganism selected from the group consisting of the genus *Schizochytrium, Oblongichytrium, Aurantiochytrium* and *Thraustochytrium*.

12. The vector of claim 11, wherein the microorganism is ONC-T18.

13. An engineered microorganism, wherein the microorganism expresses a heterologous nucleic acid molecule having a sequence that is at least 90% identical to the nucleic acid sequence of SEQ ID NO:70 and encodes a polypeptide having Δ12 desaturase activity.

14. The engineered microorganism of claim 13, wherein the microorganism is selected from the group consisting of the genus *Schizochytrium, Oblongichytrium, Aurantiochytrium* and *Thraustochytrium*.

15. The engineered microorganism of claim 14, wherein the microorganism is ONC-T18.

16. The engineered microorganism of claim 13, wherein the heterologous nucleic acid sequence is operatively linked to a heterologous promoter.

17. The engineered microorganism of claim 16, wherein the heterologous promoter is at least 90% identical to SEQ ID NO: 71 or SEQ ID NO:69.

18. The engineered microorganism of claim 16, wherein the heterologous promoter is selected from the group consisting of a bacterial promoter, yeast promoter, eukaryotic viral promoter, or promoter element isolated from microalgae.

19. The engineered microorganism of claim 13, wherein the heterologous nucleic acid sequence is over-expressed.

20. The engineered microorganism of claim 13, wherein the heterologous nucleic acid sequence is introduced into the microorganism by an expression vector.

21. The engineered microorganism of claim 13, further comprising at least one heterologous enzyme-encoding nucleic acid sequence, wherein the enzyme-encoding nucleic acid encodes an enzyme polypeptide involved in polyunsaturated fatty acid biosynthesis.

22. The engineered microorganism of claim 21, wherein the enzyme polypeptide is selected from the group consisting of fatty acid synthase (FAS), Δ5 elongase, Δ4 desaturase, and polyketide PUFA synthase (PKS).

23. An engineered microorganism, wherein the microorganism expresses at least one polyunsaturated fatty acid biosynthesis polynucleotide operatively linked to a heterologous promoter and wherein the promoter is at least 90% identical to the nucleic acid sequence of SEQ ID NO:69 or SEQ ID NO:71.

24. The engineered microorganism of claim 23, wherein the at least one polyunsaturated fatty acid biosynthesis polynucleotide is endogenous to the microorganism.

25. The engineered microorganism of claim 23, wherein the at least one endogenous polyunsaturated fatty acid biosynthesis polynucleotide is operatively linked to the heterologous promoter by homologous recombination.

26. The engineered microorganism of claim 23, wherein the at least one polyunsaturated fatty acid biosynthesis polynucleotide is exogenous to the microorganism.

27. The engineered microorganism of claim 23, wherein the at least one polyunsaturated fatty acid biosynthesis polynucleotide encodes an enzyme polypeptide selected from the group consisting of fatty acid synthase (FAS), Δ5 elongase, Δ5 desaturase, Δ12 desaturase, Δ4 desaturase, and polyketide PUFA synthase (PKS).

28. The engineered microorganism of claim 23, wherein the engineered microorganism further over-expresses a nucleic acid molecule having a sequence that is at least 90% identical to the nucleic acid sequence of SEQ ID NO:70 or SEQ ID NO:72.

29. A method for producing polyunsaturated fatty acids, the method comprising:
providing an engineered *Thraustochytrium* cell, wherein the engineered *Thraustochytrium* cell expresses a heterologous nucleic acid molecule having a sequence that is at least 90% identical to the nucleic acid sequence of SEQ ID NO:70 and encodes a polypeptide having Δ12 desaturase activity, and culturing the engineered *Thraustochytrium* cell under conditions and for a time sufficient to achieve production of the one or more polyunsaturated fatty acids through heterologous expression, wherein the heterologous expression of the heterologous nucleic acid changes production of one or more polyunsaturated fatty acids by the engineered cell as compared with a reference cell cultured under comparable conditions.

30. The method of claim 29, wherein the one or more polyunsaturated fatty acids is selected from the group consisting of alpha linolenic acid, arachidonic acid, docosahexaenoic acid, docosapentaenoic acid, eicosapentaenoic acid, gamma-linolenic acid, linoleic acid and/or linolenic acid.

31. The method of claim 29, further comprising expressing at least one heterologous polynucleotide encoding an enzyme polypeptide or part of an enzyme polypeptide complex selected from the group consisting of fatty acid synthase (FAS), Δ5 elongase, Δ5 desaturase, Δ4 desaturase, and polyketide PUFA synthase (PKS).

32. The method of claim 31, wherein the heterologous nucleic acid molecule is over-expressed.

33. A method for producing polyunsaturated fatty acids, the method comprising:
providing an engineered *Thraustochytrium* cell, wherein the engineered *Thraustochytrium* cell expresses at least one polyunsaturated fatty acid biosynthesis polynucleotide operatively linked to a heterologous promoter, wherein the promoter is at least 90% identical to the nucleic acid sequence of SEQ ID NO: 69 or is at least 90% identical to the nucleic acid sequence of SEQ ID NO: 71; and culturing the engineered *Thraustochytrium* cell under conditions and for a time sufficient to achieve production of the one or more polyunsaturated fatty acids, wherein the operative linkage of the heterologous promoter changes production of one or more polyunsaturated fatty acids by the engineered cell as compared with a reference cell cultured under comparable conditions.

34. The method of claim 33, wherein the one or more polyunsaturated fatty acids is selected from the group consisting of alpha linolenic acid, arachidonic acid, docosahexaenoic acid, docosapentaenoic acid, eicosapentaenoic acid, gamma-linolenic acid, linoleic acid and/or linolenic acid.

35. The method of claim 33, further comprising expressing at least one heterologous enzyme-encoding polynucleotide, wherein the enzyme-encoding polynucleotide encodes an enzyme selected from the group consisting of fatty acid synthase (FAS), Δ5 elongase, Δ5 desaturase, Δ12 desaturase, Δ4 desaturase, and polyketide PUFA synthase (PKS).

36. The method of claim 35, wherein the encoded enzyme is over-expressed.

37. The method of claim 33, wherein the at least one polyunsaturated fatty acid biosynthesis polynucleotide encodes an enzyme polypeptide selected from the group consisting of fatty acid synthase (FAS), Δ5 elongase, Δ5 desaturase, Δ4 desaturase, and polyketide PUFA synthase (PKS).

* * * * *

SEQUENCE LISTING

<160> NUMBER OF SEQ ID NOS: 105

<210> SEQ ID NO 1

-continued

```
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
cgcggcttcc cgtctccaag c                                              21

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
ccgagtccat ggtgcccggc                                                20

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 3
gaccatgatt acgccaagct ct                                             22

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 4
gttttcccag tcacgacgt                                                 19

<210> SEQ ID NO 5
<211> LENGTH: 724
<212> TYPE: DNA
<213> ORGANISM: Thraustochytrium sp.

<400> SEQUENCE: 5
cgcggcttcc cgtctccaag cttcgtctcg gtagagattc tatcttcgcc cggcagcccg    60
ccgccgtccg gcaagtgtag aacggcagaa agcccacttg cacggaacgc cgacaagtt   120 gacgaaagcg gcccgcaagt gcggcagccc ggctggtttt tcctcgcggc gaggccaaac   180
cgccaacgcc accaagccag acaccaggta tgtgccgcac gcgccgccgc acgcgagccc   240
cgaggatgcc ccgtacgcgc tgacgccttt ctccgccccg ccgcgagaa gacgcgctcc    300 ggcaacggcg ggagccgagc gaacgggcga ggattgatcg agtagctgca ggttgagaaa   360
aaaggaaaac cgccgagatg gacaacggct ggatggacga aagacgcac gaggacgcga    420 ggactgacga tgatcacgtg cgcaggaaga cttgaaaaga agcaaggaag gtagaaaaaa   480
aagaagaaat caagcaagat gcgcgagatc gttcacattc agggcggcca gtgcggcaac   540
caggtcggcg ccaagttctg ggaggtcatc tccgatgagc acggtgtgga tcccaccggc   600
tcgtaccatg gcgactcgga cctccagctc gagcgcatca acgtctactt caacgaggcc   660
accggcggtc gctacgtgcc ccgcgccatc ctcatggacc tcgagcccggg caccatggac   720 tcgg                                                                724
```

<210> SEQ ID NO 6
<211> LENGTH: 490
<212> TYPE: DNA
<213> ORGANISM: Thraustochytrium sp.

<400> SEQUENCE: 6

```
cgcggcttcc cgtctccaag cttcgtctcg gtagagattc tatcttcgcc cggcagcccg      60
ccgccgtccg gcaagtgtag aacggcagaa agcccacttg cacggaacgc ccgacaagtt     120
gacgaaagcg gcccgcaagt gcggcagccc ggctggtttt tcctcgcggc gaggccaaac     180
cgccaacgcc accaagccag acaccaggta tgtgccgcac gcgccgccgc acgcgagccc     240
cgaggatgcc ccgtacgcgc tgacgccttt ctccgccccg cccgcgagaa gacgcgctcc     300
ggcaacggcg ggagccgagc gaacgggcga ggattgatcg agtagctgca ggttgagaaa     360
aaaggaaaac cgccgagatg gacaacggct ggatggacga aagacgcac gaggacgcga      420
ggactgacga tgatcacgtg cgcaggaaga cttgaaaaga agcaaggaag gtagaaaaaa     480
aagaagaaat                                                            490
```

<210> SEQ ID NO 7
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 7

```
ggcctgtctc ccttggccat cc                                               22
```

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 8

```
gggcatctgg ccgtccggc                                                   19
```

<210> SEQ ID NO 9
<211> LENGTH: 1115
<212> TYPE: DNA
<213> ORGANISM: Thraustochytrium sp.

<400> SEQUENCE: 9

```
ggcctgtctc ccttggccat ccattgcgct gcggaagcat tggattgcga actgcgtcgg      60
ccagatcgct tggtttccca acatgagacg cgctctgtcg gcaagaccat ttccgccccc     120
ggctttgctc acaaccaact cgtagtagat tttgtaaaga acactgcacg tctgactgct     180
cccagcccgc acgcattgcg cttggcagcc tcggtcccaa accgtcacgg tcgctgcccg     240
gtccacggga aaaataact tttgtccgcg agcggccgtt caaggcgcag ccgcgagcgt      300
gccaaccgtc cgtcccgcat tcttttccca atgttggatt cattcattct tgccaggcca     360
gatcatctgt gcctccctcg cgtgcccttc cttagcgtgc gcagatctct tcttcccaga     420
gcccgcgcgg cgcttcgtgg agtcggcgtc catgtcatgc gcgcgcggcg tcttgacccc     480
ctcggcccct ttggttcgcg gctgcgcaac gagccgtttc acgccattgc gaccaaccgc     540
gcgctaaaat cggattggcc gttgcacgcc gattttgcag cacctctggg ctgtgaggga     600
```

```
cgaccgtcca ctttacccg cacagagtgg actttcaccc cctcactcca ctgaagccaa      660
cttttcgccg tcttcccaac ccaaagttta tgctagccct catgccgcaa cggacgtcac      720
ccccatttcc actggcgacg tggggacctg ggcgcaataa ggcgcgagaa ggaaattacg      780
acggcacact ggggccagaa gagggcacta ggagcggcaa cccactggcg cggcacagcg      840
gtttggcgcg gggatcaaag caaaacccgg ctcatccaga gcaaacccga atcagccttc      900
agacggtcgt gcctaacaac acgccgttct acccccgcctt ccttgcgtcc ctcgcctccc      960
ccgagcccaa gtcttccgcc cgctcctaac gccaaccaag caagatgcgt gaggtcatct     1020
ccatccacat cggccaggcc ggtgtccagg tcggtaacgc ctgctgggag ctctactgcc     1080
tcgagcatgg catccagccg gacggccaga tgccc                                1115

<210> SEQ ID NO 10
<211> LENGTH: 1004
<212> TYPE: DNA
<213> ORGANISM: Thraustochytrium sp.

<400> SEQUENCE: 10
ggcctgtctc ccttggccat ccattgcgct gcggaagcat tggattgcga actgcgtcgg       60
ccagatcgct tggtttccca acatgagacg cgctctgtcg gcaagaccat ttccgccccc      120
ggctttgctc acaaccaact cgtagtagat tttgtaaaga cactgcacg tctgactgct       180 cccagcccgc acgcattgcg cttggcagcc tcggtcccaa accgtcacgg tcgctgcccg      240
gtccacggga aaaataact tttgtccgcg agcggccgtt caaggcgcag ccgcgagcgt       300
gccaaccgtc cgtcccgcat tcttttccca atgttggatt cattcattct tgccaggcca      360
gatcatctgt gcctccctcg cgtgcccttc cttagcgtgc gcagatctct tcttcccaga      420
gcccgcgcgc cgcttcgtgg agtcggcgtc catgtcatgc gcgcgcggcg tcttgacccc      480
ctcggcccct ttggttcgcg gctgcgcaac gagccgtttc acgccattgc gaccaaccgc      540
gcgctaaaat cggattggcc gttgcacgcc gattttgcag cacctctggg ctgtgaggga      600
cgaccgtcca ctttacccg cacagagtgg actttcaccc cctcactcca ctgaagccaa       660
cttttcgccg tcttcccaac ccaaagttta tgctagccct catgccgcaa cggacgtcac      720
ccccatttcc actggcgacg tggggacctg ggcgcaataa ggcgcgagaa ggaaattacg      780
acggcacact ggggccagaa gagggcacta ggagcggcaa cccactggcg cggcacagcg      840
gtttggcgcg gggatcaaag caaaacccgg ctcatccaga gcaaacccga atcagccttc      900
agacggtcgt gcctaacaac acgccgttct acccccgcctt ccttgcgtcc ctcgcctccc      960
ccgagcccaa gtcttccgcc cgctcctaac gccaaccaag caag                      1004

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 11
ggtacgtcgg tgagggtatg gag                                               23

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 12
gccgctaaac cgcagactgg    20

<210> SEQ ID NO 13
<211> LENGTH: 727
<212> TYPE: DNA
<213> ORGANISM: Thraustochytrium sp.

<400> SEQUENCE: 13
ggtacgtcgg tgagggtatg gagagggtga gttctccgag gccccgtgag gatctcgccg    60
ccctcgagaa ggattacgag gaggtcggcg ccgagaccgc cgagggcgag gacgaggagg    120
agggcgagga gttctaaatg cattcgcatg ctccgcacc accacacacc accgcccctc    180
ttctttcctt gctcactcga tccatagcca cttacctgcc ccttccctct accactgcca    240
cgtgcggcgt atgagcgcgc ttgcacccgc aaccttctct ctagttgttc acaattacac    300
ccgctatcaa tactcacgca ttcatcttcc ccttttttc tactttacgt accggtgctc    360
acttacttac acctgcccgc cttgttcatt cattcttctc gatgacaacg gcaggctctg    420
cttgcggcgc gcgcacgcat cccttactcc gccgcgcacc gacaagcctg cgcaaaaaac    480
aaaaaaaact tatcttcgct cgcggctccg atgtcgcggc ggcgtacgag accgcgccga    540
gttccgcccg ccatgcgatc gagagtctct ctcgtaggag cgggaccgcg agcgacctcg    600
gtgcctccga tagccagctg ggcttctaga ccggctgggg gaccgcccgc ggcgtacctc    660
tgcgcttcgg tggcccttaa aaggctgatc gtggaaaagg tcgctctcca gtctgcggtt    720
tagcggc    727

<210> SEQ ID NO 14
<211> LENGTH: 590
<212> TYPE: DNA
<213> ORGANISM: Thraustochytrium sp.

<400> SEQUENCE: 14
atgcattcgc atggctccgc accaccacac accaccgccc ctcttctttc cttgctcact    60
cgatccatag ccacttacct gccccttccc tctaccactg ccacgtgcgg cgtatgagcg    120
cgcttgcacc cgcaaccttc tctctagttg ttcacaatta cacccgctat caatactcac    180
gcattcatct tccccttttt ttctactttta cgtaccggtg ctcacttact tacacctgcc    240
cgccttgttc attcattctt ctcgatgaca acggcaggct ctgcttgcgg cgcgcgcacg    300
catcccttac tccgccgcgc accgacaagc ctgcgcaaaa aacaaaaaaa acttatcttc    360
gctcgcggct ccgatgtcgc ggcggcgtac gagaccgcgc cgagttccgc ccgccatgcg    420
atcgagagtc tctctcgtag gagcgggacc gcgagcgacc tcggtgcctc cgatagccag    480
ctgggcttct agaccggctg ggggaccgcc cgcggcgtac ctctgcgctt cggtggccct    540
taaaaggctg atcgtggaaa aggtcgctct ccagtctgcg gtttagcggc    590

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
cggcaacacc accgccgtcc    20

<210> SEQ ID NO 16
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 16
cggagaccaa gccgcccatc acc                                              23

<210> SEQ ID NO 17
<211> LENGTH: 869
<212> TYPE: DNA
<213> ORGANISM: Thraustochytrium sp.

<400> SEQUENCE: 17
cggcaacacc accgccgtcc aggagatgtt caagcgcgtc tcggagcagt tcaccagcat        60
gttccgccgc aaggccttcc ttcactggta caccggcgag ggcatggacg agatggagtt       120
caccgaggcc gagtcgaaca tgaacgacct tgtctccgag taccagcagt accaggacgc       180
caccgccgag gaggaaggcg agttcgacga ggacgaggag gagtactaag cgccttcagg       240
caggctgatc cctactgtgg gggctctgac ggacggccgg tctttgtacg taaacaggcg       300
cttcttcgcg gcccgccgag gggggcggca acgagccggg tggcgtggca cggacaaggc       360
aagagccttt ccatcccgca taaagtgatg caccattttg accttgttga tcgttttgt        420 gtgtttagag cggccccgtg cgggtaggcg aagtgcgctt ctgagcaagg aagagagagg       480
tgcagcttct tcttgatcag tgtggtaatc ttcaacggcc acgctcgctt attcgatacc       540
tgtaaagcta ccggtgcacc cgtgcaagtt gggcaccacg tagttgtact ggtgaatcca       600
aatgttagcc gctagcttgg tgccctttc gacaggaagg gcttggtgaa aagccatgct        660
gtcgatctcc cttgggtcct cgttcgtgac gctaggccag agaatagctg tgtgccgcgc       720
agtcgaagcc agcgcgcgcg cgtcggggcc gagcatagag ttagcaattc agttgtttcg       780
ggctcttgat gaggccgcca gagagcgaag aaggatgaac ttaccagatc cgcgctccgg       840
tgtattggtg atgggcggct tggtctccg                                         869

<210> SEQ ID NO 18
<211> LENGTH: 640
<212> TYPE: DNA
<213> ORGANISM: Thraustochytrium sp.

<400> SEQUENCE: 18
gcgccttcag gcaggctgat ccctactgtg ggggctctga cggacggccg gtctttgtac        60
gtaaacaggc gcttcttcgc ggcccgccga ggggggcggc aacgagccgg gtggcgtggc       120
acggacaagg caagagcctt tccatcccgc ataaagtgat gcaccatttt gaccttgttg       180 atcgttttg tgtgtttaga gcggccccgt gcgggtaggc gaagtgcgct tctgagcaag        240
gaagagagag gtgcagcttc ttcttgatca gtgtggtaat cttcaacggc cacgctcgct       300
tattcgatac ctgtaaagct accggtgcac ccgtgcaagt gggcaccac gtagttgtac        360 tggtgaatcc aaatgttagc cgctagcttg gtgccctttt cgacaggaag gcttggtga        420 aaagccatgc tgtcgatctc ccttgggtcc tcgttcgtga cgctaggcca gagaatagct       480
gtgtgccgcg cagtcgaagc cagcgcgcgc gcgtcggggc cgagcataga gttagcaatt       540
cagttgtttc gggctcttga tgaggccgcc agagagcgaa gaaggatgaa cttaccagat       600
ccgcgctccg gtgtattggt gatgggcggc ttggtctccg                             640

<210> SEQ ID NO 19
<211> LENGTH: 950
<212> TYPE: DNA
<213> ORGANISM: Thraustochytrium sp.

<400> SEQUENCE: 19

| | | | | | |
|---|---|---|---|---|---|
| caacgccatc | ctcgaccaca | gcaaggacac | gcaccgcttc | ggctacggta | tccagatcgg | 60 |
| ataaatatta | taccgcccct | tccgctctcc | ttttcttttt | tgctcgtctg | gatgccagac | 120 |
| taaggagtcc | ttgctcctct | gcgcaaggct | gctcacccag | agtctctgcc | tgtggttgag | 180 |
| cgccaccaa | caggttaaag | cgaaccaggg | ccgccccgtt | gccgctgcga | tgtcgctgct | 240 |
| cttgcgagac | tcttcattag | atcggcggaa | tgctgccgca | ggactgaccg | cctcttcgtt | 300 |
| cgttcgtttg | tacgcgagcg | gtgcgagcgg | cttcgttgtt | ggcagatagg | cagaacgcga | 360 |
| gcagttcacg | tttctttgca | gctttatcta | tccgcaaatt | cgcctcagcg | tctgcaactt | 420 |
| tccggtgagg | acagcagagc | tgcagttctg | atcgtctcca | tcttttggag | cgcatgtcga | 480 |
| cgtcccccag | ctcgtctccg | tctcccctgg | agtggacggt | ctctttcaca | gtgcctgggt | 540 |
| gcggccattt | ccctaaatag | gttgcgcagc | cgagtttcct | taaacgtgcc | tggtccgcgt | 600 |
| gcttccgcct | tactacctga | acgcgcagta | gctcggcgcg | tgccgcttta | aggcgggcgg | 660 |
| ggtggctgct | cttgcttacg | ccaggcgcgt | acgtcagcag | cgccggcgcc | atgctgccca | 720 |
| tagcggccac | agaatcgtag | gcgctgcaat | cgggaactgc | caagatggca | atcgagacga | 780 |
| tcccccaaaa | gtggacaagc | accgtcaaag | taacctggct | gatgatgcc | gggaccgcct | 840 |
| ggtgacggcc | agccggcaaa | accggaatct | atcacgagga | ctgggcagat | caagggccta | 900 |
| gtgctagcga | gcagctcgag | cgaaagaagc | gcgccagcag | cgcaggcacg | | 950 |

<210> SEQ ID NO 20
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 20
tatatatcta gacaacgcca tcctcgacca cag                                33

<210> SEQ ID NO 21
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 21
tatataccat ggcgtgcctg cgctgctggc                                    30

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gatgctcgtc aggggggcgg                                               20

<210> SEQ ID NO 23

-continued

```
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 23
cccggaccac accggcg                                                        17

<210> SEQ ID NO 24
<211> LENGTH: 1216
<212> TYPE: DNA
<213> ORGANISM: Thraustochytrium sp.

<400> SEQUENCE: 24
gtgaccaaaa gccgtgaacg ggcgtggccg aggctacagc acgcagcggt gttctctgcg        60
tattatattt ttcgcaaggt ttcccgacgg ctggtccgcg tgcccgcgcc gcgcgcacgc       120
tctcactaga cgttggtcat gagtgtttcg agtcaagacc tcggagaaga attggggcgc       180
acaccttccg tgcgcgcacc cctgccactg tataccgtgc gtaccccacc agacagaagg       240
tcaccacccg tgctctcttc gtcagctata ccgtgtgctg tagatcgtcg caggattcgg       300
gttgtgcaca ccgcgctccg tgggctgggg gccctggcgc ggcggcttcc taggatatag       360
tctataaaac ccagcgaatt ttacacacag agcggttcat ttgcgctggg tccggtgcgc       420
aatttcgggg cacagcctgc acgtttacat cgacgtaaca gccacagtca tcgtcgccag       480
cctcttcggc cttcccaccg acccggctgc tgcccgcctt cctggctggc tgatgaacta       540
tcgcggcctg cctggcacgt acgtgcccct cccatttctc cccggtcctc cagaaatgcg       600
cctccggccc caatgaaagc aggcgttggc catgcggcgc ccgacatctg ggtcctcgcg       660
ccttctttga tgacatcgtc ctcatcgtcg tcggcgacct ggtcttcgtg atcgcttgtt       720
gatcacgcgc ttggcatctt gcgaggagaa ccgtctgcac tcttttggcg cggccgaggt       780
gccttccggg gtgcaggcca gtcgccagac cagacctgct gcaaagcccg aacatcgccg       840
tcgaggtaga ccattaggta cgtacgtacg cacgtcttca tgatcgacgc caacgtcatg       900
cggtcgatgc cccgccacgc gatggcgcta gcagccagga gcgcgtgtgt acgggcgcgg       960
agcttcgctc gcaagcaaag ctgggcgctt gggccgggga tcgggccact acttggacga      1020
acgaacgaaa cgcatgacgt catccttggc agtaaatctt gccggagcgc gcaaaaccca      1080
ggctggacgc gctgggtgcg attgagaacc gcaagctttg gagcctttca ctgagcaggg      1140
ggaactgacg ctggagcgcg cgaccgtagg cgaaggaatt tgatcgaagt aggcaggact      1200
gcccgcaggg gtcagg                                                     1216

<210> SEQ ID NO 25
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 25
tatatactcg aggtgaccaa aagccgtgaa cgg                                      33

<210> SEQ ID NO 26
<211> LENGTH: 30
<212> TYPE: DNA
<213> ORGANISM: Artificial sequence
<220> FEATURE:
<223> OTHER INFORMATION: Synthetic oligonucleotide
```

<400> SEQUENCE: 26
tatataccat ggcctgaccc ctgcgggcag                               30

<210> SEQ ID NO 27
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 27
caacctggtt gatcctgcca gta                                      23

<210> SEQ ID NO 28
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 28
caacctggtt gatcctgcca gtagccc                                  27

<210> SEQ ID NO 29
<211> LENGTH: 1764
<212> TYPE: DNA
<213> ORGANISM: Thraustochytrium sp.

<400> SEQUENCE: 29
tcactacgga aaccttgtta cgacttcacc ttcctctaaa caataagatt cacccgagtt    60
ctgacccccc tcgcgaacaa acgctcaaaa ggtcatccca tggtttcatc ggaccgttca   120
atcggtaggt gcgacgggcg gtgtgtacaa agggcaggga cgtattcaat gcaagctgat   180
gacttgcgtt tactaggaat tcctcgttgg agattaataa ttgcaaaaat ctagccccag   240
cacgatgggc gttgaaagga tttgccatgc cttccggcaa agcacctcgc tgcgaacaac   300
gatgaccacc cgttgaaccc atcagtgtag cgcgcgtgcg gcccagaaca tctaagggca   360
tcacagacct gttattgcct cgaacttcct gctcgtatac cgaacatgtc cctctaagaa   420
gcgtacgcaa gtatgtcgcc atacccaccg ctatttagta ggccgaggtc tcgttcgtta   480
acggaattaa ccagacaaat cactccacca actaagaacg ccatgcacc accacccata    540 gaatcaagaa agagctctca atctgtcaat cctacctatg tctggacctg gtaagttttc   600
ccgtgttgag tcaaattaag ccgcaggctc cactcctggt ggtgcccttc cgtcaattcc   660
tttaagtttc agccttgcga ccatactccc cccggaaccc aaagactttg atttctcatg   720
tgctgctgcg agggtccaat acaaacaccc cgcaatcgca agtcggcatc gtttacggtc   780
tagactacga tggtatctaa tcatcttcga tccccagact ttcgttcttg attaatgaaa   840
acatgcttgg taaatgcctt cgctgtagtt cgtctttcgg aaatccaaga atttcacctc   900
tagctcctaa atacgaatac ccccaactgt tcctattcat cattactcag atgtgcaaac   960
caacaaaata gcacccgagc cctatctgat catcccataa taaacatcca ggtcatacga  1020
cctgcttgga acactctgct ttaattacag tgaacgacgc cactaaaaaa agaggcgagg  1080
atggcagagg agccgctcgg caaacagagc gcagtcgcgc aaagaccggg gctcccgccc  1140
cagaaattca actacgagct ttttaactgc aacaactttta gcatacgctt ctggagctgg  1200
aattaccgcg gctgctggca ccagacttgc cctccagttg atcctcgatg agggttttac  1260

```
attgctctca ttccaatagc aagacgcgaa gcgccccgca ttgatatttc tcgtcactac   1320
ctcgtggagt ccacattggg taatttacgc gcctgctgcc ttccttggat gtggtagccg   1380
tctctcaggc tccctctccg gagtcgagcc ctaactcccc gtcacccgtt atagtcaccg   1440
tagtccaata cactaccgtc gacaactgat ggggcagaaa ctcaaacgat tcatcgctcc   1500
aaacaagcga tctgctcaat tatcatgact caccatctta cttggcttca actctaataa   1560
gtgcggccct cccgaacagt cgggccctct cagcatgtat taattccaga attactgcag   1620
gtatccatat aaagaaaata ccgaagaaat cataactgat ataatgagcc gttcgcagtc   1680
tcacagtata atcgcttata cttacacatg catggcttaa tctttgagac gagcgtaggg   1740
ctactggcag atcaaccag gttg                                           1764

<210> SEQ ID NO 30
<211> LENGTH: 4235
<212> TYPE: DNA
<213> ORGANISM: Thraustochytrium sp.

<400> SEQUENCE: 30
gacgaaaggg cctcgtgata cgcctatttt tataggttaa tgtcatgata ataatggttt     60
cttagacgtc aggtggcact tttcggggaa atgtgcgcgg aaccccctatt tgtttatttt    120 tctaaataca ttcaaatatg tatccgctca tgagacaata accctgataa atgcttcaat    180
aatattgaaa aaggaagagt atgagtattc aacatttccg tgtcgccctt attcccttt     240 ttgcggcatt ttgccttcct gttttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttttaatt taaaaggatc taggtgaaga   1140 tccttttga taatctcatg accaaaatcc cttaacgtga gttttcgttc cactgagcgt   1200
cagaccccgt agaaaagatc aaaggatctt cttgagatcc ttttttctg cgcgtaatct   1260 gctgcttgca acaaaaaaa ccaccgctac cagcggtggt ttgtttgccg gatcaagagc   1320
taccaactct ttttccgaag gtaactggct tcagcagagc gcagatacca atactgtcc   1380 ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctga acggggggtt   1560 cgtgcacaca gcccagcttg gagcgaacga cctacaccga actgagatac ctacagcgtg   1620
```

```
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttttgtga tgctcgtcag   1800 gggggcggag cctatggaaa aacgccagca acgcggcctt tttacggttc ctggccttt    1860 gctggccttt tgctcacatg tgtgctgggc ccagccggcc agatctgagc tcgcggccgc    1920
gatatcgcta gctcgaggtg accaaaagcc gtgaacgggc gtggccgagg ctacagcacg    1980
cagcggtgtt ctctgcgtat tatattttc gcaaggtttc ccgacggctg gtccgcgtgc    2040
ccgcgccgcg cgcacgctct cactagacgt tggtcatgag tgtttcgagt caagacctcg    2100
gagaagaatt ggggcgcaca ccttccgtgc gcgcacccct gccactgtat accgtgcgta    2160
ccccaccaga cagaaggtca ccacccgtgc tctcttcgtc agctataccg tgtgctgtag    2220
atcgtcgcag gattcgggtt gtgcacaccg cgctccgtgg gctggggcc ctggcgcggc     2280 ggcttcctag gatatagtct ataaaaccca gcgaattta cacacagagc ggttcatttg     2340
cgctgggtcc ggtgcgcaat tcggggcac agcctgcacg tttacatcga cgtaacagcc     2400
acagtcatcg tcgccagcct cttcggcctt cccaccgacc cggctgctgc ccgccttcct    2460
ggctggctga tgaactatcg cggcctgcct ggcacgtacg tgcccctccc atttctcccc    2520
ggtcctccag aaatgcgcct ccggcccaa tgaaagcagg cgttggccat gcggcgcccg     2580
acatctgggt cctcgcgcct tctttgatga catcgtcctc atcgtcgtcg cgacctggt    2640 cttcgtgatc gcttgttgat cacgcgcttg gcatcttgcg aggagaaccg tctgcactct    2700
tttggcgcgg ccgaggtgcc ttccggggtg caggccagtc gccagaccag acctgctgca    2760
aagcccgaac atcgccgtcg aggtagacca ttaggtacgt acgtacgcac gtcttcatga    2820
tcgacgccaa cgtcatgcgg tcgatgcccc gccacgcgat ggcgctagca gccaggagcg    2880
cgtgtgtacg ggcgcggagc ttcgctcgca agcaaagctg ggcgcttggg ccggggatcg    2940
ggccactact tggacgaacg aacgaaacgc atgacgtcat ccttggcagt aaatcttgcc    3000
ggagcgcgca aaacccaggc tggacgcgct gggtgcgatt gagaaccgca agctttggag    3060
cctttcactg agcaggggga actgacgctg gagcgcgcga ccgtaggcga aggaatttga    3120
tcgaagtagg caggactgcc cgcagggtc aggccatggc caagttgacc agtgccgttc     3180
cggtgctcac cgcgcgcgac gtcgccgag cggtcgagtt ctggaccgac cggctcgggt     3240
tctcccggga cttcgtggag gacgacttcg ccggtgtggt ccgggacgac gtgaccctgt    3300
tcatcagcgc ggtccaggac caggtggtgc cggacaacac cctggcctgg gtgtgggtgc    3360
gcggcctgga cgagctgtac gccgagtggt cggaggtcgt gtccacgaac ttccgggacg    3420
cctccgggcc ggccatgacc gagatcgcg agcagccgtg ggggcgggag ttcgccctgc     3480
gcgacccggc cggcaactgc gtgcacttcg tggccgagga gcaggactga cacgtgctac    3540
gagatttcga ttccaccgcc gccttctatg aaaggttggg cttcggaatc gttttccggg    3600
acgccggctg gatgatcctc cagcgcgggg atctcatgct ggagttcttc gcccacccca    3660
acttgtttat tgcagcttat aatggttaca aataaagcaa tagcatcaca aatttcacaa    3720
ataaagcatt tttttcactg cattctagtt gtggtttgtc caaactcatc aatgtatctt    3780
atcatgtctg aattcccggg gatcctctag agtcgacctg caggcatgca agcttggcac    3840
tggccgtcgt tttacaacgt cgtgactggg aaaaccctgg cgttacccaa cttaatcgcc    3900
ttgcagcaca tccccctttc gccagctggc gtaatagcga agaggcccgc accgatcgcc    3960
```

```
cttcccaaca gttgcgcagc ctgaatggcg aatggcgcct gatgcggtat tttctcctta    4020
cgcatctgtg cggtatttca caccgcatat atggtgcact ctcagtacaa tctgctctga    4080
tgccgcatag ttaagccagc cccgacaccc gccaacaccc gctgacgcgc cctgacgggc    4140
ttgtctgctc ccggcatccg cttacagaca agctgtgacc gtctccggga gctgcatgtg    4200
tcagaggttt tcaccgtcat caccgaaacg cgcga                              4235

<210> SEQ ID NO 31
<211> LENGTH: 3964
<212> TYPE: DNA
<213> ORGANISM: Thraustochytrium sp.

<400> SEQUENCE: 31
gacgaaaggg cctcgtgata cgcctatttt tataggttaa tgtcatgata ataatggttt      60
cttagacgtc aggtggcact tttcggggaa atgtgcgcgg aaccccctatt tgtttatttt    120 tctaaataca ttcaaatatg tatccgctca tgagacaata accctgataa atgcttcaat     180
aatattgaaa aggaagagt atgagtattc aacatttccg tgtcgccctt attccctttt      240
ttgcggcatt tgccttcct gttttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgctttttttg cacaacatgg    660 gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggccctttc cggctggctg gtttattgct gataaatctg    900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc attttaatt taaaaggatc taggtgaaga    1140 tccttttga taatctcatg accaaaatcc cttaacgtga gttttcgttc cactgagcgt    1200
cagaccccgt agaaaagatc aaaggatctt cttgagatcc ttttttttctg cgcgtaatct    1260 gctgcttgca acaaaaaaaa ccaccgctac cagcggtggt ttgtttgccg gatcaagagc    1320
taccaactct ttttccgaag gtaactggct tcagcagagc gcagatacca aatactgtcc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg atttttgtga tgctcgtcag    1800
gggggcggag cctatggaaa aacgccagca acgcggcctt tttacggttc ctggccttttt   1860
```

```
gctggccttt tgctcacatg tgtgctgggc ccagccggcc agatctgagc tcgcggccgc   1920
gatatcgcta gacaacgcca tcctcgacca cagcaaggac acgcaccgct tcggctacgg   1980
tatccagatc ggataaatat tataccgccc cttccgctct ccttttcttt tttgctcgtc   2040
tggatgccag actaaggagt ccttgctcct ctgcgcaagg ctgctcaccc agagtctctg   2100
cctgtggttg agcgcccacc aacaggttaa agcgaaccag ggccgccccg ttgccgctgc   2160
gatgtcgctg ctcttgcgag actcttcatt agatcggcgg aatgctgccg caggactgac   2220
cgcctcttcg ttcgttcgtt tgtacgcgag cggtgcgagc ggcttcgttg ttggcagata   2280
ggcagaacgc gagcagttca cgtttctttg cagctttatc tatccgcaaa ttcgcctcag   2340
cgtctgcaac tttccggtga ggacagcaga gctgcagttc tgatcgtctc catcttttgg   2400
agcgcatgtc gacgtccccc agctcgtctc cgtctcccct ggagtggacg gtctctttca   2460
cagtgcctgg gtgcggccat ttccctaaat aggttgcgca gccgagtttc cttaaacgtg   2520
cctggtccgc gtgcttccgc cttactacct gaacgcgcag tagctcggcg cgtgccgctt   2580
taaggcgggc ggggtggctg ctcttgctta cgccaggcgc gtacgtcagc agcgccggcg   2640
ccatgctgcc catagcggcc acagaatcgt aggcgctgca atcgggaact gccaagatgg   2700
caatcgagac gatcccccaa aagtggacaa gcaccgtcaa agtaacctgg ctgatgatgg   2760
ccgggaccgc ctggtgacgg ccagccggca aaaccggaat ctatcacgag gactgggcag   2820
atcaagggcc tagtgctagc gagcagctcg agcgaaagaa gcgcgccagc agcgcaggca   2880
cgccatggcc aagttgacca gtgccgttcc ggtgctcacc gcgcgcgacg tcgccggagc   2940
ggtcgagttc tggaccgacc ggctcgggtt ctcccgggac ttcgtggagg acgacttcgc   3000
cggtgtggtc cgggacgacg tgaccctgtt catcagcgcg gtccaggacc aggtggtgcc   3060
ggacaacacc ctggcctggg tgtgggtgcg cggcctggac gagctgtacg ccgagtggtc   3120
ggaggtcgtg tccacgaact tccgggacgc ctccgggccg gccatgaccg agatcggcga   3180
gcagccgtgg gggcgggagt tcgccctgcg cgacccggcc ggcaactgcg tgcacttcgt   3240
ggccgaggag caggactgac acgtgctacg agatttcgat tccaccgccg ccttctatga   3300
aaggtttggc ttcggaatcg ttttccggga cgccggctgg atgatcctcc agcgcgggga   3360
tctcatgctg gagttcttcg cccaccccaa cttgtttatt gcagcttata atggttacaa   3420
ataaagcaat agcatcacaa atttcacaaa taaagcattt ttttcactgc attctagttg   3480
tggtttgtcc aaactcatca atgtatctta tcatgtctga attcccgggg atcctctaga   3540
gtcgacctgc aggcatgcaa gcttggcact ggccgtcgtt ttacaacgtc gtgactggga   3600
aaaccctggc gttacccaac ttaatcgcct tgcagcacat ccccctttcg ccagctggcg   3660
taatagcgaa gaggcccgca ccgatcgccc ttcccaacag ttgcgcagcc tgaatggcga   3720
atggcgcctg atgcggtatt ttctccttac gcatctgtgc ggtatttcac accgcatata   3780
tggtgcactc tcagtacaat ctgctctgat gccgcatagt taagccagcc ccgacacccg   3840
ccaacacccg ctgacgcgcc ctgacgggct tgtctgctcc cggcatccgc ttacagacaa   3900
gctgtgaccg tctccgggag ctgcatgtgt cagaggtttt caccgtcatc accgaaacgc   3960
gcga                                                                3964
```

<210> SEQ ID NO 32
<211> LENGTH: 4319
<212> TYPE: DNA
<213> ORGANISM: Thraustochytrium sp.

<400> SEQUENCE: 32

```
gacgaaaggg cctcgtgata cgcctatttt tataggttaa tgtcatgata ataatggttt    60
cttagacgtc aggtggcact tttcggggaa atgtgcgcgg aaccctatt tgtttatttt   120
tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gttttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga caccacgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggga gtcaggcaac tatggatgaa cgaaatagac  1020
agatcgctga gataggtgcc tcactgatta agcattggta actgtcagac caagtttact  1080
catatatact ttagattgat ttaaaacttc atttttaatt taaaaggatc taggtgaaga  1140
tcctttttga taatctcatg accaaaatcc cttaacgtga gttttcgttc cactgagcgt  1200
cagaccccgt agaaaagatc aaaggatctt cttgagatcc ttttttttctg cgcgtaatct  1260
gctgcttgca aacaaaaaaa ccaccgctac cagcggtggt ttgtttgccg gatcaagagc  1320
taccaactct ttttccgaag gtaactggct tcagcagagc gcagatacca aatactgtcc  1380
ttctagtgta gccgtagtta ggccaccact tcaagaactc tgtagcaccg cctacatacc  1440
tcgctctgct aatcctgtta ccagtggctg ctgccagtgg cgataagtcg tgtcttaccg  1500
ggttggactc aagacgatag ttaccggata aggcgcagcg gtcgggctga acggggggtt  1560
cgtgcacaca gcccagcttg gagcgaacga cctacaccga actgagatac ctacagcgtg  1620
agcattgaga aagcgccacg cttcccgaag ggagaaaggc ggacaggtat ccggtaagcg  1680
gcagggtcgg aacaggagag cgcacgaggg agcttccagg gggaaacgcc tggtatcttt  1740
atagtcctgt cgggtttcgc cacctctgac ttgagcgtcg attttgtga tgctcgtcag  1800
gggggcggag cctatggaaa aacgccagca acgcggcctt tttacggttc ctggccttt   1860
gctggccttt tgctcacatg tgtgctgggc ccagccggcc agatctgagc tcgcggccgc  1920
gatatcgcta gacaacgcca tcctcgacca cagcaaggac acgcaccgct tcggctacgg  1980
tatccagatc ggataaatat tataccgccc cttccgctct ccttttcttt tttgctcgtc  2040
tggatgccag actaaggagt ccttgctcct ctgcgcaagg ctgctcaccc agagtctctg  2100
cctgtggttg agcgcccacc aacaggttaa agcgaaccag ggccgccccg ttgccgctgc  2160
gatgtgcgct ctcttgcgag actcttcatt agatcggcgg aatgctgccg caggactgac  2220
cgcctcttcg ttcgttcgtt tgtacgcgag cggtgcgagc ggcttcgttg ttggcagata  2280
ggcagaacgc gagcagttca cgtttctttg cagctttatc tatccgcaaa ttcgcctcag  2340
```

```
cgtctgcaac tttccggtga ggacagcaga gctgcagttc tgatcgtctc catcttttgg    2400
agcgcatgtc gacgtccccc agctcgtctc cgtctcccct ggagtggacg gtctctttca    2460
cagtgcctgg gtgcggccat ttccctaaat aggttgcgca gccgagtttc cttaaacgtg    2520
cctggtccgc gtgcttccgc cttactacct gaacgcgcag tagctcggcg cgtgccgctt    2580
taaggcgggc ggggtggctg ctcttgctta cgccaggcgc gtacgtcagc agcgccggcg    2640
ccatgctgcc catagcggcc acagaatcgt aggcgctgca atcgggaact gccaagatgg    2700
caatcgagac gatcccccaa aagtggacaa gcaccgtcaa agtaacctgg ctgatgatgg    2760
ccgggaccgc ctggtgacgg ccagccggca aaaccggaat ctatcacgag gactgggcag    2820
atcaagggcc tagtgctagc gagcagctcg agcgaaagaa gcgcgccagc agcgcaggca    2880
cgatgagtaa aggagaagaa cttttcactg gagttgtccc aattcttgtt gaattagatg    2940
gtgatgttaa tgggcacaaa ttttctgtca gtggagaggg tgaaggtgat gcaacatacg    3000
gaaaacttac ccttaaattt atttgcacta ctggaaaact acctgttcca tggccaacac    3060
ttgtcactac tttcacttat ggtgttcaat gcttttcaag atacccagat catatgaagc    3120
ggcacgactt cttcaagagc gccatgcctg agggatacgt gcaggagagg accatctctt    3180
tcaaggacga cgggaactac aagacacgtg ctgaagtcaa gtttgaggga gacaccctcg    3240
tcaacaggat cgagcttaag ggaatcgatt tcaaggagga cggaaacatc ctcggccaca    3300
agttggaata caactacaac tcccacaacg tatacatcac ggcagacaaa caaaagaatg    3360
gaatcaaagc taacttcaaa attagacaca acattgaaga tggaagcgtt caactagcag    3420
accattatca acaaaatact ccaattggcg atggccctgt cctttttacca gacaaccatt    3480 acctgtccac acaatctgcc ctttcgaaag atcccaacga aaagagagac cacatggtcc    3540
ttcttgagtt tgtaacagct gctgggatta cacatggcat ggatgaacta tacaaataag    3600
gtacctctac gcgtcacgtg ctacgagatt tcgattccac cgccgccttc tatgaaaggt    3660
tgggcttcgg aatcgttttc cgggacgccg gctggatgat cctccagcgc ggggatctca    3720
tgctggagtt cttcgcccac cccaacttgt ttattgcagc ttataatggt tacaaataaa    3780
gcaatagcat cacaaatttc acaaataaag cattttttc actgcattct agttgtggtt    3840
tgtccaaact catcaatgta tcttatcatg tctgaattcc cggggatcct ctagagtcga    3900
cctgcaggca tgcaagcttg gcactggccg tcgttttaca acgtcgtgac tgggaaaacc    3960
ctggcgttac ccaacttaat cgccttgcag cacatccccc tttcgccagc tggcgtaata    4020
gcgaagaggc ccgcaccgat cgcccttccc aacagttgcg cagcctgaat ggcgaatggc    4080
gcctgatgcg gtattttctc cttacgcatc tgtgcggtat ttcacaccgc atatatggtg    4140
cactctcagt acaatctgct ctgatgccgc atagttaagc cagccccgac acccgccaac    4200
acccgctgac gcgccctgac gggcttgtct gctcccggca tccgcttaca gacaagctgt    4260
gaccgtctcc gggagctgca tgtgtcagag gttttcaccg tcatcaccga aacgcgcga    4319

<210> SEQ ID NO 33
<211> LENGTH: 78
<212> TYPE: DNA
<213> ORGANISM: Artificial sequence
<220> FEATURE:
<223> OTHER INFORMATION: Synthetic oligonucleotide

<400> SEQUENCE: 33
gagcagctcg agcgaaagaa gcgcgccagc agcgcaggca cgatgagtaa aggagaagaa    60
```

```
cttttcactg gagttgtc                                                    78
```

<210> SEQ ID NO 34
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 34

```
gtgacgcgta gaggtacctt atttgtatag ttcatccatg ccatgtgtaa tccc           54
```

<210> SEQ ID NO 35
<211> LENGTH: 7032
<212> TYPE: DNA
<213> ORGANISM: Thraustochytrium sp. ONC-T18

<400> SEQUENCE: 35

```
agctgtttcc tgtgtgaaat tgttatccgc tcacaattcc acacaacata cgagccggaa     60
gcataaagtg taaagcctgg ggtgcctaat gagtgagcta actcacatta attgcgttgc    120
gctcactgcc cgctttccag tcgggaaacc tgtcgtgcca gctgcattaa tgaatcggcc    180
aacgcgcggg gagaggcggt ttgcgtattg ggcgctcttc cgcttcctcg ctcactgact    240
cgctgcgctc ggtcgttcgg ctgcggcgag cggtatcagc tcactcaaag gcggtaatac    300
ggttatccac agaatcaggg gataacgcag gaaagaacat gtgagcaaaa ggccagcaaa    360
aggccaggaa ccgtaaaaag gccgcgttgc tggcgttttt ccataggctc cgcccccctg    420
acgagcatca caaaaatcga cgctcaagtc agaggtggcg aaacccgaca ggactataaa    480
gataccaggc gtttccccct ggaagctccc tcgtgcgctc tcctgttccg accctgccgc    540
ttaccggata cctgtccgcc tttctccctt cgggaagcgt ggcgctttct catagctcac    600
gctgtaggta tctcagttcg gtgtaggtcg ttcgctccaa gctgggctgt gtgcacgaac    660
cccccgttca gcccgaccgc tgcgccttat ccggtaacta tcgtcttgag tccaacccgg    720
taagacacga cttatcgcca ctggcagcag ccactggtaa caggattagc agagcgaggt    780
atgtaggcgg tgctacagag ttcttgaagt ggtggcctaa ctacggctac actagaagga    840
cagtatttgg tatctgcgct ctgctgaagc cagttacctt cggaaaaaga gttggtagct    900
cttgatccgg caaacaaacc accgctggta gcggtggttt ttttgtttgc aagcagcaga    960
ttacgcgcag aaaaaaagga tctcaagaag atcctttgat cttttctacg ggtctgacg   1020
ctcagtggaa cgaaaactca cgttaaggga ttttggtcat gaattaattc ttagaaaaac   1080
tcatcgagca tcaaatgaaa ctgcaattta ttcatatcag gattatcaat accatatttt   1140
tgaaaaagcc gtttctgtaa tgaaggagaa aactcaccga gcagttcca taggatggca   1200
agatcctggt atcggtctgc gattccgact cgtccaacat caatacaacc tattaatttc   1260
ccctcgtcaa aaataaggtt atcaagtgag aaatcaccat gagtgacgac tgaatccggt   1320
gagaatggca aaagtttatg catttctttc cagacttgtt caacaggcca gccattacgc   1380
tcgtcatcaa atcactcgc atcaaccaaa ccgttattca ttcgtgattg cgcctgagcg   1440
agacgaaata cgcgatcgct gttaaaagga caattacaaa caggaatcga atgcaaccgg   1500
cgcaggaaca ctgccagcgc atcaacaata ttttcacctg aatcaggata ttcttctaat   1560
acctggaatg ctgttttccc ggggatcgca gtggtgagta accatgcatc atcaggagta   1620
cggataaaat gcttgatggt cggaagaggc ataaattccg tcagccagtt tagtctgacc   1680
atctcatctg taacatcatt ggcaacgcta cctttgccat gtttcagaaa caactctggc   1740
```

-continued

```
gcatcgggct tcccatacaa tcgatagatt gtcgcacctg attgcccgac attatcgcga    1800
gcccatttat acccatataa atcagcatcc atgttggaat ttaatcgcgg cctagagcaa    1860
gacgtttccc gttgaatatg gctcataaca ccccttgtat tactgtttat gtaagcagac    1920
agttttattg ttcatgagat tatcaaaaag gatcttcacc tagatccttt taaattaaaa    1980
atgaagtttt aaatcaatct aaagtatata tgagtaaact tggtctgaca gttaccaatg    2040
cttaatcagt gaggcaccta tctcagcgat ctgtctattt cgttcatcca tagttgcctg    2100
actccccgtc gtgtagataa ctacgatacg ggagggctta ccatctggcc ccagtgctgc    2160
aatgataccg cgagacccac gctcaccggc tccagattta tcagcaataa accagccagc    2220
cggaagggcc gagcgcagaa gtggtcctgc aactttatcc gcctccatcc agtctattaa    2280
ttgttgccgg gaagctagag taagtagttc gccagttaat agtttgcgca acgttgttgc    2340
cattgctaca ggcatcgtgg tgtcacgctc gtcgtttggt atggcttcat tcagctccgg    2400
ttcccaacga tcaaggcgag ttacatgatc ccccatgttg tgcaaaaaag cggttagctc    2460
cttcggtcct ccgatcgttg tcagaagtaa gttggccgca gtgttatcac tcatggttat    2520
ggcagcactg cataattctc ttactgtcat gccatccgta agatgctttt ctgtgactgg    2580
tgagtactca accaagtcat tctgagaata gtgtatgcgg cgaccgagtt gctcttgccc    2640
ggcgtcaata cgggataata ccgcgccaca tagcagaact ttaaaagtgc tcatcattgg    2700
aaaacgttct cggggcgaaa actctcaag gatcttaccg ctgttgagat ccagttcgat    2760
gtaacccact cgtgcaccca actgatcttc agcatctttt actttcacca gcgtttctgg    2820
gtgagcaaaa acaggaaggc aaaatgccgc aaaaaaggga ataagggcga cacggaaatg    2880
ttgaatactc atactcttcc tttttcaata ttattgaagc atttatcagg gttattgtct    2940
catgagcgga tacatatttg aatgtattta gaaaaataaa caaataggg ttccgcgcac    3000 atttccccga aaagtgccac ctgacgcgcc ctgtagcggc gcattaagcg cggcgggtgt    3060
ggtggttacg cgcagcgtga ccgctacact tgccagcgcc ctagcgcccg ctcctttcgc    3120
tttcttccct tcctttctcg ccacgttcgc cggctttccc cgtcaagctc taaatcgggg    3180
gctcccttta gggttccgat ttagtgcttt acggcacctc gaccccaaaa aacttgatta    3240
gggtgatggt tcacgtagtg ggccatcgcc ctgatagacg ttttttcgcc ctttgacgtt    3300
ggagtccacg ttctttaata gtggactctt gttccaaact ggaacaacac tcaaccctat    3360
ctcggtctat tcttttgatt tataagggat tttgccgatt tcggcctatt ggttaaaaaa    3420
tgagctgatt taacaaaaat ttaacgcgaa ttttaacaaa atattaacgc ttacaatttc    3480
cattcgccat tcaggctgcg caactgttgg gaagggcgat cggtgcgggc ctcttcgcta    3540
ttacgccagc tggcgaaagg gggatgtgct gcaaggcgat taagttgggt aacgccaggg    3600
ttttcccagt cacgacgttg taaaacgacg gccagtgaat tgtgcggccg cgagctcggg    3660
cccccacacg tgtggtctag agctagccta ggctcgagaa gcttggcctg tctcccttgg    3720
ccatccattg cgctgcggaa gcattggatt gcgaactgcg tcggccagat cgcttggttt    3780
cccaacatga gacgcgctct gtcggcaaga ccatttccgc ccccggcttt gctcacaacc    3840
aactcgtagt agattttgta aagaacactg cacgtctgac tgctcccagc ccgcacgcat    3900
tgcgcttggc agcctcggtc ccaaaccgtc acggtcgctg cccggtccac gggaaaaaat    3960
aacttttgtc cgcgagcggc cgttcaaggc gcagccgcga gcgtgccaac cgtccgtccc    4020
gcattctttt cccaatgttg gattcattca ttcttgccag gccagatcat ctgtgcctcc    4080
```

```
ctcgcgtgcc cttccttagc gtgcgcagat ctcttcttcc cagagcccgc gcggcgcttc    4140
gtggagtcgg cgtccatgtc atgcgcgcgc ggcgtcttga ccccctcggc cccttttggtt    4200 cgcggctgcg caacgagccg tttcacgcca ttgcgaccaa ccgcgcgcta aaatcggatt    4260
ggccgttgca cgccgatttt gcagcacctc tgggctgtga gggacgaccg tccactttta    4320
cccgcacaga gtggactttc accccctcac tccactgaag ccaactttc gccgtcttcc     4380 caacccaaag tttatgctag ccctcatgcc gcaacgacg tcaccccat ttccactggc      4440 gacgtgggga cctgggcgca ataaggcgcg agaaggaaat tacgacggca cactgggcc     4500 agaagagggc actaggagcg gcaacccact ggcgcggcac agcggtttgg cgcggggatc    4560
aaagcaaaac ccggctcatc cagagcaaac ccgaatcagc cttcagacgg tcgtgcctaa    4620
caacacgccg ttctaccccg ccttccttgc gtccctcgcc tccccgagc ccaagtcttc     4680 cgcccgctcc taacgccaac caagcaagat ggccaagttg accagtgccg ttccggtgct    4740
caccgcgcgc gacgtcgccg gagcggtcga gttctggacc gaccggctcg ggttctcccg    4800
ggacttcgtg gaggacgact tcgccggtgt ggtccgggac gacgtgaccc tgttcatcag    4860
cgcggtccag gaccaggtgg tgccggacaa cacccctggcc tgggtgtggg tgcgcggcct   4920
ggacgagctg tacgccgagt ggtcggaggt cgtgtccacg aacttccggg acgcctccgg    4980
gccggccatg accgagatcg gcgagcagcc gtggggcgg gagttcgccc tgcgcgaccc     5040
ggccggcaac tgcgtgcact tcgtggccga ggagcaggac taacacgtgc tacgagattt    5100
cgattccacc gccgccttct atgaaaggtt gggcttcgga atcgttttcc gggacgccgg    5160
ctggatgatc ctccagcgcg gggatctcat gctggagttc ttcgcccacc ccaacttgtt    5220
tattgcagct tataatggtt acaaataaag caatagcatc acaaatttca caaataaagc    5280
atttttttca ctgcattcta gttgtggttt gtccaaactc atcaatgtat cttatcatgt    5340
ctgagggccc gactgttcgg gagggccgca cttattagag ttgaagccaa gtaagatggt    5400
gagtcatgat aattgagcag atcgcttgtt tggagcgatg aatcgtttga gtttctgccc    5460
catcagttgt cgacggtagt gtattggact acggtgacta taacgggtga cggggagtta    5520
gggctcgact ccggagaggg agcctgagag acggctacca catccaagga aggcagcagg    5580
cgcgtaaatt acccaatgtg gactccacga ggtagtgacg agaaatatca atgcggggcg    5640
cttcgcgtct tgctattgga atgagagcaa tgtaaaaccc tcatcgagga tcaactggag    5700
ggcaagtctg gtgccagcag ccgcggtaat tccagctcca gaagcgtatg ctaaagttgt    5760
tgcagttaaa aagctcgtag ttgaatttct ggggcgggag ccccggtctt tgcgcgactg    5820
cgctctgttt gccgagcggc tcctctgcca tcctcgcctc tttttttagt ggcgtcgttc    5880
actgtaatta agcagagtg ttccaagcag gtcgtatgac ctggatgttt attatgggat     5940
gatcagatag ggctcgggtg ctattttgtt ggtttgcaca tctgagtaat gatgaatagg    6000
aacagttggg ggtattcgta tttaggagct agaggtgaaa ttcttggatt tccgaaagac    6060
gaactacagc gaaggcattt accaagcatg ttttcattaa tcaagaacga aagtctgggg    6120
atcgaagatg attagatacc atcgtagtct agaccgtaaa cgatgccgac ttgcgattgc    6180
ggggtgtttg tattgacccc tcgcagcagc acatgagaaa tcaaagtctt tgggttccgg    6240
ggggagtatg gtcgcaaggc tgaaacttaa aggaattgac ggaagggcac caccaggagt    6300
ggagcctgcg gcttaatttg actcaacacg ggaaaactta ccaggtccag acataggtag    6360
gattgacaga ttgagagctc tttcttgatt ctatgggtgg tggtgcatgg ccgttcttag    6420
ttggtggagt gatttgtctg gttaattccg ttaacgaacg agacctcggc ctactaaata    6480
```

-continued

```
gcggtgggta tggcgacata cttgcgtacg cttcttagag ggacatgttc ggtatacgag      6540
caggaagttc gaggcaataa caggtctgtg atgcccttag atgttctggg ccgcacgcgc      6600
gctacactga tgggttcaac gggtggtcat cgttgttcgc agcgaggtgc tttgccggaa      6660
ggcatggcaa atcctttcaa cgcccatcgt gctggggcta gattttttgca attattaatc    6720 tccaacgagg aattcctagt aaacgcaagt catcagcttg cattgaatac gtccctgccc      6780
tttgtacaca ccgcccgtcg cacctaccga ttgaacggtc cgatgaaacc atgggatgac     6840
cttttgagcg tttgttcgcg aggggggtca gaactcgggt gaatcttatt gtttagagga     6900
aggtgaagtc gtaacaaggt ttccgtagtg aatcacgaat tctggatccg atacgtaacg    6960
cgtctgcagc atgcgtggta ccgagctttc cctatagtga gtcgtattag agcttggcgt     7020
aatcatggtc at                                                          7032
```

<210> SEQ ID NO 36
<211> LENGTH: 53
<212> TYPE: DNA
<213> ORGANISM: Artificial sequence
<220> FEATURE:
<223> OTHER INFORMATION: Synthetic oligonucleotide

<400> SEQUENCE: 36
ggtctagagc tagcctaggc tcgagaagct tggcctgtct cccttggcca tcc         53

<210> SEQ ID NO 37
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 37
ggaacggcac tggtcaactt ggccatcttg cttggttggc gttaggagcg g           51

<210> SEQ ID NO 38
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 38
ccgctcctaa cgccaaccaa gcaagatggc caagttgacc agtgccgttc c           51

<210> SEQ ID NO 39
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 39
ggccctcccg aacagtcggg ccctcagaca tgataagata cattgatgag tttgg       55

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
ggccaagttg accagtgccg                                                    20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
cagtcctgct cctcggccac                                                    20

<210> SEQ ID NO 42
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 42
catgaccgag atcggcgag                                                     19

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ccgtcgacaa ctgatggggc                                                    20

<210> SEQ ID NO 44
<211> LENGTH: 7360
<212> TYPE: DNA
<213> ORGANISM: Thraustochytrium sp. ONC-T18

<400> SEQUENCE: 44
agctgtttcc tgtgtgaaat tgttatccgc tcacaattcc acacaacata cgagccggaa        60
gcataaagtg taaagcctgg ggtgcctaat gagtgagcta actcacatta attgcgttgc       120
gctcactgcc cgctttccag tcgggaaacc tgtcgtgcca gctgcattaa tgaatcggcc       180
aacgcgcggg gagaggcggt ttgcgtattg ggcgctcttc cgcttcctcg ctcactgact       240
cgctgcgctc ggtcgttcgg ctgcggcgag cggtatcagc tcactcaaag gcggtaatac       300
ggttatccac agaatcaggg gataacgcag gaaagaacat gtgagcaaaa ggccagcaaa       360
aggccaggaa ccgtaaaaag gccgcgttgc tggcgttttt ccataggctc cgcccccctg       420
acgagcatca caaaaatcga cgctcaagtc agaggtggcg aaacccgaca ggactataaa       480
gataccaggc gtttccccct ggaagctccc tcgtgcgctc tcctgttccg accctgccgc       540
ttaccggata cctgtccgcc tttctccctt cgggaagcgt ggcgctttct catagctcac       600
gctgtaggta tctcagttcg gtgtaggtcg ttcgctccaa gctgggctgt gtgcacgaac       660
cccccgttca gcccgaccgc tgcgccttat ccggtaacta tcgtcttgag tccaacccgg       720
taagacacga cttatcgcca ctggcagcag ccactggtaa caggattagc agagcgaggt       780
atgtaggcgg tgctacagag ttcttgaagt ggtggcctaa ctacggctac actagaagga       840
cagtatttgg tatctgcgct ctgctgaagc cagttacctt cggaaaaaga gttggtagct       900
cttgatccgg caaacaaacc accgctggta gcggtggttt ttttgtttgc aagcagcaga       960
ttacgcgcag aaaaaaagga tctcaagaag atcctttgat cttttctacg ggtctgacg      1020

```
ctcagtggaa cgaaaactca cgttaaggga ttttggtcat gaattaattc ttagaaaaac    1080
tcatcgagca tcaaatgaaa ctgcaattta ttcatatcag gattatcaat accatatttt    1140
tgaaaaagcc gtttctgtaa tgaaggagaa aactcaccga ggcagttcca taggatggca    1200
agatcctggt atcggtctgc gattccgact cgtccaacat caatacaacc tattaatttc    1260
ccctcgtcaa aaataaggtt atcaagtgag aaatcaccat gagtgacgac tgaatccggt    1320
gagaatggca aaagtttatg catttctttc cagacttgtt caacaggcca gccattacgc    1380
tcgtcatcaa aatcactcgc atcaaccaaa ccgttattca ttcgtgattg cgcctgagcg    1440
agacgaaata cgcgatcgct gttaaaagga caattacaaa caggaatcga atgcaaccgg    1500
cgcaggaaca ctgccagcgc atcaacaata ttttcacctg aatcaggata ttcttctaat    1560
acctggaatc tgttttccc ggggatcgca gtggtgagta accatgcatc atcaggagta    1620
cggataaaat gcttgatggt cggaagaggc ataaattccg tcagccagtt tagtctgacc    1680
atctcatctg taacatcatt ggcaacgcta cctttgccat gtttcagaaa caactctggc    1740
gcatcgggct tcccatacaa tcgatagatt gtcgcacctg attcccgac attatcgcga    1800 gcccatttat acccatataa atcagcatcc atgttggaat ttaatcgcgg cctagagcaa    1860
gacgtttccc gttgaatatg gctcataaca ccccttgtat tactgtttat gtaagcagac    1920
agttttattg ttcatgagat tatcaaaaag gatcttcacc tagatccttt taaattaaaa    1980
atgaagtttt aaatcaatct aaagtatata tgagtaaact tggtctgaca gttaccaatg    2040
cttaatcagt gaggcaccta tctcagcgat ctgtctattt cgttcatcca tagttgcctg    2100
actccccgtc gtgtagataa ctacgatacg ggagggctta ccatctggcc ccagtgctgc    2160
aatgataccg cgagacccac gctcaccggc tccagattta tcagcaataa accagccagc    2220
cggaagggcc gagcgcagaa gtggtcctgc aactttatcc gcctccatcc agtctattaa    2280
ttgttgccgg gaagctagag taagtagttc gccagttaat agtttgcgca acgttgttgc    2340
cattgctaca ggcatcgtgg tgtcacgctc gtcgtttggt atggcttcat tcagctccgg    2400
ttcccaacga tcaaggcgag ttacatgatc ccccatgttg tgcaaaaaag cggttagctc    2460
cttcggtcct ccgatcgttg tcagaagtaa gttggccgca gtgttatcac tcatggttat    2520
ggcagcactg cataattctc ttactgtcat gccatccgta agatgctttt ctgtgactgg    2580
tgagtactca accaagtcat tctgagaata gtgtatgcgg cgaccgagtt gctcttgccc    2640
ggcgtcaata cgggataata ccgcgccaca tagcagaact ttaaaagtgc tcatcattgg    2700
aaaacgttct cggggcgaa aactctcaag gatcttaccg ctgttgagat ccagttcgat    2760
gtaacccact cgtgcaccca actgatcttc agcatctttt actttcacca gcgtttctgg    2820
gtgagcaaaa acaggaaggc aaaatgccgc aaaaaaggga ataagggcga cacggaaatg    2880
ttgaatactc atactcttcc tttttcaata ttattgaagc atttatcagg gttattgtct    2940
catgagcgga tacatatttg aatgtattta gaaaaataaa caaataggggg ttccgcgcac    3000 atttccccga aaagtgccac ctgacgcgcc ctgtagcggc gcattaagcg cggcgggtgt    3060
ggtggttacg cgcagcgtga ccgctacact tgccagcgcc ctagcgcccg ctcctttcgc    3120
tttcttccct tcctttctcg ccacgttcgc cggctttccc cgtcaagctc taaatcgggg    3180
gctcccttta gggttccgat ttagtgcttt acggcacctc gaccccaaaa aacttgatta    3240
gggtgatggt tcacgtagtg gccatcgccc tgatagacg gttttttcgcc ctttgacgtt    3300 ggagtccacg ttctttaata gtggactctt gttccaaact ggaacaacac tcaaccctat    3360
```

```
ctcggtctat tcttttgatt tataagggat tttgccgatt tcggcctatt ggttaaaaaa    3420
tgagctgatt taacaaaaat ttaacgcgaa ttttaacaaa atattaacgc ttacaatttc    3480
cattcgccat tcaggctgcg caactgttgg gaagggcgat cggtgcgggc ctcttcgcta    3540
ttacgccagc tggcgaaagg gggatgtgct gcaaggcgat taagttgggt aacgccaggg    3600
ttttcccagt cacgacgttg taaaacgacg gccagtgaat tgtgcggccg cgagctcggg    3660
cccccacacg tgtggtctag agctagccta ggctcgagaa gcttggcctg tctcccttgg    3720
ccatccattg cgctgcggaa gcattggatt gcgaactgcg tcggccagat cgcttggttt    3780
cccaacatga gacgcgctct gtcggcaaga ccatttccgc ccccggcttt gctcacaacc    3840
aactcgtagt agattttgta agaacactg cacgtctgac tgctcccagc ccgcacgcat    3900
tgcgcttggc agcctcggtc ccaaaccgtc acgtcgctg cccggtccac gggaaaaaat    3960
aacttttgtc cgcgagcggc cgttcaaggc gcagccgcga gcgtgccaac cgtccgtccc    4020
gcattctttt cccaatgttg gattcattca ttcttgccag gccagatcat ctgtgcctcc    4080
ctcgcgtgcc cttccttagc gtgcgcagat ctcttcttcc cagagcccgc gcggcgcttc    4140
gtggagtcgg cgtccatgtc atgcgcgcgc ggcgtcttga ccccctcggc cccttggtt     4200 cgcggctgcg caacgagccg tttcacgcca ttgcgaccaa ccgcgcgcta aaatcggatt    4260
ggccgttgca cgccgatttt gcagcacctc tgggctgtga gggacgaccg tccacttta     4320 cccgcacaga gtggactttc accccctcac tccactgaag ccaacttttc gccgtcttcc    4380
caacccaaag tttatgctag ccctcatgcc gcaacggacg tcaccccat ttccactggc     4440 gacgtgggga cctgggcgca ataaggcgcg agaaggaaat tacgacggca cactggggcc    4500
agaagagggc actaggagcg gcaacccact ggcgcggcac agcggtttgg cgcggggatc    4560
aaagcaaaac ccggctcatc cagagcaaac ccgaatcagc cttcagacgg tcgtgcctaa    4620
caacacgccg ttctaccccg ccttccttgc gtccctcgcc tccccgagc ccaagtcttc     4680 cgcccgctcc taacgccaac caagcaagat ggccaagttg accagtgccg ttccggtgct    4740
caccgcgcgc gacgtcgccg gagcggtcga gttctggacc gaccggctcg ggttctcccg    4800
ggacttcgtg gaggacgact tcgccggtgt ggtccgggac gacgtgaccc tgttcatcag    4860
cgcggtccag gaccaggtgg tgccggacaa caccctggcc tgggtgtggg tgcgcggcct    4920
ggacgagctg tacgccgagt ggtcggaggt cgtgtccacg aacttccggg acgcctccgg    4980
gccggccatg accgagatcg gcgagcagcc gtggggggcgg gagttcgccc tgcgcgaccc    5040
ggccggcaac tgcgtgcact tcgtggccga ggagcaggac taaatgcatt cgcatggctc    5100
cgcaccacca cacaccaccg cccctcttct ttccttgctc actcgatcca tagccactta    5160
cctgcccctt ccctctacca ctgccacgtg cggcgtatga gcgcgcttgc acccgcaacc    5220
ttctctctag ttgttcacaa ttacacccgc tatcaatact cacgcattca tcttccctt     5280 tttttctact ttacgtaccg gtgctcactt acttacacct gccgccttg ttcattcatt     5340 cttctcgatg acaacggcag gctctgcttg cggcgcgcgc acgcatccct tactccgccg    5400
cgcaccgaca agcctgcgca aaaacaaaa aaaacttatc ttcgctcgcg gctccgatgt     5460
cgcggcggcg tgcgagaccg cgccgagttc cgcccgccat gcgatcgaga gtctctctcg    5520
taggagcggg accgcgagcg acttcggtgc ctccgatagc cagctgggct tctagaccgg    5580 ctggggggacc gccgcggcg tacctctgcg cttcggtggc ccttaaaagg ctgatcgtgg    5640
aaaaggtcgc tctccagtct gcggtttagc ggagggcccg actgttcggg agggccgcac    5700
ttattagagt tgaagccaag taagatggtg agtcatgata attgagcaga tcgcttgttt    5760
```

```
ggagcgatga atcgtttgag tttctgcccc atcagttgtc gacggtagtg tattggacta    5820
cggtgactat aacgggtgac ggggagttag ggctcgactc cggagaggga gcctgagaga    5880
cggctaccac atccaaggaa ggcagcaggc gcgtaaatta cccaatgtgg actccacgag    5940
gtagtgacga gaaatatcaa tgcggggcgc ttcgcgtctt gctattggaa tgagagcaat    6000
gtaaaaccct catcgaggat caactggagg gcaagtctgg tgccagcagc cgcggtaatt    6060
ccagctccag aagcgtatgc taaagttgtt gcagttaaaa agctcgtagt tgaatttctg    6120
gggcgggagc cccggtcttt gcgcgactgc gctctgtttg ccgagcggct cctctgccat    6180
cctcgcctct ttttttagtg gcgtcgttca ctgtaattaa agcagagtgt tccaagcagg    6240
tcgtatgacc tggatgttta ttatgggatg atcagatagg gctcgggtgc tattttgttg    6300
gtttgcacat ctgagtaatg atgaatagga acagttgggg gtattcgtat ttaggagcta    6360
gaggtgaaat tcttggattt ccgaaagacg aactacagcg aaggcattta ccaagcatgt    6420
tttcattaat caagaacgaa agtctgggga tcgaagatga ttagatacca tcgtagtcta    6480
gaccgtaaac gatgccgact tgcgattgcg gggtgtttgt attggaccct cgcagcagca    6540
catgagaaat caaagtcttt gggttccggg gggagtatgg tcgcaaggct gaaacttaaa    6600
ggaattgacg gaagggcacc accaggagtg gagcctgcgg cttaatttga ctcaacacgg    6660
gaaaacttac caggtccaga cataggtagg attgacagat tgagagctct ttcttgattc    6720
tatgggtggt ggtgcatggc cgttcttagt tggtggagtg atttgtctgg ttaattccgt    6780
taacgaacga gacctcggcc tactaaatag cggtgggtat ggcgacatac ttgcgtacgc    6840
ttcttagagg gacatgttcg gtatacgagc aggaagttcg aggcaataac aggtctgtga    6900
tgcccttaga tgttctgggc cgcacgcgcg ctacactgat gggttcaacg ggtggtcatc    6960
gttgttcgca gcgaggtgct tgccggaag gcatggcaaa tcctttcaac gcccatcgtg    7020
ctggggctag attttttgcaa ttattaatct ccaacgagga attcctagta aacgcaagtc    7080
atcagcttgc attgaatacg tccctgccct ttgtacacac cgcccgtcgc acctaccgat    7140
tgaacggtcc gatgaaacca tgggatgacc ttttgagcgt tgttcgcga ggggggtcag    7200 aactcgggtg aatcttattg tttagaggaa ggtgaagtcg taacaaggtt tccgtagtga    7260
atcacgaatt ctggatccga tacgtaacgc gtctgcagca tgcgtggtac cgagctttcc    7320
ctatagtgag tcgtattaga gcttggcgta atcatggtca    7360
```

<210> SEQ ID NO 45
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 45
ggtgcggagc catgcgaatg catttagtcc tgctcctcgg ccacgaag         48

<210> SEQ ID NO 46
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 46
cttcgtggcc gaggagcagg actaaatgca ttcgcatggc tccgcacc         48

<210> SEQ ID NO 47
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 47

| | |
|---|---|
| ggccctcccg aacagtcggg ccctccgcta aaccgcagac tggagagcg | 49 |

<210> SEQ ID NO 48
<211> LENGTH: 7199
<212> TYPE: DNA
<213> ORGANISM: Thraustochytrium sp. ONC-T18

<400> SEQUENCE: 48

| | |
|---|---|
| agctgtttcc tgtgtgaaat tgttatccgc tcacaattcc acacaacata cgagccggaa | 60 |
| gcataaagtg taaagcctgg ggtgcctaat gagtgagcta actcacatta attgcgttgc | 120 |
| gctcactgcc cgctttccag tcgggaaacc tgtcgtgcca gctgcattaa tgaatcggcc | 180 |
| aacgcgcggg gagaggcggt ttgcgtattg ggcgctcttc cgcttcctcg ctcactgact | 240 |
| cgctgcgctc ggtcgttcgg ctgcggcgag cggtatcagc tcactcaaag gcggtaatac | 300 |
| ggttatccac agaatcaggg gataacgcag gaaagaacat gtgagcaaaa ggccagcaaa | 360 |
| aggccaggaa ccgtaaaaag gccgcgttgc tggcgttttt ccataggctc cgcccccctg | 420 |
| acgagcatca aaaaatcga cgctcaagtc agaggtggcg aaacccgaca ggactataaa | 480 |
| gataccaggc gtttccccct ggaagctccc tcgtgcgctc tcctgttccg accctgccgc | 540 |
| ttaccggata cctgtccgcc tttctccctt cgggaagcgt ggcgctttct catagctcac | 600 |
| gctgtaggta tctcagttcg gtgtaggtcg ttcgctccaa gctgggctgt gtgcacgaac | 660 |
| ccccgttca gcccgaccgc tgcgccttat ccggtaacta tcgtcttgag tccaacccgg | 720 |
| taagacacga cttatcgcca ctggcagcag ccactggtaa caggattagc agagcgaggt | 780 |
| atgtaggcgg tgctacagag ttcttgaagt ggtggcctaa ctacggctac actagaagga | 840 |
| cagtatttgg tatctgcgct ctgctgaagc cagttacctt cggaaaaaga gttggtagct | 900 |
| cttgatccgg caaacaaacc accgctggta gcggtggttt ttttgtttgc aagcagcaga | 960 |
| ttacgcgcag aaaaaaagga tctcaagaag atcctttgat cttttctacg gggtctgacg | 1020 |
| ctcagtggaa cgaaaactca cgttaaggga ttttggtcat gaattaattc ttagaaaaac | 1080 |
| tcatcgagca tcaaatgaaa ctgcaattta ttcatatcag gattatcaat accatatttt | 1140 |
| tgaaaaagcc gtttctgtaa tgaaggagaa aactcaccga gcagttcca taggatggca | 1200 |
| agatcctggt atcggtctgc gattccgact cgtccaacat caatacaacc tattaatttc | 1260 |
| ccctcgtcaa aaataaggtt atcaagtgag aaatcaccat gagtgacgac tgaatccggt | 1320 |
| gagaatggca aaagtttatg catttctttc cagacttgtt caacaggcca gccattacgc | 1380 |
| tcgtcatcaa aatcactcgc atcaaccaaa ccgttattca ttcgtgattg cgcctgagcg | 1440 |
| agacgaaata cgcgatcgct gttaaaagga caattacaaa caggaatcga atgcaaccgg | 1500 |
| cgcaggaaca ctgccagcgc atcaacaata ttttcacctg aatcaggata ttcttctaat | 1560 |
| acctggaatg ctgttttccc ggggatcgca gtggtgagta accatgcatc atcaggagta | 1620 |
| cggataaaat gcttgatggt cggaagaggc ataaattccg tcagccagtt tagtctgacc | 1680 |
| atctcatctg taacatcatt ggcaacgcta cctttgccat gtttcagaaa caactctggc | 1740 |
| gcatcgggct tcccatacaa tcgatagatt gtcgcacctg attgcccgac attatcgcga | 1800 |

| | | | | |
|---|---|---|---|---|
| gcccatttat | acccatataa | atcagcatcc | atgttggaat | ttaatcgcgg  cctagagcaa | 1860 |
| gacgtttccc | gttgaatatg | gctcataaca | cccttgtat | tactgtttat  gtaagcagac | 1920 |
| agttttattg | ttcatgagat | tatcaaaaag | gatcttcacc | tagatccttt  taaattaaaa | 1980 |
| atgaagtttt | aaatcaatct | aaagtatata | tgagtaaact | tggtctgaca  gttaccaatg | 2040 |
| cttaatcagt | gaggcaccta | tctcagcgat | ctgtctattt | cgttcatcca  tagttgcctg | 2100 |
| actccccgtc | gtgtagataa | ctacgatacg | ggagggctta | ccatctggcc  ccagtgctgc | 2160 |
| aatgataccg | cgagacccac | gctcaccggc | tccagattta | tcagcaataa  accagccagc | 2220 |
| cggaagggcc | gagcgcagaa | gtggtcctgc | aactttatcc | gcctccatcc  agtctattaa | 2280 |
| ttgttgccgg | gaagctagag | taagtagttc | gccagttaat | agtttgcgca  acgttgttgc | 2340 |
| cattgctaca | ggcatcgtgg | tgtcacgctc | gtcgtttggt | atggcttcat  tcagctccgg | 2400 |
| ttcccaacga | tcaaggcgag | ttacatgatc | ccccatgttg | tgcaaaaaag  cggttagctc | 2460 |
| cttcggtcct | ccgatcgttg | tcagaagtaa | gttggccgca | gtgttatcac  tcatggttat | 2520 |
| ggcagcactg | cataattctc | ttactgtcat | gccatccgta | agatgctttt  ctgtgactgg | 2580 |
| tgagtactca | accaagtcat | tctgagaata | gtgtatgcgg | cgaccgagtt  gctcttgccc | 2640 |
| ggcgtcaata | cgggataata | ccgcgccaca | tagcagaact | ttaaaagtgc  tcatcattgg | 2700 |
| aaaacgttct | cggggcgaaa | actctcaag | gatcttaccg | ctgttgagat  ccagttcgat | 2760 |
| gtaacccact | cgtgcaccca | actgatcttc | agcatctttt | actttcacca  gcgtttctgg | 2820 |
| gtgagcaaaa | acaggaaggc | aaaatgccgc | aaaaaaggga | ataagggcga  cacggaaatg | 2880 |
| ttgaatactc | atactcttcc | tttttcaata | ttattgaagc | atttatcagg  gttattgtct | 2940 |
| catgagcgga | tacatatttg | aatgtattta | gaaaaataaa | caaatagggg  ttccgcgcac | 3000 |
| atttccccga | aaagtgccac | ctgacgcgcc | ctgtagcggc | gcattaagcg  cggcgggtgt | 3060 |
| ggtggttacg | cgcagcgtga | ccgctacact | tgccagcgcc | ctagcgcccg  ctcctttcgc | 3120 |
| tttcttccct | tcctttctcg | ccacgttcgc | cggctttccc | cgtcaagctc  taaatcgggg | 3180 |
| gctcccttta | gggttccgat | ttagtgcttt | acggcacctc | gaccccaaaa  aacttgatta | 3240 |
| gggtgatggt | tcacgtagtg | ggccatcgcc | ctgatagacg | gtttttcgcc  ctttgacgtt | 3300 |
| ggagtccacg | ttctttaata | gtggactctt | gttccaaact | ggaacaacac  tcaaccctat | 3360 |
| ctcggtctat | tcttttgatt | tataagggat | tttgccgatt | tcggcctatt  ggttaaaaaa | 3420 |
| tgagctgatt | taacaaaaat | ttaacgcgaa | ttttaacaaa | atattaacgc  ttacaatttc | 3480 |
| cattcgccat | tcaggctgcg | caactgttgg | gaagggcgat | cggtgcgggc  ctcttcgcta | 3540 |
| ttacgccagc | tggcgaaagg | gggatgtgct | gcaaggcgat | taagttgggt  aacgccaggg | 3600 |
| ttttcccagt | cacgacgttg | taaaacgacg | gccagtgaat | tgtgcggccg  cgagctcggg | 3660 |
| cccccacacg | tgtggtctag | agctagccta | ggctcgagaa | gcttggcctg  tctcccttgg | 3720 |
| ccatccattg | cgctgcggaa | gcattggatt | gcgaactgcg | tcggcagat  cgcttggttt | 3780 |
| cccaacatga | gacgcgctct | gtcggcaaga | ccatttccgc | ccccggcttt  gctcacaacc | 3840 |
| aactcgtagt | agattttgta | aagaacactg | cacgtctgac | tgctcccagc  ccgcacgcat | 3900 |
| tgcgcttggc | agcctcggtc | ccaaaccgtc | acggtcgctg | cccggtccac  gggaaaaaat | 3960 |
| aacttttgtc | cgcgagcggc | cgttcaaggc | gcagccgcga | gcgtgccaac  cgtccgtccc | 4020 |
| gcattctttt | cccaatgttg | gattcattca | ttccttgccag | gccagatcat  ctgtgcctcc | 4080 |
| ctcgcgtgcc | cttccttagc | gtgcgcagat | ctcttcttcc | cagagcccgc  gcggcgcttc | 4140 |

```
gtggagtcgg cgtccatgtc atgcgcgcgc ggcgtcttga ccccctcggc cccttttggtt    4200
cgcggctgcg caacgagccg tttcacgcca ttgcgaccaa ccgcgcgcta aaatcggatt    4260
ggccgttgca cgccgatttt gcagcacctc tgggctgtga gggacgaccg tccactttta    4320
cccgcacaga gtggactttc accccctcac tccactgaag ccaacttttc gccgtcttcc    4380
caacccaaag tttatgctag ccctcatgcc gcaacggacg tcaccccat ttccactggc     4440
gacgtgggga cctgggcgca ataaggcgcg agaaggaaat tacgacggca cactggggcc    4500
agaagagggc actaggagcg gcaacccact ggcgcggcac agcggtttgg cgcggggatc    4560
aaagcaaaac ccggctcatc cagagcaaac ccgaatcagc cttcagacgg tcgtgcctaa    4620
caacacgccg ttctaccccg ccttccttgc gtccctcgcc tcccccgagc ccaagtcttc    4680
cgcccgctcc taacgccaac caagcaagat ggccaagttg accagtgccg ttccggtgct    4740
caccgcgcgc gacgtcgccg gagcggtcga gttctggacc gaccggctcg ggttctcccg    4800
ggacttcgtg gaggacgact cgccggtgt ggtccgggac gacgtgaccc tgttcatcag     4860
cgcggtccag gaccaggtgg tgccggacaa caccctgggc tgggtgtggg tgcgcggcct    4920
ggacgagctg tacgccgagt ggtcggaggt cgtgtccacg aacttccggg acgcctccgg    4980
gccggccatg accgagatcg gcgagcagcc gtggggcgg gagttcgccc tgcgcgaccc     5040
ggccggcaac tgcgtgcact tcgtggccga ggagcaggac taagcgcctt caggcaggct    5100
gatccctact gtggggctc tgacggacgg ccggtctttg tacgtaaaca ggcgcttctt     5160
cgcggcccgc cgaggggggc ggcaacgagc cgggtggcgt ggcacggaca aggcaagagc    5220
ctttccatcc cgcataaagt gatgcaccat tttgaccttg ttgatcgttt ttgtgtgttt    5280
agagcggccc cgtgcgggta ggcgaagtgc gcttctgagc aaggaagaga gaggtgcagc    5340
ttcttcttga tcagtgtggt aatcttcaac ggccacgctc gcttattcga tacctgtaaa    5400
gctaccggtg cacccgtgca agttgggcac cacgtagttg tactggtgaa tccaaatgtt    5460
agccgctagc ttggtgccct tttcgacagg aagggcttgg tgaaaagccg agggcccgac    5520
tgttcgggag gccgcacttt attagagttg aagccaagta agatggtgag tcatgataat    5580
tgagcagatc gcttgtttgg agcgatgaat cgtttgagtt tctgccccat cagttgtcga    5640
cggtagtgta ttggactacg gtgactataa cgggtgacgg ggagttaggg ctcgactccg    5700
gagagggagc ctgagagacg gctaccacat ccaaggaagg cagcaggcgc gtaaattacc    5760
caatgtggac tccacgaggt agtgacgaga atatcaatg cggggcgctt cgcgtcttgc     5820
tattggaatg agagcaatgt aaaaccctca tcgaggatca actggagggc aagtctggtg    5880
ccagcagccg cggtaattcc agctccagaa gcgtatgcta aagttgttgc agttaaaaag    5940
ctcgtagttg aatttctggg gcgggagccc cggtctttgc gcgactgcgc tctgtttgcc    6000
gagcggctcc tctgccatcc tcgcctcttt ttttagtggc gtcgttcact gtaattaaag    6060
cagagtgttc caagcaggtc gtatgacctg gatgtttatt atgggatgat cagataggc     6120
tcgggtgcta ttttgttggt ttgcacatct gagtaatgat gaataggaac agttgggggt    6180
attcgtattt aggagctaga ggtgaaattc ttggatttcc gaaagacgaa ctacagcgaa    6240
ggcatttacc aagcatgttt tcattaatca agaacgaaag tctggggatc gaagatgatt    6300
agataccatc gtagtctaga ccgtaaacga tgccgacttg cgattgcggg gtgtttgtat    6360
tggaccctcg cagcagcaca tgagaaatca aagtctttgg gttccggggg gagtatggtc    6420
gcaaggctga aacttaaagg aattgacgga agggcaccac caggagtgga gcctgcggct    6480
taatttgact caacacggga aaacttacca ggtccagaca taggtaggat tgacagattg    6540
```

-continued

```
agagctcttt cttgattcta tgggtggtgg tgcatggccg ttcttagttg gtggagtgat    6600
ttgtctggtt aattccgtta acgaacgaga cctcggccta ctaaatagcg gtgggtatgg    6660
cgacatactt gcgtacgctt cttagaggga catgttcggt atacgagcag gaagttcgag    6720
gcaataacag gtctgtgatg cccttagatg ttctgggccg cacgcgcgct acactgatgg    6780
gttcaacggg tggtcatcgt tgttcgcagc gaggtgcttt gccggaaggc atggcaaatc    6840 cttttcaacgc ccatcgtgct ggggctagat ttttgcaatt attaatctcc aacgaggaat    6900
tcctagtaaa cgcaagtcat cagcttgcat tgaatacgtc cctgccctt gtacacaccg     6960 cccgtcgcac ctaccgattg aacgtccga tgaaaccatg gatgacctt ttgagcgttt      7020 gttcgcgagg ggggtcagaa ctcgggtgaa tcttattgtt tagaggaagg tgaagtcgta    7080
acaaggtttc cgtagtgaat cacgaattct ggatccgata cgtaacgcgt ctgcagcatg    7140
cgtggtaccg agctttccct atagtgagtc gtattagagc ttggcgtaat catggtcat    7199
```

<210> SEQ ID NO 49
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 49

```
gggatcagcc tgcctgaagg cgcttagtcc tgctcctcgg ccacgaag                 48
```

<210> SEQ ID NO 50
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 50

```
cttcgtggcc gaggagcagg actaagcgcc ttcaggcagg ctgatccc                 48
```

<210> SEQ ID NO 51
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 51

```
ggccctcccg aacagtcggg ccctcggctt ttcaccaagc ccttcctg                 48
```

<210> SEQ ID NO 52
<211> LENGTH: 6526
<212> TYPE: DNA
<213> ORGANISM: Thraustochytrium sp. ONC-T18

<400> SEQUENCE: 52

```
agctgtttcc tgtgtgaaat tgttatccgc tcacaattcc acacaacata cgagccggaa    60
gcataaagtg taaagcctgg ggtgcctaat gagtgagcta actcacatta attgcgttgc    120
gctcactgcc cgctttccag tcgggaaacc tgtcgtgcca gctgcattaa tgaatcggcc    180
aacgcgcggg gagaggcggt ttgcgtattg ggcgctcttc cgcttcctcg ctcactgact    240
cgctgcgctc ggtcgttcgg ctgcggcgag cggtatcagc tcactcaaag gcggtaatac    300
ggttatccac agaatcaggg gataacgcag gaaagaacat gtgagcaaaa ggccagcaaa    360
```

| | |
|---|---|
| aggccaggaa ccgtaaaaag gccgcgttgc tggcgttttt ccataggctc cgccccctg | 420 |
| acgagcatca caaaaatcga cgctcaagtc agaggtggcg aaacccgaca ggactataaa | 480 |
| gataccaggc gtttccccct ggaagctccc tcgtgcgctc tcctgttccg accctgccgc | 540 |
| ttaccggata cctgtccgcc tttctccctt cgggaagcgt ggcgctttct catagctcac | 600 |
| gctgtaggta tctcagttcg gtgtaggtcg ttcgctccaa gctgggctgt gtgcacgaac | 660 |
| cccccgttca gcccgaccgc tgcgccttat ccggtaacta tcgtcttgag tccaacccgg | 720 |
| taagacacga cttatcgcca ctggcagcag ccactggtaa caggattagc agagcgaggt | 780 |
| atgtaggcgg tgctacagag ttcttgaagt ggtggcctaa ctacggctac actagaagga | 840 |
| cagtatttgg tatctgcgct ctgctgaagc cagttacctt cggaaaaaga gttggtagct | 900 |
| cttgatccgg caaacaaacc accgctggta gcggtggttt ttttgtttgc aagcagcaga | 960 |
| ttacgcgcag aaaaaaagga tctcaagaag atcctttgat cttttctacg gggtctgacg | 1020 |
| ctcagtggaa cgaaaactca cgttaaggga ttttggtcat gaattaattc ttagaaaaac | 1080 |
| tcatcgagca tcaaatgaaa ctgcaattta ttcatatcag gattatcaat accatatttt | 1140 |
| tgaaaaagcc gtttctgtaa tgaaggagaa aactcaccga gcagttcca taggatggca | 1200 |
| agatcctggt atcggtctgc gattccgact cgtccaacat caatacaacc tattaatttc | 1260 |
| ccctcgtcaa aataaggtt atcaagtgag aaatcaccat gagtgacgac tgaatccggt | 1320 |
| gagaatggca aaagtttatg catttctttc cagacttgtt caacaggcca gccattacgc | 1380 |
| tcgtcatcaa aatcactcgc atcaaccaaa ccgttattca ttcgtgattg cgcctgagcg | 1440 |
| agacgaaata cgcgatcgct gttaaaagga caattacaaa caggaatcga atgcaaccgg | 1500 |
| cgcaggaaca ctgccagcgc atcaacaata ttttcacctg aatcaggata ttcttctaat | 1560 |
| acctggaatg ctgttttccc ggggatcgca gtggtgagta accatgcatc atcaggagta | 1620 |
| cggataaaat gcttgatggt cggaagaggc ataaattccg tcagccagtt tagtctgacc | 1680 |
| atctcatctg taacatcatt ggcaacgcta cctttgccat gtttcagaaa caactctggc | 1740 |
| gcatcgggct tcccatacaa tcgatagatt gtcgcacctg attgcccgac attatcgcga | 1800 |
| gcccatttat acccatataa atcagcatcc atgttggaat ttaatcgcgg cctagagcaa | 1860 |
| gacgtttccc gttgaatatg gctcataaca ccccttgtat tactgtttat gtaagcagac | 1920 |
| agttttattg ttcatgagat tatcaaaaag gatcttcacc tagatccttt taaattaaaa | 1980 |
| atgaagtttt aaatcaatct aaagtatata tgagtaaact tggtctgaca gttaccaatg | 2040 |
| cttaatcagt gaggcaccta tctcagcgat ctgtctattt cgttcatcca tagttgcctg | 2100 |
| actccccgtc gtgtagataa ctacgatacg ggagggctta ccatctggcc ccagtgctgc | 2160 |
| aatgataccg cgagacccac gctcaccggc tccagattta tcagcaataa accagccagc | 2220 |
| cggaagggcc gagcgcagaa gtggtcctgc aactttatcc gcctccatcc agtctattaa | 2280 |
| ttgttgccgg gaagctagag taagtagttc gccagttaat agtttgcgca acgttgttgc | 2340 |
| cattgctaca ggcatcgtgg tgtcacgctc gtcgtttggt atggcttcat tcagctccgg | 2400 |
| ttcccaacga tcaaggcgag ttacatgatc ccccatgttg tgcaaaaaag cggttagctc | 2460 |
| cttcggtcct ccgatcgttg tcagaagtaa gttggccgca gtgttatcac tcatggttat | 2520 |
| ggcagcactg cataattctc ttactgtcat gccatccgta agatgctttt ctgtgactgg | 2580 |
| tgagtactca accaagtcat tctgagaata gtgtatgcgg cgaccgagtt gctcttgccc | 2640 |
| ggcgtcaata cgggataata ccgcgccaca tagcagaact ttaaaagtgc tcatcattgg | 2700 |
| aaaacgttct cggggcgaa aactctcaag gatcttaccg ctgttgagat ccagttcgat | 2760 |

```
gtaacccact cgtgcaccca actgatcttc agcatctttt actttcacca gcgtttctgg    2820
gtgagcaaaa acaggaaggc aaaatgccgc aaaaaaggga ataagggcga cacggaaatg    2880
ttgaatactc atactcttcc tttttcaata ttattgaagc atttatcagg gttattgtct    2940
catgagcgga tacatatttg aatgtattta gaaaaataaa caaatagggg ttccgcgcac    3000
atttccccga aaagtgccac ctgacgcgcc ctgtagcggc gcattaagcg cggcgggtgt    3060
ggtggttacg cgcagcgtga ccgctacact tgccagcgcc ctagcgcccg ctcctttcgc    3120
tttcttccct tcctttctcg ccacgttcgc cggctttccc cgtcaagctc taaatcgggg    3180
gctcccttta gggttccgat ttagtgcttt acggcacctc gaccccaaaa aacttgatta    3240
gggtgatggt tcacgtagtg gccatcgcc ctgatagacg ttttt cgcc ctttgacgtt    3300 ggagtccacg ttctttaata gtggactctt gttccaaact ggaacaacac tcaaccctat    3360
ctcggtctat tcttttgatt tataagggat tttgccgatt tcggcctatt ggttaaaaaa    3420
tgagctgatt taacaaaaat ttaacgcgaa ttttaacaaa atattaacgc ttacaatttc    3480
cattcgccat tcaggctgcg caactgttgg gaagggcgat cggtgcgggc ctcttcgcta    3540
ttacgccagc tggcgaaagg gggatgtgct gcaaggcgat taagttgggt aacgccaggg    3600
ttttcccagt cacgacgttg taaaacgacg gccagtgaat tgtgcggccg cgagctcggg    3660
cccccacacg tgtggtctag agctagccta ggctcgagaa gcttcgcggc ttcccgtctc    3720
caagcttcgt ctcggtagag attctatctt cgcccggcag cccgccgccg tccggcaagt    3780
gtagaacggc agaaagccca cttgcacgga acgcccgaca agttgacgaa agcggcccgc    3840
aagtgcggca gcccggctgg ttttttcctcg cggcgaggcc aaaccgccaa cgccaccaag    3900
ccagacacca ggtatgtgcc gcacgcgccg ccgcacgcga gccccgagga tgccccgtac    3960
gcgctgacgc ctttctccgc cccgcccgcg agaagacgcg ctccggcaac ggcgggagcc    4020
gagcgaacgg gcgaggattg atcgagtagc tgcaggttga gaaaaaagga aaaccgccga    4080
gatggacaac ggctggatgg acgagaagac gcacgaggac gcgaggactg acgatgatca    4140
cgtgcgcagg aagacttgaa agaagcaag gaaggtagaa aaaaagaag aaatcaagca    4200 agatggccaa gttgaccagt gccgttccgg tgctcaccgc gcgcgacgtc gccggagcgg    4260
tcgagttctg gaccgaccgg ctcgggttct cccgggactt cgtggaggac gacttcgccg    4320
gtgtggtccg ggacgacgtg accctgttca tcagcgcggt ccaggaccag gtggtgccgg    4380
acaacaccct ggcctgggtg tgggtgcgcg gcctggacga gctgtacgcc gagtggtcgg    4440
aggtcgtgtc cacgaacttc cgggacgcct ccgggccggc catgaccgag atcggcgagc    4500
agccgtgggg gcgggagttc gccctgcgcg accggccgg caactgcgtg cacttcgtgg    4560
ccgaggagca ggactaacac gtgctacgag atttcgattc caccgccgcc ttctatgaaa    4620
ggttgggctt cggaatcgtt ttccgggacg ccggctggat gatcctccag cgcggggatc    4680
tcatgctgga gttcttcgcc caccccaact tgtttattgc agcttataat ggttacaaat    4740
aaagcaatag catcacaaat ttcacaaata aagcattttt ttcactgcat tctagttgtg    4800
gtttgtccaa actcatcaat gtatcttatc atgtctgagg gcccgactgt tcgggagggc    4860
cgcacttatt agagttgaag ccaagtaaga tggtgagtca tgataattga gcagatcgct    4920
tgtttggagc gatgaatcgt ttgagtttct gccccatcag ttgtcgacgg tagtgtattg    4980
gactacggtg actataacgg gtgacgggga gttagggctc gactccggag agggagcctg    5040
agagacggct accacatcca aggaaggcag caggcgcgta aattacccaa tgtggactcc    5100
```

-continued

```
acgaggtagt gacgagaaat atcaatgcgg ggcgcttcgc gtcttgctat tggaatgaga      5160
gcaatgtaaa accctcatcg aggatcaact ggagggcaag tctggtgcca gcagccgcgg      5220
taattccagc tccagaagcg tatgctaaag ttgttgcagt taaaaagctc gtagttgaat      5280
ttctggggcg ggagcccegg tctttgcgcg actgcgctct gtttgccgag cggctcctct      5340
gccatcctcg cctcttttt tagtggcgtc gttcactgta attaaagcag agtgttccaa      5400
gcaggtcgta tgacctggat gtttattatg ggatgatcag ataggctcg ggtgctattt      5460 tgttggtttg cacatctgag taatgatgaa taggaacagt tgggggtatt cgtatttagg      5520
agctagaggt gaaattcttg gatttccgaa agacgaacta cagcgaaggc atttaccaag      5580
catgttttca ttaatcaaga acgaaagtct ggggatcgaa gatgattaga taccatcgta      5640
gtctagaccg taaacgatgc cgacttgcga ttgcggggtg tttgtattgg accctcgcag      5700
cagcacatga gaaatcaaag tctttgggtt ccggggggag tatggtcgca aggctgaaac      5760
ttaaaggaat tgacgaagg gcaccaccag gagtggagcc tgcggcttaa tttgactcaa      5820
cacgggaaaa cttaccaggt ccagacatag gtaggattga cagattgaga gctctttctt      5880
gattctatgg gtggtggtgc atggccgttc ttagttggtg gagtgatttg tctggttaat      5940
tccgttaacg aacgagacct cggcctacta aatagcggtg gtatggcga catacttgcg      6000 tacgcttctt agagggacat gttcggtata cgagcaggaa gttcgaggca ataacaggtc      6060
tgtgatgccc ttagatgttc tgggccgcac gcgcgctaca ctgatgggtt caacgggtgg      6120
tcatcgttgt tcgcagcgag gtgctttgcc ggaaggcatg gcaaatcctt tcaacgccca      6180
tcgtgctggg gctagatttt tgcaattatt aatctccaac gaggaattcc tagtaaacgc      6240
aagtcatcag cttgcattga atacgtccct gcccttttgta cacaccgccc gtcgcaccta      6300
ccgattgaac ggtccgatga aaccatggga tgaccttttg agcgtttgtt cgcgagggg      6360 gtcagaactc gggtgaatct tattgtttag aggaaggtga agtcgtaaca aggtttccgt      6420
agtgaatcac gaattctgga tccgatacgt aacgcgtctg cagcatgcgt ggtaccgagc      6480
tttccctata gtgagtcgta ttagagcttg gcgtaatcat ggtcat                    6526
```

<210> SEQ ID NO 53
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 53

```
ggtctagagc tagcctaggc tcgagaagct tcgcggcttc ccgtctc                    47
```

<210> SEQ ID NO 54
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 54

```
ggaacggcac tggtcaactt ggccatcttg cttgatttct tcttttttt ctaccttcc       59
```

<210> SEQ ID NO 55
<211> LENGTH: 7374
<212> TYPE: DNA
<213> ORGANISM: Thraustochytrium sp.

<400> SEQUENCE: 55

-continued

| | |
|---|---|
| agctgtttcc tgtgtgaaat tgttatccgc tcacaattcc acacaacata cgagccggaa | 60 |
| gcataaagtg taaagcctgg ggtgcctaat gagtgagcta actcacatta attgcgttgc | 120 |
| gctcactgcc cgctttccag tcgggaaacc tgtcgtgcca gctgcattaa tgaatcggcc | 180 |
| aacgcgcggg gagaggcggt ttgcgtattg ggcgctcttc cgcttcctcg ctcactgact | 240 |
| cgctgcgctc ggtcgttcgg ctgcggcgag cggtatcagc tcactcaaag gcggtaatac | 300 |
| ggttatccac agaatcaggg gataacgcag gaaagaacat gtgagcaaaa ggccagcaaa | 360 |
| aggccaggaa ccgtaaaaag gccgcgttgc tggcgttttt ccataggctc cgcccccctg | 420 |
| acgagcatca caaaaatcga cgctcaagtc agaggtggcg aaacccgaca ggactataaa | 480 |
| gataccaggc gtttccccct ggaagctccc tcgtgcgctc tcctgttccg accctgccgc | 540 |
| ttaccggata cctgtccgcc tttctccctt cgggaagcgt ggcgctttct catagctcac | 600 |
| gctgtaggta tctcagttcg gtgtaggtcg ttcgctccaa gctgggctgt gtgcacgaac | 660 |
| cccccgttca gcccgaccgc tgcgccttat ccggtaacta tcgtcttgag tccaacccgg | 720 |
| taagacacga cttatcgcca ctggcagcag ccactggtaa caggattagc agagcgaggt | 780 |
| atgtaggcgg tgctacagag ttcttgaagt ggtggcctaa ctacggctac actagaagga | 840 |
| cagtatttgg tatctgcgct ctgctgaagc cagttacctt cggaaaaaga gttggtagct | 900 |
| cttgatccgg caaacaaacc accgctggta gcggtggttt ttttgtttgc aagcagcaga | 960 |
| ttacgcgcag aaaaaaagga tctcaagaag atcctttgat cttttctacg gggtctgacg | 1020 |
| ctcagtggaa cgaaaactca cgttaaggga ttttggtcat gaattaattc ttagaaaaac | 1080 |
| tcatcgagca tcaaatgaaa ctgcaattta ttcatatcag gattatcaat accatatttt | 1140 |
| tgaaaaagcc gtttctgtaa tgaaggagaa aactcaccga ggcagttcca taggatggca | 1200 |
| agatcctggt atcggtctgc gattccgact cgtccaacat caatacaacc tattaatttc | 1260 |
| ccctcgtcaa aaataaggtt atcaagtgag aaatcaccat gagtgacgac tgaatccggt | 1320 |
| gagaatggca aaagtttatg catttctttc cagacttgtt caacaggcca gccattacgc | 1380 |
| tcgtcatcaa aatcactcgc atcaaccaaa ccgttattca ttcgtgattg cgcctgagcg | 1440 |
| agacgaaata cgcgatcgct gttaaaagga caattacaaa caggaatcga atgcaaccgg | 1500 |
| cgcaggaaca ctgccagcgc atcaacaata ttttcacctg aatcaggata ttcttctaat | 1560 |
| acctggaatg ctgtttttcc ggggatcgca gtggtgagta accatgcatc atcaggagta | 1620 |
| cggataaaat gcttgatggt cggaagaggc ataaattccg tcagccagtt tagtctgacc | 1680 |
| atctcatctg taacatcatt ggcaacgcta cctttgccat gtttcagaaa caactctggc | 1740 |
| gcatcgggct tcccatacaa tcgatagatt gtcgcacctg attgcccgac attatcgcga | 1800 |
| gcccatttat acccatataa atcagcatcc atgttggaat ttaatcgcgg cctagagcaa | 1860 |
| gacgtttccc gttgaatatg gctcataaca ccccttgtat tactgtttat gtaagcagac | 1920 |
| agttttattg ttcatgagat tatcaaaaag gatcttcacc tagatccttt taaattaaaa | 1980 |
| atgaagtttt aaatcaatct aaagtatata tgagtaaact tggtctgaca gttaccaatg | 2040 |
| cttaatcagt gaggcaccta tctcagcgat ctgtctattt cgttcatcca tagttgcctg | 2100 |
| actccccgtc gtgtagataa ctacgatacg ggagggctta ccatctggcc ccagtgctgc | 2160 |
| aatgataccg cgagacccac gctcaccggc tccagattta tcagcaataa accagccagc | 2220 |
| cggaagggcc gagcgcagaa gtggtcctgc aactttatcc gcctccatcc agtctattaa | 2280 |
| ttgttgccgg gaagctagag taagtagttc gccagttaat agtttcgcca acgttgttgc | 2340 |

```
cattgctaca ggcatcgtgg tgtcacgctc gtcgtttggt atggcttcat tcagctccgg   2400
ttcccaacga tcaaggcgag ttacatgatc ccccatgttg tgcaaaaaag cggttagctc   2460
cttcggtcct ccgatcgttg tcagaagtaa gttggccgca gtgttatcac tcatggttat   2520
ggcagcactg cataattctc ttactgtcat gccatccgta agatgctttt ctgtgactgg   2580
tgagtactca accaagtcat tctgagaata gtgtatgcgg cgaccgagtt gctcttgccc   2640
ggcgtcaata cggataata ccgcgccaca tagcagaact ttaaaagtgc tcatcattgg   2700
aaaacgttct tcggggcgaa aactctcaag gatcttaccg ctgttgagat ccagttcgat   2760
gtaacccact cgtgcaccca actgatcttc agcatctttt actttcacca gcgtttctgg   2820
gtgagcaaaa acaggaaggc aaaatgccgc aaaaaaggga ataagggcga cacggaaatg   2880
ttgaatactc atactcttcc ttttcaata ttattgaagc atttatcagg gttattgtct   2940
catgagcgga tacatatttg aatgtattta gaaaaataaa caaatagggg ttccgcgcac   3000
atttccccga aaagtgccac ctgacgcgcc ctgtagcggc gcattaagcg cggcgggtgt   3060
ggtggttacg cgcagcgtga ccgctacact tgccagcgcc ctagcgcccg ctcctttcgc   3120
tttcttccct tcctttctcg ccacgttcgc cggctttccc cgtcaagctc taaatcgggg   3180 gctccctta gggttccgat ttagtgcttt acggcacctc gaccccaaaa aacttgatta   3240
gggtgatggt tcacgtagtg gccatcgcc ctgatagacg ttttcgcc ctttgacgtt   3300 ggagtccacg ttctttaata gtggactctt gttccaaact ggaacaacac tcaaccctat   3360
ctcggtctat tcttttgatt tataagggat tttgccgatt tcggcctatt ggttaaaaaa   3420
tgagctgatt taacaaaaat ttaacgcgaa ttttaacaaa atattaacgc ttacaatttc   3480
cattcgccat tcaggctgcg caactgttgg gaagggcgat cggtgcgggc ctcttcgcta   3540
ttacgccagc tggcgaaagg gggatgtgct gcaaggcgat taagttgggt aacgccaggg   3600
ttttcccagt cacgacgttg taaaacgacg gccagtgaat tgtgcggccg cgagctcggg   3660
cccccacacg tgtggtctag agctagccta ggctcgagaa gcttggcctg tctcccttgg   3720
ccatccattg cgctgcggaa gcattggatt gcgaactgcg tcggccagat cgcttggttt   3780
cccaacatga gacgcgctct gtcggcaaga ccatttccgc cccggctttt gctcacaacc   3840
aactcgtagt agattttgta aagaacactg cacgtctgac tgctcccagc ccgcacgcat   3900
tgcgcttggc agcctcggtc ccaaaccgtc acgtcgctg cccggtccac gggaaaaaat   3960
aacttttgtc cgcgagcggc cgttcaaggc gcagccgcga gcgtgccaac cgtccgtccc   4020
gcattctttt cccaatgttg gattcattca ttcttgccag gccagatcat ctgtgcctcc   4080
ctcgcgtgcc cttccttagc gtgcgcagat ctcttcttcc cagagcccgc gcggcgcttc   4140
gtggagtcgg cgtccatgtc atgcgcgcgc ggcgtcttga cccctcggc ccctttggtt   4200 cgcggctgcg caacgagccg tttcacgcca ttgcgaccaa ccgcgcgcta aaatcggatt   4260
ggccgttgca cgccgatttt gcagcacctc tgggctgtga gggacgaccg tccacttta   4320 cccgcacaga gtggactttc accccctcac tccactgaag ccaacttttc gccgtcttcc   4380
caacccaaag tttatgctag ccctcatgcc gcaacggacg tcaccccat ttccactggc   4440 gacgtgggga cctgggcgca ataaggcgcg agaggaaat tacgacggca cactgggcc   4500 agaagagggc actaggagcg gcaacccact ggcgcggcac agcggtttgg cgcggggatc   4560
aaagcaaaac ccggctcatc cagagcaaac ccgaatcagc cttcagacgg tcgtgcctaa   4620
caacacgccg ttctacccg ccttccttgc gtccctcgcc tccccgagc caagtcttc   4680 cgcccgctcc taacgccaac caagcaagat gagtaaagga gaagaacttt tcactggagt   4740
```

```
tgtcccaatt cttgttgaat tagatggtga tgttaatggg cacaaatttt ctgtcagtgg    4800
agagggtgaa ggtgatgcaa catacggaaa acttaccctt aaatttattt gcactactgg    4860
aaaactacct gttccatggc caacacttgt cactactttc acttatggtg ttcaatgctt    4920
ttcaagatac ccagatcata tgaagcggca cgacttcttc aagagcgcca tgcctgaggg    4980
atacgtgcag gagaggacca tctctttcaa ggacgacggg aactacaaga cacgtgctga    5040
agtcaagttt gagggagaca ccctcgtcaa caggatcgag cttaagggaa tcgatttcaa    5100
ggaggacgga aacatcctcg gccacaagtt ggaatacaac tacaactccc acaacgtata    5160
catcacggca gacaaacaaa agaatggaat caaagctaac ttcaaaatta gacacaacat    5220
tgaagatgga agcgttcaac tagcagacca ttatcaacaa atactccaa ttggcgatgg    5280 ccctgtcctt ttaccagaca accattacct gtccacacaa tctgcccttt cgaaagatcc    5340
caacgaaaag agagaccaca tggtccttct tgagtttgta acagctgctg ggattacaca    5400
tggcatggat gaactataca aataacacgt gctacgagat ttcgattcca ccgccgcctt    5460
ctatgaaagg ttgggcttcg gaatcgtttt ccggacgcc ggctggatga tcctccagcg    5520
cggggatctc atgctggagt tcttcgccca ccccaacttg tttattgcag cttataatgg    5580
ttacaaataa agcaatagca tcacaaattt cacaaataaa gcatttttt cactgcattc    5640 tagttgtggt ttgtccaaac tcatcaatgt atcttatcat gtctgagggc ccgactgttc    5700
gggagggccg cacttattag agttgaagcc aagtaagatg gtgagtcatg ataattgagc    5760
agatcgcttg tttggagcga tgaatcgttt gagtttctgc cccatcagtt gtcgacggta    5820
gtgtattgga ctacggtgac tataacgggt gacggggagt tagggctcga ctccggagag    5880
ggagcctgag agacggctac cacatccaag gaaggcagca ggcgcgtaaa ttacccaatg    5940
tggactccac gaggtagtga cgagaaatat caatgcgggg cgcttcgcgt cttgctattg    6000
gaatgagagc aatgtaaaac cctcatcgag gatcaactgg agggcaagtc tggtgccagc    6060
agccgcggta attccagctc cagaagcgta tgctaaagtt gttgcagtta aaaagctcgt    6120
agttgaattt ctgggcggg agccccggtc tttgcgcgac tgcgctctgt ttgccgagcg    6180
gctcctctgc catcctcgcc tcttttttta gtggcgtcgt tcactgtaat taaagcagag    6240
tgttccaagc aggtcgtatg acctggatgt ttattatggg atgatcagat agggctcggg    6300
tgctattttg ttggtttgca catctgagta atgatgaata ggaacagttg ggggtattcg    6360
tatttaggag ctagaggtga aattcttgga tttccgaaag acgaactaca gcgaaggcat    6420
ttaccaagca tgtttcatt aatcaagaac gaaagtctgg ggatcgaaga tgattagata    6480
ccatcgtagt ctagaccgta aacgatgccg acttgcgatt gcggggtgtt tgtattggac    6540
cctcgcagca gcacatgaga aatcaaagtc tttgggttcc gggggagta tggtcgcaag    6600 gctgaaactt aaaggaattg acggaagggc accaccagga gtggagcctg cggcttaatt    6660
tgactcaaca cggaaaaact taccaggtcc agacataggt aggattgaca gattgagagc    6720
tctttcttga ttctatgggt ggtggtgcat ggccgttctt agttggtgga gtgatttgtc    6780
tggttaattc cgttaacgaa cgagacctcg gcctactaaa tagcggtggg tatggcgaca    6840
tacttgcgta cgcttcttag agggacatgt tcggtatacg agcaggaagt tcgaggcaat    6900
aacaggtctg tgatgcccct agatgttctg ggccgcacgc gcgctacact gatgggttca    6960
acgggtggtc atcgttgttc gcagcgaggt gctttgccgg aaggcatggc aaatcctttc    7020
aacgcccatc gtgctggggc tagatttttg caattattaa tctccaacga ggaattccta    7080
```

```
gtaaacgcaa gtcatcagct tgcattgaat acgtccctgc cctttgtaca caccgcccgt    7140
cgcacctacc gattgaacgg tccgatgaaa ccatgggatg acctttttgag cgtttgttcg   7200 cgagggggt cagaactcgg gtgaatctta ttgtttagag gaaggtgaag tcgtaacaag     7260
gtttccgtag tgaatcacga attctggatc cgatacgtaa cgcgtctgca gcatgcgtgg   7320
taccgagctt tccctatagt gagtcgtatt agagcttggc gtaatcatgg tcat          7374
```

<210> SEQ ID NO 56
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 56

```
ccagtgaaaa gttcttctcc tttactcatc ttgcttggtt ggcgttagga gcgg          54
```

<210> SEQ ID NO 57
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 57

```
ccgctcctaa cgccaaccaa gcaagatgag taaaggagaa gaacttttca ctgg          54
```

<210> SEQ ID NO 58
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 58

```
ggtggaatcg aaatctcgta gcacgtgtta tttgtatagt tcatccatgc catg          54
```

<210> SEQ ID NO 59
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 59

```
catggcatgg atgaactata caaataacac gtgctacgag atttcgattc cacc          54
```

<210> SEQ ID NO 60
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 60

```
cgtcctcctt gaaatcgatt ccc                                            23
```

<210> SEQ ID NO 61
<211> LENGTH: 6011
<212> TYPE: DNA
<213> ORGANISM: Thraustochytrium sp.

<400> SEQUENCE: 61

```
gacgaaaggg cctcgtgata cgcctatttt tataggttaa tgtcatgata ataatggttt    60
```

| | |
|---|---|
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attcccttt | 240 |
| ttgcggcatt ttgccttcct gttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag cggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc attttttaatt taaaaggatc taggtgaaga | 1140 |
| tcctttttga taatctcatg accaaaatcc cttaacgtga gttttcgttc cactgagcgt | 1200 |
| cagaccccgt agaaaagatc aaaggatctt cttgagatcc ttttttttctg cgcgtaatct | 1260 |
| gctgcttgca acaaaaaaa ccaccgctac cagcggtggt ttgtttgccg gatcaagagc | 1320 |
| taccaactct ttttccgaag gtaactggct tcagcagagc gcagatacca aatactgtcc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg tcgggctga acggggggtt | 1560 |
| cgtgcacaca gcccagcttg gagcgaacga cctacaccga actgagatac ctacagcgtg | 1620 |
| agcattgaga aagcgccacg cttcccgaag ggagaaaggc ggacaggtat ccggtaagcg | 1680 |
| gcagggtcgg aacaggagag cgcacgaggg agcttccagg gggaaacgcc tggtatcttt | 1740 |
| atagtcctgt cgggtttcgc cacctctgac ttgagcgtcg attttttgtga tgctcgtcag | 1800 |
| gggggcggag cctatggaaa aacgccagca acgcggcctt tttacggttc ctggccttt | 1860 |
| gctggccttt tgctcacatg tgtgctgggc ccagccggcc agatctgagc tcgcggccgc | 1920 |
| gatatcgcta gctcgaggtg accaaaagcc gtgaacgggc gtggccgagg ctacagcacg | 1980 |
| cagcggtgtt ctctgcgtat tatatttttc gcaaggtttc ccgacggctg gtccgcgtgc | 2040 |
| ccgcgccgcg cgcacgctct cactagacgt tggtcatgag tgtttcgagt caagacctcg | 2100 |
| gagaagaatt ggggcgcaca ccttccgtgc gcgcacccct gccactgtat accgtgcgta | 2160 |
| ccccaccaga cagaaggtca ccacccgtgc tctcttcgtc agctataccg tgtgctgtag | 2220 |
| atcgtcgcag gattcgggtt gtgcacaccg cgctccgtgg gctggggcc ctggcgcggc | 2280 |
| ggcttcctag gatatagtct ataaaaccca gcgaatttta cacacagagc ggttcatttg | 2340 |
| cgctgggtcc ggtgcgcaat ttcggggcac agcctgcacg tttacatcga cgtaacagcc | 2400 |

-continued

```
acagtcatcg tcgccagcct cttcggcctt cccaccgacc cggctgctgc ccgccttcct    2460
ggctggctga tgaactatcg cggcctgcct ggcacgtacg tgcccctccc atttctcccc    2520
ggtcctccag aaatgcgcct ccggcccaa tgaaagcagg cgttggccat gcggcgcccg     2580
acatctgggt cctcgcgcct ctttgatga catcgtcctc atcgtcgtcg gcgacctggt     2640
cttcgtgatc gcttgttgat cacgcgcttg gcatcttgcg aggagaaccg tctgcactct    2700
tttggcgcgg ccgaggtgcc ttccggggtg caggccagtc gccagaccag acctgctgca    2760
aagcccgaac atcgccgtcg aggtagacca ttaggtacgt acgtacgcac gtcttcatga    2820
tcgacgccaa cgtcatgcgg tcgatgcccc gccacgcgat ggcgctagca gccaggagcg    2880
cgtgtgtacg ggcgcggagc ttcgctcgca agcaaagctg ggcgcttggg ccggggatcg    2940
ggccactact tggacgaacg aacgaaacgc atgacgtcat ccttggcagt aaatcttgcc    3000
ggagcgcgca aacccaggc tggacgcgct gggtgcgatt gagaaccgca agctttggag     3060
cctttcactg agcaggggga actgacgctg gagcgcgcga ccgtaggcga aggaatttga    3120
tcgaagtagg caggactgcc cgcagggtc aggccatggc caagttgacc agtgccgttc     3180
cggtgctcac cgcgcgcgac gtcgccggag cggtcgagtt ctggaccgac cggctcgggt    3240
tctcccggga cttcgtggag gacgacttcg ccggtgtggt ccgggacgac gtgaccctgt    3300
tcatcagcgc ggtccaggac caggtggtgc cggacaacac cctggcctgg gtgtgggtgc    3360
gcggcctgga cgagctgtac gccgagtggt cggaggtcgt gtccacgaac ttccgggacg    3420
cctccgggcc ggccatgacc gagatcggcg agcagccgtg ggggcgggag ttcgccctgc    3480
gcgacccggc cggcaactgc gtgcacttcg tggccgagga gcaggactga cacgtgctac    3540
gagatttcga ttccaccgcc gccttctatg aaaggttggg cttcggaatc gttttccggg    3600
acgccggctg gatgatcctc cagcgcgggg atctcatgct ggagttcttc gcccacccca    3660
acttgtttat tgcagcttat aatggttaca aataaagcaa tagcatcaca aatttcacaa    3720
ataaagcatt ttttcactg cattctagtt gtggtttgtc caaactcatc aatgtatctt     3780
atcatgtctg aattcccggg gatcctctag agtcgagaag cttgtcgacg aattcagatg    3840
tagtcatacg ctcgtctcaa agattaagcc atgcatgtgt aagtataagc gattatactg    3900
tgagactgcg aacggctcat tatatcagtt atgatttctt cggtattttc tttatatgga    3960
tacctgcagt aattctggaa ttaatacatg ctgagagggc ccgactgttc gggagggccg    4020
cacttattag agttgaagcc aagtaagatg gtgagtcatg ataattgagc agatcgcttg    4080
tttggagcga tgaatcgttt gagtttctgc cccatcagtt gtcgacggta gtgtattgga    4140
ctacggtgac tataacgggt gacggggagt tagggctcga ctccggagag ggagcctgag    4200
agacggctac cacatccaag gaaggcagca ggcgcgtaaa ttaccaatg tggactccac     4260 gaggtagtga cgagaaatat caatgcgggg cgcttcgcgt cttgctattg gaatgagagc    4320
aatgtaaaac cctcatcgag gatcaactgg agggcaagtc tggtgccagc agccgcggta    4380
attccagctc cagaagcgta tgctaaagtt gttgcagtta aaaagctcgt agttgaattt    4440
ctggggcggg agcccggtc tttgcgcgac tgcgtctgt ttgccgagcg gctcctctgc      4500
catcctcgcc tcttttttta gtggcgtcgt tcactgtaat taaagcagag tgttccaagc    4560
aggtcgtatg acctggatgt ttattatggg atgatcagat agggctcggg tgctattttg    4620 ttggttttgca catctgagta atgatgaata ggaacagttg ggggtattcg tatttaggag   4680
ctagaggtga aattcttgga tttccgaaag acgaactaca gcgaaggcat ttaccaagca    4740
tgttttcatt aatcaagaac gaaagtctgg ggatcgaaga tgattagata ccatcgtagt    4800
```

```
ctagaccgta aacgatgccg acttgcgatt gcggggtgtt tgtattggac cctcgcagca    4860
gcacatgaga aatcaaagtc tttgggttcc gggggagta tggtcgcaag gctgaaactt    4920
aaaggaattg acggaagggc accaccagga gtggagcctg cggcttaatt tgactcaaca    4980
cgggaaaact taccaggtcc agacataggt aggattgaca gattgagagc tctttcttga    5040
ttctatgggt ggtggtgcat ggccgttctt agttggtgga gtgatttgtc tggttaattc    5100
cgttaacgaa cgagacctcg gcctactaaa tagcggtggg tatggcgaca tacttgcgta    5160
cgcttcttag agggacatgt tcggtatacg agcaggaagt tcgaggcaat aacaggtctg    5220
tgatgccctt agatgttctg ggccgcacgc gcgctacact gatgggttca acgggtggtc    5280
atcgttgttc gcagcgaggt gctttgccgg aaggcatggc aaatcctttc aacgcccatc    5340
gtgctggggc tagattttg caattattaa tctccaacga ggaattccta gtaaacgcaa    5400
gtcatcagct tgcattgaat acgtccctgc cctttgtaca caccgcccgt cgcacctacc    5460
gattgaacgg tccgatgaaa ccatgggatg accttttgag cgtttgttcg cgagggggt    5520 cagaactcgg gtgaatctta ttgtttagag gaaggtgaag tcatcacgaa ttctggatcc    5580
gatacgtaac gcgtctgcag catgcaagct tggcactggc cgtcgtttta caacgtcgtg    5640
actgggaaaa ccctggcgtt acccaactta atcgccttgc agcacatccc cctttcgcca    5700
gctggcgtaa tagcgaagag gcccgcaccg atcgcccttc ccaacagttg cgcagcctga    5760
atggcgaatg gcgcctgatg cggtatttc tccttacgca tctgtgcggt atttcacacc    5820
gcatatatgg tgcactctca gtacaatctg ctctgatgcc gcatagttaa gccagccccg    5880
acacccgcca acacccgctg acgcgccctg acgggcttgt ctgctcccgg catccgctta    5940
cagacaagct gtgaccgtct ccgggagctg catgtgtcag aggttttcac cgtcatcacc    6000
gaaacgcgcg a                                                          6011
```

<210> SEQ ID NO 62
<211> LENGTH: 6661
<212> TYPE: DNA
<213> ORGANISM: Thraustochytrium sp.

<400> SEQUENCE: 62

```
gacgaaaggg cctcgtgata cgcctatttt tataggttaa tgtcatgata ataatggttt      60
cttagacgtc aggtggcact tttcggggaa atgtgcgcgg aacccctatt tgtttatttt    120
tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga ccacacgatg cctgtagcaa tggcaacaac gttgcgcaaa ctattaactg    780
gcgaactact tactctagct tcccggcaac aattaataga ctggatggag gcggataaag    840
```

-continued

```
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260 gctgcttgca acaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttttgtga tgctcgtcag   1800 gggggcggag cctatggaaa aacgccagca acgcggcctt tttacggttc ctggccttttt   1860 gctggccttt tgctcacatg tgtgctgggc ccagccggcc agatctgagc tcgcggccgc   1920
gatatcgcta gacaacgcca tcctcgacca cagcaaggac acgcaccgct tcggctacgg   1980
tatccagatc ggataaatat tataccgccc cttccgctct cctttttcttt tttgctcgtc   2040 tggatgccag actaaggagt ccttgctcct ctgcgcaagg ctgctcaccc agagtctctg   2100
cctgtggttg agcgcccacc aacaggttaa agcgaaccag ggccgccccg ttgccgctgc   2160
gatgtcgctg ctcttgcgag actcttcatt agatcggcgg aatgctgccg caggactgac   2220
cgcctcttcg ttcgttcgtt tgtacgcgag cggtgcgagc ggcttcgttg ttggcagata   2280
ggcagaacgc gagcagttca cgtttctttg cagctttatc tatccgcaaa ttcgcctcag   2340
cgtctgcaac tttccggtga ggacagcaga gctgcagttc tgatcgtctc catcttttgg   2400
agcgcatgtc gacgtccccc agctcgtctc cgtctcccct ggagtggacg gtctctttca   2460
cagtgcctgg gtgcggccat ttccctaaat aggttgcgca gccgagtttc cttaaacgtg   2520
cctggtccgc gtgcttccgc cttactacct gaacgcgcag tagctcggcg cgtgccgctt   2580
taaggcgggc ggggtggctg ctcttgctta cgccaggcgc gtacgtcagc agcgccggcg   2640
ccatgctgcc catagcggcc acagaatcgt aggcgctgca atcgggaact gccaagatgg   2700
caatcgagac gatcccccaa agtggacaa gcaccgtcaa agtaacctgg ctgatgatgg   2760
ccgggaccgc ctggtgacgg ccagccggca aaaccggaat ctatcacgag gactgggcag   2820
atcaagggcc tagtgctagc gagcagctcg agcgaaagaa gcgcgccagc agcgcaggca   2880
cgccatggcc aagactagtg gcggtaccgg tacgcgtgga catatggcag catgcgcttc   2940
gcgagttttc gaaggggggat cctaacacgt gctacgagat ttcgattcca ccgccgcctt   3000
ctatgaaagg ttgggcttcg gaatcgtttt ccgggacgcc ggctggatga tcctccagcg   3060
cggggatctc atgctggagt tcttcgccca ccccaacttg tttattgcag cttataatgg   3120
ttacaaataa agcaatagca tcacaaattt cacaaataaa gcattttttt cactgcattc   3180
tagttgtggt ttgtccaaac tcatcaatgt atcttatcat gtctgaattc ctcgttggag   3240
```

| | |
|---|---|
| attaataatt gcaaaaatct agccccagca cgatgggcgt tgaaaggatt tgccatgcct | 3300 |
| tccggcaaag cacctcgctg cgaacaacga tgaccacccg ttgaacccat cagtgtagcg | 3360 |
| cgcgtgcggc ccagaacatc taagggcatc acagacctgt tattgcctcg aacttcctgc | 3420 |
| tcgtataccg aacatgtccc tctaagaagc gtacgcaagt atgtcgccat acccaccgct | 3480 |
| atttagtagg ccgaggtctc gttcgttaac ggaattaacc agacaaatca ctccaccaac | 3540 |
| taagaacggc catgcaccac cacccataga atcaagaaag agctctcaat ctgtcaatcc | 3600 |
| tacctatgtc tggacctggt aagttttccc gtgttgagtc aaattaagcc gcaggctcca | 3660 |
| ctcctggtgg tgcccttccg tcaattcctt taagtttcag ccttgcgacc atactccccc | 3720 |
| cggaacccaa agactttgat ttctcatgtg ctgctgcgag ggtccaatac aaacaccccg | 3780 |
| caatcgcaag tcggcatcgt ttacggtcta gactacgatg gtatctaatc atcttcgatc | 3840 |
| cccagacttt cgttcttgat taatgaaaac atgcttggta aatgccttcg ctgtagttcg | 3900 |
| tctttcggaa atccaagaat ttcacctcta gctcctaaat acgaataccc ccaactgttc | 3960 |
| ctattcatca ttactcagat gtgcaaacca acaaaatagc acccgagccc tatctgatca | 4020 |
| tcccataata aacatccagg tcatacgacc tgcttggaac actctgcttt aattacagtg | 4080 |
| aacgacgcca ctaaaaaaag aggcgaggat ggcagaggag ccgctcggca aacagagcgc | 4140 |
| agtcgcgcaa agaccggggc tcccgcccca gaaattcaac tacgagcttt ttaactgcaa | 4200 |
| caactttagc atacgcttct ggagctggaa ttaccgcggc tgctggcacc agacttgccc | 4260 |
| tccagttgat cctcgatgag ggttttacat tgctctcatt ccaatagcaa gacgcgaagc | 4320 |
| gccccgcatt gatatttctc gtcactacct cgtggagtcc acattgggta atttacgcgc | 4380 |
| ctgctgcctt ccttggatgt ggtagccgtc tctcaggctc cctctccgga gtcgagccct | 4440 |
| aactccccgt cacccgttat agtcaccgta gtccaataca ctaccgtcga caactgatgg | 4500 |
| ggcagaaact caaacgattc atcgctccaa acaagcgatc tgctcaatta tcatgactca | 4560 |
| ccatcttact tggcttcaac tctaataagt gcggccctcc cgaacagtcg ggccctcaga | 4620 |
| catgataaga tacattgatg agtttggaca aaccacaact agaatgcagt gaaaaaaatg | 4680 |
| ctttatttgt gaaatttgtg atgctattgc tttatttgta accattataa gctgcaataa | 4740 |
| acaagttggg gtgggcgaag aactccagca tgagatcccc gcgctggagg atcatccagc | 4800 |
| cggcgtcccg gaaaacgatt ccgaagccca acctttcata gaaggcggcg gtggaatcga | 4860 |
| aatctcgtag cacgtgttag tcctgctcct cggccacgaa gtgcacgcag ttgccggccg | 4920 |
| ggtcgcgcag ggcgaactcc cgcccccacg gctgctcgcc gatctcggtc atggccggcc | 4980 |
| cggaggcgtc ccggaagttc gtggacacga cctccgacca ctcggcgtac agctcgtcca | 5040 |
| ggccgcgcac ccacacccag gccagggtgt tgtccgcac cacctggtcc tggaccgcgc | 5100 |
| tgatgaacag ggtcacgtcg tcccggacca caccggcgaa gtcgtcctcc acgaagtccc | 5160 |
| gggagaaccc gagccggtcg gtccagaact cgaccgctcc ggcgacgtcg cgcgcggtga | 5220 |
| gcaccggaac ggcactggtc aacttggcca tcttgcttgg ttggcgttag gagcgggcgg | 5280 |
| aagacttggg ctcggggag gcgagggacg caaggaaggc ggggtagaac ggcgtgttgt | 5340 |
| taggcacgac cgtctgaagg ctgattcggg tttgctctgg atgagccggg ttttgctttg | 5400 |
| atccccgcgc caaaccgctg tgccgcgcca gtgggttgcc gctcctagtg ccctcttctg | 5460 |
| gccccagtgt gccgtcgtaa tttccttctc gcgccttatt gcgcccaggt ccccacgtcg | 5520 |
| ccagtggaaa tggggtgac gtccgttgcg gcatgagggc tagcataaac tttgggttgg | 5580 |

-continued

| | |
|---|---|
| gaagacggcg aaaagttggc ttcagtggag tgaggggggtg aaagtccact ctgtgcgggt | 5640 |
| aaaagtggac ggtcgtccct cacagcccag aggtgctgca aaatcggcgt gcaacggcca | 5700 |
| atccgatttt agcgcgcggt tggtcgcaat ggcgtgaaac ggctcgttgc gcagccgcga | 5760 |
| accaaagggg ccgagggggt caagacgccg cgcgcgcatg acatggacgc cgactccacg | 5820 |
| aagcgccgcg cgggctctgg aagaagaga tctgcgcacg ctaaggaagg gcacgcgagg | 5880 |
| gaggcacaga tgatctggcc tggcaagaat gaatgaatcc aacattggga aaagaatgcg | 5940 |
| ggacggacgg ttggcacgct cgcggctgcg ccttgaacgg ccgctcgcgg acaaaagtta | 6000 |
| ttttttcccg tggaccgggc agcgaccgtg acggtttggg accgaggctg ccaagcgcaa | 6060 |
| tgcgtgcggg ctgggagcag tcagacgtgc agtgttcttt acaaaatcta ctacgagttg | 6120 |
| gttgtgagca aagccggggg cggaaatggt cttgccgaca gagcgcgtct catgttggga | 6180 |
| aaccaagcga tctggccgac gcagttcgca atccaatgct tccgcagcgc aatggatggc | 6240 |
| caagggagac aggccaagct tggcactggc cgtcgtttta caacgtcgtg actgggaaaa | 6300 |
| ccctggcgtt acccaactta atcgccttgc agcacatccc cctttcgcca gctggcgtaa | 6360 |
| tagcgaagag gcccgcaccg atcgcccttc ccaacagttg cgcagcctga atggcgaatg | 6420 |
| gcgcctgatg cggtattttc tccttacgca tctgtgcggt atttcacacc gcatatatgg | 6480 |
| tgcactctca gtacaatctg ctctgatgcc gcatagttaa gccagccccg acacccgcca | 6540 |
| acacccgctg acgcgccctg acgggcttgt ctgctcccgg catccgctta cagacaagct | 6600 |
| gtgaccgtct ccgggagctg catgtgtcag aggttttcac cgtcatcacc gaaacgcgcg | 6660 |
| a | 6661 |

<210> SEQ ID NO 63
<211> LENGTH: 85
<212> TYPE: DNA
<213> ORGANISM: Artificial sequence
<220> FEATURE:
<223> OTHER INFORMATION: Synthetic oligonucleotide

<400> SEQUENCE: 63

| | |
|---|---|
| ttatacgcgt ggacatatgg cagcatgcgc ttcgcgagtt ttcgaagggg gatcctaaca | 60 |
| cgtgctacga gatttcgatt ccacc | 85 |

<210> SEQ ID NO 64
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 64

| | |
|---|---|
| atatccacgc gtaccggtac cgccactagt cttggccatg gcgtgcctgc gctgctggc | 59 |

<210> SEQ ID NO 65
<211> LENGTH: 3670
<212> TYPE: DNA
<213> ORGANISM: Thraustochytrium sp.

<400> SEQUENCE: 65

| | |
|---|---|
| gacgaaaggg cctcgtgata cgcctatttt tataggttaa tgtcatgata ataatggttt | 60 |
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attccctttt | 240 |

```
ttgcggcatt ttgccttcct gttttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260 gctgcttgca acaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acgggggggtt   1560 cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttttgtga tgctcgtcag   1800 gggggcggag cctatggaaa aacgccagca acgcggcctt tttacggttc ctggccttt    1860 gctggccttt tgctcacatg tgtgctgggc ccagccggcc agatctgagc tcgcggccgc   1920
gatatcgcta gacaacgcca tcctcgacca cagcaaggac acgcaccgct tcggctacgg   1980
tatccagatc ggataaatat taccgcccc cttccgctct ccttttcttt tttgctcgtc   2040
tggatgccag actaaggagt ccttgctcct ctgcgcaagg ctgctcaccc agagtctctg   2100
cctgtggttg agcgcccacc aacaggttaa agcgaaccag ggccgccccg ttgccgctgc   2160
gatgtcgctg ctcttgcgag actcttcatt agatcggcgg aatgctgccg caggactgac   2220
cgcctcttcg ttcgttcgtt tgtacgcgag cggtgcgagc ggcttcgttg ttggcagata   2280
ggcagaacgc gagcagttca cgtttctttg cagctttatc tatccgcaaa ttcgcctcag   2340
cgtctgcaac tttccggtga ggacagcaga gctgcagttc tgatcgtctc catcttttgg   2400
agcgcatgtc gacgtccccc agctcgtctc cgtctcccct ggagtggacg gtctctttca   2460
cagtgcctgg gtgcggccat ttccctaaat aggttgcgca gccgagtttc cttaaacgtg   2520
cctggtccgc gtgcttccgc cttactacct gaacgcgcag tagctcggcg cgtgccgctt   2580
```

```
taaggcgggc ggggtggctg ctcttgctta cgccaggcgc gtacgtcagc agcgccggcg    2640
ccatgctgcc catagcggcc acagaatcgt aggcgctgca atcgggaact gccaagatgg    2700
caatcgagac gatcccccaa aagtggacaa gcaccgtcaa agtaacctgg ctgatgatgg    2760
ccgggaccgc ctggtgacgg ccagccggca aaaccggaat ctatcacgag gactgggcag    2820
atcaagggcc tagtgctagc gagcagctcg agcgaaagaa gcgcgccagc agcgcaggca    2880
cgccatggcc aagactagtg gcggtaccgg tacgcgtgga catatggcag catgcgcttc    2940
gcgagttttc gaaggsggat cctaacacgt gctacgagat ttcgattcca ccgccgcctt    3000
ctatgaaagg ttgggcttcg gaatcgtttt ccgggacgcc ggctggatga tcctccagcg    3060
cggggatctc atgctggagt tcttcgccca ccccaacttg tttattgcag cttataatgg    3120
ttacaaataa agcaatagca tcacaaattt cacaaataaa gcattttttt cactgcattc    3180
tagttgtggt ttgtccaaac tcatcaatgt atcttatcat gtctgaattc ccggggatcc    3240
tctagagtcg acctgcaggc atgcaagctt ggcactggcc gtcgttttac aacgtcgtga    3300
ctgggaaaac cctggcgtta cccaacttaa tcgccttgca gcacatcccc ctttcgccag    3360
ctggcgtaat agcgaagagg cccgcaccga tcgcccttcc caacagttgc gcagcctgaa    3420
tggcgaatgg cgcctgatgc ggtattttct ccttacgcat ctgtgcggta tttcacaccg    3480
catatatggt gcactctcag tacaatctgc tctgatgccg catagttaag ccagccccga    3540
cacccgccaa cacccgctga cgcgccctga cgggcttgtc tgctcccggc atccgcttac    3600
agacaagctg tgaccgtctc cgggagctgc atgtgtcaga ggttttcacc gtcatcaccg    3660
aaacgcgcga                                                           3670
```

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ggccaagttg accagtgccg                                                  20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
cagtcctgct cctcggccac                                                  20

<210> SEQ ID NO 68
<211> LENGTH: 1724
<212> TYPE: DNA
<213> ORGANISM: Artificial sequence
<220> FEATURE:
<223> OTHER INFORMATION: Synthetic construct

<400> SEQUENCE: 68

```
dgtagtcata cgctcgtctc aaagattaag ccatgcatgt gtaagtataa gcgattatac      60
tgtgagactg cgaacggctc attatatcag ttatgatttc ttcggtattt tctttatatg     120
gatacctgca gtaattctgg aattaataca tgctgagagg gcccgactgt tcgggagggc     180
cgcacttatt agagttgaag ccaagtaaga tggtgagtca tgataattga gcagatcgct     240
```

```
tgtttggagc gatgaatcgt ttgagtttct gccccatcag ttgtcgacgg tagtgtattg      300
gactacggtg actataacgg gtgacgggga gttagggctc gactccggag agggagcctg      360
agagacggct accacatcca aggaaggcag caggcgcgta aattacccaa tgtggactcc      420
acgaggtagt gacgagaaat atcaatgcgg ggcgcttcgc gtcttgctat tggaatgaga      480
gcaatgtaaa accctcatcg aggatcaact ggagggcaag tctggtgcca gcagccgcgg      540
taattccagc tccagaagcg tatgctaaag ttgttgcagt taaaaagctc gtagttgaat      600
ttctggggcg ggagccccgg tctttgcgcg actgcgctct gtttgccgag cggctcctct      660
gccatcctcg cctcttttt tagtggcgtc gttcactgta attaaagcag agtgttccaa       720
gcaggtcgta tgacctggat gtttattatg ggatgatcag atagggctcg ggtgctattt      780
tgttggtttg cacatctgag taatgatgaa taggaacagt tgggggtatt cgtatttagg      840
agctagaggt gaaattcttg gatttccgaa agacgaacta cagcgaaggc atttaccaag      900
catgttttca ttaatcaaga acgaaagtct ggggatcgaa gatgattaga taccatcgta      960
gtctagaccg taaacgatgc cgacttgcga ttgcggggtg tttgtattgg accctcgcag     1020
cagcacatga gaaatcaaag tctttgggtt ccgggggag tatggtcgca aggctgaaac      1080
ttaaaggaat tgacggaagg gcaccaccag gagtggagcc tgcggcttaa tttgactcaa     1140
cacgggaaaa cttaccaggt ccagacatag gtaggattga cagattgaga gctctttctt     1200
gattctatgg gtggtggtgc atggccgttc ttagttggtg gagtgatttg tctggttaat     1260
tccgttaacg aacgagacct cggcctacta aatagcggtg ggtatggcga catacttgcg     1320
tacgcttctt agagggacat gttcggtata cgagcaggaa gttcgaggca ataacaggtc     1380
tgtgatgccc ttagatgttc tgggccgcac gcgcgctaca ctgatgggtt caacgggtgg     1440
tcatcgttgt tcgcagcgag gtgctttgcc ggaaggcatg gcaaatcctt tcaacgccca     1500
tcgtgctggg gctagatttt tgcaattatt aatctccaac gaggaattcc tagtaaacgc     1560
aagtcatcag cttgcattga atacgtccct gcccttgta cacaccgccc gtcgcaccta      1620
ccgattgaac ggtccgatga aaccatggga tgaccttttg agcgtttgtt cgcgaggggg     1680
gtcagaactc gggtgaatct tattgtttag aggaaggtga agtc                      1724
```

<210> SEQ ID NO 69
<211> LENGTH: 3247
<212> TYPE: DNA
<213> ORGANISM: Thraustochytrium sp.

<400> SEQUENCE: 69

```
cggacggcgt gcttagtaac tgaatgaata attataccag ctgggattc tgcgaatgcg       60 aacgacgctt ccctttgca gcgacgcgt gccgcgcgcg atacttgctt                  120
ctattctagc aaagcccaac gcaaggcttg cctactcctt gtcgagcttg tacatgtcct     180
tggaggtgta cccattcgcg atgaggctct cgtacgcggc ttcgacctgc tccttgtagg     240
agcggtactc gccgaggccg aggccgccct cgctggtcgg tttgagggac ttttcgacgt     300
tgtagcgagt gcggtgtggc ggcggcgccc ccgagccggg tgcgggaagc ttcgggtcca    360
cctcggtagg aagctctttt ttccggtcct cagaaacctt gttagactcg cgcaaaacct    420
ggacaatttc ttcgcgcatg ggggcaccgc caataagaag gaagcgctcg ccccagccct    480
tccagtcaaa gtccatctgt gcggcgttga cgtgggcgcg cgccacatcg cgcacgtccg    540
tgatgcaggc gttggcctgt tgaaccttgg aggcgccaaa gtatgctagc acggagaccg    600
```

| | |
|---|---|
| agctggtgtt gagctcgggg aggccgggaa gcatggggcc gtagatgaag ctcgggttga | 660 |
| gcgcagcaag cttgaaagag ctctccttgg cgatctccca ggccgttttc tcggcgagga | 720 |
| gcttggaaag gccatagtag ttcttttct cctcgaggac cttgtcgtcg gtccagtcct | 780 |
| cttcgctgta gacgtactcg gggggcttcg cgccgtacgt gatgtagatg ttggcgatcg | 840 |
| aggcggtaag cacgaccttt tccacaccga gcttctcgca ggactcaagc acgttgcgcg | 900 |
| tgcccttcac ggccggctcg acgagtttct ggcgcgccga ctcgtcgttt atgcggataa | 960 |
| agggcgacgc cgagtggatc accgtggggc atcccttgat ggcctcatcg aagctgccct | 1020 |
| gctccaggag atcgcagcca gtgaaaagct tgagccgctc ctgggcgcca tcgagctttt | 1080 |
| gcagaaagtc cacctttttg ccggaccgcg tcgttccgtg cacctcgaag ccggcctcca | 1140 |
| gcgcgtactt gactacccac gagcccagga aaccggtaca ccccgtcacg cacacgcgtt | 1200 |
| tcgcctccgg caccgacatg ctgcttgttt gtccacctcc tcggctcttg ctccgctcgc | 1260 |
| gtataggcca ggcggctggc tagctgctcg ggctcgggac caaaacgttt ctgcaagttt | 1320 |
| cgagactgcg gcttcagctg ggattttgtg gcgtttgcct cggcctcacc gtcatcgcct | 1380 |
| catcccgtgc gcgcagatga cgacgatgcc gccgacctcg cacgacctca gcggttcag | 1440 |
| gagtcgttcg ctgcgccaag aaatgggcag cgcaacgcac gccgctcgag gtgggctgtg | 1500 |
| agcgcctcgg gcacgcgact aataagcccc agggcgctcg ggatgccctc cttccgccgc | 1560 |
| acgcgttgca ttcttgcttg cttgcttgct tgcttgcttg cttgcttgct tgcctgcgcg | 1620 |
| gagaagtgtt ggttttccg atcgacggca aagataacgc gcgtgtacta gcgtcgatcg | 1680 |
| cgagtccctt gacctgcctg cctccgtcag catgctgcca agggttgatg cgagtagcgc | 1740 |
| ggcgccgcgt tgctgcgaga tgcgcgcgcg gagtggtccg cgtccttgct gcctgcgatc | 1800 |
| gacacgacgc tgatgagggt cgagcttcct tcttcccttc cggcgccgtt gaacccgccc | 1860 |
| acccatgttg gcgaggtgaa tctggagccc gtgccggcgg ccggcggcac cgtgggccac | 1920 |
| ccgcacgcgc gctaccaagc acgctttgcg cggcggggc accgcccgcg aaacgcgttg | 1980 |
| cgcagacacc catttccagc atttcgaggt actgaggcta accgacgacg cgacgcagcg | 2040 |
| acggcgcccc cggcatgacg cggctcggga gcgtttgttt tggcgtgcgt tgctcgcgcg | 2100 |
| gcggacgttc acgaaacccg tgtcgggccg ggatccgcgc tggtccgggc gctcgacatc | 2160 |
| gatttccttt cgagcgcgct gccgcgtcga aggggctccg ggtcgcgcta ggtcttctgg | 2220 |
| cctaggaaag gaaagaaaac gggaaggagg atcaaagtca tactatgcgt acacgccgcg | 2280 |
| ttcggaaacc ctagctggtt caaccagttc cctcttctga ttccctcgct gggttctgcg | 2340 |
| ggccacgctc aagccgtccg ggacgtcatg gacgtcgcgc tgccctgcgt cgttcttcta | 2400 |
| cgcgtacgca caagaaggcg tcaccgccgc gcccgcgccg aagacctccc tcccgatcga | 2460 |
| aggtcctggt tctcgggagg cgctgtgcgt ggtatgtcga cgcgctcggc tctgcgctgg | 2520 |
| agagcgcaag gcggcttttt gaccaggttg cctgcctcct accacgtgcc cgtagggagg | 2580 |
| gggaatgtac cgcagtgcgg tggtccgcca agcaagaaac cccgcagaga aggcgtaaag | 2640 |
| tggaagaaaa acagcgtcgt atgccgccgt cgtcgcaggt gctcgtcgtc gcctcgtcga | 2700 |
| tgggacccat catgcgctga gagtctgctg caaaagaggg agggactcgg gaaggacctg | 2760 |
| gttcgcgctg gctggggaat cagtaatcgc atttcggaca tggatgcgga gacgctcccc | 2820 |
| gatgacgatg ctccaggaat cgcgcggcac gttttacggc ggcgagagag aaagtctcag | 2880 |
| cttcttttcg agggtatact ccgtggcggg ttatcatcat gtgagagatg tatcgacgcg | 2940 |
| atggagaagc atcgggtctt cgtcgaacat ccggggtcgc cggttcgtca cgaagccagc | 3000 |

```
tcatgcctcc acatgtctca caagaccacc gaaaaactgt cgaacttgat tctttaggtc    3060
tctcggacgc aaataaaaag catcggcgcg ctcgcgttca ccagcaagca gacaaaacca    3120
atatcagcct attggccgac caaaaccaag cagcagttcc tcaactcggc tctgctcaac    3180
tcagcaaact gccaacgcgt actagcagac aaggattcac cccagcttcg gttgaaacta    3240
caagatc                                                             3247
```

<210> SEQ ID NO 70
<211> LENGTH: 1239
<212> TYPE: DNA
<213> ORGANISM: Thraustochytrium sp.

<400> SEQUENCE: 70

```
atgtgcaagg tggagcccac gcggcacgag cagacggctg cggccaagcc gcaagagcag      60
cagcagcagc gtcagagtcc catcatccat ggcaagcaca acccggacct gccgacgctc     120
ggcgagattc cgccgtggt gccgaagcac tgctttgagc gctcgctcgt gacgagctcg      180
ctttacctgg ccgcgacct tctcatggca gccaccctct tcttcctcgc cagacaattc      240
cttcccgttt acgacatggg cctctcgggc gcgctcgcct ggactgtcta cgtctgtgtg     300
cagggtaccg tcggtgccgg cctttgggtg cttgggcatg aatgcggtca ccaggccttt     360
tccaactaca ggatcgtcaa cgacggcgtc ggctttctgg tccacacgag cctgttggtg     420
ccttatttca gctgggcgta cacgcacggc ttgcaccatg cccgcgtcaa ccacatgctc     480
gacggcgagt cgcacacgcc gaacctgaag aagaaggtgg ccgccaactt caaaagttc     540 tgcgacatga tgggcgatga ggcgtttgcc gttcttcacg tcttcgtcta ccttctcctg     600
gcctggccgc tttacatcat caacgggagc ggcgcgtcca agcgcaacca cgagggaaag     660
cgctggtcga aggatttctg gaagcgcccc aaccactttt tgcccacctc ggagctcttt     720
ccggacaaga tgcgcctcaa ggccgccgtc tccacgatcg gcgtccttac cgtcattgcc     780
ggcctctgct actgggctc tatcgagggc gggcgcaccg tgctgctcca gtactttctg     840
ccctacctgg tggtcaatgc ctatctcatt gggtttacct ggatgcaaca cacccacccg     900
gacgtcccgc acctcggcga ggacgagtgg tcctgggtcg cgggcactgt gctccaccgtc    960 gatcgcccct acccgccttt tatcgacgtt ctgacccacc gcatcgggtc tacgcacgtg    1020
gcgcatcacc tcttctccaa gatgccgtgg taccacgcgc gcgaggctac gacccacatc    1080
cggaccctcc tcgagcccaa gggcgtctac aactatgacc cgatgccctt ttacaaggcc    1140
ttgtttcaca ctgctaagta ctgccactac atggagggcg tcgacggtat tcagttcttc    1200
aaacatgccg ctgcccagcc caaggccaag gagctctaa                           1239
```

<210> SEQ ID NO 71
<211> LENGTH: 1066
<212> TYPE: DNA
<213> ORGANISM: Thraustochytrium sp.

<400> SEQUENCE: 71

```
gatatgtatt tacgtgatca acaaccaatc agccacgacg ttatcgtcgt tgtcggcctt      60
gtcgtcgttg tcgaagcaga ggttggagaa cgacagcaac aacgcgacgg ggagaatgtt     120
gattacgccc cgtcaatctc ggaagggccg acctagccca gaagtcctcg gcagcctttg     180
gttaacttcg gagcccgcaa cgttctggga ctgtctttgc tctaatgtaa tgcgatgccg     240
cgccttgcga ccaaggttct gccccgtcgg cgttgaagtc ttcgctcgag ggcttctgga     300
```

| | |
|---|---:|
| tgttggagaa ctgattgcac ccaatgcgat cgccaatcga tcgatgcgcg ctccgggcga | 360 |
| ccttcttctc gccgtgccgc ttttgcctcc tttgcagcca ggtacgtagc ctcgcacctg | 420 |
| gggctgtcct cgaccatggt ctcgtggccc atctcgaagc aaacgaaaag cagcgcacca | 480 |
| ccttcgtttt cggcccttt cgccgcattc ccccggcatc gtgaaacttg cgcgccggcc | 540 |
| ccggctaaag tgcgcgtgac acattgatcg cccaggacca ggctgcacat tgggggtaga | 600 |
| aaacttagtg tcgcgcggc cctgcgtgcg tcagcagcat acgtaagcca gcatcctcgc | 660 |
| cctaagtgtg cactgaaaac gcacactcct tggtcatgtg tggggacacc cgacggggac | 720 |
| tcagcgagga cggtgtcccc acctccgcgt accggcaacg tagagggcaa ggcaaaatcg | 780 |
| ttggatcctc acgacaacag gccacgccca ggtcaccctc cattccattg taccgtccgt | 840 |
| ttcgactggc ggctaacgaa aagcctatag ccgttctcgt ttgccattta ttgacgactc | 900 |
| tgcccggatg aatcccaaac acgattcata tgcgcggtct gctccgtctt atggatgacg | 960 |
| ctggatggat gggaaaaggt aaaataggcg ttctttactg tcagggtctt gcagtcgtct | 1020 |
| tgtgttgctt ggccgagtaa tcgtcacgcg caaacgatcg gcgcct | 1066 |

<210> SEQ ID NO 72
<211> LENGTH: 1338
<212> TYPE: DNA
<213> ORGANISM: Thraustochytrium sp.

<400> SEQUENCE: 72

| | |
|---|---:|
| atgggcaagg gaagcgaggg ccgcagcgcg gagcgcgaga tgtcggccga ggcgagcggc | 60 |
| gacaagcgga aaacaatttt gatcgagggc gtcctgtatg acgtgacgaa ctttaagcac | 120 |
| ccgggcggtt cgatcatcaa cttttttgacc gagggcgagg ccggcgtgga cgcgacacag | 180 |
| gcgtaccgcg agttccatca gcggtccggc aaggctgaca agtacctcaa gtcgctgccg | 240 |
| aaactggatg cgtccaaggt ggagtcgcgg ttctcggcca aggagcaggc gcggcgcgac | 300 |
| gccatgacgc gcgactatgc ggccttcgc gaggagctca tcgccgaggg gtactttgac | 360 |
| ccgtcgatcc cacacatgat tttccgcgtc gtcgagattg tggcgctctt tgcgctctcg | 420 |
| ttctggctca tgagcaaggc ctcgcccagc tcgctcgtgc tgggcgtggt gatgaacggc | 480 |
| attgcgcagg gccggtgcgg ctgggtcatg cacgagatgg ccacgggtc gttcacgggc | 540 |
| gtcatttggc tcgacgaccg gctgtgcgag ttcttttacg gagccggctg cggcatgagc | 600 |
| gggcactact ggaagaacca gcacagcaag caccacgccg cgcccaaccg cctcgagcac | 660 |
| gatgtcgatc tcaacacgtt gccctggtc gcctttaacg agcgcgttgt gcgcaaggtc | 720 |
| aagccggggt ctctgcttgc gctctggctg cgtgtgcagg cgtacctctt tgcgcccgtc | 780 |
| tcgtgcctgc tcattggcct cggctggacg ctgtacctgc acccgcgcta catgctgcgc | 840 |
| accaagcggc acatggagtt tgtctggatc tttgcgcgct atcttggttg gttctcgctc | 900 |
| atgggcgctc tcggttacac gccgggccgc tcgatcggga tgtacctgtg ctcgtttggc | 960 |
| ctcggctgca tttacatttt cctgcagttc gccgtcagcc acacgcacct gccggtgact | 1020 |
| aacccagagg accagctgca ctggctcgag tacgcggcgg accacacggt gaacattagc | 1080 |
| accaagtcct ggttcgtcac atggtggatg tcgaacctga actttcagat cgagcaccac | 1140 |
| cttttccccca cggcgccgca gtttcgcttc atggaaatca gccctcgcgt cgaggccctc | 1200 |
| ttcaagcgcc acaacctccc atactacgac ctgccctaca cgagcgcggt ctcgaccacc | 1260 |
| tttgccaacc tttattccgt cggcactcg gtcggcgact cggtcggcgc cgacaccgac | 1320 |
| gccaagaagc aagactag | 1338 |

<210> SEQ ID NO 73
<211> LENGTH: 445
<212> TYPE: PRT
<213> ORGANISM: Thraustochytrium sp.

<400> SEQUENCE: 73

```
Met Gly Lys Gly Ser Glu Gly Arg Ser Ala Glu Arg Glu Met Ser Ala
1               5                   10                  15

Glu Ala Ser Gly Asp Lys Arg Lys Thr Ile Leu Ile Glu Gly Val Leu
            20                  25                  30

Tyr Asp Val Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Ile Ala Glu Gly Tyr Phe Asp Pro Ser Ile Pro His Met Ile Phe
        115                 120                 125

Arg Val Val Glu Ile Val Ala Leu Phe Ala Leu Ser Phe Trp Leu Met
    130                 135                 140

Ser Lys Ala Ser Pro Ser Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Leu Cys Glu Phe Phe
            180                 185                 190

Tyr Gly Ala Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Leu Gly Trp Phe Ser Leu Met Gly Ala Leu
    290                 295                 300

Gly Tyr Thr Pro Gly Arg Ser Ile Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Phe Val Thr Trp
        355                 360                 365

Trp Met Ser Asn Leu Asn Phe Gln Ile Glu His His Leu Phe Pro Thr
```

```
                370                 375                 380
Ala Pro Gln Phe Arg Phe Met Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
                420                 425                 430

Asp Ser Val Gly Ala Asp Thr Asp Ala Lys Lys Gln Asp
            435                 440                 445
```

<210> SEQ ID NO 74
<211> LENGTH: 50
<212> TYPE: DNA
<213> ORGANISM: Thraustochytrium sp.

<400> SEQUENCE: 74
gcaccgccaa taagaaggaa gcgctcgccc cagcccttcc agtcaaagtc         50

<210> SEQ ID NO 75
<211> LENGTH: 50
<212> TYPE: DNA
<213> ORGANISM: Thraustochytrium sp.

<400> SEQUENCE: 75
gtttatgcgg ataaagggcg acgccgagtg gatcaccgtg gggcatccct         50

<210> SEQ ID NO 76
<211> LENGTH: 50
<212> TYPE: DNA
<213> ORGANISM: Thraustochytrium sp.

<400> SEQUENCE: 76
gggcacgcga ctaataagcc ccagggcgct cgggatgccc tccttccgcc         50

<210> SEQ ID NO 77
<211> LENGTH: 50
<212> TYPE: DNA
<213> ORGANISM: Thraustochytrium sp.

<400> SEQUENCE: 77
aaagtggaag aaaacagcg tcgtatgccg ccgtcgtcgc aggtgctcgt          50

<210> SEQ ID NO 78
<211> LENGTH: 50
<212> TYPE: DNA
<213> ORGANISM: Thraustochytrium sp.

<400> SEQUENCE: 78
ctctcggacg caaataaaaa gcatcggcgc gctcgcgttc accagcaagc         50

<210> SEQ ID NO 79
<211> LENGTH: 50
<212> TYPE: DNA
<213> ORGANISM: Thraustochytrium sp.

<400> SEQUENCE: 79
ctcgccgccg taaaacgtgc cgcgcgattc ctggagcatc gtcatcgggg         50

<210> SEQ ID NO 80
<211> LENGTH: 50
<212> TYPE: DNA
<213> ORGANISM: Thraustochytrium sp.

```
<400> SEQUENCE: 80
gcaacctggt caaaaagccg ccttgcgctc tccagcgcag agccgagcgc       50

<210> SEQ ID NO 81
<211> LENGTH: 50
<212> TYPE: DNA
<213> ORGANISM: Thraustochytrium sp.

<400> SEQUENCE: 81
tgcgtacgcg tagaagaacg acgcagggca gcgcgacgtc catgacgtcc       50

<210> SEQ ID NO 82
<211> LENGTH: 50
<212> TYPE: DNA
<213> ORGANISM: Thraustochytrium sp.

<400> SEQUENCE: 82
gcgccctggg gcttattagt cgcgtgcccg aggcgctcac agcccacctc       50

<210> SEQ ID NO 83
<211> LENGTH: 50
<212> TYPE: DNA
<213> ORGANISM: Thraustochytrium sp.

<400> SEQUENCE: 83
ctacaacgtc gaaaagtccc tcaaaccgac cagcgagggc ggcctcggcc       50

<210> SEQ ID NO 84
<211> LENGTH: 50
<212> TYPE: DNA
<213> ORGANISM: Thraustochytrium sp.

<400> SEQUENCE: 84
gccggccccg gctaaagtgc gcgtgacaca ttgatcgccc aggaccaggc       50

<210> SEQ ID NO 85
<211> LENGTH: 50
<212> TYPE: DNA
<213> ORGANISM: Thraustochytrium sp.

<400> SEQUENCE: 85
gaaaaggtaa aataggcgtt ctttactgtc agggtcttgc agtcgtcttg       50

<210> SEQ ID NO 86
<211> LENGTH: 50
<212> TYPE: DNA
<213> ORGANISM: Thraustochytrium sp.

<400> SEQUENCE: 86
cagagtcgtc aataaatggc aaacgagaac ggctataggc ttttcgttag       50

<210> SEQ ID NO 87
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 87
ggatcaaagt catactatgc gtacacg                                27

<210> SEQ ID NO 88
```

```
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 88
ggtaccgtga atacagtcga ggtagc                                          26

<210> SEQ ID NO 89
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 89
gacaaggatt caccccagct tcggttgaaa ctacaagatc atggccaagt tgaccagtgc      60

<210> SEQ ID NO 90
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 90
cgaatctcgc cgagcgtcgg caggtccggg ttgtgcttgc catgcagaca tgataagata      60
cattg                                                                 65

<210> SEQ ID NO 91
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 91
cctccacatg tctcacaaga ccaccg                                          26

<210> SEQ ID NO 92
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 92
gcaagcaatg ctcgatttcc tacc                                            24

<210> SEQ ID NO 93
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 93
ggatcaaagt catactatgc gtacacg                                         27

<210> SEQ ID NO 94
<211> LENGTH: 53
<212> TYPE: DNA
<213> ORGANISM: Artificial Sequence
<220> FEATURE:
<223> OTHER INFORMATION: Synthetic oligonucleotide
```

<400> SEQUENCE: 94
atctatgtta accgaatgca attgcgtccg agagacctaa agaatcaagt tcg        53

<210> SEQ ID NO 95
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 95
tatcatcaat tgatgtaggt taacgccatt tctagctcga gctgc                 45

<210> SEQ ID NO 96
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 96
atgtgccaat ttggtaccgt gaatacagtc g                                31

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
atgggcaagg gaagcgaggg                                             20

<210> SEQ ID NO 98
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 98
ctagtcttgc ttcttggcgt c                                           21

<210> SEQ ID NO 99
<211> LENGTH: 929
<212> TYPE: DNA
<213> ORGANISM: Thraustochytrium sp.

<400> SEQUENCE: 99
gccgtgcggc acgacggtcc gtgagtcgtg ggagacaatc cgtgctggca tcgactgcct    60
gtcggacctc cccgaggacc gcgtcgacgt gacggcctac tttgacccgg tcaagacgac   120
caaggacaag atctactgca agcgcggcgg cttcatcccc gactacgact ttgacgctcg   180
ggagttcggc cttaacatgt tccagatgga ggactcggac gcaaaccaga ccatttcgct   240
cctcaaggtc aaggaggccc tccaggatgc cggcatcgac gccctctcca aggagaagaa   300
gaacatcggc tgcgtcctcg gcattggcgg cggccagaag tcgagccacg agttctattc   360
gcgccttaat tatgttgtcg tcgagaaggt cctccgcaaa atgggcatgc ccgagaagga   420
cgtgaaggtg gccgtcgaaa agtacaaggc caactttccc gagtggcgcc tcgactcctt   480
ccccggcttc ctcggcaatg ttaccgccgg acgctgcacc aacaccttta acctcgacgg   540

| | |
|---|---|
| catgaactgc gtcgtcgacg ccgcctgcgc ctcgtcactc atcgccgtca aggtcgccat | 600 |
| cgacgagctc ctacacggcg actgcgacat gatggtgact ggcgccacct gcacggacaa | 660 |
| ctccatcggc atgtacatgg ccttctccaa gacgccggtg ttctccaccg accccagcgt | 720 |
| ccgcgcctac gacgagaaga caaagggtat gcttatcggc gagggctcgg ccatgctcgt | 780 |
| cctcaagcgc tacgccgacg ccgtacgcga cggcgacgag atccacgccg tcatccgtgg | 840 |
| ctgcgcctcc tcgagcgatg gtaaggccgc cggcatctac acgcccacca tctcggggca | 900 |
| ggaggaggcc ctccgccgcg cctacaacc | 929 |

<210> SEQ ID NO 100
<211> LENGTH: 34
<212> TYPE: DNA
<213> ORGANISM: Artificial Sequence
<220> FEATURE:
<223> OTHER INFORMATION: Synthetic oligonucleotide
<400> SEQUENCE: 100
atactcgagc cgtgcggcac gacggtccgt gagt                                34

<210> SEQ ID NO 101
<211> LENGTH: 36
<212> TYPE: DNA
<213> ORGANISM: Artificial Sequence
<220> FEATURE:
<223> OTHER INFORMATION: Synthetic oligonucleotide
<400> SEQUENCE: 101
tatccatggc cgtcgaggtt aaaggtgttg gtgcag                              36

<210> SEQ ID NO 102
<211> LENGTH: 31
<212> TYPE: DNA
<213> ORGANISM: Artificial Sequence
<220> FEATURE:
<223> OTHER INFORMATION: Synthetic oligonucleotide
<400> SEQUENCE: 102
atagaattcg atatgtattt acgtgatcaa c                                   31

<210> SEQ ID NO 103
<211> LENGTH: 45
<212> TYPE: DNA
<213> ORGANISM: Artificial Sequence
<220> FEATURE:
<223> OTHER INFORMATION: Synthetic oligonucleotide
<400> SEQUENCE: 103
ggcggcgtcg acgacgcagt tcataggcgc cgatcgtttg cgcgt                    45

<210> SEQ ID NO 104
<211> LENGTH: 45
<212> TYPE: DNA
<213> ORGANISM: Artificial Sequence
<220> FEATURE:
<223> OTHER INFORMATION: Synthetic oligonucleotide
<400> SEQUENCE: 104
acgcgcaaac gatcggcgcc tatgaactgc gtcgtcgacg ccgcc                    45

<210> SEQ ID NO 105
<211> LENGTH: 38
<212> TYPE: DNA
<213> ORGANISM: Artificial Sequence

```
<220> FEATURE:
<223> OTHER INFORMATION: Synthetic oligonucleotide

<400> SEQUENCE: 105
tatctgcagg ttgtaggcgc ggcggagggc ctcctcct                              38
```